United States Patent
Hildebrand et al.

(10) Patent No.: US 7,521,202 B2
(45) Date of Patent: Apr. 21, 2009

(54) METHOD AND APPARATUS FOR THE PRODUCTION OF SOLUBLE MHC ANTIGENS AND USES THEREOF

(75) Inventors: William H. Hildebrand, Edmond, OK (US); Kiley R. Prilliman, San Diego, CA (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 71 days.

(21) Appl. No.: 11/099,283

(22) Filed: Apr. 4, 2005

(65) Prior Publication Data
US 2006/0134744 A1    Jun. 22, 2006

Related U.S. Application Data

(63) Continuation of application No. 10/022,066, filed on Dec. 18, 2001, now abandoned, and a continuation-in-part of application No. 09/974,366, filed on Oct. 10, 2001, and a continuation-in-part of application No. 09/465,321, filed on Dec. 17, 1999, now abandoned.

(60) Provisional application No. 60/327,907, filed on Oct. 9, 2001, provisional application No. 60/256,410, filed on Dec. 18, 2000, provisional application No. 60/256,409, filed on Dec. 18, 2000.

(51) Int. Cl.
  C07K 14/74   (2006.01)
  C07K 1/00    (2006.01)
  C12P 1/00    (2006.01)
(52) U.S. Cl. .................. 435/41; 435/69.1; 435/71.1; 435/383; 530/402; 530/403
(58) Field of Classification Search .................. None
  See application file for complete search history.

(56) References Cited

U.S. PATENT DOCUMENTS

| | | | |
|---|---|---|---|
| 4,683,202 | A | 7/1987 | Mullis |
| 5,256,541 | A | 10/1993 | Pouletty et al. |
| 5,270,169 | A | 12/1993 | Chang et al. |
| 5,292,641 | A | 3/1994 | Pouletty |
| 5,482,841 | A | 1/1996 | Buelow |
| 5,710,248 | A | 1/1998 | Grose |
| 5,750,367 | A | 5/1998 | Chan |
| 5,776,746 | A | 7/1998 | Denney, Jr. |
| 5,798,209 | A | 8/1998 | Chan |
| 6,001,365 | A | 12/1999 | Peterson et al. |
| 6,255,073 | B1 | 7/2001 | Cai et al. |

FOREIGN PATENT DOCUMENTS

| | | |
|---|---|---|
| WO | WO 95/11702 | 5/1995 |
| WO | WO 97/46256 | 12/1997 |
| WO | WO 98/06749 | 2/1998 |
| WO | WO 00/23053 | 4/2000 |

OTHER PUBLICATIONS

Robinson, MA and TJ Kindt in "Fundamental Immunology, Second Edition." [1989] ed. by WE Paul. Raven Press, New York pp. 489-491.*
"Molecular Cloning A Laboratory Manual", Maniatis et al., Selected Text "RNA -Dependent DNA Polymerase" p. 129, "Isolation of mRNA from Mammalian Cells" pp. 191-193, Cold Harbor Spring Laboratory (1982).
"Large Scale Production of Murine Monoclonal Antibodies Using Hollow Fiber Bioreactors", Evans et al., BioTechniques, 6(8):763-767 (1988).
"HIV-1 Reverse Transcriptase is a Target for Cytotoxic T Lymphocytes in Infected Individuals", Walker et al., Science, 240(4848):64-66 (1988).
"Assembly of MHC Class I Molecules Analyzed in Vitro", Townsend et al., Cell, 62(6):285-295 (1990).
"Allele-Specific Motifs Revealed by Sequencing of Self-Peptides Eluted From MHC Molecules", Falk et al., Nature, 351(6324):290-296, (1991).
"Characterization of Peptides Bound to the Class I MHC Molecule HLA-A2.1 By Mass Spectrometry", Hunt et al., Science, 255(5049):1261-1263 (1992).
"Peptide Binding to HLA-A2 and HLA-B27 Isolated From *Escherichia coli*", Parker et al., The Journal of Biological Chemistry, 267(8):5451-5459 (1992).
"Endogenous Peptides of Soluble Major Histocompatibilty Complex Class I Molecule, H-2Lds: Sequence Motif, Quantitative Binding, and Molecular Modeling of the Complex", Corr et al., J. Exp. Med., 176(6):1681-1682 (1992).
"The Specificity and Efficiency of Endogenous Peptides in the Induction of HLA Class I Alpha Chain Refolding", Tanigaki, Eur J. Immunol., 22(8):2177-2180 (1992).
"Can One Predict Antigenic Peptides for MHC Class I-Restricted Cytotoxic T Lymphocytes Useful for Vaccination?", Calin-Laurens et al., Vaccine, 11(9): 974-978 (1993).
"Direct Identification of an Endogenous Peptide Recognized by Multiple HLA-A2.1-Specific Cytotoxic T Cells", Henderson et al., Proc. Natl. Acad. Sci. USA, 90:10275-10279 (1993).
"Characterization of Endogenous Peptides Eluted From the Class I MHC Molecule HLA-B7 Determined by Mass Spectrometry and Computer Modeling", Huczko et al., J. Immunol., 151(5):2572-2587 (1993).
"Flow-Cytometric Determination of Peptide-Class I Complex Formation Identification of p53 Peptides That Bind to HLA-A2", Zeh et al., Human Immunology, 39:79-86 (1994).

(Continued)

*Primary Examiner*—David A. Saunders
*Assistant Examiner*—F. Pierre VanderVegt
(74) *Attorney, Agent, or Firm*—Dunlap, Codding, P.C.

(57) ABSTRACT

The field of the invention relates in general to at least one method and apparatus for the production of soluble MHC antigens and more particularly, but not by way of limitation, to at least one method and apparatus for the production of soluble Class I and II HLA molecules. The field of the invention also includes such produced soluble Class I and II HLA molecules and their use. According to the methodology of the present invention, the soluble Class I and II HLA molecules can be produced from either gDNA or cDNA starting material.

12 Claims, 86 Drawing Sheets

OTHER PUBLICATIONS

"Peptide Binding to the Most Frequent HLA-A Class I Alleles Measured By Quantitative Molecular Binding Assays", Sette et al., Molecular Immunology, 31(11): 813-822 (1994).

"Binding of a Peptide Antigen to Multiple HLA Alleles Allows Definition of an A2-Like Supertype", del Guercio et al., J Immunol., 154(2):685-693 (1995).

"An HLA Class I Peptide-Binding Assay Based on Competition for Binding to Class I Molecules on Intact Human B Cells Identification of Conserved HIV-I Polymerase Peptides Binding to HLA-A*0301", van der Burg et al., Human Immunology, 44:189-198 (1995).

"Measuring Interactions of MHC Class I Molecules Using Surface Plasmon Resonance", Khllko et al., J. Immunol. Methods, 183(1):77-94 (1995).

"Peptide Motifs of HLA-B58, B60, B61, and B62 Molecules", Falk et al., Immunogenetics, 41(2-3):165-168 (1995).

"An Empirical Method for the Prediction of T-Cell Epitopes", Davenport et al., Immunogenetics, 42(5):392-397 (1995).

"Peptide Motifs of HLA-B38 and B39 Molecules", Falk et al., Immunogenetics, 41(2-3):162-164, (1995).

"Detailed Motifs for Peptide Binding to HLA-A*0201 Derived From Large Random Sets of Peptides Using Cellular Binding Assay", Driifhout et al., Human Immunolgy, 43(1):1-12, (1995).

"Analysis of the Structure of Naturally Processed Peptides Bound by Class I and Class II Major Histocompatibility Complex Molecules", Appella et al., EXS., 73:105-119 (1995).

"Mapping and Ranking of Potential Cytotoxic T Epitopes in the p53 Protein: Effect of Mutations and Polymorphism on Peptide Binding to Purified and Refolded HLA Molecules", Gnjatic et al., Eur. J. Immunol., 25(6):1638-1642 (1995).

"Simplified High-Sensitivity Sequencing of a Major Histocompatibility Complex Class I-Associated Immunoreactive Peptide Using Matrix-Assisted Laser Desorption/Ionization Mass Spectrometry", Woods et al., 226(1):15-25 (1995).

"Probing HLA-B7 Conformational Shifts Induced by Peptide-Binding Groove Mutations and Bound Peptide With Anti-HLA Monoclonal Antibodies", Smith et al., 157(6):2470-2478 (1996).

"Mass Spectrometry. Ionization Methods and Instrumentation", Chapman, Methods Mol Biol., 61:9-28 (1996).

"HLA Allele Selection for Designing Peptide Vaccines", Kamalakar et al, Genetic Analysis: Biomolecular Engineering, 13:81-86 (1996).

"Class I-Restricted Presentation of an HIV-1 gp41 Epitope Containing an N-Linked Glycosylation Site. Implications for the Mechanism of Processing of Viral Envelope Proteins", Ferris et al., J Immunol., 156(2):834-840 (1996).

"Evaluation of Hollow Fiber Bioreactors as an Alternative to Murine Ascites Production for Small Scale Monoclonal Antibody Production", Jackson et al., J. Immunol. Methods, 189(2):217-231 (1996).

"T-Cell Epitope Determination", Walden, Curr Opin Immunol., 8(1):68-74 (1996).

"Large-Scale Production of Class I Bound Peptides: Assigning a Signature to HLA-B*1501", Prilliman et al., Immunogentics, 45(6):379-385 (1997).

"HLA Class I Binding Motifs Derived From Random Peptide Libraries Differ at the Cooh Terminus From Those of Eluted Peptides", Davenport et al., J. Exp. Med., 185(2): 367-371 (1997).

"Stability of Empty and Peptide-Loaded Class II Major Histocompatibility Complex Molecules at Neutral and Endosomal pH: Comparison to Class I Proteins", Reich et al., Proc. Natl. Acad. Sci. USA, 94:2495-2500 (1997).

"Human Peptide Transporter Deficiency: Importance of HLA-B in the Presentation of Tap-Independent EBV Antigens", de la Salle et al., J. Immunol., 158(10):4555-4563 (1997).

"A Novel, Highly Efficient Peptide-HLA Class I Binding Assay Using Unfolded Heavy Chain Molecules: Identification of HIV-1 Derived Peptides That Bind to HLA-A*0201 and HLA-A*0301", Tan et al., J. Immunol. Methods, 205(2): 201-209 (1997).

"Synthetic Peptides Based on Chlamydia Trachomatis Antigens Identify Cytotoxic T Lymphocyte Responses in Subjects From a Trachoma-Endemic Population", Holland et al., Clin. Exp. Immunol., 107(1):44-49 (1997).

"Complexity Among Constituents of the HLA-B*1501 Peptide Motif", Prilliman et al., Immunogenetics, 48:89-97 (1998).

"A Microcapillary Column Switching HPLC- Electrospray Ionization MS System for the Direct Identification of Peptides Presented by Major Histocompatibility Complex Class I Molecules", van der Heeft et al., Anal. Chem., 70:3742-3751 (1998).

"Synthetic Peptides of Human Papillomavirus Type 18 E6 Harboring HLA-A2.1 Motif Can Induce Peptide-Specific Cytotoxic T-Cells From Peripheral Blood Mononuclear Cells of Healthy Donors", Yoon et al., Virus Research, 54:23-29 (1998).

"MHCPEP, A Database of MHC-Binding Peptides: Update 1997", Brusic et al., Nucleic Acids Research, 26(1):368-371 (1998).

"Prediction of MHC Class II-Binding Peptides Using an Evolutionary Algorithm and Artificial Neural Network", Brusic et al., Bioinformatics, 14(2): 121-130 (1998).

"Efficient Generation of Major Histocompatibility Complex Class I-Peptide Complexes Using Synthetic Peptide Libraries", Stevens et al., The Journal of Biological Chemistry, 273(5):2874-2884 (1998).

"Neural Network-Based Prediction of Candidate T-Cell Epitopes", Honeyman et al., Nat. Biotechnol., 16(10): 966-969 (1998).

"Direct Identification of Major Histocompatibility Complex Class I-Bound Tumor-Associated Peptide Antigens of a Renal Carcinoma Cell Line by a Novel Mass Spectrometric Method", Flad et al., Cancer Research, 58(24):5803-5811 (1998).

"Structure and Function of a Membrane-Bound Murine MHC Class I Molecule", Cella et al., Proc. Natl. Acad. Sci. USA, 96:5634-5639 (1999).

"Identification of HLA-A3 and -B7-Restricted CTL Response to Hepatitis C Virus in Patients with Acute and Chronic Hepitis C", Chang et al., J. Immunol., 162(2):1156-1164 (1999).

"HLA-B15 Peptide Ligands are Preferentially Anchored at Their C Termini", Prilliman et al., J. Immunol., 162(12):7277-7284 (1999).

"Structure and Function of a Membrane-Bound Muring MHC Class I Molecule", Proc. Natl. Acad. Sci. USA, 96:5634-5639 (1999).

"Alpha-2 Domain Polymorphism and HLA Class I Peptide Loading", Prilliman et al., Tissue Antigens, 54(5):450-460 (1999).

"Syfpeithi: A Database for MHC Ligands and Peptide Motifs", Rammensee et al., Immunogenetics, 50:213-219 (1999).

"Peptide Motif of the Class I Molecule HLA-B*1503", Prilliman et al., Immunogenetics, 49:144-146 (1999).

"Clad Against all Clades- Can Vaccinomics Build a World HIV Vaccine?", Hollon, The Scientist, 14(18):1 (2000).

"Human Immunology- 26th Annual Ashi Meeting Abstracts 2000", 61: Supplement 2 (2000).

"C-Terminal Epitope Tagging Facilitates Comparative Ligand Mapping From MHC Class I Positive Cells", Hickman et al., Human Immunology, 61:1339-1346 (2000).

"Production and Application of Individual HLA Protein", Hildebrand et al., Human Immunology, abstract, vol. 61, No. Suppl 2, p. S81 XP008007733 (2000).

"Fimm, a database of functional molecular immunology", C Schonbach et al., Nucleic Acids Research, vol. 28, No. 1, Jan. 2000, pp. 222-224, XP002242984 Oxford, UK figure 1; table 1.

"Rapid Determination of HLA B*07 Ligands From the West Nile Virus NY99 Genome", De Groot et al., Emerging Infectious Diseases, 7(4):706-713 (2001).

"Examination of Possible Structural Constraints of MHC-Binding Peptides by Assessment of Their Native Structure Within Their Source Proteins", Schueler-Furman et al., Proteins: Structure, Function, and Genetics, 45:47-54 (2001).

"Use of Fluorescence Polarization to Monitor MHC-Peptide Interactions in Solution", Dedier et al., Journal of Immunological Methods, 255:57-66 (2001).

"Peptide/MHC Monomers Can be Inserted Into Artificial Lipid Bilayers as Artificial Antigen Presentation Constructs", Jiang et al., Section of Transplantation Immunology, BMT Department, M.D. Anderson Cancer Center, Houston, Texas, Abstract # 2126 (2001).

"Neural Network Method for Predicting Peptides That Bind Major Histocompatibility Complex Molecules", Gulukota et al., Methods Mol. Biol., 156:201-209 (2001).

"Molecular Cloning a Laboratory Manual", Maniatis et al., Selected Text "Synthesis and Cloning of DNA" vol. 1, pp. 211-246, Cold Harbor Spring Laboratory (1982).

"A Soluble Divalent Class I Major Histocompatibility Complex Molecule Inhibits Aloreactive T Cell at Nonmolar Concentrations", Dal Porto et al., Proc. Natl. Acad. Sci. USA, 90:6671-6675 (1993).

"Targeted Amplification of Alternatively Spliced Transcripts of Major Histocompatibility Complexes Class I Heavy Chain", Yang et al., Journal of Immunological Methods, 175:265-279 (1994).

"Prediction of Well-Conserved HIV-1 Ligands Using a Matrix-Based Algorithm, Epimatrix", Schafer et al., Vaccine, 16(19):1880-1884 (1998).

"Unisyn Strives for Flexibility and Scale", Prompt, Membrane and Separation Technology News, ISSN 0737-8483, Mar. 1, 1998.

"In Vitro Peptide Binding to Soluble Empty Class I Major Histocompatibility Complex Molecules Isolated From Transfected Drosophila Melanogaster Cells", Matsumura et al., The Journal Of Biological Chemistry, vol. 267, ISS Nov. 25:23589-23595 (1992).

"A Mutant Human B-2-Microglobulin Can be Used to Generate Diverse Multmeric Class I Peptide Complexes as Specific Probes for Cell Receptors", Walter et al., Journal of Immunological Methods 214:41-50 (1998).

* cited by examiner

A *(W6/32-purified B*1501 complexes)*

| position: | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| *dominant* | — | | Q(8.0) | K(3.0)<br>F(5.0)<br>R(4.0) | — | — | — | — | — | Y(4.0) | — | — | — | — | — |
| *strong* | — | | M(3.0)<br>L(2.0)<br>V(2.0) | Y(3.0)<br>P(2.0)<br>N(2.0)<br>H(2.0) | P(2.5)<br>D(2.5)<br>G(2.0)<br>E(2.0) | G(2.0) | — | — | — | F(3.0) | — | — | — | — | — |

FIG. 15

B (BBM.1-purified B*1501 complexes)

| position: | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| dominant | — | Q(7.5) | — | — | — | — | — | — | Y(4.0) | — | — | — | — | — |
| strong | — | P(3.5) | F(2.5) | P(2.2) | I(2.0) | — | — | — | F(3.0) | — | — | — | — | — |
| | | L(2.5) | K(2.5) | D(2.0) | | | | | | | | | | |
| | | V(2.0) | R(2.0) | G(2.0) | | | | | | | | | | |
| | | | P(2.0) | | | | | | | | | | | |
| | | | N(2.0) | | | | | | | | | | | |

FIG. 15 CONT'D.

Fraction 10

| | 2 | 3 | 4 | 5 | 6 | 7 | 8 | 9 | 10 | 11 | 12 |
|---|---|---|---|---|---|---|---|---|---|---|---|
| dominant | P<br>Q | - | - | - | - | - | - | - | - | - | - |
| strong | W | K<br>R<br>H | G<br>F | - | - | - | - | - | - | - | - |
| weak | S<br>I | E | D<br>N<br>M<br>I | S<br>W<br>P | H<br>S | V<br>T | I | Y | K | V | E |

Fraction 15

| | 2 | 3 | 4 | 5 | 6 | 7 | 8 | 9 | 10 | 11 | 12 |
|---|---|---|---|---|---|---|---|---|---|---|---|
| dominant | P<br>Q | - | - | - | - | - | - | - | - | - | - |
| strong | W | K<br>R<br>H | G<br>F | - | - | - | - | - | - | - | - |
| weak | S<br>I | E | D<br>N<br>M<br>I | S<br>W<br>P | H<br>S | V<br>T | I | Y | K | V | E |

Fraction 28

| position: | 2 | 3 | 4 | 5 | 6 | 7 | 8 | 9 | 10 | 11 | 12 |
|---|---|---|---|---|---|---|---|---|---|---|---|
| dominant | K | - | - | - | - | - | - | - | - | - | - |
| strong | Q<br>V<br>P | H<br>N<br>R | G | L<br>S<br>H | R | I | D<br>N | K | V | E | - |
| weak | - | P<br>F<br>K<br>D | E | P<br>E | V<br>A<br>F | P<br>M | Q<br>E<br>A<br>H<br>W | Y<br>F | - | F<br>P | S<br>K |

Fraction 31

| position: | 2 | 3 | 4 | 5 | 6 | 7 | 8 | 9 | 10 |
|---|---|---|---|---|---|---|---|---|---|
| dominant | - | K | - | W | - | - | - | - | - |
| strong | S | H | N | R | S | F | - | G | F |
|  | Q |  |  | M | Y | V |  |  |  |
|  | P |  |  |  |  |  |  |  |  |
| weak | L | Y | A | - | L | - | Y | Y | - |
|  |  | L |  |  | K |  | S |  |  |
|  |  | V |  |  |  |  | K |  |  |

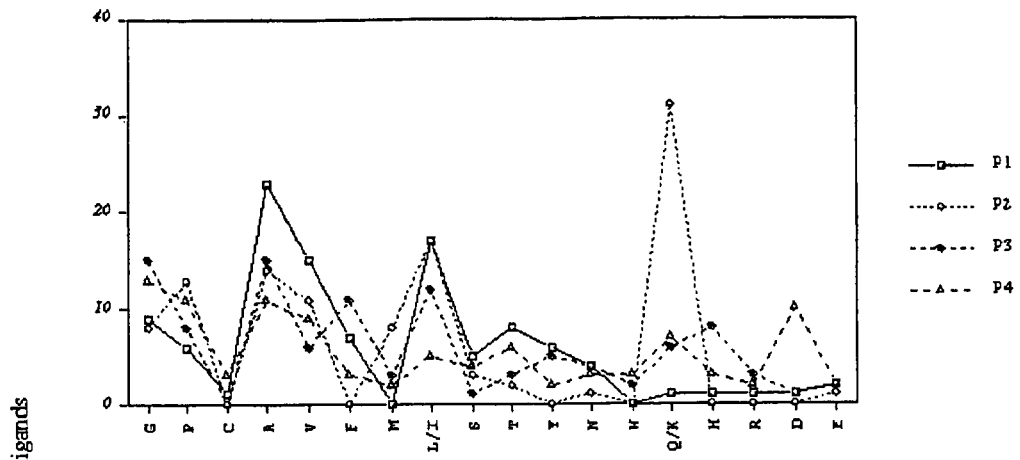
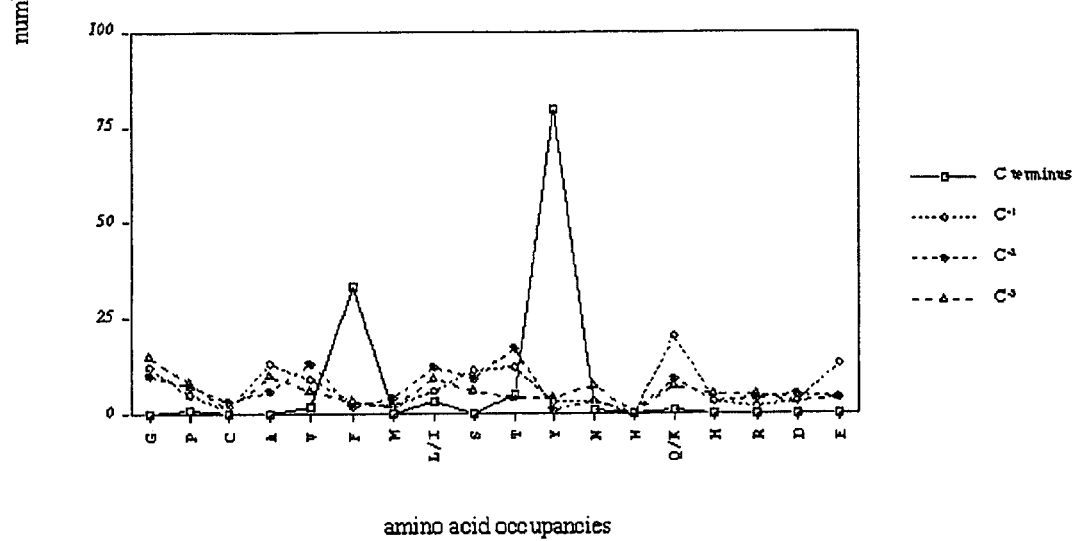
FIG. 21

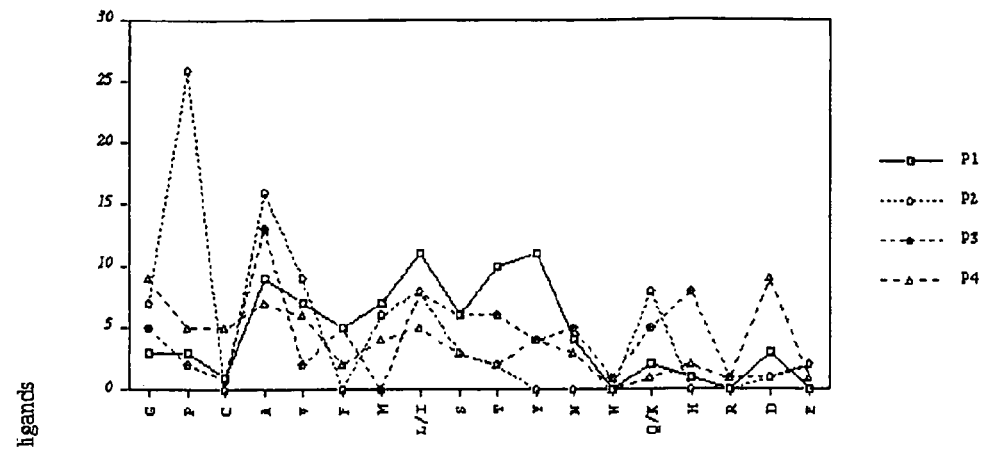
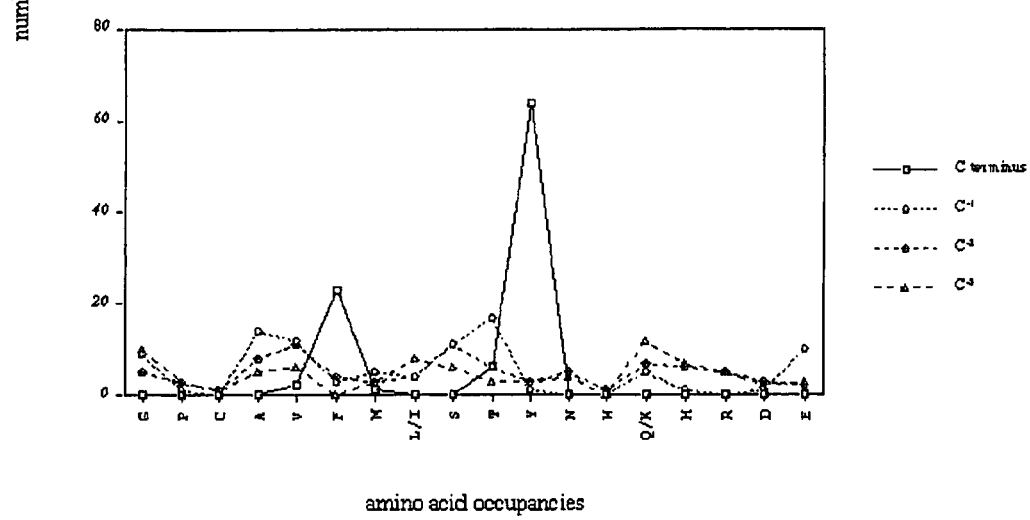
FIG. 23

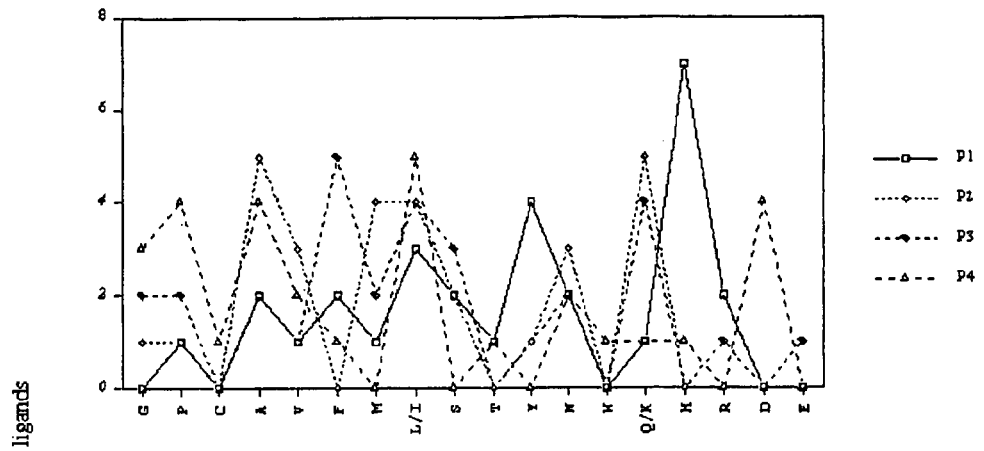
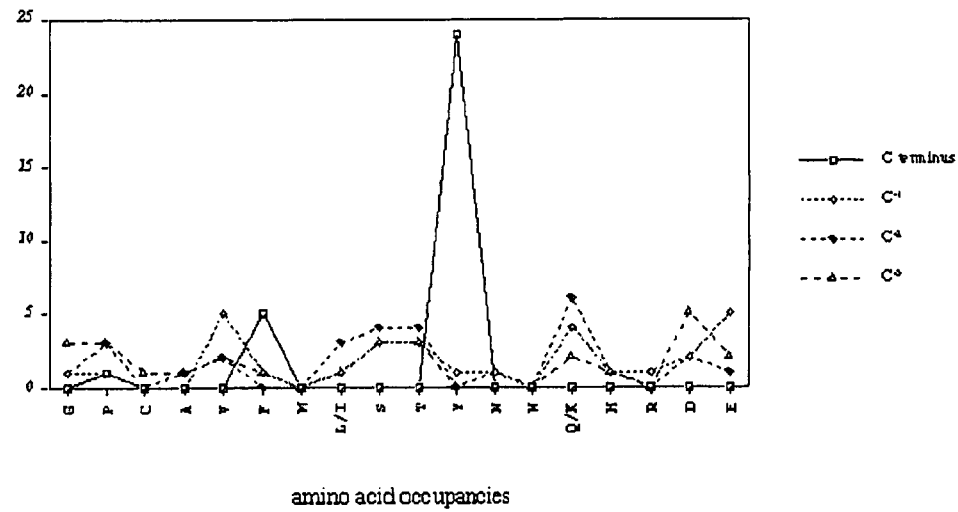
FIG. 25

FIG. 29 PCR Strategy

GDNA FIG. 5

TABLE 1

| consensus | 24 | 45 | 46 | 63 | 67 | S | W | E | W | ethnicity |
|---|---|---|---|---|---|---|---|---|---|---|
| | A | M | A | E | S | S | W | E | W | |
| B*1512 | – | – | – | – | – | – | – | D | G | Thai |
| B*1508 | – | – | – | N | F | – | – | – | – | Iranian/Indian/Amerindian |
| B*1501 | – | – | – | – | – | – | – | – | – | Caucasian |
| B*1503 | S | E | E | – | – | – | L | – | – | Black |
| B*1518 | S | E | E | N | C | – | L | – | – | Indian |
| B*1510 | S | E | E | N | C | Y | L | – | – | Black |

| primer | type | sequence (5'→3') |
| --- | --- | --- |
| HLA5UT | PCR (5'; inserts *Sal*I site) | GGGCGTCGACGGACTCAGAATCTCCCCAGACGCCGAG |
| sHLA3TM | PCR (3'; inserts stop codon and *Hind*III site) | CCCGAAGCTTTCATCTCAGGGTGAG |
| 5PXI | PCR (5'; inserts *Xba*I site) | GGGCTCTAGAGGACTCAGAATCTCCCCAGACGCCGAG |
| 3PEI | PCR (3'; inserts stop codon and *Eco*RI site) | CCCGGAATTCTCATCTCAGGGTGAG |
| M13 universal | sequencing (mp18, end through α$_3$) (mp19, leader through α$_2$) | TGTAAAACGACGGCCAGT |
| 3S | sequencing (α$_2$ through α$_3$) | CGGCAAGGATTACATCGCCCTG |
| JD3S | sequencing (α$_3$ through end) | CCCCATCGTGGGCATCGTTG |
| 3N | sequencing (α$_2$ through leader) | CAGGGCGATGTAATCCTTGCCG |
| 4N | sequencing (α$_3$ through α$_2$) | GCCAGTCAGTGTGATCTCCGC |
| T7 promoter | sequencing (T7 promoter forward priming site) | TAATACGACTCACTATAGGG |
| pcDNA3.1/BGH | sequencing (BGH reverse priming site) | TAGAAGGCACAGTCGAGG |

TABLE 2

TABLE 3

| allele | # fractions | P2 extras | P9 extras | >9 cycles? |
|---|---|---|---|---|
| B*1501 | 7 | P | - | yes (14) |
| B*1508 | 8 | QVKRS | IVMQ | yes (14) |
| B*1503 | 3 | P | MNL | yes (14) |
| B*1510 | 3 | PR | MIY | yes (14) |

| ligand | source protein | allele(s) characterized from |
|---|---|---|
| HLA ligands | | |
| VGYVDDTQF | HLA-I α (49-57) | B*1501, 1508 |
| IAVGYVDDTQF | HLA-I α (47-57) | B*1501, B*1512 |
| IKADHVSTY | HLA-II DPα (32-40) | B*1503 |
| GSHSMRYF | HLA-I α (25-32) | B*1503 |
| Replication/transcription/translation ligands | | |
| GQRKGAGSVF | 60S ribosomal protein L8 (7-16) | B*1501, 1503 |
| AQAESLRY | 40S ribosomal protein S3 (100-107) | B*1501 |
| GKVRTDITY | 40S ribosomal protein S4 (73-81) | B*1503 |
| SHAQTVVL | 40S ribosomal protein S27 (48-55) | B*1510 |
| SQFGGGSQY | eIF3-p66 (61-69) | B*1501, 1503, 1508, B*1512 |
| VQGPVGTDF | zinc finger transcription factor (296-304) | B*1501 |
| APPPPPPPP | transcription factor ZFM1 (581-589) | B*1501 |
| YQHTGAVL | spleen mitotic checkpoint BUB3 (53-60) | B*1510 |
| AHGRKMSKSL | valyl-tRNA synthetase (859-868) | B*1510 |
| LPHQPLATY | Oct-binding factor 1 (52-60) | B*1508 |
| AKYSTPATL | probable ATP-dependent RNA helicase DDX10 (280-288) | B*1503 |
| AKAGITTTL | DNA replication licensing factor MCM5 (470-478) | B*1503 |
| TQAPGNPVL | splicing factor U2AF large chain (179-187) | B*1510 |
| SHQRQLLL | Kin17 (49-56) | B*1510 |
| NQFQALLQY | polypyrimidine tract-binding protein (220-228) | B*1512 |
| Biosynthetic/degradative modification ligands | | |
| FVSNHAY | aldolase A (358-364) | B*1501, 1508 |
| ILGPPGSVY | ubiquitin-protein ligase (83-91) | B*1501, B*1502, 1508, B*1512 |
| YMIDPSGVSY | proteasome subunit C8 (150-159) | B*1501, B*1502, 1508, B*4601, B*1512 |
| NHAIVSTSV | 26S protease (S4) regulatory subunit (741-749) | B*1510 |
| IHTPENPVI | lanosterol 14-alpha demethylase (488-496) | B*1510 |

TABLE 4

| | | |
|---|---|---|
| AHSNLASVL | O-linked GlcNAc transferase (237-245) | B*1510 |
| *Signalling/modulatory ligands* | | |
| VVAPITTGY | calcyclin binding protein (63-71) | B*1501, 1508 |
| GHSPPTSSL | tyrosine-protein kinase JAK3 (491-499) | B*1510 |
| LPPPPPPPP | Fas antigen ligand (54-62) | B*1503 |
| NHANGLTL | serine/threonine protein phosphatase PP2A (α and β) (229-236) | B*1510 |
| *Transporter/chaperone ligands* | | |
| EHVASSPAL | 13S Golgi transport complex 90 kD subunit (741-749) | B*1510 |
| HHSDGSVSL | tapasin (354-362) | B*1509, B*1510 |
| QPGPQIVY | GABA/noradrenaline transporter (261-268) | B*1503 |
| *Structural/cytokinesis ligands* | | |
| NMNDLVSEY | tubulin β chain (414-422) | B*1508 |
| THTQPGVQL | septin 2 homolog (70-78) | B*1509, B*1510 |
| SHANSAVVL | β-adaptin (249-257) | B*1509, B*1510 |
| *Unknown function ligands* | | |
| GQYPTQPTY | KIAA0058 (5-13); like *Mus muluscus* proline-rich protein | B*1503 |
| VKVIQQESY | mammary tumor-associated protein INT6 (278-286) | B*1503 |
| AKYPHVEDY | Ki nuclear autoantigen (207-215) | B*1503 |
| AMNPTNTVF | heat shock cognate 71 kD protein (60-68) | B*1503 |
| CPLSCFT | human HTGS database | B*1501, B*1503, B*1508 |
| MPHSGYGF | human EST | B*1508 |
| CHSAFAL | human HTGS database | B*1510 |
| LHLLTLEA | human EST | B*1510 |
| KNANLVQLY | human EST | B*1512 |

TABLE 4 CONT'D.

| fraction | ion for MS/MS | derived peptide sequence |
|---|---|---|
| 7 | 504.1 (+2) | H M S G Z P T S Y |
| 7 | 549.2 (+2) | H N Z A A H Z E Y |
| 8 | 526.0 (+2) | H A A X Y S Z V Y |
| 10 | 484.3 (+2) | Y Q S D H R Y |
| 11 | 424.3 (+2) | H X S T Z D F |
| 11 | 464.3 (+2) | H A P P T D P P P |
| 11 | 550.0 (+2) | H G P A N R D S V F |
| 11 | 563.3 (+2) | F P Y P T D P Z Y |
| 12 | 531.2 (+2) | Z N A N X V Z X Y |
| 14 | 585.6 (+2) | R S F X X E N E Y |
| 16 | 488.7 (+2) | H M Z N P T S Y |
| 16 | 661.9 (+2) | Y V X F – I – V Y |
| 17 | 577.6 (+2) | R S M X R C P E Y |
| 18 | 523.0 (+2) | – E V T A Z T Y |
| 20 | 582.4 (+2) | M Y N C N E X D Y |
| 25 | 562.8 (+2) | N Q F Q A L L Q Y |

TABLE 5

Table 6

| ALLELE | 7 | 9 | 24 | 25 | 26 | 34 | 35 | 36 | 45 | 62 | 63 | 66 | 67 | 70 | 74 | 77 | 80 | P2 MOTIF (dominant/strong) |
|---|---|---|---|---|---|---|---|---|---|---|---|---|---|---|---|---|---|---|
| consensus | Y | Y | A | V | G | V | R | F | M | R | E | I | S | N | Y | Y | L | W |
| B*1508 | - | - | - | - | - | - | - | - | - | - | N | - | F | - | - | - | - | PA |
| B*1513 | - | - | - | - | - | - | - | - | - | - | - | - | - | - | - | - | - | ILQVP |
| B*1502 | - | - | - | - | - | - | - | - | - | - | N | - | - | - | - | - | - | LVQP |
| B*1501 | - | - | - | - | - | - | - | - | - | - | - | - | - | - | - | - | - | QMLV |
| B*1512 | - | - | - | - | - | - | - | - | - | - | - | - | - | - | - | - | G | QLM |
| B*1503 | - | - | S | - | - | - | - | - | E | - | - | - | - | - | - | - | - | QKM |
| B*1518 | - | - | S | - | - | - | - | - | E | - | N | - | C | - | - | - | - | H |
| B*1509 | - | - | S | - | - | - | - | - | E | - | N | - | C | - | - | - | - | H |
| B*1510 | - | - | S | - | - | - | - | - | E | - | N | - | C | - | - | - | - | H |
| B*1517 | - | - | - | - | - | - | - | - | - | - | - | N | M | S | - | - | - | TS |
| B*1516 | - | - | - | - | - | - | - | - | - | - | - | N | M | S | - | - | - | T |
| B*4601 | - | - | - | - | - | - | - | - | - | - | - | K | Y | Q | - | - | - | MI |

TABLE 7

| ALLELE | 70 | 73 | 74 | 76 | 77 | 80 | 81 | 84 | 95 | 96 | 97 | 113 | 114 | 116 | 123 | 143 | 145 | 146 | 147 | P9 MOTIF (dominant/strong) |
|---|---|---|---|---|---|---|---|---|---|---|---|---|---|---|---|---|---|---|---|---|
| consensus | N | T | Y | E | S | N | L | Y | L | Q | R | D | S | Y | Y | I | T | K | W | |
| B*1502 | - | - | - | - | - | - | - | - | I | - | - | - | - | - | - | - | - | - | - | YFM |
| B*1501 | - | - | - | - | - | - | - | - | - | - | - | - | - | - | - | - | - | - | - | YF |
| B*1503 | - | - | - | - | - | - | - | - | - | - | - | - | - | - | - | - | - | - | - | YF |
| B*1508 | - | - | - | - | - | - | - | - | - | - | - | - | - | - | - | - | - | - | - | YF |
| B*1512 | - | - | - | - | - | - | - | - | - | - | - | - | - | - | - | - | - | - | - | YF |
| B*1518 | - | - | - | - | - | - | - | - | - | - | - | - | - | - | - | - | - | - | - | YF |
| B*4601 | Q | - | D | V | - | - | - | - | - | - | - | - | - | - | - | - | - | - | - | YF |
| B*1517 | S | - | - | - | N | I | A | - | - | - | - | H | D | - | - | - | - | - | - | YF |
| B*1516 | S | - | - | - | N | I | A | - | W | - | - | - | - | - | - | - | - | - | - | Y |
| B*1509 | - | - | - | - | - | - | - | - | - | - | - | N | Y | - | - | - | - | - | - | LF |
| B*1510 | - | - | - | - | - | - | - | - | - | - | - | - | Y | - | - | - | - | - | - | LF |
| B*1513 | - | - | - | N | I | A | - | I | - | - | - | - | - | - | - | - | - | - | - | W |

| fraction | ion for MS/MS | derived peptide sequence |
|---|---|---|
| 9 | 490.3 (+2) | A G G Z P A T P P A X |
| 9 | 513.1 (+2) | S H Z G C V Z P A V |
| 10 | 433.8 (+2) | G H D P S P A A |
| 10 | 455.4 (+2) | E H V A S S P A L |
| 10 | 482.6 (+2) | M C Z - G M P A X |
| 10 | 482.8 (+2) | G H G A N N D P A X |
| 10 | 495.7 (+2) | X H S Z P A G P A X |
| 11 | 448.9 (+2) | M H A D N P V X |
| 11 | 482.8 (+2) | G H <u>C</u> <u>P</u> R N P A X |
| 11 | 495.7 (+2) | X H S G A P Z A P X |
| 11 | 516.7 (+2) | X H <u>T</u> <u>E</u> <u>H</u> A P X |
| 12 | 448.4 (+2) | T Q A P G N P V L |
| 12 | 460.3 (+2) | T Z A <u>G</u> <u>C</u> <u>M</u> <u>V</u> P X |
| 13 | 464.8 (+2) | M V - - H P V X |
| 14 | 456.7 (+2) | A H S V P S P A F |
| 14 | 477.7 (+2) | M H T - - P A P V |
| 14 | 482.8 (+2) | P G A A V V P S X |
| 15 | 510.1 (+2) | I H T P E N P V I |
| 16 | 456.7 (+2) | S H <u>D</u> <u>G</u> <u>S</u> V P T X |
| 16 | 522.7 (+2) | - - - - - - P V X |
| 16 | 523.3 (+2) | M A H S - - P V F |
| 17 | 523.2 (+2) | - H - - - - P V F |
| 18 | 474.8 (+2) | M X <u>G</u> <u>X</u> S F P A X |
| 18 | 491.2 (+2) | V H T C V N P V X |
| 18 | 515.8 (+2) | E W <u>H</u> <u>X</u> P V S X |
| 19 | 496.6 (+2) | <u>E</u> <u>T</u> <u>P</u> <u>E</u> H A P V X |

TABLE 8

TABLE 9

| side chain | P1 | P2 | P3 | P4 | | | | | side chain |
|---|---|---|---|---|---|---|---|---|---|
| G | — | — | 11.90% | 10.32% | 11.90% | — | — | — | G |
| P | — | 10.32% | — | — | — | — | — | — | P |
| C | — | — | — | — | — | — | — | — | C |
| A | 18.25% | 11.11% | 11.90% | — | — | — | 10.32% | — | A |
| V | 11.90% | — | — | — | — | 10.32% | — | — | V |
| F | — | — | — | — | — | — | — | 26.19% | F |
| M | — | — | — | — | — | — | — | — | M |
| I/L | 13.49% | 13.49% | — | — | — | — | — | — | I/L |
| S | — | — | — | — | — | — | — | — | S |
| T | — | — | — | — | — | 13.49% | — | — | T |
| Y | — | — | — | — | — | — | — | 63.49% | Y |
| N | — | — | — | — | — | — | — | — | N |
| W | — | — | — | — | — | — | — | — | W |
| Q/K | — | 24.60% | — | — | — | — | 15.87% | — | Q/K |
| H | — | — | — | — | — | — | — | — | H |
| R | — | — | — | — | — | — | — | — | R |
| D | — | — | — | — | — | — | — | — | D |
| E | — | — | — | — | — | — | 10.32% | — | E |
| N value | 13.64 | 19.52 | 3.80 | 0.32 | 1.90 | 3.81 | 6.51 | 69.68 | C value |
| $N_{sum}$ | 37.28 | | | | 81.90 | | | | $C_{sum}$ |

B*1501 $N_{sum}/C_{sum}$ = 0.46

TABLE 10

| side chain | P1 | P2 | P3 | P4 | C-term | | | G-term | side chain | C value |
|---|---|---|---|---|---|---|---|---|---|---|
| G | 12.16% | — | — | — | 12.16% | — | — | — | G | |
| P | — | 10.81% | 12.16% | 13.51% | 10.81% | — | — | — | P | |
| C | 31.08% | — | — | 12.16% | — | — | — | — | C | |
| A | — | — | — | — | — | — | — | — | A | |
| V | — | — | — | — | — | — | — | — | V | |
| F | — | — | — | — | — | — | — | 20.27% | F | |
| M | — | — | — | — | — | — | 13.51% | — | M | |
| I/L | — | — | — | — | — | — | 10.81% | — | I/L | |
| S | — | — | — | — | — | 13.51% | 17.57% | — | S | |
| T | — | — | — | — | — | — | — | — | T | |
| Y | — | — | — | — | — | — | — | 68.92% | Y | |
| N | — | — | — | — | — | — | — | — | N | |
| W | — | — | — | — | — | — | — | — | W | |
| Q/K | — | 43.24% | — | — | 13.51% | 12.16% | 14.86% | — | Q/K | |
| H | — | — | — | — | — | — | — | — | H | |
| R | — | — | — | — | — | — | — | — | R | |
| D | — | — | — | — | — | — | — | — | D | |
| E | — | — | — | — | — | — | — | — | E | |
| N value | 23.24 | 34.05 | 2.16 | 5.67 | 6.48 | 9.99 | 12.43 | 69.19 | C value | |
| $N_{sum}$ | 65.12 | | | | | | | | $C_{sum}$ | |

B*1503  $N_{sum}/C_{sum} = 0.66$

| side chain | P1 | P2 | P3 | P4 | C | C | C | side chain |
|---|---|---|---|---|---|---|---|---|
| G | – | – | – | – | 10.42% | – | – | G |
| P | – | 27.08% | – | – | – | – | – | P |
| C | – | – | – | – | – | – | – | C |
| A | – | 16.67% | 13.54% | – | – | – | – | A |
| V | – | – | – | – | – | 14.58% | – | V |
| F | – | – | – | – | – | 12.50% | 23.96% | F |
| M | – | – | – | – | – | – | – | M |
| I/L | 11.46% | – | – | – | – | – | – | I/L |
| S | – | – | – | – | – | 11.46% | – | S |
| T | 10.42% | – | – | – | – | 17.71% | – | T |
| Y | 11.46% | – | – | – | – | – | 66.67% | Y |
| N | – | – | – | – | – | – | – | N |
| W | – | – | – | – | – | – | – | W |
| Q/K | – | – | – | – | 12.50% | – | – | Q/K |
| H | – | – | – | – | – | – | – | H |
| R | – | – | – | – | – | – | – | R |
| D | – | – | – | – | – | – | – | D |
| E | – | – | – | – | – | 10.42% | – | E |
| N value | 3.34 | 23.75 | 3.54 | 0.00 | 2.92 | 2.92 | 70.63 | C value |
| $N_{sum}$ | 30.63 | | | | | | | $C_{sum}$ |

B*1508 $N_{sum}/C_{sum} = 0.33$

TABLE 11

| side chain | P1 | P2 | P3 | P4 | | C-Term | side chain |
|---|---|---|---|---|---|---|---|
| G | 10.57% | - | 10.57% | 10.57% | 11.38% | - | G |
| P | - | - | - | 12.20% | - | - | P |
| C | - | - | - | - | - | - | C |
| A | - | - | 19.51% | - | - | - | A |
| V | - | - | - | - | - | 14.63% | V |
| F | - | - | - | - | - | - | F |
| M | 11.38% | - | - | - | - | 22.76% | 10.57% | M |
| I/L | 12.20% | - | - | - | - | 12.20% | 70.73% | I/L |
| S | 11.38% | - | - | - | - | 15.45% | - | S |
| T | - | - | - | - | - | - | T |
| Y | - | - | - | - | - | - | Y |
| N | - | - | - | - | - | - | N |
| W | - | - | - | - | - | - | W |
| Q/K | - | 58.54% | - | - | - | - | Q/K |
| H | - | - | - | - | - | - | H |
| R | - | - | - | - | - | - | R |
| D | - | - | - | - | - | - | D |
| E | - | - | - | - | - | - | E |
| N value | 5.53 | 48.54 | 10.08 | 2.77 | 1.38 | 18.46 | 25.04 | 61.3 | C value |
| $N_{sum}$ | 66.92 | | | | | 105.18 | | | $C_{sum}$ |

B*1510 $N_{sum}/C_{sum}$ = 0.63

TABLE 12

TABLE 13

| side chain | P1 | P2 | P3 | P4 | C1' | C2' | C3' | side chain | C value |
|---|---|---|---|---|---|---|---|---|---|
| G | - | - | - | - | - | - | - | G | - |
| P | - | - | - | 13.33% | - | - | - | P | - |
| C | - | - | - | - | - | - | - | C | - |
| A | - | 16.67% | - | 13.33% | - | - | - | A | - |
| V | - | - | - | - | - | - | - | V | - |
| F | - | - | 16.67% | - | - | 16.67% | - | F | 16.67% |
| M | - | 13.33% | - | - | - | - | - | M | - |
| I/L | - | 13.33% | 13.33% | 16.67% | - | - | - | I/L | - |
| S | - | - | - | - | - | 13.33% | - | S | - |
| T | - | - | - | - | - | 13.33% | - | T | - |
| Y | 13.33% | - | - | - | - | - | 80.00% | Y | - |
| N | - | - | - | - | - | - | - | N | - |
| W | - | - | - | - | - | 20.00% | - | W | - |
| Q/K | 23.33% | 16.67% | 13.33% | - | - | - | - | Q/K | 13.33% |
| H | - | - | - | - | - | - | - | H | - |
| R | - | - | - | - | - | - | - | R | - |
| D | - | - | - | 13.33% | - | - | - | D | 16.67% |
| E | - | - | - | - | 16.67% | - | - | E | 16.67% |
| N value | 16.66 | 20.00 | 13.33 | 16.66 | 6.67 | 16.66 | 16.67 | C value | 76.67 |
| $N_{sum}$ | 66.65 | | | | | | | $C_{sum}$ | 116.67 |

$B*1512 \quad N_{sum}/C_{sum} = 0.57$

| fraction | ion for MS/MS | derived peptide sequence | alleles overlapping |
|---|---|---|---|
| 6 | 398.2 (+3) | - - W D R H T X F | B*1501/B*1508 |
| 6 | 448.2 (+2) | - - - - - Y T | B*1501/B*1508 |
| 7 | 418.7 (+2) | A Q F A S G A G Z | B*1501/B*1503 |
| 8 | 402.2 (+2) | - G - - C D Y | B*1501/B*1503 |
| 8 | 418.7 (+2) | G S H F G V A Y | B*1501/B*1508 |
| 8 | 516.7 (+2) | N Q Z H G S A E Y | B*1501/B*1503/B*1508/B*1512 |
| 8 | 642.7 (+2) | P M N D W X M T Z T Y | B*1501/B*1512 |
| 9 | 331.4 (+3) | A P M A R G Z Y | B*1501/B*1503 |
| 9 | 418.7 (+2) | F V S N H A Y | B*1501/B*1508 |
| 9 | 433.2 (+2) | N P P A Z Z P N | B*1501/B*1503 |
| 9 | 437.0 (+2) | T G - - - - A Y | B*1501/B*1508 |
| 9 | 441.2 (+2) | - Q - D P P P D M Z Y | B*1501/B*1503 |
| 9 | 446.6 (+2) | G Q Z Z A V D F | B*1501/B*1503 |
| 9/10 | 465.2 (+2) | S Q F G G G S Q Y | B*1501/B*1503/B*1508/B*1512 |
| 9 | 476.2 (+2) | S Q F D H V T Y | B*1501/B*1508 |
| 9 | 578.0 (+2) | T P X G E P Y Z S Y | B*1501/B*1503/B*1508 |
| 10 | 398.3 (+2) | X A N - - V T | B*1501/B*1508 |
| 10 | 456.8 (+2) | C P L S C F T | B*1501/B*1503/B*1508 |
| 10 | 509.0 (+2) | F L Z A M Z S T Y | B*1501/B*1508/B*1512 |
| 10 | 532.0 (+2) | T V X D S Z T H Y | B*1501/B*1508/B*1512 |
| 13 | 503.6 (+2) | G Q R K G A G S V F | B*1501/B*1503 |
| 14 | 460.7 (+2) | V V A P I T T G Y | B*1501/B*1508 |
| 14 | 475.1 (+2) | V V A C V - - - Y | B*1501/B*1508 |
| 14 | 525.3 (+2) | P L A - N - H T Y | B*1501/B*1508 |
| 15 | 514.2 (+2) | F Q A R X T E Y | B*1501/B*1508 |
| 16 | 522.0 (+2) | V G Y V D D T Q F | B*1501/B*1508 |
| 17 | 351.3 (+3) | A A F C G - - - X V | B*1501/B*1508 |
| 17 | 408.7 (+2) | Y L H - - E T | B*1501/B*1508 |
| 17/18 | 451.4 (+2) | I L G P P G S V Y | B*1501/B*1508/B*1512 |
| 17 | 462.4 (+2) | X L G D V N M Y | B*1501/B*1508 |
| 17 | 507.0 (+2) | - - - - X V E F | B*1501/B*1508 |
| 17 | 519.2 (+2) | T A R V X S V E Y | B*1501/B*1508 |
| 18 | 565.7 (+2) | A E F W A C Z X Y | B*1501/B*1503 |
| 18/19 | 566.2 (+2) | Y M I D P S G V S Y | B*1501/B*1508/B*1512 |
| 19/20 | 560.0 (+2) | X V E X T T D Y Y | B*1501/B*1512 |
| 20/21 | 448.2 (+2) | A A G X G P T F Y | B*1501/B*1512 |
| 20/21 | 614.0 (+2) | I A V G Y V D D T Q F | B*1501/B*1512 |
| 21/22 | 507.2 (+2) | V A F V X F V G Y | B*1501/B*1512 |
| 21/22 | 557.2 (+2) | Y N R W S X E F | B*1501/B*1512 |
| 22/23 | 510.8 (+2) | A L M P - - X N Y | B*1501/B*1512 |

TABLE 14

| allele | ion overlaps collided | positive overlaps | overlap frequency |
|---|---|---|---|
| B*1512 | 20 | 14 | *70%* |
| B*1508 | 286 | 25 | *9%* |
| B*1503 | 88 | 12 | *14%* |
| B*1510 | 26 | 0 | *0%* |

TABLE 15

| motif P2/P9 | + length variation only | + P2 variation only |
|---|---|---|
| DLASMLNRY (64-72) | MQLLCVF (1-7) | DIEGHASHY (28-36) |
| MLNRYKLIY (68-76) | HLDIEGHASHY (26-36) | SAPLEKQLF (123-131) |
| PLEKQLFYY (125-133) | MLSAPLEKQLF (121-131) | APLEKQLFY (124-132) |
| YQLRCHLSY (149-157) | PLEKQLF (125-131) | LPNTRPHSY (138-146) |
| ALSINGDKF (159-167) | PLEKQLFY (125-132) | NTRPHSYVF (140-148) |
| DLPDLRGPF (203-211) | TMLPNTRPHSY (136-146) | SINGDKFQY (161-169) |
| FVPNLKDMF (242-250) | MLPNTRPHSY (137-146) | YTGAMTSKF (169-177) |
| AVTMTAASY (253-261) | QLRCHLSY (150-157) | TSKFLMGTY (174-182) |
| TMFEVSVAF (290-298) | YVALSINGDKF (157-167) | LTSAQSGDY (216-224) |
| DLRWLAKSF (314-322) | FQYTGAMTSKF (167-177) | YSLVIVTTF (224-232) |
| HLTTEKQEY (366-374) | AMTSKFLMGTY (172-182) | VIVTTFVHY (227-235) |
| ALRLATVGY (375-383) | HVLSLVF (192-198) | TTFVHYANF (238-246) |
| ALGTESGLF (467-475) | SLTSAQSGDY (215-224) | MTAASYARY (256-264) |
| AVSNAVDGF (505-513) | SLVIVTTF (225-232) | DTETLTTMF (284-292) |
| ALYEASTTY (564-572) | LVIVTTF (226-232) | ATVKGMQSY (338-346) |
| RQIPKIQNF (597-605) | IVTTFVHY (228-235) | ATSVLLSAY (396-404) |
| ILSSNYFDF (643-651) | IVTTFVHYANF (228-238) | SAYNRHPLF (402-410) |
| TVMEIAGLY (666-674) | FVHYANFHNF (232-241) | HTVMRETLF (414-422) |
| HVVLAIILY (679-687) | FVHYANFHNFY (232-242) | ESGLFSPCY (471-479) |
| VVLAIILYF (680-688) | TMTAASY (255-261) | SPCYLSLRF (476-484) |
| FLVHKIVMF (696-704) | TMTAASYARY (255-264) | IIPLINVTF (544-552) |
| LVHKIVMFF (697-705) | ELDTETLTTMF (282-292) | TTYLSSSLF (570-578) |
| | TMFEVSVAFF (290-399) | NSILSSNYF (641-649) |
| | TVLKDIIGICY (326-326) | AIILYFIAF (683-691) |
| | VLKDIIGICY (327-326) | FIAFALGIF (688-696) |
| | TVKGMQSY (339-346) | |
| | RLATVGY (377-383) | |
| | TVGYPKAGVY (380-389) | |
| | LLSAYNRHPLF (400-410) | |
| | PLHTVMRETLF (412-422) | |
| | VMRETLF (416-422) | |
| | GLALGTESGLF (465-475) | |
| | GLFSPCY (473-479) | |
| | LMIIPLINVTF (542-552) | |
| | PLINVTF (546-552) | |
| | EVRGSALY (559-566) | |
| | YLSSSLF (572-578) | |
| | TQKSCIF (608-614) | |
| | TQKSCIFCGF (608-617) | |
| | GLETTTY (627-633) | |
| | VQNSILSSNY (639-648) | |
| | VQNSILSSNYF (639-649) | |
| | ILSSNYF (643-649) | |
| | VMEIAGLY (667-674) | |
| | VVLAIILY (680-687) | |
| | VVLAIILYF (680-688) | |
| | VLAIILY (681-687) | |
| | VLAIILYF (681-688) | |
| | VLAIILYFIAF (681-691) | |
| | ILYFIAF (685-691) | |
| | FLVHKIVMFF (696-705) | |

TABLE 16

TABLE 17

| Primer name | Sequence 5'-3' | Locus | Cut site | Annealing site |
|---|---|---|---|---|
| PP5UTA | GCGCTCTAGACCCAGACGCCGAGGATGGCC | A | XbaI | 5UT |
| 3PPI4A | GCCCTGACCCTGCTAAAGGT | A | | Intron 4 |
| PP5UTB | GCGCTCTAGACCACCCGGACTCAGAATCTCCT | B | XbaI | 5UT |
| 3PPI4B | TGCTTTCCCTGAGAAGAGAT | B | | Intron 4 |
| 5UTB39 | AGGCGAATTCCAGAGTCTCCTCAGACGCG | B*39 | EcoRI | 5UT B39 |
| 5PKCE | GGGCGAATTCCCGCCGCCACCATGCGGGTCATGGCGCC | C | EcoRI | 5UT |
| 3PPI4C | TTCTGCTTTCCTGAGAAGAC | C | | Intron 4 |
| PP5UT | GGGCGAATTCGGACTCAGAATCTCCCAGACGCCGAG | B | EcoRI | 5UT |
| PP3PEI | CCGCGAATTCTCATCTCAGGGTGAGGGCT | A,B,C | EcoRI | Exon 4 |
| PP3PEIH | CCGCAAGCTTTCATCTCAGGGTGAGGGCT | A,B,C | HindIII | Exon 4 |
| 3PEIHC7 | CCGCAAGCTTTCAGCTCAGGGTGAGGGGCT | Cw*07 | HindIII | Exon 4 |

| Primer Name | Sequence 5'-3' |
|---|---|
| T7Prom | TAATACGACTCACTATAGGG |
| BGHrev | TAGAAGGCACAGTCGAGG |
| PPI2E2R | GTCGTGACCTGCGCCCC |
| PPI2E2F | TTTCATTTTCAGTTTAGGCCA |
| ABCI3E4F | GGTGTCCTGTCCATTCTCA |

5'CY5 Sequencing Primers

TABLE 18

TABLE 19

| Sample | OD 260nm | OD 280nm | 260nm/280nm | Dilution factor | Concentration ug/ml |
|---|---|---|---|---|---|
| 3A394 | 0.0346 | 0.0202 | 1.7111 | 20 | 34.5821 |

TABLE 20

| Sample | OD 260nm | OD 280nm | 260nm/280nm | Dilution factor | Concentration ug/ml |
|---|---|---|---|---|---|
| 3A394TPC1 | 0.2821 | 0.1505 | 1.8739 | 20 | 282.0960 |

TABLE 21

| Sample | OD 260nm | OD 280nm | 260nm/280nm | Dilution factor | Concentration ug/ml |
|---|---|---|---|---|---|
| 3A394TPC1 | 0.6919 | 0.3625 | 1.9087 | 50 | 1729.8492 |

TABLE 22

| Sample | Decay time milliseconds | # live cells/ml | # dead cells/ml | Viability % |
|---|---|---|---|---|
| 3A394TPC1 | 19.8 | $1.12 \times 10^6$ | $1.65 \times 10^5$ | 87.16 |

TABLE 23

| Sample | Optical Density 492nm | Dilution | Concentration of soluble HLA ng/ml |
|---|---|---|---|
| 3A394TP C1 well 1 | 1.278<br>1.388 (over range) | 1.0 | 247.270 |
| 3A394TP C1 well 2 | 1.227<br>1.274 | 1.0 | 229.855 |
| 3A394TP C1 well 3 | 1.021<br>1.042 | 1.0 | 154.403 |
| 3A394TP C1 well 4 | 1.108<br>1.070 | 1.0 | 169.001 |

TABLE 24

| Allele | Allele Allele AlleleConcentration by ELISA ug/ml | Concentration by ELISA ug/ml Concentration by ELISA ug/ml Concentration by ELISA ug/mlTotal amount made mg |
|---|---|---|
| Total amount made mg Total amount made mg Total amount made mgHLA-A*0301 | 545.4 | 3.47 |
| HLA-A*1102 | 888.5 | 2.57 |
| HLA-A*2902 | 476.8 | 2.58 |
| HLA-A*3002 | 50.3 | 3.38 |
| HLA-A*3201 | 1382.0 | 9.61 |
| HLA-A*3301 | 40.0 | 0.8 |
| HLA-B*0801 | 66.0 | 21.0 |
| HLA-B*1302 | 55.0 | 9.0 |
| HLA-B*1401 | 146.0 | 50.0 |
| HLA-B*1801 | 587.6 | 0.4 |
| HLA-B*3701 | 1831.0 | 119.0 |
| HLA-B*3801 | 128.0 | 66.0 |
| HLA-B*3905 | 1400.0 | 120.0 |
| HLA-B*40012 | 59.0 | 10.0 |
| HLA-B*4002 | 400.0 | 180.0 |
| HLA-B*4101 | 288.4 | 8.8 |
| HLA-B*4402 | 59.0 | 10.0 |

TABLE A

| fraction | ion for MS/MS | derived peptide sequence |
|---|---|---|
| 6 | 398.2 (+3) | - - W D R H T X F |
| 6 | 448.2 (+2) | - - - - - Y T |
| 7 | 382.7 (+2) | V Q F E A A T |
| 7 | 418.7 (+2) | A Q F A S G A G Z |
| 7 | 455.2 (+2) | A L G A - - R G Y |
| 7 | 489.1 (+2) | - - V - - G H X Y |
| 7 | 506.8 (+2) | X S - - - C E Y |
| 8 | 402.2 (+2) | - G - - C D Y |
| 8 | 419.2 (+2) | G S H F G V A Y |
| 8 | 433.8 (+2) | A P P P P P P P P |
| 8 | 455.2 (+2) | - - - Z A R G Y |
| 8 | 462.2 (+2) | D P H A P P Z Y |
| 8 | 507.2 (+2) | A V P S X H X X Y |
| 8 | 512.3 (+2) | X A Z V Z M T A Y |
| 8 | 512.8 (+2) | A L N G R V T M Y |
| 8 | 516.9 (+2) | N Q Z H G S A E Y |
| 8 | 522.9 (+2) | F G X A C X A T S Y |
| 8 | 642.7 (+2) | P M N D W X M T Z T Y |
| 9 | 331.4 (+3) | A P M A R G Z Y |
| 9 | 418.7 (+2) | F V S N H A Y |
| 9 | 426.2 (+3) | - - - - - - - - S Y |
| 9 | 433.3 (+2) | N P P A Z Z P N |
| 9 | 437.0 (+2) | T G - - - - A Y |
| 9 | 441.2 (+3) | - Q - D P P P D M Z Y |
| 9 | 446.6 (+2) | G Q Z Z A V D F |
| 9 | 453.6 (+2) | X Q - - A G G Z Y |
| 9 | 465.2 (+2) | S Q F G G G S Q Y |
| 9 | 476.2 (+2) | S Q F D H V T Y |
| 9 | 481.0 (+2) | G Q H A S V X S Y |
| 9 | 514.2 (+2) | - - A A H V P P G Y |
| 9 | 550.2 (+2) | F M D V G A P T V Y |
| 9 | 578.0 (+2) | T P X G E P Y Z S Y |
| 10 | 398.3 (+2) | X A N - - V T |
| 10 | 448.2 (+2) | A Q A A P F A G Y |
| 10 | 448.4 (+2) | V V V F G V Z F |
| 10 | 450.4 (+2) | A Q M - - S E Y |
| 10 | 456.8 (+2) | C P L S C F T |
| 10 | 464.7 (+2) | - - - - F G H Y |
| 10 | 473.7 (+2) | A L W - - P Z F |
| 10 | 486.4 (+2) | V P H Z N A Y |

TABLE A CONT'D.

| | | |
|---|---|---|
| 10 | 498.7 (+2) | - - - - - G H G G Y |
| 10 | 509.0 (+2) | F L Z A M Z S T Y |
| 10 | 527.7 (+2) | G Q Y V V Z P T Y |
| 10 | 532.0 (+2) | T V X D S Z T H Y |
| 10 | 540.2 (+2) | P M F D P P Z T F |
| 11 | 469.2 (+2) | A Q A E S L R Y |
| 11 | 480.6 (+2) | X A V G H S G G T Y |
| 11 | 511.2 (+2) | - - - - - P T Y |
| 11 | 516.7 (+2) | E S X P N N V P Y |
| 12 | 383.0 (+3) | L A H T E C P R G Y |
| 12 | 435.0 (+2) | - - - - P S Y |
| 12 | 473.2 (+2) | V Q G P V G V Q Y |
| 12 | 475.0 (+2) | R G X G V A G T A F |
| 12 | 505.0 (+2) | T G A P V S E E G Y |
| 12 | 513.7 (+2) | V Q X Y Y G S V V |
| 12 | 519.0 (+2) | E P A M V X Z C F |
| 12 | 531.2 (+2) | G Q P G A P X G G Z Y |
| 12 | 541.0 (+2) | G P P H N G X R A Y |
| 12 | 542.2 (+2) | A A H W H V E A Y |
| 12 | 553.7 (+2) | T P P T R R E S Y |
| 12 | 577.2 (+2) | F P T D R R S Q F |
| 13 | 363.0 (+3) | Y T G V S Y X H F |
| 13 | 447.0 (+2) | A Q A S A P D A Y |
| 13 | 465.0 (+2) | V Q Y Y X P F |
| 13 | 503.6 (+2) | G Q R K G A G S V F |
| 13 | 553.2 (+2) | X Q Z X - - D V Y |
| 13 | 590.8 (+2) | A T G T A Z N X N Z Y |
| 14 | 460.7 (+2) | V V A P I T T G Y |
| 14 | 471.5 (+2) | V V A C V - - - Y |
| 14 | 495.2 (+2) | X Q Y T V G Y F |
| 14 | 525.3 (+2) | P L A - N - H T Y |
| 14 | 541.3 (+2) | P L F G Q T A G Q Y |
| 14 | 550.4 (+2) | A - - - - Q X E Y |
| 14 | 577.2 (+2) | Z G Y G N P X N G A Y |
| 15 | 459.8 (+2) | V Q G P V G T D F |
| 15 | 470.9 (+2) | V A G G W - - - F |
| 15 | 514.2 (+2) | F Q A R X T E Y |
| 15 | 536.6 (+2) | X A G F F X X E Y |
| 15 | 544.2 (+2) | X Q - - - - Z Y |
| 15 | 564.2 (+2) | S G A X D R A Y Z F |
| 16 | 467.1 (+2) | F Q - - - - T X |
| 16 | 500.4 (+2) | T P - - - A Z A F |
| 16 | 501.0 (+2) | V V A T Z N Z Z X |
| 16 | 503.6 (+2) | Y M V T - - - F |
| 16 | 517.4 (+2) | A L G S Z A X M P F |
| 16 | 521.3 (+2) | A P A V - - - V G Y |
| 16 | 522.0 (+2) | V G Y V D D T Q F |
| 16 | 525.6 (+2) | - - - - - - T G F |

TABLE A CONT'D.

| | | |
|---|---|---|
| 16 | 536.0 (+2) | P V P N V R X N Y |
| 16 | 544.4 (+2) | - - - - - - T X S X |
| 16 | 557.6 (+2) | T L E G W M S Z Y |
| 16 | 561.5 (+2) | Y M V C N A E E Y |
| 16 | 596.7 (+2) | - - - - - X R D X Y |
| 16 | 596.9 (+2) | S L X - - - - - F |
| 17 | 343.2 (+3) | A Q H P S A X R F |
| 17 | 351.3 (+3) | A A F C G - - - X V |
| 17 | 408.7 (+2) | Y L H - - E T |
| 17 | 441.2 (+2) | - - - - - Z A Y |
| 17 | 451.4 (+2) | I L G P P G S V Y |
| 17 | 455.0 (+2) | G L G Z T S A E F |
| 17 | 462.4 (+2) | X L G D V N M Y |
| 17 | 483.8 (+2) | V M G X T N A N F |
| 17 | 490.2 (+2) | N A X G R E S S F |
| 17 | 497.2 (+2) | A M N P T N T V F |
| 17 | 507.0 (+2) | - - - - X V E F |
| 17 | 511.2 (+2) | X Q A P A X F V Y |
| 17 | 519.2 (+2) | T A R V X S V E Y |
| 17 | 526.8 (+2) | A L F - - - F T Y |
| 17 | 542.8 (+2) | X Q X N A Y X S Y |
| 17 | 563.2 (+2) | G L A R C S Z V E Y |
| 18 | 503.8 (+2) | S Q X A A G V D V F |
| 18 | 511.7 (+2) | P Q G Z M A - - Y |
| 18 | 519.6 (+2) | - V F V S H T T F |
| 18 | 538.8 (+2) | H X T G N E A T S F |
| 18 | 565.7 (+2) | A E F W A C Z X Y |
| 18 | 566.2 (+2) | Y M I D P S G V S Y |
| 18 | 581.2 (+2) | X Q G H H E M F Y |
| 20 | 448.2 (+2) | A A G X G P T F Y |
| 20 | 560.0 (+2) | X V E X T T D Y Y |
| 20 | 614.0 (+2) | I A V G Y V D D T Q F |
| 21 | 507.2 (+2) | V A F V X F V G Y |
| 22 | 510.8 (+2) | A L M P - - X N Y |
| 22 | 557.2 (+2) | Y N R W S X E F |
| 24 | 546.3 (+2) | - - Z D R N V T F |
| 25 | 546.3 (+2) | V V T M - - - Z Y |

\* Dashes represent positions at which amino acids could not be unambiguously assigned through NanoES-MS/MS fragmentation patterns and/or Edman data obtained. Underlined residues designate tentative assignments.

TABLE B

| fraction | ion for MS/MS | derived peptide sequence |
|---|---|---|
| 6 | 471.8 (+2) | A Z V E C E T Y |
| 7 | 418.7 (+2) | A Q F A S G A G Z |
| 7 | 504.2 (+2) | Z G X G G G P A T S Y |
| 8 | 402.2 (+2) | - G - - C D Y |
| 8 | 441.2 (+2) | - - - - - Z S F |
| 8 | 516.9 (+2) | N Q Z H G S A E Y |
| 9 | 331.4 (+3) | A P M A R G Z Y |
| 9 | 349.4 (+3) | - - - - - - G F Y |
| 9 | 418.7 (+2) | A Z V N S G - Y |
| 9 | 426.2 (+3) | A A S S Z V - - P P Z Y |
| 9 | 433.3 (+2) | N P P A Z Z P N |
| 9 | 437.0 (+2) | A C G G C G Z D Y |
| 9 | 441.2 (+3) | - Z - D P P P D M Z Y |
| 9 | 446.6 (+2) | G Q Z Z A V D F |
| 9 | 578.0 (+2) | T P X G E P Y Z S Y |
| 10 | 426.5 (+2) | G P - - - P Z Y |
| 10 | 443.2 (+2) | A P Z Y P P P P |
| 10 | 448.3 (+2) | G Z V C T P G S F |
| 10 | 456.8 (+2) | C P L S C F T |
| 10 | 464.7 (+2) | S Q F G G G S Q Y |
| 10 | 465.4 (+2) | A S G F N G S Z Y |
| 10 | 503.8 (+2) | - Z - - Y T A Y |
| 10 | 508.7 (+2) | G Z P P H N G F Y |
| 10 | 517.0 (+2) | I K A D H V S T Y |
| 10 | 527.7 (+2) | X Z A D H V X P Y |
| 10 | 540.2 (+2) | - - - - P G Z V Y |
| 10 | 549.2 (+2) | Z S V - - - Z T G Y |
| 11 | 437.0 (+2) | H X G N Q A A Y |
| 11 | 511.4 (+2) | Z A G T T V P V S Y |
| 11 | 527.4 (+2) | G Q Y P T Q P T Y |
| 11 | 581.4 (+2) | F A G S Z S N T S T Y |
| 12 | 494.8 (+2) | S Z G G - - - T G Y |
| 12 | 526.8 (+2) | Z G P P N Y X T Y |
| 12 | 547.1 (+2) | V K V I Q Q E S Y |
| 13 | 454.6 (+2) | L P P P P P P P P |
| 13 | 476.0 (+2) | A K Y S T P A T L |
| 13 | 503.6 (+2) | G Q R K G A G S V F |
| 13 | 513.1 (+2) | R Z S A N H E A X |
| 13 | 526.4 (+2) | G K V R T D I T Y |
| 13 | 553.2 (+2) | V V X P A V R S T Y |

TABLE B CONT'D.

| | | |
|---|---|---|
| 13 | 561.0 (+2) | A K Y P H V E D Y |
| 13 | 571.3 (+2) | A Z N X S A Y V X Y |
| 13 | 601.2 (+2) | E V V G D T Z Y |
| 14 | 438.2 (+2) | A K A G I T T T L |
| 14 | 490.8 (+2) | V - - T Z A G S A F |
| 14 | 517.2 (+2) | A Z A A A N V X X Y |
| 14 | 531.5 (+2) | A N H S V R D T Y |
| 14 | 535.3 (+2) | E - - - G X R Z Y |
| 14 | 552.8 (+2) | X Z H N D Z S T Y |
| 14 | 577.2 (+2) | A N E Z X G - - - Y |
| 15 | 497.3 (+2) | A A G P T A Z E S Y |
| 15 | 514.2 (+2) | V A G X V F M Z Y |
| 15 | 527.0 (+2) | A Z Y Z A Z V V F |
| 15 | 564.2 (+2) | A Z F - - - Z X Y |
| 15 | 577.2 (+2) | Z G Y G N P X N Z Y |
| 15 | 626.0 (+2) | - - - - - Z A P C H Y |
| 16 | 521.6 (+2) | A H A V Q R V V Y |
| 16 | 525.6 (+2) | T Z X T V V X N Y |
| 17 | 446.8 (+2) | A Z Z A S G X A F |
| 17 | 492.8 (+2) | G S H S M R Y F |
| 17 | 503.8 (+2) | Y G Y G A T V E F |
| 17 | 967.6 (+1) | V Z - - - T T F |
| 18 | 451.4 (+2) | Q P G P Q I V Y |
| 18 | 455.2 (+2) | N G Z X S N N Y |
| 18 | 475.2 (+2) | A N X V Z X E Y |
| 18 | 489.1 (+2) | G Z - - - Z G X X Y |
| 18 | 497.8 (+2) | A M N P T N T V F |
| 18 | 525.2 (+2) | Y N - - - Z X F |
| 18 | 538.8 (+2) | - M - - S Y Z N F |
| 18 | 565.7 (+2) | A E E W A C Z X Y |
| 19 | 521.6 (+2) | S Z F G C P T R F |
| 19 | 524.6 (+2) | X G A X S N - - E F |
| 19 | 571.2 (+2) | R Z A A Y R X T Y |
| 19 | 646.2 (+2) | T N X H D G D G A T Z Y |

\* Dashes represent positions at which amino acids could not be unambiguously assigned through NanoES-MS/MS fragmentation patterns and/or Edman data obtained. Underlined residues designate tentative assignments.

TABLE C

| fraction | ion for MS/MS | derived peptide sequence |
|---|---|---|
| 6 | 398.2 (+3) | - - W D R H T X F |
| 6 | 448.2 (+2) | - - - - - Y T |
| 8 | 419.2 (+2) | G S H F G V A Y |
| 8 | 441.2 (+2) | V P C G Z Z S Y |
| 8 | 473.2 (+2) | T A Z X H R G Y |
| 8 | 512.8 (+2) | X A Z Y E H T Y |
| 8 | 516.9 (+2) | N Q Z H G S A E Y |
| 8 | 546.8 (+2) | N G X A M H W T Y |
| 9 | 418.7 (+2) | F V S N H A Y |
| 9 | 437.0 (+2) | T G - - - - A Y |
| 9 | 465.2 (+2) | S Q F G G G S Q Y |
| 9 | 476.2 (+2) | S Q F D H V T Y |
| 9 | 481.0 (+2) | - P - - G Z D E V |
| 9 | 514.2 (+2) | N G Y D G P N A G Y |
| 9 | 578.0 (+2) | T P X G E P Y Z S Y |
| 10 | 398.3 (+2) | X A N - - V T |
| 10 | 448.3 (+2) | M P H S G Y G F |
| 10 | 450.4 (+2) | V D X - - - Y |
| 10 | 456.8 (+2) | C P L S C F T |
| 10 | 464.7 (+2) | - - - - P G F Y |
| 10 | 486.2 (+2) | - A - P H P M G Y |
| 10 | 494.2 (+2) | A Q T V G Y G E Y |
| 10 | 508.7 (+2) | - - - - - S V Y |
| 10 | 509.0 (+2) | F L Z A M Z S T Y |
| 10 | 532.0 (+2) | T V X D S Z T H Y |
| 11 | 444.1 (+2) | T P - - A R A P T |
| 11 | 469.2 (+2) | S E H D R M Y |
| 11 | 480.6 (+2) | T G N C S G T G T Y |
| 11 | 496.8 (+2) | A Q V N P S X T Y |
| 11 | 532.3 (+2) | S P G A E T R A X Y |
| 12 | 473.2 (+2) | Y L G - - - G A F |
| 12 | 494.8 (+2) | X T S F M Z V Y |
| 12 | 499.0 (+2) | - P - - - P S S G Y |
| 12 | 505.0 (+2) | T P - - - G R M Y |
| 12 | 513.7 (+2) | P M F D Z Z V Y |
| 12 | 519.0 (+2) | Y L - - - R T F |
| 12 | 531.2 (+2) | A Q E H G C A A Z F |
| 12 | 542.2 (+2) | - M - - - G V H D Y |
| 12 | 550.2 (+2) | Y V S - - R N Q Y |
| 12 | 553.7 (+2) | A Q Y A A G E S F Y |

TABLE C CONT'D.

| | | |
|---|---|---|
| 12 | 564.0 (+2) | T P H T Z H D E Y |
| 12 | 565.2 (+2) | Y M - - - E M Y |
| 13 | 396.1 (+3) | D P H Y V S G H Z F |
| 13 | 401.2 (+2) | M V G X X P A T |
| 13 | 526.4 (+2) | Z A S P G E X T S Y |
| 14 | 460.7 (+2) | V V A P I T T G Y |
| 14 | 471.5 (+2) | V V A C V - - - Y |
| 14 | 525.3 (+2) | P L A - N - H T Y |
| 14 | 543.2 (+2) | X A X Y R R M Y |
| 14 | 550.4 (+2) | P L A M Z X Y T Y |
| 15 | 460.6 (+2) | - P - M P G X A Y |
| 15 | 461.0 (+2) | H T T S Z N A Y |
| 15 | 506.0 (+2) | M A A M V G V A V Y |
| 15 | 508.4 (+2) | G P Z V M Z H G Y |
| 15 | 514.2 (+2) | F Q A R X T E Y |
| 15 | 520.0 (+2) | L P H Q P L A T Y |
| 15 | 525.2 (+2) | A A A X V - - - V T Y |
| 15 | 536.6 (+2) | X P E M G Z F S Y |
| 15 | 544.2 (+2) | Y V - - V R - V F |
| 15 | 564.2 (+2) | F V T X N X E E Y |
| 16 | 489.0 (+2) | A A P V G A X E S Y |
| 16 | 500.4 (+2) | G S - - - S Y T Y |
| 16 | 522.0 (+2) | V G Y V D D T Q F |
| 16 | 525.7 (+2) | Y V A - - - P A F |
| 16 | 533.0 (+2) | V G Y - - A H P G F |
| 16 | 535.7 (+2) | Z A T N S V T S T Y |
| 16 | 537.0 (+2) | - - - - - - S T Y |
| 16 | 545.8 (+2) | Y A T A G E M M A F |
| 16 | 547.0 (+2) | S P T Y T H A V A F |
| 16 | 557.0 (+2) | M P A - - M V M A F |
| 17 | 351.3 (+3) | A A F C G - - - X V |
| 17 | 393.7 (+2) | S P N E D X M Z V F |
| 17 | 403.2 (+2) | V A A T A G A V F |
| 17 | 408.7 (+2) | Y L H - - E T |
| 17 | 414.8 (+2) | T A F P F V F |
| 17 | 451.4 (+2) | I L G P P G S V Y |
| 17 | 462.4 (+2) | X L G D V N M Y |
| 17 | 476.2 (+2) | Y G - - - V X S M |
| 17 | 490.8 (+2) | X P H C S C S S F |
| 17 | 504.0 (+2) | D P P C W G V S F |
| 17 | 507.0 (+2) | - - - - X V E F |
| 17 | 511.2 (+2) | - - - - A H D A Y |
| 17 | 519.2 (+2) | T A R V X S V E Y |
| 17 | 526.8 (+2) | X S D G R Z X T Y |
| 17 | 542.8 (+2) | N M N D L V S E Y |
| 17 | 557.2 (+2) | M P A A D Y E V A F |
| 18 | 474.8 (+2) | A E I L Q V I Y |
| 18 | 503.8 (+2) | A P - - - X V S Y |

TABLE C CONT'D.

| 18 | 514.7 (+2) | M P A G Y N N V Y |
| 18 | 519.6 (+2) | Y M S G X Y G T F |
| 18 | 526.8 (+2) | - - - A V V A Z S Y |
| 18 | 538.8 (+2) | X P V V P A A Z T Y |
| 18 | 566.2 (+2) | Y M I D P S G V S Y |
| 18 | 616.3 (+2) | F A N G V Z G C A F A F |

\* Dashes represent positions at which amino acids could not be unambiguously assigned through NanoES-MS/MS fragmentation patterns and/or Edman data obtained. Underlined residues designate tentative assignments.

TABLE D

| fraction | ion for MS/MS | derived peptide sequence |
|---|---|---|
| 6 | 493.0 (+2) | N H A V G - - V S M |
| 6 | 557.8 (+2) | H N V F Z P T S N A |
| 7 | 434.8 (+2) | S V C E T E S X |
| 7 | 481.3 (+2) | T H P S Z A C A F |
| 7 | 489.1 (+2) | - H - - S P X X |
| 8 | 420.1 (+2) | A N X E G P H T |
| 8 | 441.7 (+2) | G H S P P T S S L |
| 8 | 494.8 (+2) | C H S A F A L |
| 8 | 511.6 (+2) | H H A F A Z V X V |
| 8 | 519.4 (+2) | D H Y Y X A G S X |
| 9 | 411.4 (+2) | E X A P H A A X |
| 9 | 424.3 (+2) | A A A X R C E X |
| 9 | 426.1 (+2) | G H Z A P A A S X |
| 9 | 441.7 (+2) | V H N P Z S S X |
| 9 | 444.2 (+2) | A G G P T X C R X |
| 9 | 455.5 (+2) | L H L L T L E A |
| 9 | 490.3 (+2) | A G G Z P A T P P A X |
| 9 | 513.1 (+2) | S H Z G C V Z P A V |
| 9 | 520.0 (+2) | X H R L C S P T X |
| 10 | 404.2 (+2) | S V S X P H A P |
| 10 | 417.1 (+2) | A P F T G G N G X |
| 10 | 433.8 (+2) | G H D P D S P A A |
| 10 | 446.2 (+2) | E H G X E N G H |
| 10 | 455.4 (+2) | E H V A S S P A L |
| 10 | 460.4 (+2) | H H A P C G V S X |
| 10 | 464.0 (+2) | N H A I V S T S V |
| 10 | 464.7 (+2) | G H Z N S V T S V |
| 10 | 465.3 (+2) | S H Z A P C T S V |
| 10 | 469.4 (+2) | F V A R F V S X |
| 10 | 469.6 (+2) | H H S D G S V S L |
| 10 | 473.7 (+2) | S H A G A P P P T X |
| 10 | 482.6 (+2) | M C Z - G M P A X |
| 10 | 482.8 (+2) | G H G A N N D P A X |
| 10 | 495.7 (+2) | X H S Z P A G P A X |
| 10 | 508.3 (+2) | X H V V S - - V X |
| 10 | 511.2 (+2) | A V X D C C Z V A V |
| 10 | 522.3 (+2) | E X G G N T N P Z X |
| 10 | 522.7 (+2) | Y H G S Z N P E X |
| 10 | 569.6 (+2) | - - - - - T Y S Y |
| 10 | 574.3 (+2) | - - - - - - - - M |

TABLE D CONT'D.

| | | |
|---|---|---|
| 11 | 405.7 (+2) | S H - - - Y F |
| 11 | 425.8 (+2) | A H P D Z A X V |
| 11 | 444.7 (+2) | G T A H Y Z V X |
| 11 | 448.9 (+2) | M H A D N P V X |
| 11 | 455.7 (+2) | S H V D R P S X |
| 11 | 459.7 (+2) | T G A A F Z N P X |
| 11 | 482.8 (+2) | G H C P R N P A X |
| 11 | 495.7 (+2) | X H S G A P Z A P X |
| 11 | 516.7 (+2) | X H D T E H A P X |
| 11 | 562.3 (+2) | - - - Y Z A Y V Y |
| 12 | 411.7 (+2) | G H G P T X A A V |
| 12 | 428.8 (+2) | V P - - - - - - |
| 12 | 444.7 (+2) | Y Q H T G A V L |
| 12 | 448.4 (+2) | T Q A P G N P V L |
| 12 | 460.3 (+2) | T Z A G C M V P X |
| 12 | 490.9 (+2) | T H T Q P G V Q L |
| 12 | 507.4 (+2) | G H A G H V P P E X |
| 12 | 511.6 )+2) | T H F R Y V S X |
| 12 | 528.1 (+2) | E H R P D R V F |
| 13 | 427.6 (+2) | S H A Q T V V L |
| 13 | 449.2 (+2) | S H A N S A V V L |
| 13 | 464.8 (+2) | M V - - H P V X |
| 13 | 487.6 (+2) | Y H H G G V S A F |
| 13 | 506.2 (+2) | - H - - G H T G Y X |
| 14 | 420.1 (+2) | N H A N G L T L |
| 14 | 438.7 (+2) | - - - - - P X X |
| 14 | 456.7 (+2) | A H S V P S P A F |
| 14 | 477.7 (+2) | M H T - - P A P V |
| 14 | 482.8 (+2) | P G A A V V P S X |
| 14 | 560.8 (+2) | G H A G M G C V F Z X |
| 14 | 592.3 (+2) | M R - - - - G X E X |
| 15 | 418.9 (+2) | S H G V P R A X |
| 15 | 439.0 (+2) | E H H M P X X |
| 15 | 454.3 (+2) | H H Z C A A G A X |
| 15 | 492.1 (+2) | X V D Z A E P X V |
| 15 | 510.1 (+2) | I H T P E N P V I |
| 15 | 520.0 (+2) | M G X P V R H M V |
| 15 | 524.2 (+2) | S H Y D W Z V X |
| 15 | 532.9 (+2) | M P H S H P F V X |
| 15 | 577.2 (+2) | Z C V R C Z N G V F |
| 16 | 412.9 (+2) | S H A G A G X V X |
| 16 | 418.3 (+2) | G H X E G P X X |
| 16 | 424.3 (+2) | X H G G D H V X |
| 16 | 448.6 (+2) | E Z A H S X V X |
| 16 | 448.9 (+2) | Y H H D X V X |
| 16 | 454.3 (+2) | M A G A W C R X |
| 16 | 456.7 (+2) | S H D G S V P T X |
| 16 | 464.2 (+2) | F H - - X X X |

TABLE D CONT'D.

| | | | | | | | | | | |
|---|---|---|---|---|---|---|---|---|---|---|
| 16 | 469.9 (+2) | E | H | - | - | - | T | V | X | |
| 16 | 472.3 (+2) | M | A | X | - | - | - | - | V | V |
| 16 | 499.0 (+2) | G | H | A | X | T | D | G | X | T | X |
| 16 | 504.1 (+2) | P | V | S | H | X | V | N | E | L |
| 16 | 507.7 (+2) | X | X | Y | T | P | G | H | T | X |
| 16 | 522.7 (+2) | - | - | - | - | - | - | P | V | X |
| 16 | 523.3 (+2) | M | A | H | S | - | - | P | V | F |
| 16 | 529.9 (+2) | X | H | Y | D | R | N | Q | X | |
| 16 | 536.2 (+2) | E | A | - | - | C | Z | V | T | T | Y |
| 16 | 547.9 (+2) | - | - | - | - | - | - | A | X | S | V |
| 16 | 552.4 (+2) | X | Z | A | P | T | S | V | F | Z | X |
| 17 | 367.7 (+3) | F | T | M | P | A | H | P | S | T | X |
| 17 | 490.8 (+2) | M | T | X | G | Y | G | E | P | X |
| 17 | 557.3 (+2) | A | H | G | R | K | M | S | K | S | L |
| 17 | 340.7 (+3) | - | H | - | - | H | A | Z | V | X |
| 17 | 367.7 (+3) | - | - | - | - | R | X | S | H | X |
| 17 | 419.8 (+2) | - | - | - | H | A | V | G | X | X |
| 17 | 462.8 (+2) | M | S | S | N | E | X | X | M | |
| 17 | 476.2 (+2) | G | H | - | - | - | - | P | C | C |
| 17 | 504.2 (+2) | X | H | V | X | A | V | N | E | X |
| 17 | 523.2 (+2) | - | H | - | - | - | - | - | P | V | F |
| 17 | 543.2 (+2) | X | H | E | V | Z | P | H | X | X |
| 17 | 590.2 (+2) | A | T | E | H | C | F | V | M | E | X |
| 18 | 456.4 (+2) | A | H | S | N | L | A | S | V | L |
| 18 | 463.3 (+2) | V | X | A | P | A | N | D | X | X |
| 18 | 474.8 (+2) | M | X | G | X | S | F | P | A | X |
| 18 | 491.2 (+2) | V | H | T | C | V | N | P | V | X |
| 18 | 497.8 (+2) | S | H | Q | R | Q | L | L | L | |
| 18 | 515.8 (+2) | E | W | H | Y | P | V | S | X | |
| 18 | 519.7 (+2) | E | H | M | D | X | Z | T | F | |
| 18 | 543.4 (+2) | X | H | E | V | Z | P | H | X | X |
| 18 | 596.8 (+2) | E | H | H | T | Z | S | N | P | X | X |
| 19 | 434.6 (+2) | - | H | G | C | P | G | M | P | X |
| 19 | 496.6 (+2) | E | T | P | E | H | A | P | V | X |
| 19 | 539.6 (+2) | M | X | P | G | N | S | A | X | Y | X |

\* Dashes represent positions at which amino acids could not be unambiguously assigned through NanoES-MS/MS fragmentation patterns and/or Edman data obtained. Underlined residues designate tentative assignments.

TABLE E

| fraction | ion for MS/MS | derived peptide sequence |
|---|---|---|
| 7  | 504.1 (+2) | H M S G Z P T S Y |
| 7  | 549.2 (+2) | H N Z A A H Z E Y |
| 8  | 517.0 (+2) | N Q Z H G S A E Y |
| 8  | 526.0 (+2) | H A A X Y S Z V Y |
| 8  | 642.7 (+2) | P M N D W X M T Z T Y |
| 10 | 465.3 (+2) | S Q F G G G S Q Y |
| 10 | 484.3 (+2) | Y Q S D H R Y |
| 10 | 509.0 (+2) | F L Z A M Z S T Y |
| 10 | 532.0 (+2) | T V X D S Z T H Y |
| 11 | 424.3 (+2) | H X S T Z D F |
| 11 | 464.3 (+2) | H A P P T D P P P |
| 11 | 550.0 (+2) | H G P A N R D S V F |
| 11 | 563.3 (+2) | F P Y P T D P Z Y |
| 12 | 531.2 (+2) | K N A N L V Q L Y |
| 14 | 585.6 (+2) | R S F X X E N E Y |
| 16 | 488.7 (+2) | H M Z N P T S Y |
| 16 | 661.9 (+2) | Y V X F - - - - V Y |
| 17 | 577.6 (+2) | R S M X R C P E Y |
| 18 | 451.1 (+2) | I L G P P G S V Y |
| 18 | 523.0 (+2) | - - E V T A Z T Y |
| 19 | 565.6 (+2) | Y M I D P S G V S Y |
| 19 | 503.8 (+2) | S Q X A A G V D V F |
| 20 | 560.0 (+2) | X V E X T T D Y Y |
| 20 | 582.4 (+2) | M Y N C N E X D Y |
| 21 | 448.2 (+2) | A A G X G P T F Y |
| 21 | 614.0 (+2) | I A V G Y V D D T Q F |
| 22 | 507.2 (+2) | V A E V X F V G Y |
| 22 | 557.2 (+2) | Y N R W S X E F |
| 23 | 510.8 (+2) | A L M P - - X N Y |
| 25 | 562.8 (+2) | N Q F Q A L L Q Y |

* Dashes represent positions at which amino acids could not be unambiguously assigned through NanoES-MS/MS fragmentation patterns and/or Edman data obtained. Underlined residues designate tentative assignments.

SEQUENCE LISTING

```
<160> NUMBER OF SEQ ID NOS: 638

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Consensus
      sequence

<400> SEQUENCE: 1

Ala Met Ala Glu Ser Ser Trp Glu Trp
 1               5

<210> SEQ ID NO 2
<211> LENGTH: 9
<212> TYPE: PRT
<213> ORGANISM: Homo sapiens
```

```
<400> SEQUENCE: 2

Ala Met Ala Glu Ser Ser Trp Asp Gly
 1               5

<210> SEQ ID NO 3
<211> LENGTH: 9
<212> TYPE: PRT
<213> ORGANISM: Homo sapiens

<400> SEQUENCE: 3

Ala Met Ala Asn Phe Ser Trp Glu Trp
 1               5

<210> SEQ ID NO 4
<211> LENGTH: 9
<212> TYPE: PRT
<213> ORGANISM: Homo sapiens

<400> SEQUENCE: 4

Ala Met Ala Glu Ser Ser Trp Glu Trp
 1               5

<210> SEQ ID NO 5
<211> LENGTH: 9
<212> TYPE: PRT
<213> ORGANISM: Homo sapiens

<400> SEQUENCE: 5

Ser Glu Glu Glu Ser Ser Leu Glu Trp
 1               5

<210> SEQ ID NO 6
<211> LENGTH: 9
<212> TYPE: PRT
<213> ORGANISM: Homo sapiens

<400> SEQUENCE: 6

Ser Glu Glu Asn Cys Ser Leu Glu Trp
 1               5

<210> SEQ ID NO 7
<211> LENGTH: 9
<212> TYPE: PRT
<213> ORGANISM: Homo sapiens

<400> SEQUENCE: 7

Ser Glu Glu Asn Cys Tyr Leu Glu Trp
 1               5

<210> SEQ ID NO 8
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 8
gggcgtcgac ggactcagaa tctccccaga cgccgag                              37

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Primer
```

```
<400> SEQUENCE: 9
ccgcaagctt tcatctcagg gtgag                                          25

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 10
gggctctaga ggactcagaa tctccccaga cgccgag                             37

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 11
ccgcgaattc tcatctcagg gtgag                                          25

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 12
tgtaaaacga cggccagt                                                  18

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 13
cggcaaggat tacatcgccc tg                                             22

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 14
ccccatcgtg ggcatcgttg                                                20

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 15
cagggcgatg taatccttgc cg                                             22
```

```
<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 16
gccaggtcag tgtgatctcc gc                                              22

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 17
taatacgact cactataggg                                                 20

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 18
tagaaggcac agtcgagg                                                   18

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic motif

<400> SEQUENCE: 19

Gln Val Lys Arg Ser
  1               5

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic motif

<400> SEQUENCE: 20

Ile Val Met Gln
  1

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Val Gly Tyr Val Asp Asp Thr Gln Phe
  1               5
```

```
<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ile Ala Val Gly Tyr Val Asp Asp Thr Gln Phe
 1               5                  10

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ile Lys Ala Asp His Val Ser Thr Tyr
 1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Ser His Ser Met Arg Tyr Phe
 1               5

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Gln Arg Lys Gly Ala Gly Ser Val Phe
 1               5                  10

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Gln Ala Glu Ser Leu Arg Tyr
 1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 27

Gly Lys Val Arg Thr Asp Ile Thr Tyr
  1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ser His Ala Gln Thr Val Val Leu
  1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Gln Phe Gly Gly Gly Ser Gln Tyr
  1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Val Gln Gly Pro Val Gly Thr Asp Phe
  1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Pro Pro Pro Pro Pro Pro Pro Pro
  1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Tyr Gln His Thr Gly Ala Val Leu
  1               5
```

```
<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala His Gly Arg Lys Met Ser Lys Ser Leu
 1               5                  10

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Leu Pro His Gln Pro Leu Ala Thr Tyr
 1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Lys Tyr Ser Thr Pro Ala Thr Leu
 1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ala Lys Ala Gly Ile Thr Thr Thr Leu
 1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Thr Gln Ala Pro Gly Asn Pro Val Leu
 1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 38

Ser His Gln Arg Gln Leu Leu Leu
  1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Asn Gln Phe Gln Ala Leu Leu Gln Tyr
  1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Phe Val Ser Asn His Ala Tyr
  1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ile Leu Gly Pro Pro Gly Ser Val Tyr
  1               5

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Tyr Met Ile Asp Pro Ser Gly Val Ser Tyr
  1               5                  10

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Asn His Ala Ile Val Ser Thr Ser Val
  1               5
```

```
<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ile His Thr Pro Glu Asn Pro Val Ile
 1               5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala His Ser Asn Leu Ala Ser Val Leu
 1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Val Val Ala Pro Ile Thr Thr Gly Tyr
 1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly His Ser Pro Pro Thr Ser Ser Leu
 1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Leu Pro Pro Pro Pro Pro Pro Pro
 1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 49

Asn His Ala Asn Gly Leu Thr Leu
  1               5

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Glu His Val Ala Ser Ser Pro Ala Leu
  1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

His His Ser Asp Gly Ser Val Ser Leu
  1               5

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gln Pro Gly Pro Gln Ile Val Tyr
  1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Asn Met Asn Asp Leu Val Ser Glu Tyr
  1               5

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Thr His Thr Gln Pro Gly Val Gln Leu
  1               5
```

```
<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser His Ala Asn Ser Ala Val Val Leu
  1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Gln Tyr Pro Thr Gln Pro Thr Tyr
  1               5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Val Lys Val Ile Gln Gln Glu Ser Tyr
  1               5

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ala Lys Tyr Pro His Val Glu Asp Tyr
  1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ala Met Asn Pro Thr Asn Thr Val Phe
  1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 60

Cys Pro Leu Ser Cys Phe Thr
  1               5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Met Pro His Ser Gly Tyr Gly Phe
  1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Cys His Ser Ala Phe Ala Leu
  1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Leu His Leu Leu Thr Leu Glu Ala
  1               5

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Lys Asn Ala Asn Leu Val Gln Leu Tyr
  1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

His Met Ser Gly Glx Pro Thr Ser Tyr
  1               5
```

```
<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

His Asn Glx Ala Ala His Glx Glu Tyr
 1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Unknown amino acid

<400> SEQUENCE: 67

His Ala Ala Xaa Tyr Ser Glx Val Tyr
 1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Tyr Gln Ser Asp His Arg Tyr
 1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Unknown amino acid

<400> SEQUENCE: 69

His Xaa Ser Thr Glx Asp Phe
 1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

His Ala Pro Pro Thr Asp Pro Pro Pro
 1               5
```

```
<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

His Gly Pro Ala Asn Arg Asp Ser Val Phe
 1               5                  10

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Phe Pro Tyr Pro Thr Asp Pro Glx Tyr
 1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Unknown amino acid
<220> FEATURE:
<221> NAME/KEY: MOD_RES
<222> LOCATION: (8)
<223> OTHER INFORMATION: Unknown amino acid

<400> SEQUENCE: 73

Glx Asn Ala Asn Xaa Val Glx Xaa Tyr
 1               5

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(5)
<223> OTHER INFORMATION: Unknown amino acid

<400> SEQUENCE: 74

Arg Ser Phe Xaa Xaa Glu Asn Glu Tyr
 1               5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 75

His Met Glx Asn Pro Thr Ser Tyr
  1               5

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Unknown amino acid
<220> FEATURE:
<221> NAME/KEY: MOD_RES
<222> LOCATION: (5)..(8)
<223> OTHER INFORMATION: Unknown amino acid

<400> SEQUENCE: 76

Tyr Val Xaa Phe Xaa Xaa Xaa Xaa Val Tyr
  1               5                  10

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Unknown amino acid

<400> SEQUENCE: 77

Arg Ser Met Xaa Arg Cys Pro Glu Tyr
  1               5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Unknown amino acid

<400> SEQUENCE: 78

Xaa Xaa Phe Val Thr Ala Glx Thr Tyr
  1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Unknown amino acid
```

```
<400> SEQUENCE: 79

Met Tyr Asn Cys Asn Glu Xaa Asp Tyr
 1               5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Asn Gln Phe Gln Ala Leu Leu Gln Tyr
 1               5

<210> SEQ ID NO 81
<211> LENGTH: 18
<212> TYPE: PRT
<213> ORGANISM: Artificial Sequence
<220> FEATURE:
<223> OTHER INFORMATION: Description of Artificial Sequence: Consensus
      sequence

<400> SEQUENCE: 81

Tyr Tyr Ala Val Gly Val Arg Phe Met Arg Glu Ile Ser Asn Tyr Tyr
 1               5                  10                  15

Leu Trp

<210> SEQ ID NO 82
<211> LENGTH: 18
<212> TYPE: PRT
<213> ORGANISM: Homo sapiens

<400> SEQUENCE: 82

Tyr Tyr Ala Val Gly Val Arg Phe Met Arg Asn Ile Phe Asn Tyr Tyr
 1               5                  10                  15

Leu Trp

<210> SEQ ID NO 83
<211> LENGTH: 18
<212> TYPE: PRT
<213> ORGANISM: Homo sapiens

<400> SEQUENCE: 83

Tyr Tyr Ala Val Gly Val Arg Phe Met Arg Asn Ile Ser Asn Tyr Tyr
 1               5                  10                  15

Leu Trp

<210> SEQ ID NO 84
<211> LENGTH: 18
<212> TYPE: PRT
<213> ORGANISM: Homo sapiens

<400> SEQUENCE: 84

Tyr Tyr Ala Val Gly Val Arg Phe Met Arg Asn Ile Ser Asn Tyr Tyr
 1               5                  10                  15

Leu Trp

<210> SEQ ID NO 85
<211> LENGTH: 18
<212> TYPE: PRT
<213> ORGANISM: Homo sapiens
```

```
<400> SEQUENCE: 85

Tyr Tyr Ala Val Gly Val Arg Phe Met Arg Glu Ile Ser Asn Tyr Tyr
 1               5                  10                  15
Leu Trp

<210> SEQ ID NO 86
<211> LENGTH: 18
<212> TYPE: PRT
<213> ORGANISM: Homo sapiens

<400> SEQUENCE: 86

Tyr Tyr Ala Val Gly Val Arg Phe Met Arg Glu Ile Ser Asn Tyr Tyr
 1               5                  10                  15
Leu Gly

<210> SEQ ID NO 87
<211> LENGTH: 18
<212> TYPE: PRT
<213> ORGANISM: Homo sapiens

<400> SEQUENCE: 87

Tyr Tyr Ser Val Gly Val Arg Phe Glu Arg Glu Ile Ser Asn Tyr Tyr
 1               5                  10                  15
Leu Trp

<210> SEQ ID NO 88
<211> LENGTH: 18
<212> TYPE: PRT
<213> ORGANISM: Homo sapiens

<400> SEQUENCE: 88

Tyr Tyr Ser Val Gly Val Arg Phe Glu Arg Asn Ile Cys Asn Tyr Tyr
 1               5                  10                  15
Leu Trp

<210> SEQ ID NO 89
<211> LENGTH: 18
<212> TYPE: PRT
<213> ORGANISM: Homo sapiens

<400> SEQUENCE: 89

Tyr Tyr Ser Val Gly Val Arg Phe Glu Arg Asn Ile Cys Asn Tyr Tyr
 1               5                  10                  15
Leu Trp

<210> SEQ ID NO 90
<211> LENGTH: 18
<212> TYPE: PRT
<213> ORGANISM: Homo sapiens

<400> SEQUENCE: 90

Tyr Tyr Ser Val Gly Val Arg Phe Glu Arg Asn Ile Cys Asn Tyr Tyr
 1               5                  10                  15
Leu Trp

<210> SEQ ID NO 91
<211> LENGTH: 18
<212> TYPE: PRT
<213> ORGANISM: Homo sapiens
```

```
<400> SEQUENCE: 91

Tyr Tyr Ala Val Gly Val Arg Phe Met Arg Glu Asn Met Ser Tyr Tyr
 1               5                  10                  15

Leu Trp

<210> SEQ ID NO 92
<211> LENGTH: 18
<212> TYPE: PRT
<213> ORGANISM: Homo sapiens

<400> SEQUENCE: 92

Tyr Tyr Ala Val Gly Val Arg Phe Met Arg Glu Asn Met Ser Tyr Tyr
 1               5                  10                  15

Leu Trp

<210> SEQ ID NO 93
<211> LENGTH: 18
<212> TYPE: PRT
<213> ORGANISM: Homo sapiens

<400> SEQUENCE: 93

Tyr Tyr Ala Val Gly Val Arg Phe Met Arg Glu Lys Tyr Gln Tyr Tyr
 1               5                  10                  15

Leu Trp

<210> SEQ ID NO 94
<211> LENGTH: 20
<212> TYPE: PRT
<213> ORGANISM: Artificial Sequence
<220> FEATURE:
<223> OTHER INFORMATION: Description of Artificial Sequence: Consensus
      sequence

<400> SEQUENCE: 94

Asn Thr Tyr Glu Ser Asn Leu Tyr Leu Gln Arg Asp Ser Tyr Tyr Ile
 1               5                  10                  15

Ile Thr Lys Trp
            20

<210> SEQ ID NO 95
<211> LENGTH: 20
<212> TYPE: PRT
<213> ORGANISM: Homo sapiens

<400> SEQUENCE: 95

Asn Thr Tyr Glu Ser Asn Leu Tyr Ile Gln Arg Asp Ser Tyr Tyr Ile
 1               5                  10                  15

Ile Thr Lys Trp
            20

<210> SEQ ID NO 96
<211> LENGTH: 20
<212> TYPE: PRT
<213> ORGANISM: Homo sapiens

<400> SEQUENCE: 96

Asn Thr Tyr Glu Ser Asn Leu Tyr Leu Gln Arg Asp Ser Tyr Tyr Ile
 1               5                  10                  15

Ile Thr Lys Trp
            20
```

```
-continued

<210> SEQ ID NO 97
<211> LENGTH: 20
<212> TYPE: PRT
<213> ORGANISM: Homo sapiens

<400> SEQUENCE: 97

Asn Thr Tyr Glu Ser Asn Leu Tyr Leu Gln Arg Asp Ser Tyr Tyr Ile
 1               5                  10                  15

Ile Thr Lys Trp
            20

<210> SEQ ID NO 98
<211> LENGTH: 20
<212> TYPE: PRT
<213> ORGANISM: Homo sapiens

<400> SEQUENCE: 98

Asn Thr Tyr Glu Ser Asn Leu Tyr Leu Gln Arg Asp Ser Tyr Tyr Ile
 1               5                  10                  15

Ile Thr Lys Trp
            20

<210> SEQ ID NO 99
<211> LENGTH: 20
<212> TYPE: PRT
<213> ORGANISM: Homo sapiens

<400> SEQUENCE: 99

Asn Thr Tyr Glu Ser Asn Leu Tyr Leu Gln Arg Asp Ser Tyr Tyr Ile
 1               5                  10                  15

Ile Thr Lys Trp
            20

<210> SEQ ID NO 100
<211> LENGTH: 20
<212> TYPE: PRT
<213> ORGANISM: Homo sapiens

<400> SEQUENCE: 100

Asn Thr Tyr Glu Ser Asn Leu Tyr Leu Gln Arg Asp Ser Tyr Tyr Ile
 1               5                  10                  15

Ile Thr Lys Trp
            20

<210> SEQ ID NO 101
<211> LENGTH: 20
<212> TYPE: PRT
<213> ORGANISM: Homo sapiens

<400> SEQUENCE: 101

Gln Thr Asp Val Ser Asn Leu Tyr Leu Gln Arg Asp Ser Tyr Tyr Ile
 1               5                  10                  15

Ile Thr Lys Trp
            20

<210> SEQ ID NO 102
<211> LENGTH: 20
<212> TYPE: PRT
<213> ORGANISM: Homo sapiens
```

```
<400> SEQUENCE: 102

Ser Thr Tyr Glu Asn Ile Ala Tyr Leu Gln Arg His Asp Tyr Tyr Ile
 1               5                  10                  15

Ile Thr Lys Trp
            20

<210> SEQ ID NO 103
<211> LENGTH: 20
<212> TYPE: PRT
<213> ORGANISM: Homo sapiens

<400> SEQUENCE: 103

Ser Thr Tyr Glu Asn Ile Ala Tyr Trp Gln Arg Asp Ser Tyr Tyr Ile
 1               5                  10                  15

Ile Thr Lys Trp
            20

<210> SEQ ID NO 104
<211> LENGTH: 20
<212> TYPE: PRT
<213> ORGANISM: Homo sapiens

<400> SEQUENCE: 104

Asn Thr Tyr Glu Ser Asn Leu Tyr Leu Gln Arg Asn Tyr Tyr Tyr Ile
 1               5                  10                  15

Ile Thr Lys Trp
            20

<210> SEQ ID NO 105
<211> LENGTH: 20
<212> TYPE: PRT
<213> ORGANISM: Homo sapiens

<400> SEQUENCE: 105

Asn Thr Tyr Glu Ser Asn Leu Tyr Leu Gln Arg Asp Tyr Tyr Tyr Ile
 1               5                  10                  15

Ile Thr Lys Trp
            20

<210> SEQ ID NO 106
<211> LENGTH: 20
<212> TYPE: PRT
<213> ORGANISM: Homo sapiens

<400> SEQUENCE: 106

Asn Thr Tyr Glu Asn Ile Ala Tyr Ile Gln Arg Asp Ser Tyr Tyr Ile
 1               5                  10                  15

Ile Thr Lys Trp
            20

<210> SEQ ID NO 107
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)
<223> OTHER INFORMATION: Unknown amino acid
```

```
<400> SEQUENCE: 107

Ala Gly Gly Glx Pro Ala Thr Pro Pro Ala Xaa
 1               5                  10

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ser His Glx Gly Cys Val Glx Pro Ala Val
 1               5                  10

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gly His Asp Pro Asp Ser Pro Ala Ala
 1               5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Glu His Val Ala Ser Ser Pro Ala Leu
 1               5

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Unknown amino acid
<220> FEATURE:
<221> NAME/KEY: MOD_RES
<222> LOCATION: (9)
<223> OTHER INFORMATION: Unknown amino acid

<400> SEQUENCE: 111

Met Cys Glx Xaa Gly Met Pro Ala Xaa
 1               5

<210> SEQ ID NO 112
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (10)
<223> OTHER INFORMATION: Unknown amino acid

<400> SEQUENCE: 112

Gly His Gly Ala Asn Asn Asp Pro Ala Xaa
 1               5                  10

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (10)
<223> OTHER INFORMATION: Unknown amino acid

<400> SEQUENCE: 113

Xaa His Ser Glx Pro Ala Gly Pro Ala Xaa
 1               5                  10

<210> SEQ ID NO 114
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Unknown amino acid

<400> SEQUENCE: 114

Met His Ala Asp Asn Pro Val Xaa
 1               5

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Unknown amino acid

<400> SEQUENCE: 115

Gly His Cys Pro Arg Asn Pro Ala Xaa
 1               5

<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (10)
<223> OTHER INFORMATION: Unknown amino acid

<400> SEQUENCE: 116

Xaa His Ser Gly Ala Pro Glx Ala Pro Xaa
 1               5                  10

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (9)
<223> OTHER INFORMATION: Unknown amino acid

<400> SEQUENCE: 117

Xaa His Asp Thr Glu His Ala Pro Xaa
 1               5

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Thr Gln Ala Pro Gly Asn Pro Val Leu
 1               5

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Unknown amino acid

<400> SEQUENCE: 119

Thr Glx Ala Gly Cys Met Val Pro Xaa
 1               5

<210> SEQ ID NO 120
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (3)..(4)
<223> OTHER INFORMATION: Unknown amino acid
<220> FEATURE:
<221> NAME/KEY: MOD_RES
<222> LOCATION: (8)
<223> OTHER INFORMATION: Unknown amino acid

<400> SEQUENCE: 120

Met Val Xaa Xaa His Pro Val Xaa
  1               5

<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ala His Ser Val Pro Ser Pro Ala Phe
  1               5

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(5)
<223> OTHER INFORMATION: Unknown amino acid

<400> SEQUENCE: 122

Met His Thr Xaa Xaa Pro Ala Pro Val
  1               5

<210> SEQ ID NO 123
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Unknown amino acid

<400> SEQUENCE: 123

Pro Gly Ala Ala Val Val Pro Ser Xaa
  1               5

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ile His Thr Pro Glu Asn Pro Val Ile
  1               5
```

```
<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Unknown amino acid

<400> SEQUENCE: 125

Ser His Asp Gly Ser Val Pro Thr Xaa
 1               5

<210> SEQ ID NO 126
<211> LENGTH: 5
<212> TYPE: PRT
<213> ORGANISM: Artificial Sequence
<220> FEATURE:
<223> OTHER INFORMATION: Description of Artificial Sequence: Synthetic
      motif

<400> SEQUENCE: 126

Ile Leu Gln Val Pro
 1               5

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(6)
<223> OTHER INFORMATION: Unknown amino acid

<400> SEQUENCE: 127

Met Ala His Ser Xaa Xaa Pro Val Phe
 1               5

<210> SEQ ID NO 128
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (3)..(7)
<223> OTHER INFORMATION: Unknown amino acid

<400> SEQUENCE: 128

Xaa His Xaa Xaa Xaa Xaa Xaa Pro Val Phe
 1               5                  10

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (2)
<223> OTHER INFORMATION: Unknown amino acid
<220> FEATURE:
<221> NAME/KEY: MOD_RES
<222> LOCATION: (4)
<223> OTHER INFORMATION: Unknown amino acid
<220> FEATURE:
<221> NAME/KEY: MOD_RES
<222> LOCATION: (9)
<223> OTHER INFORMATION: Unknown amino acid

<400> SEQUENCE: 129

Met Xaa Gly Xaa Ser Phe Pro Ala Xaa
  1               5

<210> SEQ ID NO 130
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Unknown amino acid

<400> SEQUENCE: 130

Val His Thr Cys Val Asn Pro Val Xaa
  1               5

<210> SEQ ID NO 131
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Unknown amino acid

<400> SEQUENCE: 131

Glu Trp His Tyr Pro Val Ser Xaa
  1               5

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Unknown amino acid

<400> SEQUENCE: 132

Glu Thr Pro Glu His Ala Pro Val Xaa
  1               5

<210> SEQ ID NO 133
<211> LENGTH: 18
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Ile or Leu
<220> FEATURE:
<221> NAME/KEY: MOD_RES
<222> LOCATION: (14)
<223> OTHER INFORMATION: Gln or Lys

<400> SEQUENCE: 133

Gly Pro Cys Ala Val Phe Met Xaa Ser Thr Tyr Asn Trp Xaa His Arg
 1               5                  10                  15

Asp Glu

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Unknown amino acid
<220> FEATURE:
<221> NAME/KEY: MOD_RES
<222> LOCATION: (8)
<223> OTHER INFORMATION: Unknown amino acid

<400> SEQUENCE: 134

Xaa Xaa Trp Asp Arg His Thr Xaa Phe
 1               5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ala Gln Phe Ala Ser Gly Ala Gly Glx
 1               5

<210> SEQ ID NO 136
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (3)..(4)
<223> OTHER INFORMATION: Unknown amino acid

<400> SEQUENCE: 136

Xaa Gly Xaa Xaa Cys Asp Tyr
 1               5
```

```
<210> SEQ ID NO 137
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Gly Ser His Phe Gly Val Ala Tyr
1               5

<210> SEQ ID NO 138
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Asn Gln Glx His Gly Ser Ala Glu Tyr
1               5

<210> SEQ ID NO 139
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: Unknown amino acid

<400> SEQUENCE: 139

Pro Met Asn Asp Trp Xaa Met Thr Glx Thr Tyr
1               5                   10

<210> SEQ ID NO 140
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ala Pro Met Ala Arg Gly Glx Tyr
1               5

<210> SEQ ID NO 141
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Phe Val Ser Asn His Ala Tyr
1               5

<210> SEQ ID NO 142
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 142

Asn Pro Pro Ala Glx Glx Pro Asn
1               5

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(6)
<223> OTHER INFORMATION: Unknown amino acid

<400> SEQUENCE: 143

Thr Gly Xaa Xaa Xaa Xaa Ala Tyr
1               5

<210> SEQ ID NO 144
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (3)
<223> OTHER INFORMATION: Unknown amino acid

<400> SEQUENCE: 144

Xaa Gln Xaa Asp Pro Pro Asp Met Glx Tyr
1               5                   10

<210> SEQ ID NO 145
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gly Gln Glx Glx Ala Val Asp Phe
1               5

<210> SEQ ID NO 146
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ser Gln Phe Gly Gly Gly Ser Gln Tyr
1               5
```

<210> SEQ ID NO 147
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Ser Gln Phe Asp His Val Thr Tyr
 1               5

<210> SEQ ID NO 148
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Unknown amino acid

<400> SEQUENCE: 148

Thr Pro Xaa Gly Glu Pro Tyr Glx Ser Tyr
 1               5                  10

<210> SEQ ID NO 149
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (4)..(5)
<223> OTHER INFORMATION: Unknown amino acid

<400> SEQUENCE: 149

Xaa Ala Asn Xaa Xaa Val Thr
 1               5

<210> SEQ ID NO 150
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Cys Pro Leu Ser Cys Phe Thr
 1               5

<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 151

Phe Leu Glx Ala Met Glx Ser Thr Tyr
1               5

<210> SEQ ID NO 152
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Unknown amino acid

<400> SEQUENCE: 152

Thr Val Xaa Asp Ser Glx Thr His Tyr
1               5

<210> SEQ ID NO 153
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Gly Gln Arg Lys Gly Ala Gly Ser Val Phe
1               5                   10

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Val Val Ala Pro Ile Thr Thr Gly Tyr
1               5

<210> SEQ ID NO 155
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(8)
<223> OTHER INFORMATION: Unknown amino acid

<400> SEQUENCE: 155

Val Val Ala Cys Val Xaa Xaa Xaa Tyr
1               5

<210> SEQ ID NO 156
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (4)
<223> OTHER INFORMATION: Unknown amino acid
<220> FEATURE:
<221> NAME/KEY: MOD_RES
<222> LOCATION: (6)
<223> OTHER INFORMATION: Unknown amino acid

<400> SEQUENCE: 156

Pro Leu Ala Xaa Asn Xaa His Thr Tyr
  1               5

<210> SEQ ID NO 157
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Unknown amino acid

<400> SEQUENCE: 157

Phe Gln Ala Arg Xaa Thr Glu Tyr
  1               5

<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Val Gly Tyr Val Asp Asp Thr Gln Phe
  1               5

<210> SEQ ID NO 159
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(9)
<223> OTHER INFORMATION: Unknown amino acid

<400> SEQUENCE: 159

Ala Ala Phe Cys Gly Xaa Xaa Xaa Xaa Val
  1               5                  10

<210> SEQ ID NO 160
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(5)
<223> OTHER INFORMATION: Unknown amino acid
```

```
<400> SEQUENCE: 160

Tyr Leu His Xaa Xaa Glu Thr
  1               5

<210> SEQ ID NO 161
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Ile Leu Gly Pro Pro Gly Ser Val Tyr
  1               5

<210> SEQ ID NO 162
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid

<400> SEQUENCE: 162

Xaa Leu Gly Asp Val Asn Met Tyr
  1               5

<210> SEQ ID NO 163
<211> LENGTH: 4
<212> TYPE: PRT
<213> ORGANISM: Artificial Sequence
<220> FEATURE:
<223> OTHER INFORMATION: Description of Artificial Sequence: Synthetic
      motif

<400> SEQUENCE: 163

Leu Val Gln Pro
  1

<210> SEQ ID NO 164
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Unknown amino acid

<400> SEQUENCE: 164

Thr Ala Arg Val Xaa Ser Val Glu Tyr
  1               5

<210> SEQ ID NO 165
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (8)
<223> OTHER INFORMATION: Unknown amino acid

<400> SEQUENCE: 165

Ala Glu Phe Trp Ala Cys Glx Xaa Tyr
 1               5

<210> SEQ ID NO 166
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Tyr Met Ile Asp Pro Ser Gly Val Ser Tyr
 1               5                  10

<210> SEQ ID NO 167
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (4)
<223> OTHER INFORMATION: Unknown amino acid

<400> SEQUENCE: 167

Xaa Val Glu Xaa Thr Thr Asp Tyr Tyr
 1               5

<210> SEQ ID NO 168
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Unknown amino acid

<400> SEQUENCE: 168

Ala Ala Gly Xaa Gly Pro Thr Phe Tyr
 1               5

<210> SEQ ID NO 169
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Ile Ala Val Gly Tyr Val Asp Asp Thr Gln Phe
 1               5                  10
```

```
<210> SEQ ID NO 170
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Unknown amino acid

<400> SEQUENCE: 170

Val Ala Phe Val Xaa Phe Val Gly Tyr
 1               5

<210> SEQ ID NO 171
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: Unknown amino acid

<400> SEQUENCE: 171

Tyr Asn Arg Trp Ser Xaa Glu Phe
 1               5

<210> SEQ ID NO 172
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(7)
<223> OTHER INFORMATION: Unknown amino acid

<400> SEQUENCE: 172

Ala Leu Met Pro Xaa Xaa Xaa Asn Tyr
 1               5

<210> SEQ ID NO 173
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Asp Leu Ala Ser Met Leu Asn Arg Tyr
 1               5

<210> SEQ ID NO 174
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 174

Met Leu Asn Arg Tyr Lys Leu Ile Tyr
  1               5

<210> SEQ ID NO 175
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Pro Leu Glu Lys Gln Leu Phe Tyr Tyr
  1               5

<210> SEQ ID NO 176
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Tyr Gln Leu Arg Cys His Leu Ser Tyr
  1               5

<210> SEQ ID NO 177
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Ala Leu Ser Ile Asn Gly Asp Lys Phe
  1               5

<210> SEQ ID NO 178
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Asp Leu Pro Asp Leu Arg Gly Pro Phe
  1               5

<210> SEQ ID NO 179
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Phe Val Pro Asn Leu Lys Asp Met Phe
  1               5
```

```
<210> SEQ ID NO 180
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Ala Val Thr Met Thr Ala Ala Ser Tyr
1               5

<210> SEQ ID NO 181
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Thr Met Phe Glu Val Ser Val Ala Phe
1               5

<210> SEQ ID NO 182
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Asp Leu Arg Trp Leu Ala Lys Ser Phe
1               5

<210> SEQ ID NO 183
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

His Leu Thr Thr Glu Lys Gln Glu Tyr
1               5

<210> SEQ ID NO 184
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Ala Leu Arg Leu Ala Thr Val Gly Tyr
1               5

<210> SEQ ID NO 185
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 185

Ala Leu Gly Thr Glu Ser Gly Leu Phe
 1               5

<210> SEQ ID NO 186
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Ala Val Ser Asn Ala Val Asp Gly Phe
 1               5

<210> SEQ ID NO 187
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ala Leu Tyr Glu Ala Ser Thr Thr Tyr
 1               5

<210> SEQ ID NO 188
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Arg Gln Ile Pro Lys Ile Gln Asn Phe
 1               5

<210> SEQ ID NO 189
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Ile Leu Ser Ser Asn Tyr Phe Asp Phe
 1               5

<210> SEQ ID NO 190
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Thr Val Met Glu Ile Ala Gly Leu Tyr
 1               5
```

```
<210> SEQ ID NO 191
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

His Val Val Leu Ala Ile Ile Leu Tyr
 1               5

<210> SEQ ID NO 192
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Val Val Leu Ala Ile Ile Leu Tyr Phe
 1               5

<210> SEQ ID NO 193
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Phe Leu Val His Lys Ile Val Met Phe
 1               5

<210> SEQ ID NO 194
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Leu Val His Lys Ile Val Met Phe Phe
 1               5

<210> SEQ ID NO 195
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Met Gln Leu Leu Cys Val Phe
 1               5

<210> SEQ ID NO 196
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 196

His Leu Asp Ile Glu Gly His Ala Ser His Tyr
 1               5                  10

<210> SEQ ID NO 197
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Met Leu Ser Ala Pro Leu Glu Lys Gln Leu Phe
 1               5                  10

<210> SEQ ID NO 198
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Pro Leu Glu Lys Gln Leu Phe
 1               5

<210> SEQ ID NO 199
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Pro Leu Glu Lys Gln Leu Phe Tyr
 1               5

<210> SEQ ID NO 200
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Thr Met Leu Pro Asn Thr Arg Pro His Ser Tyr
 1               5                  10

<210> SEQ ID NO 201
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Met Leu Pro Asn Thr Arg Pro His Ser Tyr
 1               5                  10
```

<210> SEQ ID NO 202
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Gln Leu Arg Cys His Leu Ser Tyr
 1               5

<210> SEQ ID NO 203
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Tyr Val Ala Leu Ser Ile Asn Gly Asp Lys Phe
 1               5                  10

<210> SEQ ID NO 204
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Phe Gln Tyr Thr Gly Ala Met Thr Ser Lys Phe
 1               5                  10

<210> SEQ ID NO 205
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Ala Met Thr Ser Lys Phe Leu Met Gly Thr Tyr
 1               5                  10

<210> SEQ ID NO 206
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

His Val Leu Ser Leu Val Phe
 1               5

<210> SEQ ID NO 207
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 207

Ser Leu Thr Ser Ala Gln Ser Gly Asp Tyr
1               5                   10

<210> SEQ ID NO 208
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Ser Leu Val Ile Val Thr Thr Phe
1               5

<210> SEQ ID NO 209
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Leu Val Ile Val Thr Thr Phe
1               5

<210> SEQ ID NO 210
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Ile Val Thr Thr Phe Val His Tyr
1               5

<210> SEQ ID NO 211
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Ile Val Thr Thr Phe Val His Tyr Ala Asn Phe
1               5                   10

<210> SEQ ID NO 212
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Phe Val His Tyr Ala Asn Phe His Asn Phe
1               5                   10
```

```
<210> SEQ ID NO 213
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Phe Val His Tyr Ala Asn Phe His Asn Phe Tyr
 1               5                  10

<210> SEQ ID NO 214
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Thr Met Thr Ala Ala Ser Tyr
 1               5

<210> SEQ ID NO 215
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Thr Met Thr Ala Ala Ser Tyr Ala Arg Tyr
 1               5                  10

<210> SEQ ID NO 216
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Glu Leu Asp Thr Glu Thr Leu Thr Thr Met Phe
 1               5                  10

<210> SEQ ID NO 217
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Thr Met Phe Glu Val Ser Val Ala Phe Phe
 1               5                  10

<210> SEQ ID NO 218
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 218

Thr Val Leu Lys Asp Ile Ile Gly Ile Cys Tyr
1               5                   10

<210> SEQ ID NO 219
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Val Leu Lys Asp Ile Ile Gly Ile Cys Tyr
1               5                   10

<210> SEQ ID NO 220
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Thr Val Lys Gly Met Gln Ser Tyr
1               5

<210> SEQ ID NO 221
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Arg Leu Ala Thr Val Gly Tyr
1               5

<210> SEQ ID NO 222
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Thr Val Gly Tyr Pro Lys Ala Gly Val Tyr
1               5                   10

<210> SEQ ID NO 223
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Leu Leu Ser Ala Tyr Asn Arg His Pro Leu Phe
1               5                   10
```

```
<210> SEQ ID NO 224
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Pro Leu His Thr Val Met Arg Glu Thr Leu Phe
 1               5                  10

<210> SEQ ID NO 225
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Val Met Arg Glu Thr Leu Phe
 1               5

<210> SEQ ID NO 226
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Gly Leu Ala Leu Gly Thr Glu Ser Gly Leu Phe
 1               5                  10

<210> SEQ ID NO 227
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Gly Leu Phe Ser Pro Cys Tyr
 1               5

<210> SEQ ID NO 228
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Leu Met Ile Ile Pro Leu Ile Asn Val Thr Phe
 1               5                  10

<210> SEQ ID NO 229
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 229

Pro Leu Ile Asn Val Thr Phe
 1               5

<210> SEQ ID NO 230
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Glu Val Arg Gly Ser Ala Leu Tyr
 1               5

<210> SEQ ID NO 231
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Tyr Leu Ser Ser Ser Leu Phe
 1               5

<210> SEQ ID NO 232
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Thr Gln Lys Ser Cys Ile Phe
 1               5

<210> SEQ ID NO 233
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Thr Gln Lys Ser Cys Ile Phe Cys Gly Phe
 1               5                  10

<210> SEQ ID NO 234
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Gly Leu Glu Thr Thr Thr Tyr
 1               5
```

```
<210> SEQ ID NO 235
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Val Gln Asn Ser Ile Leu Ser Ser Asn Tyr
 1               5                  10

<210> SEQ ID NO 236
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Val Gln Asn Ser Ile Leu Ser Ser Asn Tyr Phe
 1               5                  10

<210> SEQ ID NO 237
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Ile Leu Ser Ser Asn Tyr Phe
 1               5

<210> SEQ ID NO 238
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Val Met Glu Ile Ala Gly Leu Tyr
 1               5

<210> SEQ ID NO 239
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Val Val Leu Ala Ile Ile Leu Tyr
 1               5

<210> SEQ ID NO 240
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 240

Val Leu Ala Ile Ile Leu Tyr
1               5

<210> SEQ ID NO 241
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Val Leu Ala Ile Ile Leu Tyr Phe
1               5

<210> SEQ ID NO 242
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Val Leu Ala Ile Ile Leu Tyr Phe Ile Ala Phe
1               5                   10

<210> SEQ ID NO 243
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Ile Leu Tyr Phe Ile Ala Phe
1               5

<210> SEQ ID NO 244
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Phe Leu Val His Lys Ile Val Met Phe Phe
1               5                   10

<210> SEQ ID NO 245
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Asp Ile Glu Gly His Ala Ser His Tyr
1               5

```
<210> SEQ ID NO 246
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Ser Ala Pro Leu Glu Lys Gln Leu Phe
 1               5

<210> SEQ ID NO 247
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Ala Pro Leu Glu Lys Gln Leu Phe Tyr
 1               5

<210> SEQ ID NO 248
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Leu Pro Asn Thr Arg Pro His Ser Tyr
 1               5

<210> SEQ ID NO 249
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Asn Thr Arg Pro His Ser Tyr Val Phe
 1               5

<210> SEQ ID NO 250
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Ser Ile Asn Gly Asp Lys Phe Gln Tyr
 1               5

<210> SEQ ID NO 251
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 251

Tyr Thr Gly Ala Met Thr Ser Lys Phe
 1               5

<210> SEQ ID NO 252
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Thr Ser Lys Phe Leu Met Gly Thr Tyr
 1               5

<210> SEQ ID NO 253
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Leu Thr Ser Ala Gln Ser Gly Asp Tyr
 1               5

<210> SEQ ID NO 254
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Tyr Ser Leu Val Ile Val Thr Thr Phe
 1               5

<210> SEQ ID NO 255
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Val Ile Val Thr Thr Phe Val His Tyr
 1               5

<210> SEQ ID NO 256
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Thr Thr Phe Val His Tyr Ala Asn Phe
 1               5
```

```
<210> SEQ ID NO 257
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Met Thr Ala Ala Ser Tyr Ala Arg Tyr
 1               5

<210> SEQ ID NO 258
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Asp Thr Glu Thr Leu Thr Thr Met Phe
 1               5

<210> SEQ ID NO 259
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Ala Thr Val Lys Gly Met Gln Ser Tyr
 1               5

<210> SEQ ID NO 260
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Ala Thr Ser Val Leu Leu Ser Ala Tyr
 1               5

<210> SEQ ID NO 261
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Ser Ala Tyr Asn Arg His Pro Leu Phe
 1               5

<210> SEQ ID NO 262
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 262

His Thr Val Met Arg Glu Thr Leu Phe
 1               5

<210> SEQ ID NO 263
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Glu Ser Gly Leu Phe Ser Pro Cys Tyr
 1               5

<210> SEQ ID NO 264
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Ser Pro Cys Tyr Leu Ser Leu Arg Phe
 1               5

<210> SEQ ID NO 265
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Ile Ile Pro Leu Ile Asn Val Thr Phe
 1               5

<210> SEQ ID NO 266
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Thr Thr Tyr Leu Ser Ser Ser Leu Phe
 1               5

<210> SEQ ID NO 267
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Asn Ser Ile Leu Ser Ser Asn Tyr Phe
 1               5
```

```
<210> SEQ ID NO 268
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Ala Ile Ile Leu Tyr Phe Ile Ala Phe
 1               5

<210> SEQ ID NO 269
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Phe Ile Ala Phe Ala Leu Gly Ile Phe
 1               5

<210> SEQ ID NO 270
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 270
gcgctctaga cccagacgcc gaggatggcc                                    30

<210> SEQ ID NO 271
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 271
gccctgaccc tgctaaaggt                                               20

<210> SEQ ID NO 272
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 272
gcgctctaga ccacccggac tcagaatctc ct                                 32

<210> SEQ ID NO 273
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 273
tgctttccct gagaagagat                                               20
```

<210> SEQ ID NO 274
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 274
aggcgaattc cagagtctcc tcagacgcg                                29

<210> SEQ ID NO 275
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 275
gggcgaattc ccgccgccac catgcgggtc atggcgcc                      38

<210> SEQ ID NO 276
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 276
ttctgctttc ctgagaagac                                          20

<210> SEQ ID NO 277
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 277
gggcgaattc ggactcagaa tctccccaga cgccgag                       37

<210> SEQ ID NO 278
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 278
ccgcgaattc tcatctcagg gtgaggggct                               30

<210> SEQ ID NO 279
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 279
ccgcaagctt tcatctcagg gtgaggggct                               30

<210> SEQ ID NO 280
<211> LENGTH: 30
<212> TYPE: DNA
<213> ORGANISM: Artificial Sequence
<220> FEATURE:
<223> OTHER INFORMATION: Description of Artificial Sequence: Primer

```
<400> SEQUENCE: 280
ccgcaagctt tcagctcagg gtgaggggct                                    30

<210> SEQ ID NO 281
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 281
taatacgact cactataggg                                               20

<210> SEQ ID NO 282
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 282
tagaaggcac agtcgagg                                                 18

<210> SEQ ID NO 283
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 283
gtcgtgacct gcgcccc                                                  17

<210> SEQ ID NO 284
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 284
tttcattttc agtttaggcc a                                             21

<210> SEQ ID NO 285
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 285
ggtgtcctgt ccattctca                                                19

<210> SEQ ID NO 286
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Val Gln Phe Glu Ala Ala Thr
 1               5
```

```
<210> SEQ ID NO 287
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(6)
<223> OTHER INFORMATION: Unknown amino acid

<400> SEQUENCE: 287

Ala Leu Gly Ala Xaa Xaa Arg Gly Tyr
 1               5

<210> SEQ ID NO 288
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Unknown amino acid
<220> FEATURE:
<221> NAME/KEY: MOD_RES
<222> LOCATION: (4)..(5)
<223> OTHER INFORMATION: Unknown amino acid
<220> FEATURE:
<221> NAME/KEY: MOD_RES
<222> LOCATION: (8)
<223> OTHER INFORMATION: Unknown amino acid

<400> SEQUENCE: 288

Xaa Xaa Val Xaa Xaa Gly His Xaa Tyr
 1               5

<210> SEQ ID NO 289
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (3)..(5)
<223> OTHER INFORMATION: Unknown amino acid

<400> SEQUENCE: 289

Xaa Ser Xaa Xaa Xaa Cys Glu Tyr
 1               5

<210> SEQ ID NO 290
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Unknown amino acid
```

```
-continued

<400> SEQUENCE: 290

Xaa Xaa Xaa Glx Ala Arg Gly Tyr
 1               5

<210> SEQ ID NO 291
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Asp Pro His Ala Pro Pro Glx Tyr
 1               5

<210> SEQ ID NO 292
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Unknown amino acid
<220> FEATURE:
<221> NAME/KEY: MOD_RES
<222> LOCATION: (7)..(8)
<223> OTHER INFORMATION: Unknown amino acid

<400> SEQUENCE: 292

Ala Val Pro Ser Xaa His Xaa Xaa Tyr
 1               5

<210> SEQ ID NO 293
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid

<400> SEQUENCE: 293

Xaa Ala Glx Val Glx Met Thr Ala Tyr
 1               5

<210> SEQ ID NO 294
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Ala Leu Asn Gly Arg Val Thr Met Tyr
 1               5

<210> SEQ ID NO 295
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Unknown amino acid
<220> FEATURE:
<221> NAME/KEY: MOD_RES
<222> LOCATION: (6)
<223> OTHER INFORMATION: Unknown amino acid

<400> SEQUENCE: 295

Phe Gly Xaa Ala Cys Xaa Ala Thr Ser Tyr
 1               5                  10

<210> SEQ ID NO 296
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (3)..(4)
<223> OTHER INFORMATION: Unknown amino acid

<400> SEQUENCE: 296

Xaa Gln Xaa Xaa Ala Gly Gly Glx Tyr
 1               5

<210> SEQ ID NO 297
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Unknown amino acid

<400> SEQUENCE: 297

Gly Gln His Ala Ser Val Xaa Ser Tyr
 1               5

<210> SEQ ID NO 298
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Unknown amino acid

<400> SEQUENCE: 298

Xaa Xaa Ala Ala His Val Pro Pro Gly Tyr
 1               5                  10
```

```
<210> SEQ ID NO 299
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Phe Met Asp Val Gly Ala Pro Thr Val Tyr
 1               5                  10

<210> SEQ ID NO 300
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Ala Gln Ala Ala Pro Phe Ala Gly Tyr
 1               5

<210> SEQ ID NO 301
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Val Val Val Phe Gly Val Glx Phe
 1               5

<210> SEQ ID NO 302
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(5)
<223> OTHER INFORMATION: Unknown amino acid

<400> SEQUENCE: 302

Ala Gln Met Xaa Xaa Ser Glu Tyr
 1               5

<210> SEQ ID NO 303
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Unknown amino acid

<400> SEQUENCE: 303

Xaa Xaa Xaa Xaa Phe Gly His Tyr
 1               5
```

```
<210> SEQ ID NO 304
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(5)
<223> OTHER INFORMATION: Unknown amino acid

<400> SEQUENCE: 304

Ala Leu Trp Xaa Xaa Pro Glx Phe
 1               5

<210> SEQ ID NO 305
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Val Pro His Glx Asn Ala Tyr
 1               5

<210> SEQ ID NO 306
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Unknown amino acid

<400> SEQUENCE: 306

Xaa Xaa Xaa Xaa Xaa Gly His Gly Gly Tyr
 1               5                  10

<210> SEQ ID NO 307
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Gly Gln Tyr Val Val Glx Pro Thr Tyr
 1               5

<210> SEQ ID NO 308
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Pro Met Phe Asp Pro Pro Glx Thr Phe
 1               5
```

```
<210> SEQ ID NO 309
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Ala Gln Ala Glu Ser Leu Arg Tyr
 1               5

<210> SEQ ID NO 310
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid

<400> SEQUENCE: 310

Xaa Ala Val Gly His Ser Gly Gly Thr Tyr
 1               5                  10

<210> SEQ ID NO 311
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Unknown amino acid

<400> SEQUENCE: 311

Glu Ser Xaa Pro Asn Asn Val Pro Tyr
 1               5

<210> SEQ ID NO 312
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Leu Ala His Thr Glu Cys Pro Arg Gly Tyr
 1               5                  10

<210> SEQ ID NO 313
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Val Gln Gly Pro Val Gly Val Gln Tyr
 1               5
```

<210> SEQ ID NO 314
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Unknown amino acid

<400> SEQUENCE: 314

Arg Gly Xaa Gly Val Ala Gly Thr Ala Phe
 1               5                  10

<210> SEQ ID NO 315
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Thr Gly Ala Pro Val Ser Glu Glu Gly Tyr
 1               5                  10

<210> SEQ ID NO 316
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Unknown amino acid

<400> SEQUENCE: 316

Val Gln Xaa Tyr Tyr Gly Ser Val Val
 1               5

<210> SEQ ID NO 317
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: Unknown amino acid

<400> SEQUENCE: 317

Glu Pro Ala Met Val Xaa Glx Cys Phe
 1               5

<210> SEQ ID NO 318
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Unknown amino acid -continued

```
<400> SEQUENCE: 318

Gly Gln Pro Gly Ala Pro Xaa Gly Gly Glx Tyr
 1               5                  10

<210> SEQ ID NO 319
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Unknown amino acid

<400> SEQUENCE: 319

Gly Pro Pro His Asn Gly Xaa Arg Ala Tyr
 1               5                  10

<210> SEQ ID NO 320
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Ala Ala His Trp His Val Glu Ala Tyr
 1               5

<210> SEQ ID NO 321
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Thr Pro Pro Thr Arg Arg Glu Ser Tyr
 1               5

<210> SEQ ID NO 322
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Phe Pro Thr Asp Arg Arg Ser Gln Phe
 1               5

<210> SEQ ID NO 323
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Unknown amino acid
```

```
<400> SEQUENCE: 323

Tyr Thr Gly Val Ser Tyr Xaa His Phe
  1               5

<210> SEQ ID NO 324
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Ala Gln Ala Ser Ala Pro Asp Ala Tyr
  1               5

<210> SEQ ID NO 325
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Unknown amino acid

<400> SEQUENCE: 325

Val Gln Tyr Tyr Xaa Pro Phe
  1               5

<210> SEQ ID NO 326
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (4)..(6)
<223> OTHER INFORMATION: Unknown amino acid

<400> SEQUENCE: 326

Xaa Gln Glx Xaa Xaa Xaa Asp Val Tyr
  1               5

<210> SEQ ID NO 327
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Unknown amino acid

<400> SEQUENCE: 327

Ala Thr Gly Thr Ala Glx Asn Xaa Asn Glx Tyr
  1               5                  10
```

```
<210> SEQ ID NO 328
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid

<400> SEQUENCE: 328

Xaa Gln Tyr Thr Val Gly Tyr Phe
 1               5

<210> SEQ ID NO 329
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Pro Leu Phe Gly Gln Thr Ala Gly Gln Tyr
 1               5                  10

<210> SEQ ID NO 330
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(5)
<223> OTHER INFORMATION: Unknown amino acid
<220> FEATURE:
<221> NAME/KEY: MOD_RES
<222> LOCATION: (7)
<223> OTHER INFORMATION: Unknown amino acid

<400> SEQUENCE: 330

Ala Xaa Xaa Xaa Xaa Gln Xaa Glu Tyr
 1               5

<210> SEQ ID NO 331
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Unknown amino acid

<400> SEQUENCE: 331

Glx Gly Tyr Gly Asn Pro Xaa Asn Gly Ala Tyr
 1               5                  10

<210> SEQ ID NO 332
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 332

Val Gln Gly Pro Val Gly Thr Asp Phe
 1               5

<210> SEQ ID NO 333
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(8)
<223> OTHER INFORMATION: Unknown amino acid

<400> SEQUENCE: 333

Val Ala Gly Gly Trp Xaa Xaa Xaa Phe
 1               5

<210> SEQ ID NO 334
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (6)..(7)
<223> OTHER INFORMATION: Unknown amino acid

<400> SEQUENCE: 334

Xaa Ala Gly Phe Phe Xaa Xaa Glu Tyr
 1               5

<210> SEQ ID NO 335
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Unknown amino acid

<400> SEQUENCE: 335

Ser Gly Ala Xaa Asp Arg Ala Tyr Glx Phe
 1               5                  10

<210> SEQ ID NO 336
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Unknown amino acid
```

```
<400> SEQUENCE: 336

Thr Pro Xaa Xaa Xaa Ala Glx Ala Phe
 1               5

<210> SEQ ID NO 337
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Unknown amino acid

<400> SEQUENCE: 337

Val Val Ala Thr Glx Asn Glx Glx Xaa
 1               5

<210> SEQ ID NO 338
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(7)
<223> OTHER INFORMATION: Unknown amino acid

<400> SEQUENCE: 338

Tyr Met Val Thr Xaa Xaa Xaa Phe
 1               5

<210> SEQ ID NO 339
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Unknown amino acid

<400> SEQUENCE: 339

Ala Leu Gly Ser Glx Ala Xaa Met Pro Phe
 1               5                  10

<210> SEQ ID NO 340
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(7)
<223> OTHER INFORMATION: Unknown amino acid

<400> SEQUENCE: 340

Ala Pro Ala Val Xaa Xaa Xaa Val Gly Tyr
 1               5                  10
```

```
<210> SEQ ID NO 341
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Unknown amino acid

<400> SEQUENCE: 341

Pro Val Pro Asn Val Arg Xaa Asn Tyr
  1               5

<210> SEQ ID NO 342
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Thr Leu Glu Gly Trp Met Ser Glx Tyr
  1               5

<210> SEQ ID NO 343
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Tyr Met Val Cys Asn Ala Glu Glu Tyr
  1               5

<210> SEQ ID NO 344
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Unknown amino acid

<400> SEQUENCE: 344

Ala Gln His Pro Ser Ala Xaa Arg Phe
  1               5

<210> SEQ ID NO 345
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Gly Leu Gly Glx Thr Ser Ala Glu Phe
  1               5
```

```
<210> SEQ ID NO 346
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Unknown amino acid

<400> SEQUENCE: 346

Val Met Gly Xaa Thr Asn Ala Asn Phe
 1               5

<210> SEQ ID NO 347
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Unknown amino acid

<400> SEQUENCE: 347

Asn Ala Xaa Gly Arg Glu Ser Ser Phe
 1               5

<210> SEQ ID NO 348
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Ala Met Asn Pro Thr Asn Thr Val Phe
 1               5

<210> SEQ ID NO 349
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (6)
<223> OTHER INFORMATION: Unknown amino acid

<400> SEQUENCE: 349

Xaa Gln Ala Pro Ala Xaa Phe Val Tyr
 1               5

<210> SEQ ID NO 350
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (5)..(7)
<223> OTHER INFORMATION: Unknown amino acid

<400> SEQUENCE: 350

Ala Leu Phe Xaa Xaa Xaa Phe Thr Tyr
 1               5

<210> SEQ ID NO 351
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (3)
<223> OTHER INFORMATION: Unknown amino acid
<220> FEATURE:
<221> NAME/KEY: MOD_RES
<222> LOCATION: (7)
<223> OTHER INFORMATION: Unknown amino acid

<400> SEQUENCE: 351

Xaa Gln Xaa Asn Ala Tyr Xaa Ser Tyr
 1               5

<210> SEQ ID NO 352
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Gly Leu Ala Arg Cys Ser Glx Val Glu Tyr
 1               5                  10

<210> SEQ ID NO 353
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Unknown amino acid

<400> SEQUENCE: 353

Ser Gln Xaa Ala Ala Gly Val Asp Val Phe
 1               5                  10

<210> SEQ ID NO 354
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (7)..(8)
<223> OTHER INFORMATION: Unknown amino acid

<400> SEQUENCE: 354

Pro Gln Gly Glx Met Ala Xaa Xaa Tyr
 1               5

<210> SEQ ID NO 355
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid

<400> SEQUENCE: 355

Xaa Val Phe Val Ser His Thr Thr Phe
 1               5

<210> SEQ ID NO 356
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Unknown amino acid

<400> SEQUENCE: 356

His Xaa Thr Gly Asn Glu Ala Thr Ser Phe
 1               5                  10

<210> SEQ ID NO 357
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid

<400> SEQUENCE: 357

Xaa Gln Gly His His Glu Met Phe Tyr
 1               5

<210> SEQ ID NO 358
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Unknown amino acid
```

```
<400> SEQUENCE: 358

Ala Ala Gly Xaa Gly Pro Thr Phe Tyr
 1               5

<210> SEQ ID NO 359
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Unknown amino acid

<400> SEQUENCE: 359

Val Ala Phe Val Xaa Phe Val Gly Tyr
 1               5

<210> SEQ ID NO 360
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(7)
<223> OTHER INFORMATION: Unknown amino acid

<400> SEQUENCE: 360

Ala Leu Met Pro Xaa Xaa Xaa Asn Tyr
 1               5

<210> SEQ ID NO 361
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: Unknown amino acid

<400> SEQUENCE: 361

Tyr Asn Arg Trp Ser Xaa Glu Phe
 1               5

<210> SEQ ID NO 362
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Unknown amino acid

<400> SEQUENCE: 362

Xaa Xaa Glx Asp Arg Asn Val Thr Phe
 1               5
```

```
<210> SEQ ID NO 363
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(7)
<223> OTHER INFORMATION: Unknown amino acid

<400> SEQUENCE: 363

Val Val Thr Met Xaa Xaa Xaa Glx Tyr
 1               5

<210> SEQ ID NO 364
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Ala Glx Val Glu Cys Glu Thr Tyr
 1               5

<210> SEQ ID NO 365
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Ala Gln Phe Ala Ser Gly Ala Gly Glx
 1               5

<210> SEQ ID NO 366
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Unknown amino acid

<400> SEQUENCE: 366

Glx Gly Xaa Gly Gly Gly Pro Ala Thr Ser Tyr
 1               5                  10

<210> SEQ ID NO 367
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (3)..(4)
<223> OTHER INFORMATION: Unknown amino acid
```

```
<400> SEQUENCE: 367

Xaa Gly Xaa Xaa Cys Asp Tyr
 1               5

<210> SEQ ID NO 368
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Asn Gln Glx His Gly Ser Ala Glu Tyr
 1               5

<210> SEQ ID NO 369
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Ala Pro Met Ala Arg Gly Glx Tyr
 1               5

<210> SEQ ID NO 370
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Unknown amino acid

<400> SEQUENCE: 370

Ala Glx Val Asn Ser Gly Xaa Tyr
 1               5

<210> SEQ ID NO 371
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(8)
<223> OTHER INFORMATION: Unknown amino acid

<400> SEQUENCE: 371

Ala Ala Ser Ser Glx Val Xaa Xaa Pro Pro Glx Tyr
 1               5                   10

<210> SEQ ID NO 372
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 372

Asn Pro Pro Ala Glx Glx Pro Asn
  1               5

<210> SEQ ID NO 373
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Ala Cys Gly Gly Cys Gly Glx Asp Tyr
  1               5

<210> SEQ ID NO 374
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (3)
<223> OTHER INFORMATION: Unknown amino acid

<400> SEQUENCE: 374

Xaa Glx Xaa Asp Pro Pro Asp Met Glx Tyr
  1               5                  10

<210> SEQ ID NO 375
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Gly Gln Glx Glx Ala Val Asp Phe
  1               5

<210> SEQ ID NO 376
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Unknown amino acid

<400> SEQUENCE: 376

Thr Pro Xaa Gly Glu Pro Tyr Glx Ser Tyr
  1               5                  10

<210> SEQ ID NO 377
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Unknown amino acid

<400> SEQUENCE: 377

Gly Pro Xaa Xaa Xaa Pro Glx Tyr
 1               5

<210> SEQ ID NO 378
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Ala Pro Glx Tyr Pro Pro Pro Pro
 1               5

<210> SEQ ID NO 379
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Gly Glx Val Cys Thr Pro Gly Ser Phe
 1               5

<210> SEQ ID NO 380
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Cys Pro Leu Ser Cys Phe Thr
 1               5

<210> SEQ ID NO 381
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Ser Gln Phe Gly Gly Gly Ser Gln Tyr
 1               5

<210> SEQ ID NO 382
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 382

Ala Ser Gly Phe Asn Gly Ser Glx Tyr
 1               5

<210> SEQ ID NO 383
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (3)..(4)
<223> OTHER INFORMATION: Unknown amino acid

<400> SEQUENCE: 383

Xaa Glx Xaa Xaa Tyr Thr Ala Tyr
 1               5

<210> SEQ ID NO 384
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Gly Glx Pro Pro His Asn Gly Phe Tyr
 1               5

<210> SEQ ID NO 385
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Ile Lys Ala Asp His Val Ser Thr Tyr
 1               5

<210> SEQ ID NO 386
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (7)
<223> OTHER INFORMATION: Unknown amino acid

<400> SEQUENCE: 386

Xaa Glx Ala Asp His Val Xaa Pro Tyr
 1               5
```

```
<210> SEQ ID NO 387
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Unknown amino acid

<400> SEQUENCE: 387

Xaa Xaa Xaa Xaa Pro Gly Glx Val Tyr
  1               5

<210> SEQ ID NO 388
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(6)
<223> OTHER INFORMATION: Unknown amino acid

<400> SEQUENCE: 388

Glx Ser Val Xaa Xaa Xaa Glx Thr Gly Tyr
  1               5                  10

<210> SEQ ID NO 389
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Unknown amino acid

<400> SEQUENCE: 389

His Xaa Gly Asn Gln Ala Ala Tyr
  1               5

<210> SEQ ID NO 390
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Glx Ala Gly Thr Thr Val Pro Val Ser Tyr
  1               5                  10

<210> SEQ ID NO 391
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 391

Gly Gln Tyr Pro Thr Gln Pro Thr Tyr
 1               5

<210> SEQ ID NO 392
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Phe Ala Gly Ser Glx Ser Asn Thr Ser Thr Tyr
 1               5                  10

<210> SEQ ID NO 393
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(7)
<223> OTHER INFORMATION: Unknown amino acid

<400> SEQUENCE: 393

Ser Glx Gly Gly Xaa Xaa Xaa Thr Gly Tyr
 1               5                  10

<210> SEQ ID NO 394
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Unknown amino acid

<400> SEQUENCE: 394

Glx Gly Pro Pro Asn Tyr Xaa Thr Tyr
 1               5

<210> SEQ ID NO 395
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Val Lys Val Ile Gln Gln Glu Ser Tyr
 1               5

<210> SEQ ID NO 396
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 396

Leu Pro Pro Pro Pro Pro Pro Pro
 1               5

<210> SEQ ID NO 397
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397

Ala Lys Tyr Ser Thr Pro Ala Thr Leu
 1               5

<210> SEQ ID NO 398
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Gly Gln Arg Lys Gly Ala Gly Ser Val Phe
 1               5                  10

<210> SEQ ID NO 399
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Unknown amino acid

<400> SEQUENCE: 399

Arg Glx Ser Ala Asn His Glu Ala Xaa
 1               5

<210> SEQ ID NO 400
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Gly Lys Val Arg Thr Asp Ile Thr Tyr
 1               5

<210> SEQ ID NO 401
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Unknown amino acid
```

```
<400> SEQUENCE: 401

Val Val Xaa Pro Ala Val Arg Ser Thr Tyr
 1               5                  10

<210> SEQ ID NO 402
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Ala Lys Tyr Pro His Val Glu Asp Tyr
 1               5

<210> SEQ ID NO 403
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Unknown amino acid
<220> FEATURE:
<221> NAME/KEY: MOD_RES
<222> LOCATION: (9)
<223> OTHER INFORMATION: Unknown amino acid

<400> SEQUENCE: 403

Ala Glx Asn Xaa Ser Ala Tyr Val Xaa Tyr
 1               5                  10

<210> SEQ ID NO 404
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Glu Val Val Gly Asp Thr Glx Tyr
 1               5

<210> SEQ ID NO 405
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Ala Lys Ala Gly Ile Thr Thr Thr Leu
 1               5

<210> SEQ ID NO 406
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (2)..(3)
<223> OTHER INFORMATION: Unknown amino acid

<400> SEQUENCE: 406

Val Xaa Xaa Thr Glx Ala Gly Ser Ala Phe
 1               5                  10

<210> SEQ ID NO 407
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(9)
<223> OTHER INFORMATION: Unknown amino acid

<400> SEQUENCE: 407

Ala Glx Ala Ala Ala Asn Val Xaa Xaa Tyr
 1               5                  10

<210> SEQ ID NO 408
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408

Ala Asn His Ser Val Arg Asp Thr Tyr
 1               5

<210> SEQ ID NO 409
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Unknown amino acid
<220> FEATURE:
<221> NAME/KEY: MOD_RES
<222> LOCATION: (6)
<223> OTHER INFORMATION: Unknown amino acid

<400> SEQUENCE: 409

Glu Xaa Xaa Xaa Gly Xaa Arg Glx Tyr
 1               5

<210> SEQ ID NO 410
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
```

```
<400> SEQUENCE: 410

Xaa Glx His Asn Asp Glx Ser Thr Tyr
 1               5

<210> SEQ ID NO 411
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Unknown amino acid
<220> FEATURE:
<221> NAME/KEY: MOD_RES
<222> LOCATION: (7)..(9)
<223> OTHER INFORMATION: Unknown amino acid

<400> SEQUENCE: 411

Ala Asn Glu Glx Xaa Gly Xaa Xaa Xaa Tyr
 1               5                  10

<210> SEQ ID NO 412
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

Ala Ala Gly Pro Thr Ala Glx Glu Ser Tyr
 1               5                  10

<210> SEQ ID NO 413
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Unknown amino acid

<400> SEQUENCE: 413

Val Ala Gly Xaa Val Phe Met Glx Tyr
 1               5

<210> SEQ ID NO 414
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 414

Ala Glx Tyr Glx Ala Glx Val Val Phe
 1               5

<210> SEQ ID NO 415
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(6)
<223> OTHER INFORMATION: Unknown amino acid
<220> FEATURE:
<221> NAME/KEY: MOD_RES
<222> LOCATION: (8)
<223> OTHER INFORMATION: Unknown amino acid

<400> SEQUENCE: 415

Ala Glx Phe Xaa Xaa Xaa Glx Xaa Tyr
  1               5

<210> SEQ ID NO 416
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Unknown amino acid

<400> SEQUENCE: 416

Glx Gly Tyr Gly Asn Pro Xaa Asn Glx Tyr
  1               5                  10

<210> SEQ ID NO 417
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Unknown amino acid

<400> SEQUENCE: 417

Xaa Xaa Xaa Xaa Xaa Glx Ala Pro Cys His Tyr
  1               5                  10

<210> SEQ ID NO 418
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 418

Ala His Ala Val Gln Arg Val Val Tyr
  1               5

<210> SEQ ID NO 419
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Unknown amino acid
```

```
<220> FEATURE:
<221> NAME/KEY: MOD_RES
<222> LOCATION: (7)
<223> OTHER INFORMATION: Unknown amino acid

<400> SEQUENCE: 419

Thr Glx Xaa Thr Val Val Xaa Asn Tyr
  1               5

<210> SEQ ID NO 420
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Unknown amino acid

<400> SEQUENCE: 420

Ala Glx Glx Ala Ser Gly Xaa Ala Phe
  1               5

<210> SEQ ID NO 421
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Gly Ser His Ser Met Arg Tyr Phe
  1               5

<210> SEQ ID NO 422
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 422

Tyr Gly Tyr Gly Ala Thr Val Glu Phe
  1               5

<210> SEQ ID NO 423
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Unknown amino acid

<400> SEQUENCE: 423

Val Glx Xaa Xaa Xaa Thr Thr Phe
  1               5

<210> SEQ ID NO 424
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 424

Gln Pro Gly Pro Gln Ile Val Tyr
 1               5

<210> SEQ ID NO 425
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Unknown amino acid

<400> SEQUENCE: 425

Asn Gly Glx Xaa Ser Asn Asn Tyr
 1               5

<210> SEQ ID NO 426
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Unknown amino acid
<220> FEATURE:
<221> NAME/KEY: MOD_RES
<222> LOCATION: (6)
<223> OTHER INFORMATION: Unknown amino acid

<400> SEQUENCE: 426

Ala Asn Xaa Val Glx Xaa Glu Tyr
 1               5

<210> SEQ ID NO 427
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Unknown amino acid
<220> FEATURE:
<221> NAME/KEY: MOD_RES
<222> LOCATION: (8)..(9)
<223> OTHER INFORMATION: Unknown amino acid

<400> SEQUENCE: 427

Gly Glx Xaa Xaa Xaa Glx Gly Xaa Xaa Tyr
 1               5                  10

<210> SEQ ID NO 428
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 428

Ala Met Asn Pro Thr Asn Thr Val Phe
  1               5

<210> SEQ ID NO 429
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Unknown amino acid
<220> FEATURE:
<221> NAME/KEY: MOD_RES
<222> LOCATION: (7)
<223> OTHER INFORMATION: Unknown amino acid

<400> SEQUENCE: 429

Tyr Asn Xaa Xaa Xaa Glx Xaa Phe
  1               5

<210> SEQ ID NO 430
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (3)..(4)
<223> OTHER INFORMATION: Unknown amino acid

<400> SEQUENCE: 430

Xaa Met Xaa Xaa Ser Tyr Glx Asn Phe
  1               5

<210> SEQ ID NO 431
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Unknown amino acid

<400> SEQUENCE: 431

Ala Glu Phe Trp Ala Cys Glx Xaa Tyr
  1               5

<210> SEQ ID NO 432
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 432

Ser Glx Phe Gly Cys Pro Thr Arg Phe
  1               5

<210> SEQ ID NO 433
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (4)
<223> OTHER INFORMATION: Unknown amino acid
<220> FEATURE:
<221> NAME/KEY: MOD_RES
<222> LOCATION: (7)..(8)
<223> OTHER INFORMATION: Unknown amino acid

<400> SEQUENCE: 433

Xaa Gly Ala Xaa Ser Asn Xaa Xaa Glu Phe
  1               5                  10

<210> SEQ ID NO 434
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Unknown amino acid

<400> SEQUENCE: 434

Arg Glx Ala Ala Tyr Arg Xaa Thr Tyr
  1               5

<210> SEQ ID NO 435
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Unknown amino acid

<400> SEQUENCE: 435

Thr Asn Xaa His Asp Gly Asp Gly Ala Thr Glx Tyr
  1               5                  10

<210> SEQ ID NO 436
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Unknown amino acid
```

```
<220> FEATURE:
<221> NAME/KEY: MOD_RES
<222> LOCATION: (8)
<223> OTHER INFORMATION: Unknown amino acid

<400> SEQUENCE: 436

Xaa Xaa Trp Asp Arg His Thr Xaa Phe
 1               5

<210> SEQ ID NO 437
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 437

Gly Ser His Phe Gly Val Ala Tyr
 1               5

<210> SEQ ID NO 438
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 438

Val Pro Cys Gly Glx Glx Ser Tyr
 1               5

<210> SEQ ID NO 439
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Unknown amino acid

<400> SEQUENCE: 439

Thr Ala Glx Xaa His Arg Gly Tyr
 1               5

<210> SEQ ID NO 440
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid

<400> SEQUENCE: 440

Xaa Ala Glx Tyr Glu His Thr Tyr
 1               5

<210> SEQ ID NO 441
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 441

Asn Gln Glx His Gly Ser Ala Glu Tyr
  1               5

<210> SEQ ID NO 442
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Unknown amino acid

<400> SEQUENCE: 442

Asn Gly Xaa Ala Met His Trp Thr Tyr
  1               5

<210> SEQ ID NO 443
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 443

Phe Val Ser Asn His Ala Tyr
  1               5

<210> SEQ ID NO 444
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(6)
<223> OTHER INFORMATION: Unknown amino acid

<400> SEQUENCE: 444

Thr Gly Xaa Xaa Xaa Xaa Ala Tyr
  1               5

<210> SEQ ID NO 445
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 445

Ser Gln Phe Gly Gly Gly Ser Gln Tyr
  1               5

<210> SEQ ID NO 446
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 446

Ser Gln Phe Asp His Val Thr Tyr
 1               5

<210> SEQ ID NO 447
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (3)..(4)
<223> OTHER INFORMATION: Unknown amino acid

<400> SEQUENCE: 447

Xaa Pro Xaa Xaa Gly Glx Asp Glu Val
 1               5

<210> SEQ ID NO 448
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 448

Asn Gly Tyr Asp Gly Pro Asn Ala Gly Tyr
 1               5                  10

<210> SEQ ID NO 449
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Unknown amino acid

<400> SEQUENCE: 449

Thr Pro Xaa Gly Glu Pro Tyr Glx Ser Tyr
 1               5                  10

<210> SEQ ID NO 450
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (4)..(5)
<223> OTHER INFORMATION: Unknown amino acid
```

```
<400> SEQUENCE: 450

Xaa Ala Asn Xaa Xaa Val Thr
 1               5

<210> SEQ ID NO 451
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 451

Met Pro His Ser Gly Tyr Gly Phe
 1               5

<210> SEQ ID NO 452
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 452

Cys Pro Leu Ser Cys Phe Thr
 1               5

<210> SEQ ID NO 453
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Unknown amino acid

<400> SEQUENCE: 453

Xaa Xaa Xaa Xaa Xaa Pro Gly Phe Tyr
 1               5

<210> SEQ ID NO 454
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (3)
<223> OTHER INFORMATION: Unknown amino acid

<400> SEQUENCE: 454

Xaa Ala Xaa Pro His Pro Met Gly Tyr
 1               5

<210> SEQ ID NO 455
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 455

Ala Gln Thr Val Gly Tyr Gly Glu Tyr
 1               5

<210> SEQ ID NO 456
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 456

Phe Leu Glx Ala Met Glx Ser Thr Tyr
 1               5

<210> SEQ ID NO 457
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Unknown amino acid

<400> SEQUENCE: 457

Thr Val Xaa Asp Ser Glx Thr His Tyr
 1               5

<210> SEQ ID NO 458
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Unknown amino acid

<400> SEQUENCE: 458

Thr Pro Xaa Xaa Ala Arg Ala Pro Thr
 1               5

<210> SEQ ID NO 459
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 459

Ser Glu His Asp Arg Met Tyr
 1               5

<210> SEQ ID NO 460
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 460

Thr Gly Asn Cys Ser Gly Thr Gly Thr Tyr
 1               5                  10

<210> SEQ ID NO 461
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Unknown amino acid

<400> SEQUENCE: 461

Ala Gln Val Asn Pro Ser Xaa Thr Tyr
 1               5

<210> SEQ ID NO 462
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Unknown amino acid

<400> SEQUENCE: 462

Ser Pro Gly Ala Glu Thr Arg Ala Xaa Tyr
 1               5                  10

<210> SEQ ID NO 463
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(6)
<223> OTHER INFORMATION: Unknown amino acid

<400> SEQUENCE: 463

Tyr Leu Gly Xaa Xaa Xaa Gly Ala Phe
 1               5

<210> SEQ ID NO 464
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
```

```
<400> SEQUENCE: 464

Xaa Thr Ser Phe Met Glx Val Tyr
 1               5

<210> SEQ ID NO 465
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (3)..(5)
<223> OTHER INFORMATION: Unknown amino acid

<400> SEQUENCE: 465

Xaa Pro Xaa Xaa Xaa Pro Ser Ser Gly Tyr
 1               5                  10

<210> SEQ ID NO 466
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Unknown amino acid

<400> SEQUENCE: 466

Thr Pro Xaa Xaa Xaa Gly Arg Met Tyr
 1               5

<210> SEQ ID NO 467
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 467

Pro Met Phe Asp Glx Glx Val Tyr
 1               5

<210> SEQ ID NO 468
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Unknown amino acid

<400> SEQUENCE: 468

Tyr Leu Xaa Xaa Xaa Arg Thr Phe
 1               5
```

```
<210> SEQ ID NO 469
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 469

Ala Gln Glu His Gly Cys Ala Ala Glx Phe
 1               5                  10

<210> SEQ ID NO 470
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (3)..(5)
<223> OTHER INFORMATION: Unknown amino acid

<400> SEQUENCE: 470

Xaa Met Xaa Xaa Xaa Gly Val His Asp Tyr
 1               5                  10

<210> SEQ ID NO 471
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(5)
<223> OTHER INFORMATION: Unknown amino acid

<400> SEQUENCE: 471

Tyr Val Ser Xaa Xaa Arg Asn Gln Tyr
 1               5

<210> SEQ ID NO 472
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 472

Ala Gln Tyr Ala Ala Gly Glu Ser Phe Tyr
 1               5                  10

<210> SEQ ID NO 473
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 473

Thr Pro His Thr Glx His Asp Glu Tyr
 1               5

<210> SEQ ID NO 474
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Unknown amino acid

<400> SEQUENCE: 474

Tyr Met Xaa Xaa Xaa Phe Met Tyr
 1               5

<210> SEQ ID NO 475
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 475

Asp Pro His Tyr Val Ser Gly His Glx Phe
 1               5                  10

<210> SEQ ID NO 476
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(5)
<223> OTHER INFORMATION: Unknown amino acid

<400> SEQUENCE: 476

Met Val Gly Xaa Xaa Pro Ala Thr
 1               5

<210> SEQ ID NO 477
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Unknown amino acid

<400> SEQUENCE: 477

Glx Ala Ser Pro Gly Glu Xaa Thr Ser Tyr
 1               5                  10

<210> SEQ ID NO 478
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 478

Val Val Ala Pro Ile Thr Thr Gly Tyr
 1               5

<210> SEQ ID NO 479
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(8)
<223> OTHER INFORMATION: Unknown amino acid

<400> SEQUENCE: 479

Val Val Ala Cys Val Xaa Xaa Xaa Tyr
 1               5

<210> SEQ ID NO 480
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Unknown amino acid
<220> FEATURE:
<221> NAME/KEY: MOD_RES
<222> LOCATION: (6)
<223> OTHER INFORMATION: Unknown amino acid

<400> SEQUENCE: 480

Pro Leu Ala Xaa Asn Xaa His Thr Tyr
 1               5

<210> SEQ ID NO 481
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (3)
<223> OTHER INFORMATION: Unknown amino acid

<400> SEQUENCE: 481

Xaa Ala Xaa Tyr Arg Arg Met Tyr
 1               5

<210> SEQ ID NO 482
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (6)
<223> OTHER INFORMATION: Unknown amino acid

<400> SEQUENCE: 482

Pro Leu Ala Met Glx Xaa Tyr Thr Tyr
 1               5

<210> SEQ ID NO 483
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (3)
<223> OTHER INFORMATION: Unknown amino acid
<220> FEATURE:
<221> NAME/KEY: MOD_RES
<222> LOCATION: (7)
<223> OTHER INFORMATION: Unknown amino acid

<400> SEQUENCE: 483

Xaa Pro Xaa Met Pro Gly Xaa Ala Tyr
 1               5

<210> SEQ ID NO 484
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 484

His Thr Thr Ser Glx Asn Ala Tyr
 1               5

<210> SEQ ID NO 485
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 485

Met Ala Ala Met Val Gly Val Ala Val Tyr
 1               5                   10

<210> SEQ ID NO 486
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 486

Gly Pro Glx Val Met Glx His Gly Tyr
 1               5
```

```
<210> SEQ ID NO 487
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Unknown amino acid

<400> SEQUENCE: 487

Phe Gln Ala Arg Xaa Thr Glu Tyr
  1               5

<210> SEQ ID NO 488
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 488

Leu Pro His Gln Pro Leu Ala Thr Tyr
  1               5

<210> SEQ ID NO 489
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Unknown amino acid
<220> FEATURE:
<221> NAME/KEY: MOD_RES
<222> LOCATION: (6)..(8)
<223> OTHER INFORMATION: Unknown amino acid

<400> SEQUENCE: 489

Ala Ala Ala Xaa Val Xaa Xaa Xaa Val Thr Tyr
  1               5                  10

<210> SEQ ID NO 490
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid

<400> SEQUENCE: 490

Xaa Pro Glu Met Gly Glx Phe Ser Tyr
  1               5

<210> SEQ ID NO 491
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (3)..(4)
<223> OTHER INFORMATION: Unknown amino acid
<220> FEATURE:
<221> NAME/KEY: MOD_RES
<222> LOCATION: (7)
<223> OTHER INFORMATION: Unknown amino acid

<400> SEQUENCE: 491

Tyr Val Xaa Xaa Val Arg Xaa Val Phe
 1               5

<210> SEQ ID NO 492
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Unknown amino acid
<220> FEATURE:
<221> NAME/KEY: MOD_RES
<222> LOCATION: (6)
<223> OTHER INFORMATION: Unknown amino acid

<400> SEQUENCE: 492

Phe Val Thr Xaa Asn Xaa Glu Glu Tyr
 1               5

<210> SEQ ID NO 493
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Unknown amino acid

<400> SEQUENCE: 493

Ala Ala Pro Val Gly Ala Xaa Glu Ser Tyr
 1               5                  10

<210> SEQ ID NO 494
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Unknown amino acid

<400> SEQUENCE: 494

Gly Ser Xaa Xaa Xaa Ser Tyr Thr Tyr
 1               5

<210> SEQ ID NO 495
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(6)
<223> OTHER INFORMATION: Unknown amino acid

<400> SEQUENCE: 495

Tyr Val Ala Xaa Xaa Xaa Pro Ala Phe
 1               5

<210> SEQ ID NO 496
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(5)
<223> OTHER INFORMATION: Unknown amino acid

<400> SEQUENCE: 496

Val Gly Tyr Xaa Xaa Ala His Pro Gly Phe
 1               5                  10

<210> SEQ ID NO 497
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 497

Glx Ala Thr Asn Ser Val Thr Ser Thr Tyr
 1               5                  10

<210> SEQ ID NO 498
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
<223> OTHER INFORMATION: Unknown amino acid

<400> SEQUENCE: 498

Xaa Xaa Xaa Xaa Xaa Xaa Ser Thr Tyr
 1               5

<210> SEQ ID NO 499
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 499

Tyr Ala Thr Ala Gly Glu Met Met Ala Phe
 1               5                  10
```

```
<210> SEQ ID NO 500
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 500

Ser Pro Thr Tyr Thr His Ala Val Ala Phe
 1               5                  10

<210> SEQ ID NO 501
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(5)
<223> OTHER INFORMATION: Unknown amino acid

<400> SEQUENCE: 501

Met Pro Ala Xaa Xaa Met Val Met Ala Phe
 1               5                  10

<210> SEQ ID NO 502
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(9)
<223> OTHER INFORMATION: Unknown amino acid

<400> SEQUENCE: 502

Ala Ala Phe Cys Gly Xaa Xaa Xaa Xaa Val
 1               5                  10

<210> SEQ ID NO 503
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: Unknown amino acid

<400> SEQUENCE: 503

Ser Pro Asn Glu Asp Xaa Met Glx Val Phe
 1               5                  10

<210> SEQ ID NO 504
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 504

Val Ala Ala Thr Ala Gly Ala Val Phe
  1               5

<210> SEQ ID NO 505
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(5)
<223> OTHER INFORMATION: Unknown amino acid

<400> SEQUENCE: 505

Tyr Leu His Xaa Xaa Glu Thr
  1               5

<210> SEQ ID NO 506
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 506

Thr Ala Phe Pro Phe Val Phe
  1               5

<210> SEQ ID NO 507
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 507

Ile Leu Gly Pro Pro Gly Ser Val Tyr
  1               5

<210> SEQ ID NO 508
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid

<400> SEQUENCE: 508

Xaa Leu Gly Asp Val Asn Met Tyr
  1               5

<210> SEQ ID NO 509
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (3)..(5)
<223> OTHER INFORMATION: Unknown amino acid
<220> FEATURE:
<221> NAME/KEY: MOD_RES
<222> LOCATION: (7)
<223> OTHER INFORMATION: Unknown amino acid

<400> SEQUENCE: 509

Tyr Gly Xaa Xaa Xaa Val Xaa Ser Met
  1               5

<210> SEQ ID NO 510
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid

<400> SEQUENCE: 510

Xaa Pro His Cys Ser Cys Ser Ser Phe
  1               5

<210> SEQ ID NO 511
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 511

Asp Pro Pro Cys Trp Gly Val Ser Phe
  1               5

<210> SEQ ID NO 512
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Unknown amino acid

<400> SEQUENCE: 512

Xaa Xaa Xaa Xaa Ala His Asp Ala Tyr
  1               5

<210> SEQ ID NO 513
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Unknown amino acid
```

-continued

```
<400> SEQUENCE: 513

Thr Ala Arg Val Xaa Ser Val Glu Tyr
 1               5

<210> SEQ ID NO 514
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (7)
<223> OTHER INFORMATION: Unknown amino acid

<400> SEQUENCE: 514

Xaa Ser Asp Gly Arg Glx Xaa Thr Tyr
 1               5

<210> SEQ ID NO 515
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 515

Asn Met Asn Asp Leu Val Ser Glu Tyr
 1               5

<210> SEQ ID NO 516
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 516

Met Pro Ala Ala Asp Tyr Glu Val Ala Phe
 1               5                  10

<210> SEQ ID NO 517
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 517

Ala Glu Ile Leu Gln Val Ile Tyr
 1               5

<210> SEQ ID NO 518
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (3)..(6)
<223> OTHER INFORMATION: Unknown amino acid

<400> SEQUENCE: 518

Ala Pro Xaa Xaa Xaa Xaa Val Ser Tyr
 1               5

<210> SEQ ID NO 519
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 519

Met Pro Ala Gly Tyr Asn Asn Val Tyr
 1               5

<210> SEQ ID NO 520
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Unknown amino acid

<400> SEQUENCE: 520

Tyr Met Ser Gly Xaa Tyr Gly Thr Phe
 1               5

<210> SEQ ID NO 521
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Unknown amino acid

<400> SEQUENCE: 521

Xaa Xaa Xaa Ala Val Val Ala Glx Ser Tyr
 1               5                  10

<210> SEQ ID NO 522
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid

<400> SEQUENCE: 522

Xaa Pro Val Val Pro Ala Ala Glx Thr Tyr
 1               5                  10
```

```
<210> SEQ ID NO 523
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 523

Tyr Met Ile Asp Pro Ser Gly Val Ser Tyr
 1               5                  10

<210> SEQ ID NO 524
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 524

Phe Ala Asn Gly Val Glx Gly Cys Ala Phe Ala Phe
 1               5                  10

<210> SEQ ID NO 525
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(7)
<223> OTHER INFORMATION: Unknown amino acid

<400> SEQUENCE: 525

Asn His Ala Val Gly Xaa Xaa Val Ser Met
 1               5                  10

<210> SEQ ID NO 526
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 526

His Asn Val Phe Glx Pro Thr Ser Asn Ala
 1               5                  10

<210> SEQ ID NO 527
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Unknown amino acid

<400> SEQUENCE: 527

Ser Val Cys Glu Thr Glu Ser Xaa
 1               5
```

```
<210> SEQ ID NO 528
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 528

Thr His Pro Ser Glx Ala Cys Ala Phe
 1               5

<210> SEQ ID NO 529
<211> LENGTH: 4
<212> TYPE: PRT
<213> ORGANISM: Artificial Sequence
<220> FEATURE:
<223> OTHER INFORMATION: Description of Artificial Sequence: Synthetic
      motif

<400> SEQUENCE: 529

Gln Met Leu Val
 1

<210> SEQ ID NO 530
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Unknown amino acid

<400> SEQUENCE: 530

Ala Asn Xaa Glu Gly Pro His Thr
 1               5

<210> SEQ ID NO 531
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 531

Gly His Ser Pro Pro Thr Ser Ser Leu
 1               5

<210> SEQ ID NO 532
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 532

Cys His Ser Ala Phe Ala Leu
 1               5

<210> SEQ ID NO 533
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Unknown amino acid

<400> SEQUENCE: 533

His His Ala Phe Ala Glx Val Xaa Val
  1               5

<210> SEQ ID NO 534
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Unknown amino acid
<220> FEATURE:
<221> NAME/KEY: MOD_RES
<222> LOCATION: (9)
<223> OTHER INFORMATION: Unknown amino acid

<400> SEQUENCE: 534

Asp His Tyr Tyr Xaa Ala Gly Ser Xaa
  1               5

<210> SEQ ID NO 535
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Unknown amino acid
<220> FEATURE:
<221> NAME/KEY: MOD_RES
<222> LOCATION: (8)
<223> OTHER INFORMATION: Unknown amino acid

<400> SEQUENCE: 535

Glu Xaa Ala Pro His Ala Ala Xaa
  1               5

<210> SEQ ID NO 536
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Unknown amino acid
<220> FEATURE:
<221> NAME/KEY: MOD_RES
<222> LOCATION: (8)
<223> OTHER INFORMATION: Unknown amino acid

<400> SEQUENCE: 536

Ala Ala Ala Xaa Arg Cys Glu Xaa
  1               5
```

```
<210> SEQ ID NO 537
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Unknown amino acid

<400> SEQUENCE: 537

Gly His Glx Ala Pro Ala Ala Ser Xaa
 1               5

<210> SEQ ID NO 538
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Unknown amino acid

<400> SEQUENCE: 538

Val His Asn Pro Glx Ser Ser Xaa
 1               5

<210> SEQ ID NO 539
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: Unknown amino acid
<220> FEATURE:
<221> NAME/KEY: MOD_RES
<222> LOCATION: (9)
<223> OTHER INFORMATION: Unknown amino acid

<400> SEQUENCE: 539

Ala Gly Gly Pro Thr Xaa Cys Arg Xaa
 1               5

<210> SEQ ID NO 540
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 540

Leu His Leu Leu Thr Leu Glu Ala
 1               5

<210> SEQ ID NO 541
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (9)
<223> OTHER INFORMATION: Unknown amino acid

<400> SEQUENCE: 541

Xaa His Arg Leu Cys Ser Pro Thr Xaa
 1               5

<210> SEQ ID NO 542
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Unknown amino acid

<400> SEQUENCE: 542

Ser Val Ser Xaa Pro His Ala Pro
 1               5

<210> SEQ ID NO 543
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Unknown amino acid

<400> SEQUENCE: 543

Ala Pro Phe Thr Gly Gly Asn Gly Xaa
 1               5

<210> SEQ ID NO 544
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Unknown amino acid

<400> SEQUENCE: 544

Glu His Gly Xaa Glu Asn Gly His
 1               5

<210> SEQ ID NO 545
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (9)
<223> OTHER INFORMATION: Unknown amino acid

<400> SEQUENCE: 545

His His Ala Pro Cys Gly Val Ser Xaa
 1               5

<210> SEQ ID NO 546
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 546

Asn His Ala Ile Val Ser Thr Ser Val
 1               5

<210> SEQ ID NO 547
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 547

Gly His Glx Asn Ser Val Thr Ser Val
 1               5

<210> SEQ ID NO 548
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 548

Ser His Glx Ala Pro Cys Thr Ser Val
 1               5

<210> SEQ ID NO 549
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Unknown amino acid

<400> SEQUENCE: 549

Phe Val Ala Arg Phe Val Ser Xaa
 1               5

<210> SEQ ID NO 550
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 550

His His Ser Asp Gly Ser Val Ser Leu
1               5

<210> SEQ ID NO 551
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)
<223> OTHER INFORMATION: Unknown amino acid

<400> SEQUENCE: 551

Ser His Ala Gly Ala Pro Pro Pro Thr Xaa
1               5                   10

<210> SEQ ID NO 552
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (6)..(7)
<223> OTHER INFORMATION: Unknown amino acid
<220> FEATURE:
<221> NAME/KEY: MOD_RES
<222> LOCATION: (9)
<223> OTHER INFORMATION: Unknown amino acid

<400> SEQUENCE: 552

Xaa His Val Val Ser Xaa Xaa Val Xaa
1               5

<210> SEQ ID NO 553
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Unknown amino acid

<400> SEQUENCE: 553

Ala Val Xaa Asp Cys Cys Glx Val Ala Val
1               5                   10

<210> SEQ ID NO 554
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Unknown amino acid
```

```
<220> FEATURE:
<221> NAME/KEY: MOD_RES
<222> LOCATION: (9)
<223> OTHER INFORMATION: Unknown amino acid

<400> SEQUENCE: 554

Glu Xaa Gly Gly Asn Thr Asn Pro Glx Xaa
 1               5                  10

<210> SEQ ID NO 555
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Unknown amino acid

<400> SEQUENCE: 555

Tyr His Gly Ser Glx Asn Pro Glu Xaa
 1               5

<210> SEQ ID NO 556
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Unknown amino acid

<400> SEQUENCE: 556

Xaa Xaa Xaa Xaa Xaa Thr Tyr Ser Tyr
 1               5

<210> SEQ ID NO 557
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Unknown amino acid

<400> SEQUENCE: 557

Ser His Xaa Xaa Xaa Tyr Phe
 1               5

<210> SEQ ID NO 558
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Unknown amino acid
```

```
<400> SEQUENCE: 558

Ala His Pro Asp Glx Ala Xaa Val
1               5

<210> SEQ ID NO 559
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Unknown amino acid

<400> SEQUENCE: 559

Gly Thr Ala His Tyr Glx Val Xaa
1               5

<210> SEQ ID NO 560
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Unknown amino acid

<400> SEQUENCE: 560

Ser His Val Asp Arg Pro Ser Xaa
1               5

<210> SEQ ID NO 561
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Unknown amino acid

<400> SEQUENCE: 561

Thr Gly Ala Ala Phe Glx Asn Pro Xaa
1               5

<210> SEQ ID NO 562
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Unknown amino acid

<400> SEQUENCE: 562

Xaa Xaa Xaa Tyr Glx Ala Tyr Val Tyr
1               5
```

<210> SEQ ID NO 563
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: Unknown amino acid

<400> SEQUENCE: 563

Gly His Gly Pro Thr Xaa Ala Ala Val
1               5

<210> SEQ ID NO 564
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 564

Tyr Gln His Thr Gly Ala Val Leu
1               5

<210> SEQ ID NO 565
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 565

Thr His Thr Gln Pro Gly Val Gln Leu
1               5

<210> SEQ ID NO 566
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)
<223> OTHER INFORMATION: Unknown amino acid

<400> SEQUENCE: 566

Gly His Ala Gly His Val Pro Pro Glu Xaa
1               5                   10

<210> SEQ ID NO 567
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Unknown amino acid

```
<400> SEQUENCE: 567

Thr His Phe Arg Tyr Val Ser Xaa
 1               5

<210> SEQ ID NO 568
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 568

Glu His Arg Pro Asp Arg Val Phe
 1               5

<210> SEQ ID NO 569
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 569

Ser His Ala Gln Thr Val Val Leu
 1               5

<210> SEQ ID NO 570
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 570

Ser His Ala Asn Ser Ala Val Val Leu
 1               5

<210> SEQ ID NO 571
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 571

Tyr His His Gly Gly Val Ser Ala Phe
 1               5

<210> SEQ ID NO 572
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (3)..(4)
<223> OTHER INFORMATION: Unknown amino acid
```

```
<220> FEATURE:
<221> NAME/KEY: MOD_RES
<222> LOCATION: (10)
<223> OTHER INFORMATION: Unknown amino acid

<400> SEQUENCE: 572

Xaa His Xaa Xaa Gly His Thr Gly Tyr Xaa
 1               5                  10

<210> SEQ ID NO 573
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 573

Asn His Ala Asn Gly Leu Thr Leu
 1               5

<210> SEQ ID NO 574
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)
<223> OTHER INFORMATION: Unknown amino acid

<400> SEQUENCE: 574

Gly His Ala Gly Met Gly Cys Val Phe Glx Xaa
 1               5                  10

<210> SEQ ID NO 575
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(6)
<223> OTHER INFORMATION: Unknown amino acid
<220> FEATURE:
<221> NAME/KEY: MOD_RES
<222> LOCATION: (8)
<223> OTHER INFORMATION: Unknown amino acid
<220> FEATURE:
<221> NAME/KEY: MOD_RES
<222> LOCATION: (10)
<223> OTHER INFORMATION: Unknown amino acid

<400> SEQUENCE: 575

Met Arg Xaa Xaa Xaa Xaa Gly Xaa Glu Xaa
 1               5                  10

<210> SEQ ID NO 576
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (8)
<223> OTHER INFORMATION: Unknown amino acid

<400> SEQUENCE: 576

Ser His Gly Val Pro Arg Ala Xaa
 1               5

<210> SEQ ID NO 577
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(7)
<223> OTHER INFORMATION: Unknown amino acid

<400> SEQUENCE: 577

Glu His His Met Pro Xaa Xaa
 1               5

<210> SEQ ID NO 578
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Unknown amino acid

<400> SEQUENCE: 578

His His Glx Cys Ala Ala Gly Ala Xaa
 1               5

<210> SEQ ID NO 579
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (8)
<223> OTHER INFORMATION: Unknown amino acid

<400> SEQUENCE: 579

Xaa Val Asp Glx Ala Glu Pro Xaa Val
 1               5

<210> SEQ ID NO 580
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (3)
<223> OTHER INFORMATION: Unknown amino acid

<400> SEQUENCE: 580

Met Gly Xaa Pro Val Arg His Met Val
 1               5

<210> SEQ ID NO 581
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Unknown amino acid

<400> SEQUENCE: 581

Ser His Tyr Asp Trp Glx Val Xaa
 1               5

<210> SEQ ID NO 582
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Unknown amino acid

<400> SEQUENCE: 582

Met Pro His Ser His Pro Phe Val Xaa
 1               5

<210> SEQ ID NO 583
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 583

Glx Cys Val Arg Cys Glx Asn Gly Val Phe
 1               5                  10

<210> SEQ ID NO 584
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Unknown amino acid
<220> FEATURE:
<221> NAME/KEY: MOD_RES
<222> LOCATION: (9)
<223> OTHER INFORMATION: Unknown amino acid
```

-continued

```
<400> SEQUENCE: 584

Ser His Ala Gly Ala Gly Xaa Val Xaa
 1               5

<210> SEQ ID NO 585
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Unknown amino acid
<220> FEATURE:
<221> NAME/KEY: MOD_RES
<222> LOCATION: (7)..(8)
<223> OTHER INFORMATION: Unknown amino acid

<400> SEQUENCE: 585

Gly His Xaa Glu Gly Pro Xaa Xaa
 1               5

<210> SEQ ID NO 586
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (8)
<223> OTHER INFORMATION: Unknown amino acid

<400> SEQUENCE: 586

Xaa His Gly Gly Asp His Val Xaa
 1               5

<210> SEQ ID NO 587
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: Unknown amino acid
<220> FEATURE:
<221> NAME/KEY: MOD_RES
<222> LOCATION: (8)
<223> OTHER INFORMATION: Unknown amino acid

<400> SEQUENCE: 587

Glu Glx Ala His Ser Xaa Val Xaa
 1               5

<210> SEQ ID NO 588
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (5)
<223> OTHER INFORMATION: Unknown amino acid
<220> FEATURE:
<221> NAME/KEY: MOD_RES
<222> LOCATION: (7)
<223> OTHER INFORMATION: Unknown amino acid

<400> SEQUENCE: 588

Tyr His His Asp Xaa Val Xaa
  1               5

<210> SEQ ID NO 589
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Unknown amino acid

<400> SEQUENCE: 589

Met Ala Gly Ala Trp Cys Arg Xaa
  1               5

<210> SEQ ID NO 590
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Unknown amino acid
<220> FEATURE:
<221> NAME/KEY: MOD_RES
<222> LOCATION: (8)
<223> OTHER INFORMATION: Unknown amino acid

<400> SEQUENCE: 590

Glu His Xaa Xaa Xaa Thr Val Xaa
  1               5

<210> SEQ ID NO 591
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(7)
<223> OTHER INFORMATION: Unknown amino acid

<400> SEQUENCE: 591

Met Ala Xaa Xaa Xaa Xaa Xaa Val Val
  1               5

<210> SEQ ID NO 592
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Unknown amino acid
<220> FEATURE:
<221> NAME/KEY: MOD_RES
<222> LOCATION: (8)
<223> OTHER INFORMATION: Unknown amino acid
<220> FEATURE:
<221> NAME/KEY: MOD_RES
<222> LOCATION: (10)
<223> OTHER INFORMATION: Unknown amino acid

<400> SEQUENCE: 592

Gly His Ala Xaa Thr Asp Gly Xaa Thr Xaa
 1               5                  10

<210> SEQ ID NO 593
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Unknown amino acid

<400> SEQUENCE: 593

Pro Val Ser His Xaa Val Asn Glu Leu
 1               5

<210> SEQ ID NO 594
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Unknown amino acid
<220> FEATURE:
<221> NAME/KEY: MOD_RES
<222> LOCATION: (9)
<223> OTHER INFORMATION: Unknown amino acid

<400> SEQUENCE: 594

Xaa Xaa Tyr Thr Pro Gly His Thr Xaa
 1               5

<210> SEQ ID NO 595
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (8)
<223> OTHER INFORMATION: Unknown amino acid
```

```
<400> SEQUENCE: 595

Xaa His Tyr Asp Arg Asn Gln Xaa
 1               5

<210> SEQ ID NO 596
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Unknown amino acid

<400> SEQUENCE: 596

Glu Ala Xaa Xaa Cys Glx Val Thr Thr Tyr
 1               5                  10

<210> SEQ ID NO 597
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (10)
<223> OTHER INFORMATION: Unknown amino acid

<400> SEQUENCE: 597

Xaa Glx Ala Pro Thr Ser Val Phe Glx Xaa
 1               5                  10

<210> SEQ ID NO 598
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)
<223> OTHER INFORMATION: Unknown amino acid

<400> SEQUENCE: 598

Phe Thr Met Pro Ala His Pro Ser Thr Xaa
 1               5                  10

<210> SEQ ID NO 599
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Unknown amino acid
<220> FEATURE:
<221> NAME/KEY: MOD_RES
<222> LOCATION: (9)
<223> OTHER INFORMATION: Unknown amino acid
```

```
<400> SEQUENCE: 599

Met Thr Xaa Gly Tyr Gly Glu Pro Xaa
 1               5

<210> SEQ ID NO 600
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 600

Ala His Gly Arg Lys Met Ser Lys Ser Leu
 1               5                  10

<210> SEQ ID NO 601
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (3)..(4)
<223> OTHER INFORMATION: Unknown amino acid
<220> FEATURE:
<221> NAME/KEY: MOD_RES
<222> LOCATION: (9)
<223> OTHER INFORMATION: Unknown amino acid

<400> SEQUENCE: 601

Xaa His Xaa Xaa His Ala Glx Val Xaa
 1               5

<210> SEQ ID NO 602
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Unknown amino acid
<220> FEATURE:
<221> NAME/KEY: MOD_RES
<222> LOCATION: (8)..(9)
<223> OTHER INFORMATION: Unknown amino acid

<400> SEQUENCE: 602

Xaa Xaa Xaa His Ala Val Gly Xaa Xaa
 1               5

<210> SEQ ID NO 603
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(7)
<223> OTHER INFORMATION: Unknown amino acid
```

-continued

```
<400> SEQUENCE: 603

Met Ser Ser Asn Glu Xaa Xaa Met
 1               5

<210> SEQ ID NO 604
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(6)
<223> OTHER INFORMATION: Unknown amino acid

<400> SEQUENCE: 604

Gly His Xaa Xaa Xaa Xaa Pro Cys Cys
 1               5

<210> SEQ ID NO 605
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (4)
<223> OTHER INFORMATION: Unknown amino acid
<220> FEATURE:
<221> NAME/KEY: MOD_RES
<222> LOCATION: (9)
<223> OTHER INFORMATION: Unknown amino acid

<400> SEQUENCE: 605

Xaa His Val Xaa Ala Val Asn Glu Xaa
 1               5

<210> SEQ ID NO 606
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (8)..(9)
<223> OTHER INFORMATION: Unknown amino acid

<400> SEQUENCE: 606

Xaa His Glu Val Glx Pro His Xaa Xaa
 1               5

<210> SEQ ID NO 607
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (10)
<223> OTHER INFORMATION: Unknown amino acid

<400> SEQUENCE: 607

Ala Thr Glu His Cys Phe Val Met Glu Xaa
  1               5                  10

<210> SEQ ID NO 608
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 608

Ala His Ser Asn Leu Ala Ser Val Leu
  1               5

<210> SEQ ID NO 609
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Unknown amino acid
<220> FEATURE:
<221> NAME/KEY: MOD_RES
<222> LOCATION: (8)..(9)
<223> OTHER INFORMATION: Unknown amino acid

<400> SEQUENCE: 609

Val Xaa Ala Pro Ala Asn Asp Xaa Xaa
  1               5

<210> SEQ ID NO 610
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 610

Ser His Gln Arg Gln Leu Leu Leu
  1               5

<210> SEQ ID NO 611
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Unknown amino acid

<400> SEQUENCE: 611

Phe His Met Asp Xaa Glx Thr Phe
  1               5
```

<210> SEQ ID NO 612
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (8)..(9)
<223> OTHER INFORMATION: Unknown amino acid

<400> SEQUENCE: 612

Xaa His Glu Val Glx Pro His Xaa Xaa
 1               5

<210> SEQ ID NO 613
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(10)
<223> OTHER INFORMATION: Unknown amino acid

<400> SEQUENCE: 613

Phe His His Thr Glx Ser Asn Pro Xaa Xaa
 1               5                  10

<210> SEQ ID NO 614
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (9)
<223> OTHER INFORMATION: Unknown amino acid

<400> SEQUENCE: 614

Xaa His Gly Cys Pro Gly Met Pro Xaa
 1               5

<210> SEQ ID NO 615
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Unknown amino acid
<220> FEATURE:
<221> NAME/KEY: MOD_RES
<222> LOCATION: (8)
<223> OTHER INFORMATION: Unknown amino acid

```
<220> FEATURE:
<221> NAME/KEY: MOD_RES
<222> LOCATION: (10)
<223> OTHER INFORMATION: Unknown amino acid

<400> SEQUENCE: 615

Met Xaa Pro Gly Asn Ser Ala Xaa Tyr Xaa
 1               5                  10

<210> SEQ ID NO 616
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 616

Asn Gln Glx His Gly Ser Ala Glu Tyr
 1               5

<210> SEQ ID NO 617
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: Unknown amino acid

<400> SEQUENCE: 617

Pro Met Asn Asp Trp Xaa Met Thr Glx Thr Tyr
 1               5                  10

<210> SEQ ID NO 618
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 618

Ser Gln Phe Gly Gly Gly Ser Gln Tyr
 1               5

<210> SEQ ID NO 619
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 619

Phe Leu Glx Ala Met Glx Ser Thr Tyr
 1               5

<210> SEQ ID NO 620
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (3)
<223> OTHER INFORMATION: Unknown amino acid

<400> SEQUENCE: 620

Thr Val Xaa Asp Ser Glx Thr His Tyr
 1               5

<210> SEQ ID NO 621
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 621

Lys Asn Ala Asn Leu Val Gln Leu Tyr
 1               5

<210> SEQ ID NO 622
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 622

Ile Leu Gly Pro Pro Gly Ser Val Tyr
 1               5

<210> SEQ ID NO 623
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 623

Tyr Met Ile Asp Pro Ser Gly Val Ser Tyr
 1               5                  10

<210> SEQ ID NO 624
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Unknown amino acid

<400> SEQUENCE: 624

Ser Gln Xaa Ala Ala Gly Val Asp Val Phe
 1               5                  10

<210> SEQ ID NO 625
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)
<223> OTHER INFORMATION: Unknown amino acid
<220> FEATURE:
<221> NAME/KEY: MOD_RES
<222> LOCATION: (4)
<223> OTHER INFORMATION: Unknown amino acid

<400> SEQUENCE: 625

Xaa Val Glu Xaa Thr Thr Asp Tyr Tyr
 1               5

<210> SEQ ID NO 626
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Unknown amino acid

<400> SEQUENCE: 626

Ala Ala Gly Xaa Gly Pro Thr Phe Tyr
 1               5

<210> SEQ ID NO 627
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Unknown amino acid

<400> SEQUENCE: 627

Val Ala Phe Val Xaa Phe Val Gly Tyr
 1               5

<210> SEQ ID NO 628
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: Unknown amino acid

<400> SEQUENCE: 628

Tyr Asn Arg Trp Ser Xaa Glu Phe
 1               5

<210> SEQ ID NO 629
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (5)..(7)
<223> OTHER INFORMATION: Unknown amino acid

<400> SEQUENCE: 629

Ala Leu Met Pro Xaa Xaa Xaa Asn Tyr
 1               5

<210> SEQ ID NO 630
<211> LENGTH: 88
<212> TYPE: DNA
<213> ORGANISM: Unknown Organism
<220> FEATURE:
<223> OTHER INFORMATION: Description of Unknown Organism: Bacterial
      expression vector
<220> FEATURE:
<221> NAME/KEY: CDS
<222> LOCATION: (35)..(85)

<400> SEQUENCE: 630
ccatggagct cgaggatccc gggcaagctt gctt ggt ggc ggt ctg aac gac atc    55
                                     Gly Gly Gly Leu Asn Asp Ile
                                      1               5 ttc gag gct cag aaa atc gaa tgg cac gaa taa                          88
Phe Glu Ala Gln Lys Ile Glu Trp His Glu
        10                  15

<210> SEQ ID NO 631
<211> LENGTH: 17
<212> TYPE: PRT
<213> ORGANISM: Unknown Organism
<220> FEATURE:
<223> OTHER INFORMATION: Description of Unknown Organism: Biotinylation
      substrate peptide

<400> SEQUENCE: 631

Gly Gly Gly Leu Asn Asp Ile Phe Glu Ala Gln Lys Ile Glu Trp His
 1               5                  10                  15

Glu

<210> SEQ ID NO 632
<211> LENGTH: 89
<212> TYPE: DNA
<213> ORGANISM: Unknown Organism
<220> FEATURE:
<223> OTHER INFORMATION: Description of Unknown Organism: Bacterial
      expression vector
<220> FEATURE:
<221> NAME/KEY: CDS
<222> LOCATION: (36)..(86)

<400> SEQUENCE: 632
ccatggagct cgaggatccc gggcaagctt gcttg ggt ggc ggt ctg aac gac       53
                                      Gly Gly Gly Leu Asn Asp
                                       1               5 atc ttc gag gct cag aaa atc gaa tgg cac gaa taa                      89
Ile Phe Glu Ala Gln Lys Ile Glu Trp His Glu
            10                  15

<210> SEQ ID NO 633
<211> LENGTH: 90
<212> TYPE: DNA
<213> ORGANISM: Unknown Organism
<220> FEATURE:
<223> OTHER INFORMATION: Description of Unknown Organism: Bacterial
      expression vector
```

<220> FEATURE:
<221> NAME/KEY: CDS
<222> LOCATION: (37)..(87)

<400> SEQUENCE: 633
ccatggagct cgaggatccc gggcaagctt ccggcg ggt ggc ggt ctg aac gac      54
                                        Gly Gly Gly Leu Asn Asp
                                        1               5 atc ttc gag gct cag aaa atc gaa tgg cac gaa taa                      90
Ile Phe Glu Ala Gln Lys Ile Glu Trp His Glu
        10                  15

<210> SEQ ID NO 634
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 634
gggcctcgag ggactcagaa tctccccaga cgccgag                             37

<210> SEQ ID NO 635
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 635
ccgcaagctt ccatctcagg gtgaggggct                                     30

<210> SEQ ID NO 636
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 636
ccgcgaattc ttattcgtgc cattcgattt tctg                                34

<210> SEQ ID NO 637
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 637

Ser Pro Arg Thr Leu Asn Ala Trp Val
 1               5

<210> SEQ ID NO 638
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 638

Trp Lys Leu Pro Ala Gly Gly
 1               5

METHOD AND APPARATUS FOR THE PRODUCTION OF SOLUBLE MHC ANTIGENS AND USES THEREOF

CROSS REFERENCE TO RELATED APPLICATIONS

This application is a continuation of U.S. Ser. No. 10/022,066, filed Dec. 18, 2001, now abandoned entitled "METHOD AND APPARATUS FOR THE PRODUCTION OF SOLUBLE MHC ANTIGENS AND USES THEREOF," now published. The application U.S. Ser. No. 10/022,066 claims priority under 35 U.S.C. § 119(e) of provisional U.S. Ser. No. 60/256,410, filed Dec. 18, 2000, entitled "HLA PRODUCTION FROM GENOMIC DNA," now converted; provisional U.S. Ser. No. 60/256,409, filed Dec. 18, 2000, entitled "HLA PROTEIN PRODUCTION FROM CDNA," now converted; and provisional U.S. Ser. No. 60/327,907, filed Oct. 9, 2001, entitled "PRODUCTION OF SOLUBLE HUMAN HLA CLASS I PROTEINS FROM GENOMIC DNA," now converted, the contents of all of which are hereby expressly incorporated in their entirety by reference.

The application U.S. Ser. No. 10/022,066 is also a continuation-in-part of U.S. Ser. No. 09/465,321, filed Dec. 17, 1999, entitled "METHOD AND APPARATUS FOR THE PRODUCTION OF SOLUBLE MHC ANTIGENS," now abandoned, the contents of which are hereby expressly incorporated in their entirety by reference.

The application U.S. Ser. No. 10/022,066 is also continuation-in-part of U.S. Ser. No. 09/974,366, filed Oct. 10, 2001, entitled "COMPARATIVE LIGAND MAPPING FROM MHC POSITIVE CELLS," now published, the contents of which are hereby expressly incorporated in their entirety by reference.

STATEMENT REGARDING FEDERALLY FUNDED RESEARCH

At least a portion of the invention was developed under funding from the National Institute of Health ("NIH") under contract Nos. No1-A1-45243 and No1-A1-95360. As such, the Government may own certain rights in and to this application.

BACKGROUND OF THE INVENTION

1. Field of the Invention

The field of the invention relates in general to at least one method and apparatus for the production of soluble MHC antigens and more particularly, but not by way of limitation, to at least one method and apparatus for the production of soluble Class I and II HLA molecules (i.e. sHLA). The field of the invention also includes such produced soluble Class I and II HLA molecules and their uses. According to the methodology of the present invention, the soluble Class I and II HLA molecules can be produced from either gDNA or cDNA starting material. One such exemplary, but non-limiting, use is the formation of a tetrameric sHLA (or other multimeric complex) complex which may be used to test immunogenicity of peptide ligands of interest—i.e. will a peptide ligand of interest provoke a CTL response and/or preferentially bind a CTL.

2. Brief Description of the Background Art

Class I HLA molecules are polymorphic human glycoproteins that endogenously bind and then extracellularly present peptide ligands to $CD8^+$ T lymphocytes. Polymorphisms within the class I peptide binding groove are positioned to moderate ligand binding and presentation to such immune system cells. To date, the small quantities of natural ligands available to those of skill in the art has limited the understanding of precisely how polymorphism alters peptide binding and in turn, vaccine development and, more basically, if a peptide ligand of interest will provoke a CTL mediated immune response. In order to address the impact of polymorphism upon antigen presentation, the inventors developed the novel approach disclosed herein—i.e. that ligand presentation overlaps exist across the polymorphisms and that these overlaps distinguish divergent class I peptide binding grooves. Utilizing this novel approach and coupling it with a unique hollow-fiber cell culture scheme and utilizing a mass spectrometric ligand mapping approach, large quantities of peptides eluted from soluble class I and class II molecules can be obtained for detailed analyses, vaccine development, and functional testing.

Initially, peptide ligands were extracted from five different HLA-B15 allotypes and subsequently examined. Mapping and characterizing the ligands obtained from these allotypes demonstrated that they: (i) vary in length from 7 to 12 residues; (ii) are more conserved at their C termini than at their N-proximal residues; and (iii) are presented as overlaps contingent on C-terminal preferences. These results provide insight into class I and class II ligand loading not available via other methods, demonstrating that an elemental role is played by a peptide ligand's C terminus during endogenous binding and provides the starting material for a multimeric complex to be used to test the functionality of a peptide ligand of interest. The data obtained, and disclosed herein, validates, and illustrates the unique methods disclosed herein for the production of sHLA from either gDNA or DNA starting material and the uses to which this sHLA material may be put.

Class I and class II MHC molecules, designated HLA class I and class II, respectively, in humans, bind and display peptide antigens upon the cell surface. The peptides they present are derived from either normal endogenous proteins ("self") or foreign proteins ("nonself"). Nonself proteins include items such as the products of malignant transformation or intracellular pathogens. In this manner, class I and class II molecules convey information regarding the internal fitness of a cell to $CD8^+$ CTLs which are activated upon interaction with "nonself" peptides. Such activation may lead the CD8+ CTLs to kill and/or suppress a cell which is malignant or contains intracellular pathogens.

Examination of HLA by serologic and molecular methods by those of ordinary skill in the art continues to demonstrate that the class I HLA-A, B, and C molecules are encoded by the most polymorphic genes in mammals. Translating class I polymorphism into the tertiary structure of the class I molecule indicates that residues positioned to affect class I peptide presentation to T lymphocytes are most frequently affected by the mutagenic events which diversify class I loci. Throughout the world, HLA class I molecules exhibit a high degree of polymorphism that is generated by systematic recombinatorial events and collectively allows for the presentation of a vast array of different peptides. Depending upon allelic composition, two individuals' molecules may not necessarily bind the same peptides with equal affinity or even at all.

While the general structure and function of MHC class I molecules has been reasonably well studied and established, their polymorphic nature and how they specifically influence the capacity of class I in peptide binding and presentation remains an issue of persistent inquiry by those of ordinary skill in the art. The nature of precise overlaps in peptide binding specificity to HLA class I is particularly ill-defined at the current time due to the complexity of peptides bound. For example, this and other issues must be clarified in order to effectively pursue vaccines capable of eliciting protective CTL responses across an extensive population range. Unraveling the functional significance of class I polymorphism is an important issue that requires an understanding of how the mutagenic events diversifying the class I binding groove differentially moderate the presentation of peptide ligands.

The heavy chains of class I molecules are encoded within the MHC and, upon assembling into heterodimers with the light chain, $\beta_2$m, are responsible for selectively gathering endogenously processed peptides. Once peptides are collected, mature class I molecules transport the bound peptides to the cell surface where receptors on CD8$^+$ T lymphocytes engage the class I molecules to inspect the ligands. CTLs may then be triggered by class I molecules bearing virus or tumor-derived peptides.

With respect to the background art, hereafter numerous references are disclosed which detail one or more aspects of the background art as it relates to the novel methods and uses of the present invention. As such, each reference listed should be understood as being wholly incorporated by reference herein in their entirety as though the reference were fully transcribed herein. In this manner, one of skill in the art given the present specification would be fully informed and could truly appreciate the novel and unprecedented nature of the invention(s) disclosed and taught herein. The full and complete citations for each reference are appended hereto after the detailed description and before the claims.

The class I molecules expressed upon the nucleated cells of all vertebrate systems studied to date (for example, Ennis et al. 1988; Winkler et al. 1989; Kaufman et al. 1990; Lawlor et al. 1990; Trowsdale 1995; Prilliman et al. 1996; Antao et al. 1999) are heterodimers composed of a glycosylated 45 kDa heavy chain ($\alpha$-chain) and a 12 kDa light chain ($\beta_2$m). In humans, heavy chains are encoded at 3 loci (B, C, and A) within the MHC on the short arm of chromosome 6 (FIG. 1A). FIG. 1B illustrates each $\alpha$-chain comprised of $\alpha_1$, $\alpha_2$, and $\alpha_3$ domains, as well as a transmembrane domain, which tethers the molecule to the cell surface and a short C-terminal cytoplasmic domain (Björkman and class I location and heavy chain coding region).

X-ray crystallography (Björkman et al. 1987a; Madden et al. 1991; Saper et al. 1991; Madden et al. 1992; Collins et al. 1995; Reid et al. 1996; Smith et al. 1996a; Smith et al. 1996b; Glithero et al. 1999) has illustrated details of the structural relationship of the extracellular $\alpha$-chain domains and $\beta_2$m (FIG. 2). The membrane-proximal domains, $\alpha_3$ and $\beta_2$m, associate in an immunoglobulin fold structure. The membrane-distal $\alpha_1$ and $\alpha_2$ domains together create a closed basket-like structure that sits atop the $\alpha_3$ and $\beta_2$m structure (FIG. 2A). It consists of two $\alpha$-helical "walls" with a "floor" created by eight anti-parallel $\beta$-sheets (Björkman et al. 1987a; Madden 1995; and FIGS. 2, B and C). In the earliest studies, detection of electron density situated in the $\alpha_1/\alpha_2$ groove helped to clarify the experimentally-suspected occupancy of peptide fragments 8-10 residues long and thus the function of class I molecules in presenting such peptides upon the cell surface (Björkman et al. 1987b). Initial crystallographic studies designated six subsites, A-F (FIG. 3), or "specificity determining pockets," that constitute the peptide binding groove (Garrett et al. 1989; Saper et al. 1991; Fremont et al. 1992; Matsumura et al. 1992; Elliott et al. 1993; Young et al. 1995). In addition to crystal structure analyses, thermodynamic stability studies indicate that networks of hydrogen bonds to structural residues lining the A- and F-pockets, which lie at opposite ends of the groove, serve to fasten a peptide by its N and C termini, respectively (Bouvier and Wiley 1994); these two pockets are thus implicated in the fixed orientation of a peptide within the binding groove.

Class I molecules primarily associate with peptide fragments, thus forming $\alpha$-chain/$\beta_2$ m/peptide trimolecular complexes, via an endogenous processing pathway during their assembly (Germain 1994; Heemels and Ploegh 1995; Lehner and Cresswell 1996; York and Rock 1996; Pamer and Cresswell 1998); in fact, the very binding of peptides is essential for the stabilization and expression of these molecules (Ljungren et al. 1990; Townsend et al. 1990; Elliott 1991). The class I $\alpha$-chain and $\beta_2$m are cotranslationally translocated into the ER lumen (Townsend et al. 1990; Germain and Margulies 1993; Neefjes et al. 1993), where the $\alpha$-chain remains anchored to the ER membrane and is stabilized prior to association with $\beta_2$m and/or peptide through interactions with various chaperone proteins, including BiP, ER-60, calnexin, calreticulin, and tapasin (Nöβner and Parham 1995; Sadasivan et al. 1996; Suh et al. 1996; Spee and Neefjes 1997; Harris et al. 1998; Lindquist et al. 1998). Although several alternative proteolytic processing and transport pathways, certainly exist (for example, Hsu et al. 1991; Henderson et al. 1992; Kozlowski et al. 1992; Roelse et al. 1994; Snyder et al. 1994; Ferris et al. 1996; Craiu et al. 1997; Luckey et al. 1998; Mosse et al. 1998; Wang et al. 1998; Young et al. 1998), it is believed that the majority of peptides the nascent class I molecules interact with are delivered to the ER in a distinct series of events.

Proteins in the cytoplasmic compartment are first enzymatically degraded into peptides of relatively uniform length by an ATP-dependent proteasome complex (Coux et al. 1996). Some proteasome components include the IFN-$\gamma$ inducible subunits LMP2 and LMP7; these are themselves encoded within the MHC (Gaczynska et al. 1994). The typically nonameric fragments produced are then actively conveyed across the ER membrane via a dimer of TAP1/TAP2, an MHC-encoded ATP-binding cassette transporter (Monaco et al. 1990; Parham 1990; Grandea III et al. 1995). Once inside the ER, a processed peptide can be captured within the $\alpha_1/\alpha_2$ groove of a class I molecule and a stable trimer is formed (Germain and Margulies 1993; Smith et al. 1995). This trimeric $\alpha$-chain/$\beta_2$m/peptide complex is then transported through the Golgi complex and ultimately to the extracellular surface. The processes of class I assembly and transport are summarized in FIG. 4.

Following cell surface localization, mature complexes of class I bearing peptide antigens become available for interaction with receptors on monocytes, B and T lymphocytes, and NK cells (Townsend and Bodmer 1989; Yokoyama 1993; Lanier and Phillips 1996; Borges et al. 1997; Cosman et al. 1997). Their primary, and to date most thoroughly examined, natural receptor appears to be the TCR of T lymphocytes bearing the CD8 heterodimer. Site-directed mutagenesis and crystallographic studies indicate that the V$\alpha$ and V$_\beta$ domains of heterodimeric TCRs associate in a diagonal fashion across the top surface of the structure formed by MHC $\alpha_1$ and $\alpha_2$ (Hogan et al. 1988; Lombardi et al. 1991; Moots 1993; Tussey et al. 1994; Garboczi et al. 1996; Garcia et al. 1996; Parham 1996; Björkman 1997; Smith and Lautz 1997; Manning et al. 1998). The hypervariable CDRs of V$_\alpha$/V$_\beta$ contact specific regions of this interface (FIG. 5). Both precursor and effector CTLs are defined as being class I-restricted in that they are only capable of recognizing and responding to antigens displayed in the context of these molecules (Zinkemagel and Doherty 1974).

Since the antigens presented to CD8$^+$ T lymphocytes are predominantly obtained through the processing of intracellular proteins as previously described, class I molecules figuratively serve as external banners that advertise the inner contents of the cells. Indeed, these antigens of peptide ligands indicate to the immune system as a whole which cells are to be eliminated and/or protected. Malignancies and/or pathogens effectively use this system to camouflage their existence and thereby escape detection and elimination by CD8+ CTLs, for example.

Thymic education of lymphocytes prevents activation in response to characteristic cell-derived peptides (Robey and Fowlkes 1994), but peptides acquired through the degradation of atypical proteins are recognized and induce cytolysis (Townsend et al. 1985; Gotch et al. 1988; Walker et al. 1988; Clark et al. 1995). Therefore, it is not surprising that CD8$^+$ T lymphocytes play a critical role in controlling and/or eliminating infected and neoplastic cells.

CD8+T lymphocytes are implicated in immunity to pathogens such as viruses, which are intracellular invaders that utilize the host cell's biosynthetic machinery to produce their own foreign proteins (Yap et al. 1978; Lin and Askonas 1981; Jamieson et al. 1987; Harty and Bevan 1992; Riddell et al. 1992; Kulkarni et al. 1995; Heslop et al. 1996; Schmitz et al. 1999). CTL responses are likewise extended to include stimulation by aberrant proteins such as those associated with malignancy (Vose and Bonnard 1982; Muul et al. 1987; Coulie et al. 1992; Melief 1992; Kittlesen et al. 1998; Shichijo et al. 1998). In fact, class I molecules are capable of binding and presenting to CTLs any protein introduced into the endogenous processing pathway by either natural or artificial means (Gooding and O'Connell 1983; Moore et al. 1988; Yewdell and Bennink 1990; Bertoletti et al. 1991; Donnelly et al. 1993; Ikonomidis et al. 1994; Ballard et al. 1996; Day et al. 1997; Goletz et al. 1997; Kim et al. 1997). This knowledge serves as a motivating factor behind the development of both protein/peptide-based vaccines and other therapeutics intended to elicit protective CTL responses to microbial pathogens and other abnormalities, which otherwise remain cytoplasmically concealed from detection.

Fully understanding the role of class I molecules in ligand presentation as described above is complicated by α-chain polymorphism. Class I structural differences resulting from genetic variation confer extreme heterogeneity upon regions of the molecule that interact with peptides. The knowledge of how polymorphism specifically impacts the natural presentation of peptide epitopes upon the cell surface is consequently limited.

Class I MHC polymorphism was first documented in mice (Gorer 1936; Gorer 1937; Nathenson et al. 1981) and next studied in humans by serology (Dausset 1958; Payne and Hackel 1961; van Rood 1969); however, first protein and then DNA sequencing studies precisely demonstrated this genetic variability to be most concentrated throughout the exons of the $\alpha_1$ and $\alpha_2$ heavy chain domains at positions affecting amino acid residues that line the walls and floor of the previously described peptide binding groove (Orr et al. 1979; Tragardh et al. 1979; Rojos et al. 1987; Parham et al. 1988; Parham et al. 1989; Parham et al. 1995). It is the more centrally-located binding pockets (B-E), together with specific residues within the F-pocket, that appear to be the most polymorphic (Chelvanayagam 1996; Kostyu et al. 1997). Changes in the physicochemical properties of amino acid side chains within the groove can influence the stability with which given peptides interact during the assembly of α-chain/β$_2$m/peptide trimers (Matsui et al. 1993; Rohren et al. 1993; Salter 1994; Young et al. 1995). Therefore, despite the overall structural conservation illustrated among class I α-chains (Björkman and Parham 1990; Madden 1995), their peptide binding grooves can vary drastically from one allelic form to another; as a result various isoforms are capable of associating with distinct arrays of peptides (Elliott et al. 1993; Smith et al. 1995; Smith et al. 1996b).

The characteristic polymorphism observed among class I molecules is thought to originate primarily through recombination and gene conversion (Kuhner et al. 1991; Parham et al. 1995); point mutations are believed to contribute more rarely to the pool of new alleles continually arising (Parham et al. 1989). Individuals inherit a set of three class I genes from each parent, and since their expression is codominant, a single person may therefore display up to six different HLA class I molecules upon his or her nucleated cells. From these alleles, new forms evolving progressively within populations can be passed on to subsequent generations and likewise serve as templates upon which yet further diversity may be introduced. This occurs through events such as single or double recombination (Parham et al. 1988) or nonreciprocal exchanges between cis-oriented gene segments during gene conversion (Parham 1992). Serological cross-reactivity studies, as well as locus-specific PCR amplification and sequencing analyses, have verified the existence of allelic subtypes, or allotypes, of closely related alleles that appear to have arisen from a common ancestral template by these molecular mechanisms (for example, Payne et al. 1978; Ooba et al. 1989; Hildebrand et al. 1994; Prilliman et al. 1996). While both inter- and intra-locus genetic events may give rise to polymorphism, the latter is most commonly observed; alleles at a locus generally tend to be more closely related to one another than to those present at other loci (Parham et al. 1988; Parham et al. 1995). The forces driving HLA class I polymorphism are believed to be those of overdominant or balancing selection (Hughes and Nei 1988; Hughes and Yeager 1998); this is based upon values of $d_N > d_S$ within the coding regions of $\alpha_1$ and $\alpha_2$ for specificity determining pocket residues positioned to interact with the peptide binding groove, while the contrary ($d_S > d_N$) is observed among the remaining $\alpha_1/\alpha_2$ residues.

Considering the manner by which class I structural polymorphisms are generated and maintained demonstrates that HLA genetic variability affords both advantages and disadvantages. It is beneficial in ensuring that at least a small portion of the human population will possess class I molecules capable of: (i) binding immunogenic peptides derived from any given pathogen; (ii) presenting those peptides to CTLs; and (iii) evoking a protective imune response. In short, annihilation of the species is guarded against by molecular diversity (Parham 1992). The concept of heterozygote advantage through polymorphism as a mechanism for effectively allowing broader peptide binding abilities and thus broader CTL recognition of pathogenic peptides has been strongly emphasized from a statistical perspective (Hughes and Nei 1988; Nei and Hughes 1992). For example, HLA heterozygosity has been correlated with diminished progression to disease following HIV infection (Carrington et al. 1999). In addition, at the level of individual allotypes the "nonrandomness" with which certain polymorphisms are maintained within populations following their evolution supports positive natural selection. This might occur in response to specific pathogenic pressures, as seen in the strong association of the West African allele HLA-B*5301 with resistance to malaria (Hill et al. 1991; Hill et al. 1992), a parasitic illness endemic to West Africa. As mentioned previously however, the polymorphic nature of class I molecules results in divergent allotypes binding and presenting different peptides. CTLs thus focus on distinct portions of any given pathogen from one individual to another. Therefore, dissecting disease susceptibilities and resistances requires a grasp of how binding groove-localized amino acid variations specifically alter ligand presentation.

Numerous previous research endeavors have been directed toward understanding the structural and functional nature of peptides bound by HLA complexes; though some progress has been made in analyzing the manner that peptide binding is specifically influenced through $\alpha_1/\alpha_2$ substitutions, this knowledge remains limited and sometimes inconsistent. The full extent that polymorphisms dictate the degrees of ligand binding ability, stringency, and/or degeneracy (and subsequently cell surface presentation) has, as a result, not been adequately resolved. Similarly, the occurrence of overlapping ligands, or identical peptides presented across the binding groove polymorphisms of multiple distinct allotypes, remains to be explored.

Ideally, characterizing functional overlaps would provide an advantage not only to explore the general effects of binding groove architecture but more specifically to understand the similarities and/or differences of what is presented to CTLs by the class I molecules of genetically diverse individuals. In the search for answers to ligand binding influences by α-chain polymorphisms, methods including pooled Edman sequencing, mass spectrometric analysis, and binding/reconstitution assays have been employed. However, each approach bears its own strengths and limitations and none so far has been significantly successful in comparatively evaluating levels of functional overlap across class I polymorphisms. The importance of understanding peptide associations with polymorphic class I molecules at a level of complexity not necessarily afforded by the currently-defined strategies is thus underscored: epitope predictions based upon methods that fail to accurately assign possibilities for natural binding groove occupancy by either aberrant or low-abundance peptides of varying binding affinities interfered with detecting presentation overlaps among various HLA class I allotypes.

Early investigations of class I peptide ligands focused on simplifying the effects of polymorphism through establishing "motifs" (Rötzschke and Falk 1991; Rammensee et al. 1993; Engelhard 1994). Motifs have typically been established by purifying surface-expressed class I molecules from detergent lysates of either transformed cells or transfectants and extracting the bound ligands with either TFA or acetic acid. The resulting peptide pools are then subjected to consecutive cycles of N-terminal Edman degradation (Falk et al. 1991; Jardetzky et al. 1991).

The resultant motifs from N-Terminal Edman degradation are invariably nine amino acids in length and describe, as based upon relative yield increases per cycle, conserved "anchor" residues, or sites of stereochemical preferences, for peptides that are bound by a class I molecule. These anchors, typically appearing to involve both P2 and P9 of the ligands, are considered to be allele-specific and thus common among nearly all of the peptides bound by a given class I allotype. The remaining positions demonstrate no overriding amino acid preferences, although the motifs of a few molecules demonstrate anchors at P3 or P5 (Rammensee et al. 1997). The P2 anchor is assumed to associate with the B-pocket of the binding groove, while P9, the C-terminal residue assignment, associates with the F-pocket. "Auxiliary" or "secondary" anchors (alternative positions frequently defined by the occupancy of chemically similar residues) are additionally included in the motifs of some class I molecules (Rammensee et al. 1997). In general, a common interpretation of this type of data is that endogenous peptide binding and/or loading requires a nonamer with particular P2 and P9 anchors. As will be discussed, many searches (and consequent failed attempts) for putative viral or tumor class I-presented epitopes have subsequently been predicated upon nonameric templates with P2 and P9 anchor assignments.

Broad efforts have been focused upon establishing and analyzing motifs from natural class I ligands (for example, Huczko et al. 1993; Fleischhauer et al. 1994; Kubo et al. 1994; Barber et al. 1995; Steinle et al. 1995; Barber et al. 1996; Tzeng et al. 1996; Tieng et al. 1997; Yagüe et al. 1998). However, motifs fail to reflect the true complexity of peptides presented by divergent class I molecules. Drawbacks are evident in that numerous characterized peptide sequences that bind class I are greater than 9 residues long, with 14 being the largest identified to date (Engelhard 1994); The binding of longer ligands likely results from stable associations at anchor positions coupled with central protrusion of the peptide outward from the groove (Fremont et al. 1992; Guo et al. 1992; Madden et al. 1993). Furthermore, other examinations of specific peptides naturally presented by class I MHC of both humans and mice have indicated that some fail to comply with their respectively defined motif anchors (Calin-Laurens et al. 1993; Henderson et al. 1993; Sadovnikova et al. 1993; Kawakami et al. 1994; Urban et al. 1994; Malarkannan et al. 1996; Mata et al. 1998), thus suggesting that both length variance and "nonanchor" residues in the peptide could play significantly more prominent roles in binding than strictly accounted for by a given pooled motif alone. Studies have also indicated that low copy-number peptides, presented by only a small proportion of the total class I molecules expressed upon the cell surface, can successfully elicit CTL responses (Cox et al. 1994; Malarkannan et al. 1996; Wang et al. 1997). Issues such as these clearly reflect the limitations posed in applying Edman sequencing to the complex mixtures of peptides extracted from class I molecules (Stevanovic and Jung 1993). As a result, pooled Edman sequencing is therefore unable either to precisely characterize individual ligands or to effectively identify overlaps in ligand presentation.

Shortly after the debut of examining class I ligands by pooled Edman sequencing, the first reports of ligand analyses via mass spectrometric sequencing of organic ions from similarly-prepared class I ligand extracts began to emerge (Henderson et al. 1992; Hunt et al. 1992; Huczko et al. 1993; Appella et al. 1995). The utilization of MS/MS on a triple quadrupole mass spectrometer provided for the precise characterization of individual constituents at sub-picomolar levels from pools of class I peptides, in contrast to the picomolar detection limits of Edman analysis. Furthermore, LC/MS prior to this step allowed for complexity estimates to be made. For example, based upon the quantitation of 200 different peptides present within HLA-A*0201 extracts, extrapolation with regard to the peptides detected versus their respective contributions to the mass spectrometric TIC obtained indicated that at least 1,000 and perhaps as many as 10,000 unique peptides are bound by this class I allotype (Hunt et al. 1992). The ability to characterize ligands as such additionally assisted in being able to identify and sequence single specific epitopes from RP-HPLC fractions demonstrating biological activity via CTL assays (Rötzschke et al. 1990; Henderson et al. 1993; Kawakami et al. 1994; Skipper et al. 1996; Simmons et al. 1997; Wang et al. 1997; Hogan et al. 1998; Paradela et al. 1998). Examination of ligands by mass spectrometry was therefore an effective development in both starting to fill the gaps often present in pooled motifs and expediting the classification of ligands potentially bearing immunological significance.

However, the routine application of mass spectrometric techniques to class I ligand examination has remained relatively isolated; it is practiced in only a handful of laboratories (for example, Woods et al. 1995; Simmons et al. 1997; Flad et al. 1998; van der Heeft et al. 1998; Yagüe et al. 1998). This appears largely due to the inherent difficulties imposed in handling the small quantities of peptides extracted for study (Henderson et al. 1993; Appella et al. 1995; van der Heeft et al. 1998) as well as the notably tedious nature of the subsequent data processing (Papayannopoulos 1995; van der Heeft et al. 1998). Other issues concern the specific instrumentation and its mode of operation, since: (i) the ability to consistently identify peptides from particular extracts relies upon dependable RP-HPLC gradients for separation; and (ii) the possible ionization and/or detection interfaces function in distinct manners that can influence the data ultimately acquired (Chapman 1996; Watson 1997). In summary, understanding the impact of polymorphism upon the binding of endogenous peptdes has historically been limited by small amounts of ligands available for analyses.

What has not been accomplished yet by mass spectrometry is the systematic definition of peptides across diverse class I allotypes. Various in vitro assays have been developed to complement mass spectrometric approaches. The assays are performed using a number of different protocols with the common theme of assessing the relative abilities in vitro of synthetically defined peptides to associate with specific class I α-chains and $\beta_2$m. In the case of binding assays, synthetic peptides as well as a peptide standard are incubated with purified class I complexes and tested in their capacities to competitively displace the ligands already bound (Chen and Parham 1989; Ruppert et al. 1993; Sette et al. 1994). This has likewise been performed by stripping ligands from class I complexes expressed on the cell surface by acid treatment and then incubating the cells with the synthetic peptides (Drijfhout et al. 1995). Another common approach to competitive binding assays involves FACS analysis with class I-specific MAbs after incubation of synthetic peptides with various cell lines including RMA-S (Townsend et al. 1989), T2 (Salter et al. 1985), Hmy2.C1R (Storkus et al. 1989), or 721.221 (Kavathas et al. 1980) transfected to express HLA α-chains (Huczko et al. 1993; Takamiya et al. 1994; Zeh III et al. 1994; Boisgerault et al. 1996; Konya et al. 1997). Alternatively, de novo reconstitution assays can be performed by incubating synthetic peptides with free α-chains and $\beta_2$m and comparing the resultant quantities of free versus complexed α-chains (Tanigaki 1992; Fruci et al. 1993). Other methods of reconstitution have also been applied (Silver et al. 1991; Parker et al. 1994; Gnjatic et al. 1995; Robbins et al. 1995; Tan et al. 1997).

While these in vitro assays with synthetic ligands have led to the development of extensive "supermotifs", or enhanced motifs that ascribe binding preferences to particular class I allotypes or groups of related allotypes (del Guercio et al. 1995; Sidney et al. 1996a; Sidney et al. 1996b), they present obvious limitations. A technical concern is that binding/reconstitution determinations are often based upon either "standard" probe peptides for each allotype examined or mean experimental values that can significantly differ from one laboratory or experiment to another. A specific illustration is based on the results generated by three different groups testing HLA-A*0201 with panels of synthetic peptides; the assignment of residues preferred or deleterious for binding at given positions varied widely (Ruppert et al. 1993; Parker et al. 1994; Drijfhout et al. 1995). In fact, only three residue similarities carried across all three studies.

Ruppert and colleagues and Drijfhout and colleagues each employed competitive binding assays; however, the former involved assessing the ability of synthetic peptides to inhibit binding of a radioiodinated standard peptide to membrane-extracted class I complexes, while the latter involved stripping peptides from class I complexes on B-LCLs and determining by FACS analysis the ability of synthetic peptides to inhibit binding of a different fluorescence-labelled standard. On the other hand, Parker and colleagues employed a reconstitution assay which measured the incorporation of radioiodinated $\beta_2$m into complexes refolded using synthetic peptides and α-chains prepared from *Escherichia coli* inclusion bodies. Of perhaps greater significance, these types of assays fail to account for the processing/loading physiology of trimolecular complex formation within the cell (Hogan et al. 1988); indeed, differences have been documented in performing comparative examinations by pooled Edman sequencing and mass spectrometry upon naturally-extracted versus artificially bound peptides (Davenport et al. 1997). In one specific case, an immunodominant HIV peptide divulged through other mechanisms completely failed to demonstrate binding to its restricting allotype via an in vitro assay (Tsomides et al. 1991). Conclusions regarding ligand presentation that are drawn from binding/reconstitution assays thus cannot be applied generally without caveat.

Thus, the present invention(s) aim to provide a methodology for the production of soluble MHC Class I and II molecules from either gDNA or cDNA starting material such that the structural and functional impact of HLA class I polymorphism on peptide binding can be assessed and, in particular, to test how natural ligand presentation overlaps exist in varying degrees across the polymorphisms of divergent class I binding grooves. Furthermore, the soluble MHC molecules can be used in the functional testing of CTL binding assays and vaccine deveopment. Utilizing this specification, one of ordinary skill in the art will able to: (i) generate ligands and hence ligand maps from the peptide pools extracted from series of distinct yet related class I HLA-B15 allotypes; (ii) compare the different ligand maps to identify potentially shared elements; and (iii) characterize the elements identified to positively or negatively validate the occurrence of overlapping ligands. One of ordinary skill in the art, given the present specification, will also realize that the ability to produce soluble MHC molecules from either gDNA or cDNA starting material also will allow for other useful assay and vaccine development such as the functional testing of peptide ligands of interest to determine if, when, and how such peptide ligands provoke and/or stimulate an immune response. All of which is directed toward the goal of identifying candidate peptide ligands that may be used singly or together as a vaccine and/or immune system primer.

BRIEF DESCRIPTION OF THE SEVERAL VIEWS OF THE DRAWINGS

FIG. 15 is a tabulation of the pooled Edman sequencing motifs for peptides extracted from B*1501 purified by two different MAbs. Data derived from the eluates of B*1501 complexes purified using either W6/32 (A) or BBM.1 (B) indicated amino acid residues that had been previously attributed to the corresponding positions in B*1501 motifs (solid characters), as well as a residue which was not included in any previous motif descriptions (Falk et al. 1995; Barber et al. 1996). Edman degradation was carried out as described hereinafter, and relative picomolar fold increases are indicated in parentheses to the right of each residue; amino acids demonstrating a 2.0 to 3.5-fold picomolar increase over the previous degradation cycle were grouped as "strong", while those demonstrating an increase of greater than 3.5-fold were grouped as "dominant". Dashes indicate that no distinct residues could be detected as either dominant or strong at the given positions.

FIG. 19 is four tabular examples of Edman sequence complexity among RP-HPLC ligand fractions from BBM.1-purified B*1501. While each of the fractions marked by dots in FIG. 15 was subjected to Edman sequencing, the results obtained from fractions 10, 15, 28, and 31 are shown here to specifically illustrate some of the diverse trends observed among constituents of the ligand mixture. Dominant and strong assignments were made as described hereinbefore for FIG. 13; weak assignments were made for amino acids demonstrating a 1.5 to less than 2.0-fold picomolar increase over previous cycles. No assignments are shown for P1 due to lower confidence since comparison with former cycles was impossible. The positional assignments in fraction 15, which are identified in bold italics, appear to correspond to a hexamer, IAVGYV, derived from HLA class I α-chain$_{23-28}$ (Prilliman et al. 1998).

FIG. 21 is two graphs showing N- and C-regional diversity observed through alignments of B*1501 ligands. Frequency of occurrence for amino acids at the first (A) and final (B) four positions among the ligands characterized from B*1501 (Table A). The graphs were generated from separate N- and C-terminal data alignments.

FIG. 23 is two graphs showing N- and C-regional diversity observed through alignments of B*1508 ligands. Frequency of occurrence for amino acids at the first (A) and final (B) four positions among the ligands characterized from B*1508 (Table C). The graphs were generated from separate N- and C-terminal data alignments.

FIG. 25 is two graphs showing N- and C-regional diversity observed through alignments of B*1512 ligands. Frequency of occurrence for amino acids at the first (A) and final (B) four positions among the ligands characterized from B*1512 (Table E). The graphs were generated from separate N- and C-terminal data alignments. The information shown here for B*1512 ligands is skewed in relation to that obtained for ligands from the other four allotypes since (i) a comparatively fewer B*1512 peptides were sequenced, and (ii) over half of the B*1512 peptides characterized were specifically investigated as ion map differences with B*1501.

Table 1. Amino acid differences among the B*1512, B*1508, B*1501, B*1503, B*1518, and B*1510 allotypes. Residues, noted across the top of the table, are numbered from the N terminus of the mature class I heavy chain for each; the 24 amino acid leader sequence is therefore not included. The residue positions are differentially highlighted in black ($\alpha_1$) or gray ($\alpha_2$). Positions of identity with the consensus sequence (italicized) drawn from B*1501 are indicated by dashes.

Table 2. PCR and sequencing primers for creating and verifying sHLA constructs. Designated restriction enzyme cut sites are underlined on the 5' and 3' PCR primers, and the regions of the 3' PCR primers that inserted a stop codonn at position 300 are shown in bold italics. Sequencing primers were Cy5-labelled; the regions that they either sequenced through or hybridized with are indicated in parentheses.

Figure 13:
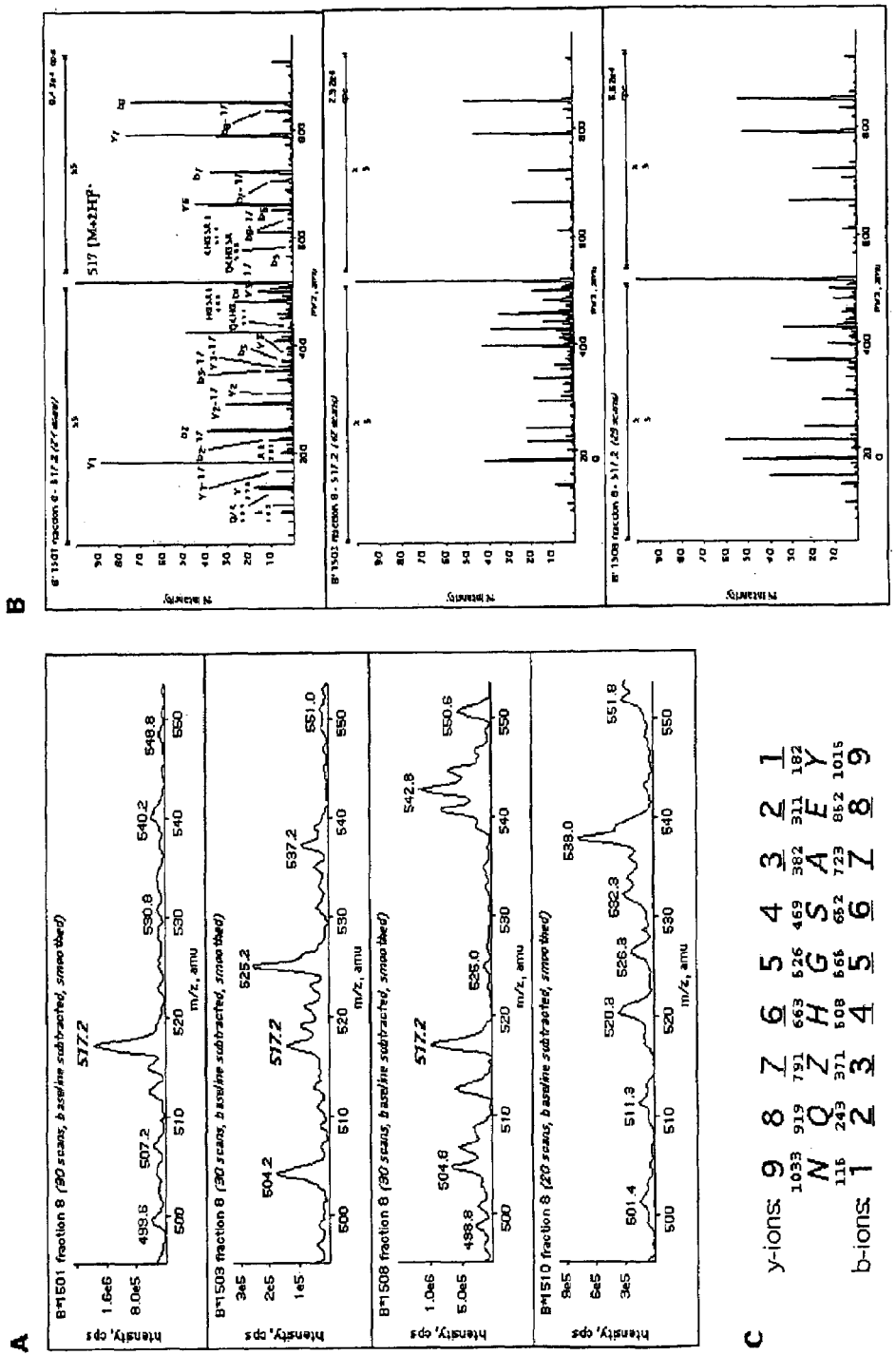
FIG. 13 includes two graphs (A and B) and chart C that show the identification and verification of a ligand overlap across divergent HLA-B15 molecules. NanoES-MS spectral ion maps obtained individually from RP-HPLC fraction 8 for each of B*1501, B*1503, B*1508, and B*1510 were aligned for comparison; an expanded view of the range 495-555 m/z, or amu, is shown in (A). The ion mass centered at 517.2 m/z matched across the spectra of B*1501, B*1503, and B*1508 (top three panels) but not B*1510 (bottom panel). This ion was subsequently selected for NanoES-MS/MS from fraction 8 of the first three class I MHC molecules. The homologous spectra resulting from fragmentation of this $[M+2H]^{2+}$ ion (B) classified the peptide as a positive match, or ligand overlap, occurring across B*1501, B*1503, and B*1508 and allowed for primary sequence derivation (C). N- and C-terminal peptide fragments present in all three NanoES-MS/MS spectra are labelled according to standard nomenclature (Roepstorff and Fohlman 1984) in the top panel of (B) and underlined in (C); immonium ions are indicated by their single-letter amino acid codes in (B), and the sequences of internal cleavage products are also specified.
Figure 16:
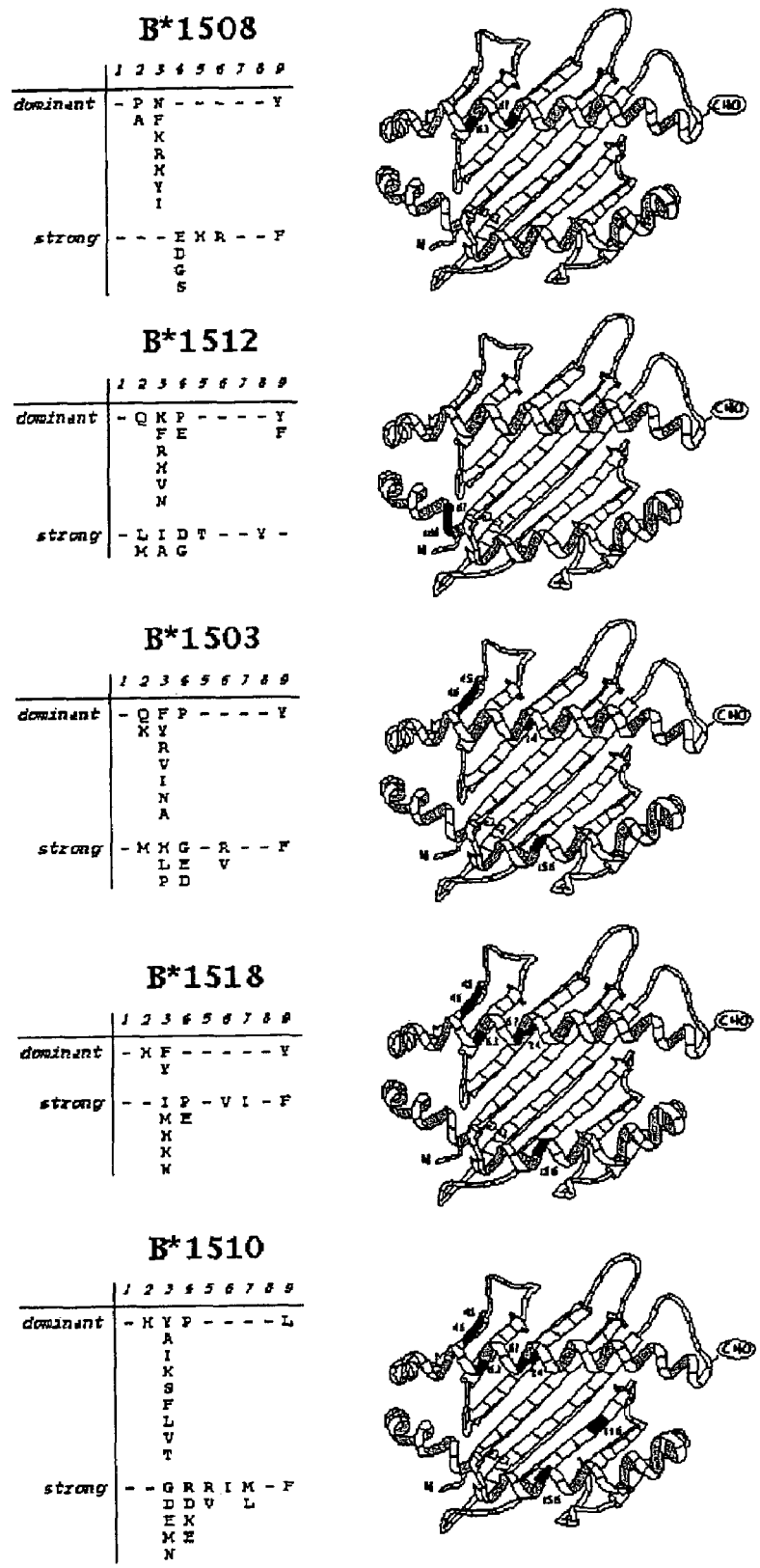
FIG. 16 is a tabulation and corresponding pictorial representation of pooled Edman sequencing motifs for peptides extracted from B*1508, B*1512, B*1503, B*1518, and B*1510. Edman degradation was carried out as described herein, and the data were analyzed as described hereinbefore with respect to FIG. 15. Ribbon diagrams of the class I antigen binding groove to the right of each motif show the structural residues of the $\alpha_1/\alpha_2$ antigen binding groove among each of the alleles which differ with respect to B*1501 according to Table 1; they are indicated in black and numbered from the N terminus of the mature class I α-chain.

Table 3. Additional P2, P9, and length variability revealed through Edman sequencing of RP-HPLC ligand fractions from W6/32-purified B*1501, B*1508, B*1503, and B*1510. The number of fractions for each which were subjected to Edman degradation as described herein and shown in FIG. 13 are shown; ligands present in the fractions from all four molecules demonstrated evidence of (i) expanded P2 and P9 occupancy, and (ii) sequence beyond the 9 residues described by their respective motifs (as shown in FIGS. 15 and 16).

Table 4. HLA-B15 ligands identically matching database source proteins, by category. The ligands are categorized according to source protein functions. Residues for the specific ligands are numbered from the initiating Met of their respective source proteins. Ligands from HLA-B15 molecules not studied here (B*1502, B*1509, and B*4601) are referenced herein.

Table 5. Ligands unique to B*1512, as compared with B*1501. Positively-charged P1 residues are indicated in bold. Dashes represent positions at which amino acids could not be unambiguously assigned through the NanoES-MS/MS fragmentation patterns and/or Edman data obtained. Underlined residues designate tentative assignments.

Table 6. Ligand binding groove residues interacting with the B-pocket among HLA-B15 allotypes bearing known Edman-derived motifs. Residues, noted across the top of the table, are numbered from the N terminus of the mature class I heavy chain for each. The residue positions are differentially highlighted in black ($\alpha_1$) or gray ($\alpha_2$); vertical hatching immediately below further distinguishes those residues located on a helix. The molecules are grouped according to dominant/strong P2 motif similarities. Structural residues specifically discussed in the text are indicated in bold italics.

Table 7. Ligand binding groove residues interacting with the F-pocket among HLA-B15 allotypes bearing known Edman-derived motifs. Residues, noted across the top of the table, are numbered from the N terminus of the mature class I heavy chain for each. The residue positions are differentially highlighted in black ($\alpha_1$) or gray ($\alpha_2$); vertical hatching immediately below further distinguishes those residues located on a helix. The molecules are grouped according to dominant/strong P9 motif similarities. Structural residues specifically discussed herein are indicated in bold italics.

Table 8. B*1510 ligands exhibiting Pro with Ala and/or Val in various C-proximal combinations. C-proximal occurrences of Pro, Ala, and Val are indicated in bold. Dashes represent positions at which amino acids could not be unambiguously assigned through the NanoES-MS/MS fragmentation patterns and/or Edman data obtained. Underlined residues designate tentative assignments.

Table 9. B*1501 ligands: N- and C-regional occupancies observed at >10% among 126 ligands. The positional occupancy percentages for residues among the ligands from Table A greater than 10% are specifically shown; dashes indicate occupany rates below 10% for the given side chains. N-regional positions and $N_{sum}$ values are highlighted in black, while C-regional positions and $C_{sum}$ values are highlighted in gray.

Table 10. B*1503 ligands: N- and C-regional occupancies observed at >10% among 74 ligands. The positional occupancy percentages for residues among the ligands from Table B greater than 10% are specifically shown; dashes indicate occupany rates below 10% for the given side chains. N-regional positions and $N_{sum}$ values are highlighted in black, while C-regional positions and $C_{sum}$ values are highlighted in gray.

Table 11. B*1508 ligands: N- and C-regional occupancies observed at >10% among 96 ligands. The positional occupancy percentages for residues among the ligands from Table C greater than 10% are specifically shown; dashes indicate occupany rates below 10% for the given side chains. N-regional positions and $N_{sum}$ values are highlighted in black, while C-regional positions and $C_{sum}$ values are highlighted in gray.

Table 12. B*1510 ligands: N- and C-regional occupancies observed at >10% among 123 ligands. The positional occupancy percentages for residues among the ligands from Table D greater than 10% are specifically shown; dashes indicate occupany rates below 10% for the given side chains. N-regional positions and $N_{sum}$ values are highlighted in black, while C-regional positions and $C_{sum}$ values are highlighted in gray.

Table 13. B*1512 ligands: N- and C-regional occupancies observed at >10% among 30 ligands. The positional occupancy percentages for residues among the ligands from Table E greater than 10% are specifically shown; dashes indicate occupany rates below 10% for the given side chains. N-regional positions and $N_{sum}$ values are highlighted in black, while C-regional positions and $C_{sum}$ values are highlighted in gray.

Table 14. Overlaps identified through RP-HPLC/NanoES-MS ligand mass mapping and characterized by NanoES-MS/MS. Dashes represent positions at which amino acids could not be unambiguously assigned through the NanoES-MS/MS fragmentation patterns and/or Edman data obtained. Underlined residues designate tentative assignments.

Table 15. Overlap frequencies observed between B*1501 and B*1512, B*1508, B*1503, or B*1510. The frequencies of ligand presentation overlap for the molecules listed with respect to B*1501 were determined from the number of total matching ion masses subjected to NanoES-MS/MS and the number of those ions collided analyzed by NanoES-MS/MS confirmed as actual overlaps. The resulting values are conservative since not all ions selected for examination successfully yielded fragments that could be used for evaluating the sequence positivity of mass matches.

Table 16. Potential B*1501 epitopes selected from the EBV gp85 structural antigen. The EBV gp85 protein (accession number 1334905, Arrand et al. 1981) was manually scanned for epitopes with consideration to B*1501. In the first column, epitope candidates matching the length and sequence constraints of the B*1501 pooled motif (FIG. 15) are listed. In the second column, epitope candidates matching the B*1501 motif-prescribed P2 and C-terminal occupancies but demonstrating relaxed length constraints (7 to 11 residues, according to the B*1501 panel in FIG. 20) are listed. In the third column, epitope candidates matching the B*1501 motif-prescribed nonameric length but demonstrating P2 flexibility (according to FIG. 21A) are listed.

Table 17 PCR of sHLA from gDNA primers.

Table 18 clone sequencing 5'CYS primers.

Table 19 optical density readings and concentration of DNA extracted from sample 3A394.

Table 20 optical density readings of positive clones.

Table 21 optical density readings of AF/102 plasmid extracted.

Table 22 viability of cells after two (2) days.

Table 23 Elisa results for positive transfectants exhibiting G418 resistance.

Table 24 HLA types and sHLA molecules preduced.

Table A derived peptide ligands from B*1501.

Table B derived peptide ligands from B*1503.

Table C derived peptide ligands from B*1508.

Table D derived peptide ligands from B*1510.

Table E derived peptide ligands from B*1512.

DETAILED DESCRIPTION OF THE INVENTION

Before explaining at least one embodiment of the invention in detail by way of exemplary drawings, experimentation, results, and laboratory procedures, it is to be understood that the invention is not limited in its application to the details of construction and the arrangement of the components set forth in the following description or illustrated in the drawings, experimentation and/or results. The invention is capable of other embodiments or of being practiced or carried out in various ways. Also, it is to be understood that the phraseology and terminology employed herein is for the purpose of description and should not be regarded as limiting.

As described hereinabove, characterizing naturally processed HLA class I and class II ligands is a key element behind the basic understanding of how polymorphism impacts ligand presentation. However, technical and scientific challenges including both extreme sample heterogeneity and limited sample sizes complicate such examinations. Thousands of distinct peptides are present within a ligand extract prepared from a single type of class I molecule, and the immunoprecipitation/extraction protocols typically employed to recover peptide ligands yield sparse quantities on the order of ~20 µg (Hunt et al. 1992; Henderson et al. 1993). These factors often require specialized biochemical expertise not necessarily available in either the common laboratory or core facility.

Class I major histocompatibility complex (MHC) molecules, designated HLA class I in humans, bind and display peptide antigens upon the cell surface. The peptides they present are derived from either normal endogenous proteins ("self") or foreign proteins ("nonself"), such as products of malignant transformation or intracellular pathogens such as viruses. In this manner, class I molecules convey information regarding the internal fitness of a cell to immune effector cells including but not limited to CD8+ cytotoxic T lymphocytes (CTLs), which are activated upon interaction with "nonself" peptides and which lyse or kill the cell presenting such "nonself" peptides.

Class II MHC molecules, designated HLA class II in humans, also bind and display peptide antigens upon the cell surface. However, unlike class I MHC molecules which are expressed on virtually all nucleated cells, class II MHC molecules are normally confined to specialized cells, such as B lymphocytes, macrophages, dendritic cells, and other antigen presenting cells which take up foreign antigens from the extracellular fluid via an endocytic pathway. Therefore, the peptides they bind and present are derived from extracellular foreign antigens, such as products of bacteria that multiply outside of cells, wherein such products include protein toxins secreted by the bacteria that have deleterious and even lethal effects on the host. In this manner, class II molecules convey information regarding the fitness of the extracellular space in the vicinity of the cell displaying the class II molecule to immune effector cells including but not limited to $CD4^+$ helper T cells, which help eliminate such pathogens both by helping B cells make antibodies against microbes as well as toxins produced by such microbes and by activating macrophages to destroy ingested microbes.

Class I and class II HLA molecules exhibit extensive polymorphism, which is generated by systematic recombinatorial and point mutation events; as such, hundreds of different HLA types exist throughout the world's population, resulting in a large immunological diversity among the population. Such extensive HLA diversity in the population results in tissue or organ transplant rejection between individuals as well as differing susceptibilities and/or resistances to infectious diseases. HLA molecules also contribute significantly to autoimmunity and cancer. Because HLA molecules mediate most, if not all, adaptive immune responses, HLA proteins are needed to study transplantation, autoimmunity, and for developing vaccines.

There are several applications in which purified, individual class I and class II MHC proteins would be highly useful. Such applications include using MHC-peptide multimers as immunodiagnostic reagents for disease resistance/autoimmunity; assessing the binding of potentially therapeutic peptides; elution of peptides from MHC molecules to identify vaccine candidates; screening transplant patients for preformed MHC specific antibodies; and removal of anti-HLA antibodies from a patient. Since every individual has different MHC molecules, the testing of numerous individual MHC molecules is a prerequisite for understanding differences in disease susceptibility between individuals. Therefore, purified MHC molecules representative of the hundreds of different HLA types existing throughout the world's population are highly desirable for unraveling disease susceptibilities and resistances and for designing therapeutics.

Currently there is no readily available source of individual HLA molecules. Until now, the quantities of HLA protein available were small and typically consist of a mixture of different HLA molecules. Production of HLA molecules traditionally involves growth and lysis of cells expressing multiple HLA molecules. Ninety percent of the population is heterozygous at each of the HLA loci; codominant expression results in multiple HLA proteins expressed at each HLA locus. To purify native class I or class II molecules from mammalian cells requires time-consuming and cumbersome purification methods, and since each cell typically expresses multiple surface-bound HLA class I or class II molecules, HLA purification results in a mixture of many different HLA class I or class II molecules. When performing experiments using such a mixture of HLA molecules or performing experiments using a cell having multiple surface-bound HLA molecules, interpretation of results cannot directly distinguish between the different HLA molecules, and one cannot be certain that any particular HLA molecule is responsible for a given result. Therefore, a need exists in the art for a method of producing substantial quantities of individual HLA class I or class II molecules so that they can be readily purified and isolated independent of other HLA class I or class II molecules. Such individual HLA molecules, when provided in sufficient quantity and purity, would provide a powerful tool for studying and measuring immune responses.

The present invention envisions a method of producing MHC molecules which are secreted from mammalian cells in a bioreactor unit. Substantial quantities of individual MHC molecules are obtained by modifying class I or class II molecules so they are secreted. Secretion of soluble MHC molecules overcomes the disadvantages and defects of the prior art in relation to the quantity and purity of MHC molecules produced. Problems of quantity are overcome because the cells producing the MHC do not need to be detergent lysed or killed in order to obtain the MHC molecule. In this way the cells producing secreted MHC remain alive and therefore continue to produce MHC. Problems of purity are overcome because the only MHC molecule secreted from the cell is the one that has specifically been constructed to be secreted. Thus, transfection of vectors encoding such secreted MHC molecules into cells which may express endogenous, surface bound MHC provides a method of obtaining a highly concentrated form of the transfected MHC molecule as it is secreted from the cells. Greater purity can be assured by transfecting the secreted MHC molecule into MHC deficient cell lines.

Production of the MHC molecules in a hollow fiber bioreactor unit allows cells to be cultured at a density substantially greater than conventional liquid phase tissue culture permits. Dense culturing of cells secreting MHC molecules further amplifies the ability to continuously harvest the transfected MHC molecules. Dense bioreactor cultures of MHC secreting cell lines allow for high concentrations of individual MHC proteins to be obtained. Highly concentrated individual MHC proteins provide an advantage in that most downstream protein purification strategies perform better as the concentration of the protein to be purified increases. Thus, the culturing of MHC secreting cells in bioreactors allows for a continuous production of individual MHC proteins in a concentrated form.

Although class I and class II ligands were first examined by Edman sequencing, the primary characterization of individual ligands has been significantly improved upon through MS/MS applications. This is frequently performed via LC/MS using a microcapillary (<1 mm i.d) HPLC column directly interfaced with a triple quadrupole mass spectrometer (Hunt et al. 1992). The rationale behind using columns of small i.d. is that a lower solvent flow rate is permitted that ultimately increases the sensitivity of mass spectrometric detection (Tomer et al. 1994).

Figure 6:
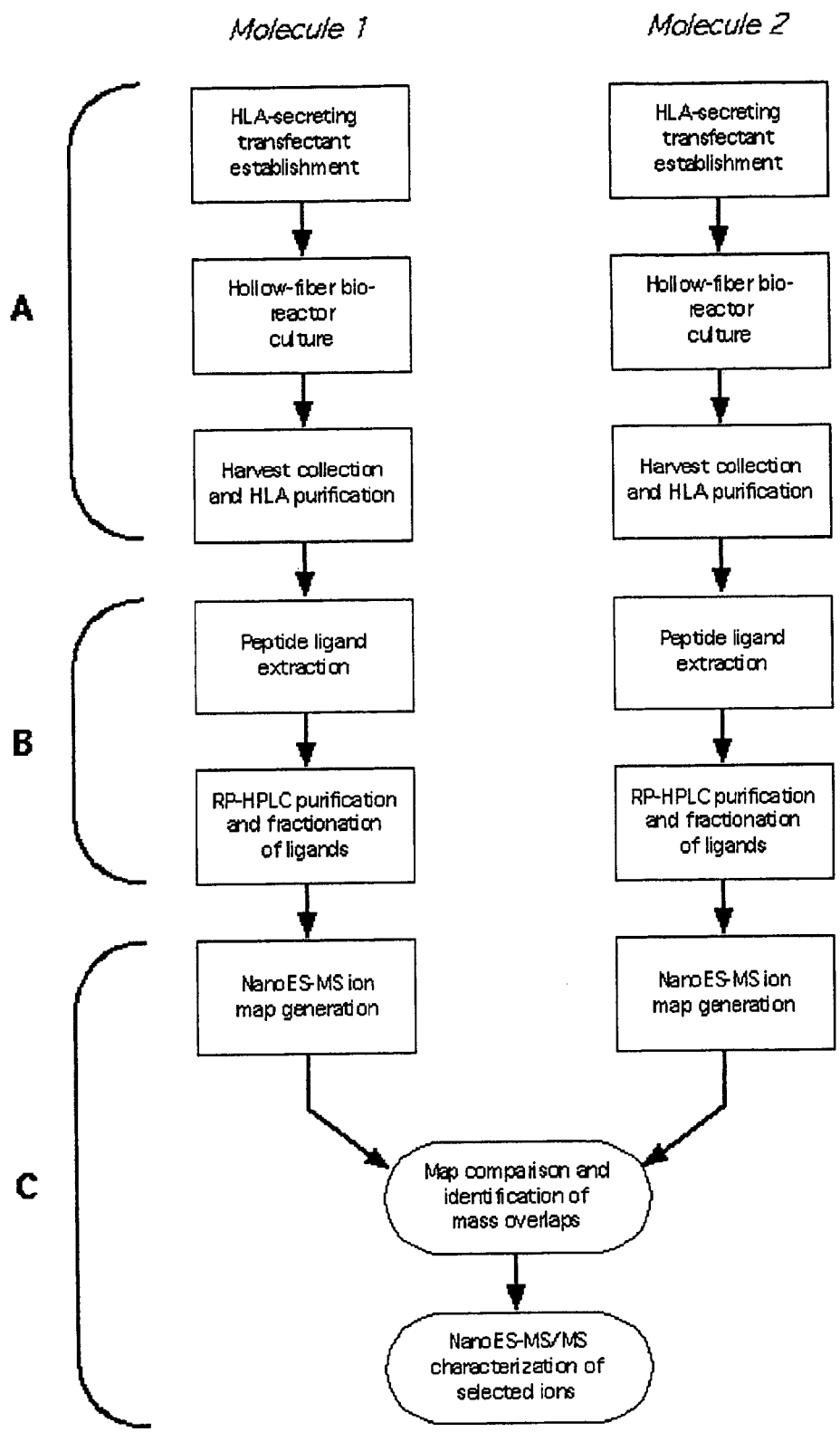
FIG. 6 is a flow diagram of the overall strategy for comparatively mapping and characterizing peptide ligands presented by class I HLA. The approach taken to address the presence of overlapping ligands across diverse class I molecules consisted of three basic parts: (A) sHLA-producing transfectant establishment and culture; (B) extraction, purification, and separation of ligands; and (C) ion map generation/comparison and characterization of individual peptides. Though only two molecules are indicated for simplification, numerous additional molecules (as indicated in the specification) were simultaneously carried through the steps shown.

Unfortunately, since sample load capacity decreases proportionately to the column diameter, such columns and LC/MS methods can be technically difficult or inconsistent for laboratories not routinely employing them to operate, more robust protocols for producing and studying class I-derived peptides have been desired. The methodology of the present invention, as described herein, solves and/or meets this need in the art by a methodology which increases the quantities of ligands extractable by producing recombinant soluble class I and class II molecules. The sample amounts subsequently available offset handling losses at the bench, which have been estimated at 50% (Veronese et al. 1996; Hogan et al. 1998; and Dr. Peter Parham, unpublished observations), and obviate the need for microcapillary LC/MS prior to MS/MS analysis. This is because significantly larger (20-fold) ligand samples are instead separated by standard offline RP-HPLC followed by NanoES-MS mapping and NanoES-MS/MS sequencing. The methodology of the present invention has proven consistent for comparatively examining peptides extracted from different class I molecules. As shown in FIG. 6, utilizing the production of soluble class I and class II molecules of the present invention, allows one of ordinary skill in the art to locate and characterize overlapping ligands among distinct allotypes (FIG. 6).

Figure 7:
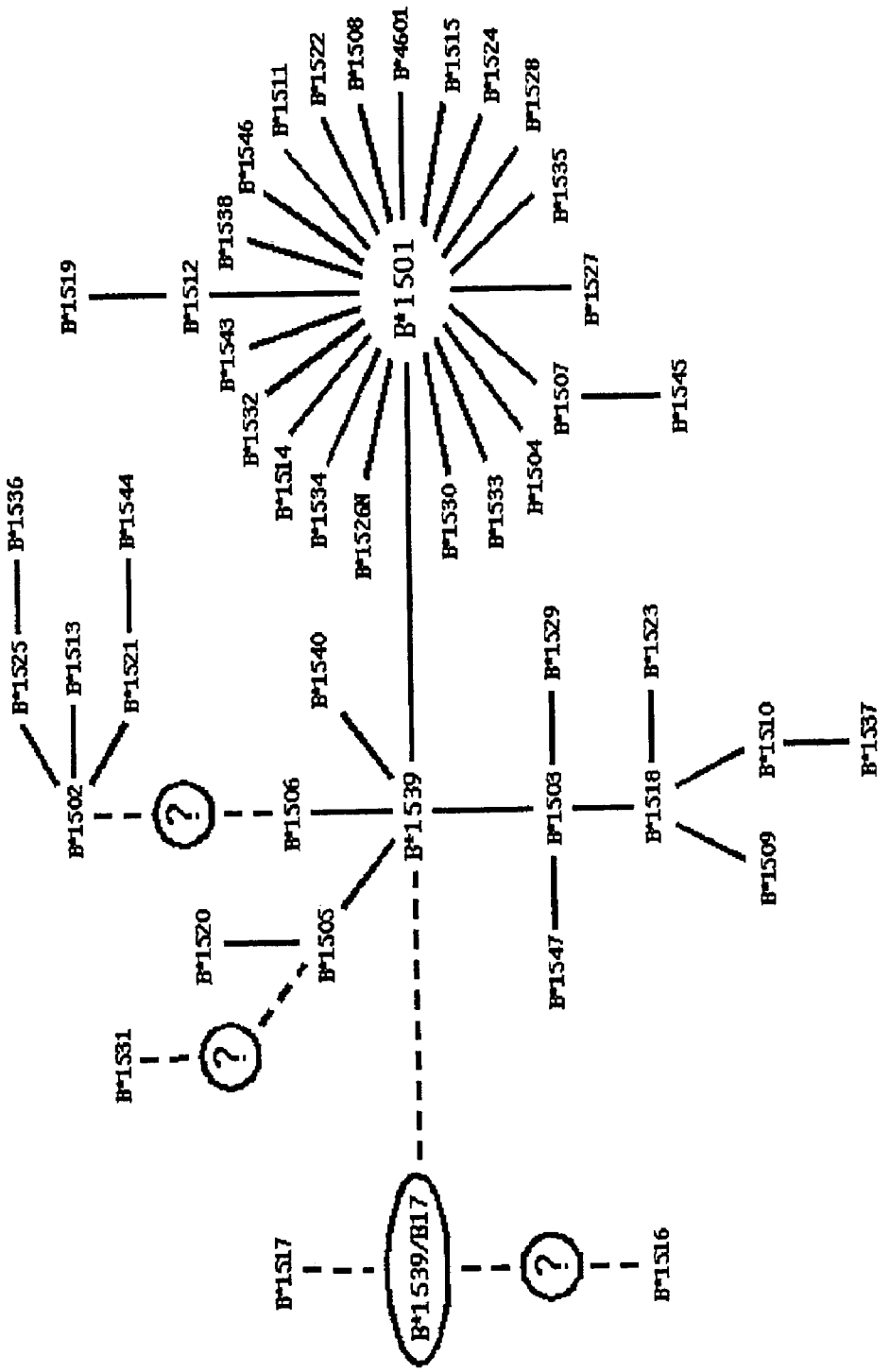
FIG. 7. Hypothesized evolutionary relationships of HLA-B15 allotypes according to expressed $\alpha$-chain polymorphisms. Shown in this scheme are the 46 allotypes whose amino acid sequences are provided in herein. Solid lines indicate single mutagenic events separating given allotypes. Dashed lines indicate that greater than one mutagenic event separates given allotypes; intermediaries are indicated by question marks unless more specifically suspected (as in the case of a probable B*1539/B17 recombinant). None of the line lengths are reflective of mutational rates.

The initial HLA molecules selected for examination and production were from the HLA-B15 family, a hypothetical schematic of which is presented in FIG. 7. The HLA-B15 family represents a broad and diverse group of molecules comprised of nearly 50 evolutionarily related allotypes differing almost sequentially by 1-15 peptide binding groove residues, and they are observed throughout numerous ethnic populations (Hildebrand et al. 1994); serological and DNA-based typing thus far confirm distribution of B15 alleles among Caucasians, Amerindians (North and South), Mexicans, Blacks (African and American), Indians, Iranians, Pakistanis, Chinese, Japanese, Koreans, and Thais. The majority of HLA B-locus polymorphisms known to exist are represented among the members of this allelic family. HLA-B*1501 appears to be the "ancestral allele."

Figure 8:
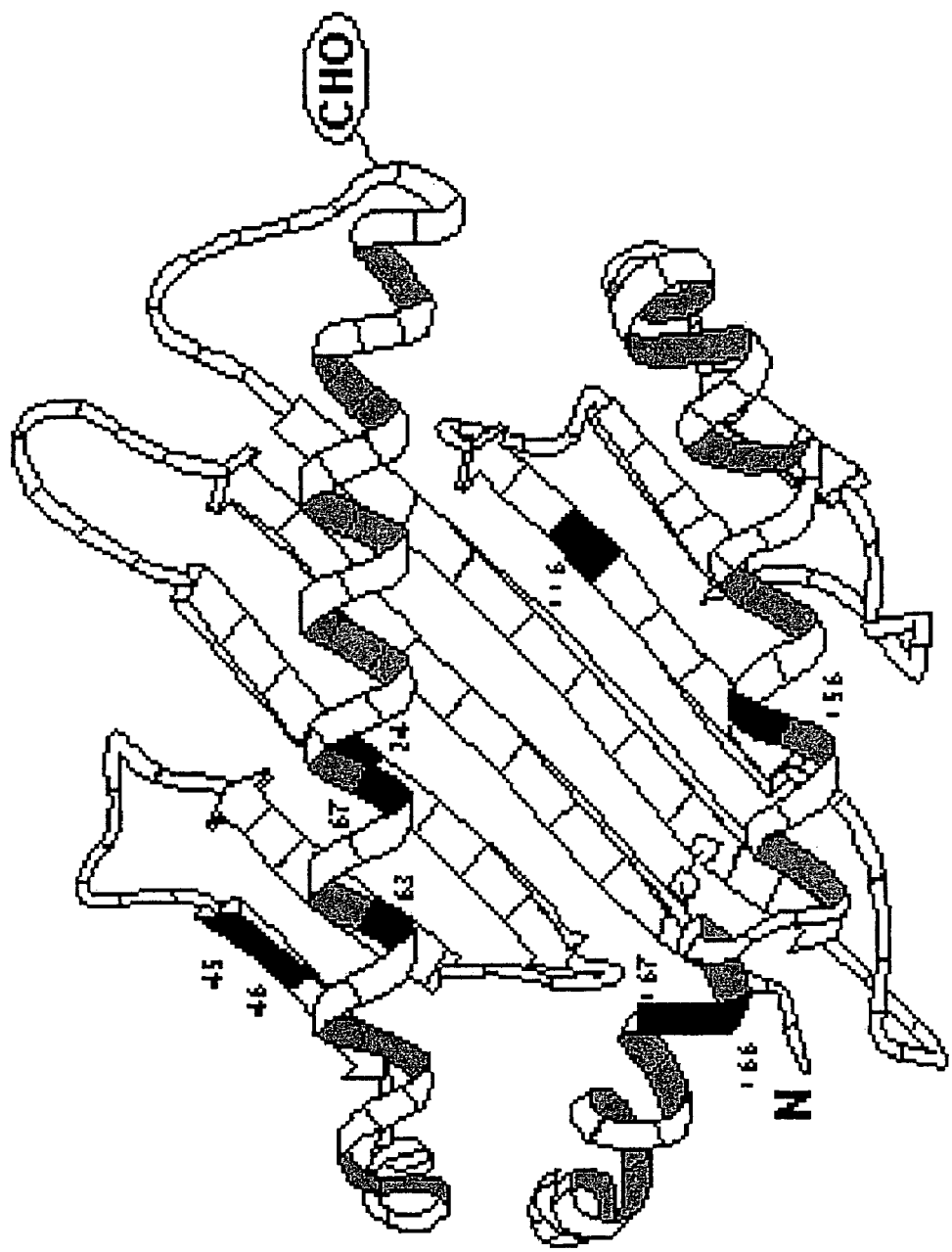
FIG. 8 is a graphical representation of the localization of antigen binding groove substitutions distinguishing the B*1512, B*1508, B*1501, B*1503, B*1518, and B*1510 allotypes. The structural residues of the antigen binding groove formed by $\alpha_1$ and $\alpha_2$ which differ among the six alleles according to Table 1 are indicated on the ribbon diagram in black and numbered from the N terminus of the mature class I $\alpha$-chain.

The specific B15 allotypes initially selected for review and use with the present invention were B*1501 (Pohla et al. 1989; Choo et al. 1993; Hildebrand et al. 1994; Lin et al. 1996), B*1503 (Domena et al. 1993), B*1508 (Hildebrand et al. 1994), B*1510 (Domena et al. 1993; Rodriguez et al. 1993; Rodriguez et al. 1996), B*1512 (Hildebrand et al. 1994), and B*1518 (formerly B*7901, Choo et al. 1991; Lin et al. 1996; Rodriguez et al. 1996) (Table 1 and FIG. 8). B*1508 differs from B*1501 by a single mutagenic event in the $\alpha_1$ helix, while B*1512 differs by a single mutagenic event in the $\alpha_2$ helix; the remaining three alleles demonstrate a progressive series of polymorphisms throughout their binding grooves imposed by sequential mutagenic events during their divergent evolution from B*1501.

Using the primer sets of HLA5UT (Domena et al. 1993) and sHLA3TM (Prilliman et al. 1997) or 5PXI and 3PEI (Table 2) and template DNA from reliable full-length cDNA clones of HLA-B15 molecules B*1501, B*1503, B*1508, B*1510, B*1512, and B*1518, truncating PCR was performed for each on a Robocycler (Stratagene) for 30 cycles as previously described (Prilliman et al. 1997). The resultant PCR products contained the leader peptide, $\alpha_1$, $\alpha_2$, and $\alpha_3$ coding domains of the HLA heavy chain.

The PCR products were introduced into mammalian expression vectors. Initial constructs (truncated B*1501, B*1503, and B*1508) were prepared with the PSRα-neo vector (Lin et al. 1990), which has formerly been used to express non-truncated HLA molecules (Barber et al. 1997; Martinez-Naves et al. 1997), while other constructs (truncated B*1501, B*1503, B*1508, B*1510, B*1512, and B*1518) were additionally prepared with either pcDNA3 or pcDNA3.1 (−) (Invitrogen). Constructs using the PSRα-neo vector were made from PCR products of the HLA5UT and sHLA3TM primers; the PCR products were subcloned into M13 (mp18 or mp19) according to standard protocols (Domena et al. 1993) so that confirmatory single-stranded DNA sequencing could be performed with Cy5-labelled versions of the primers M13 universal, 4N, and 3N (mp 18) or M13 universal, 3S, and JD3S (mp19), listed in Table 2 and described previously (Ennis et al. 1990; Domena et al. 1993), using the AutoLoad sequencing kit and ALFexpress automated sequencer (both Amersham Pharmacia Biotech). The insert was then prepared and purified, and this was followed by subcloning into PSRα-neo. Constructs using the pcDNA3 vector were made from PCR products of the 5PXI and 3PEI primers; these PCR products were subcloned into M13 and sequenced as above, following which the insert was subcloned into pcDNA3. Constructs using the pcDNA3.1 (−) vector were made from products of the 5PXI and 3PEI primers; PCR products were directly subcloned into pcDNA3.1 (−), following which double-stranded DNA sequence analysis was performed with Cy5-labelled versions of the primers 3S, 4N, T7 promoter, and pcDNA3.1/BGH (Table 2).

DNA from each of the construct clones was prepared using Qiagen Midi kits for transfection of the class I-negative B-LCL 721.221. Cells growing in log phase in RPMI-1640+2 mM L-glutamine+phenol red+20% FCS were pelleted and electroporation was performed as described (Gumperz et al. 1995) prior to beginning selection with 1.5 mg/mL G418. Upon establishment of confluent growth after approximately 3 weeks, putative transfectant wells were screened for sHLA production using a sandwich ELISA (Prilliman et al. 1997). Transfectant wells positive for sHLA production were then subcloned by limiting dilution to establish cell lines optimally secreting greater than 1 μg/mL of class I molecules in static culture over 48 h. Satisfactorily subcloned transfectants were then expanded, frozen in RPMI-1640+20% FCS+10% DMSO, and stored at −135° C.

Figure 9:
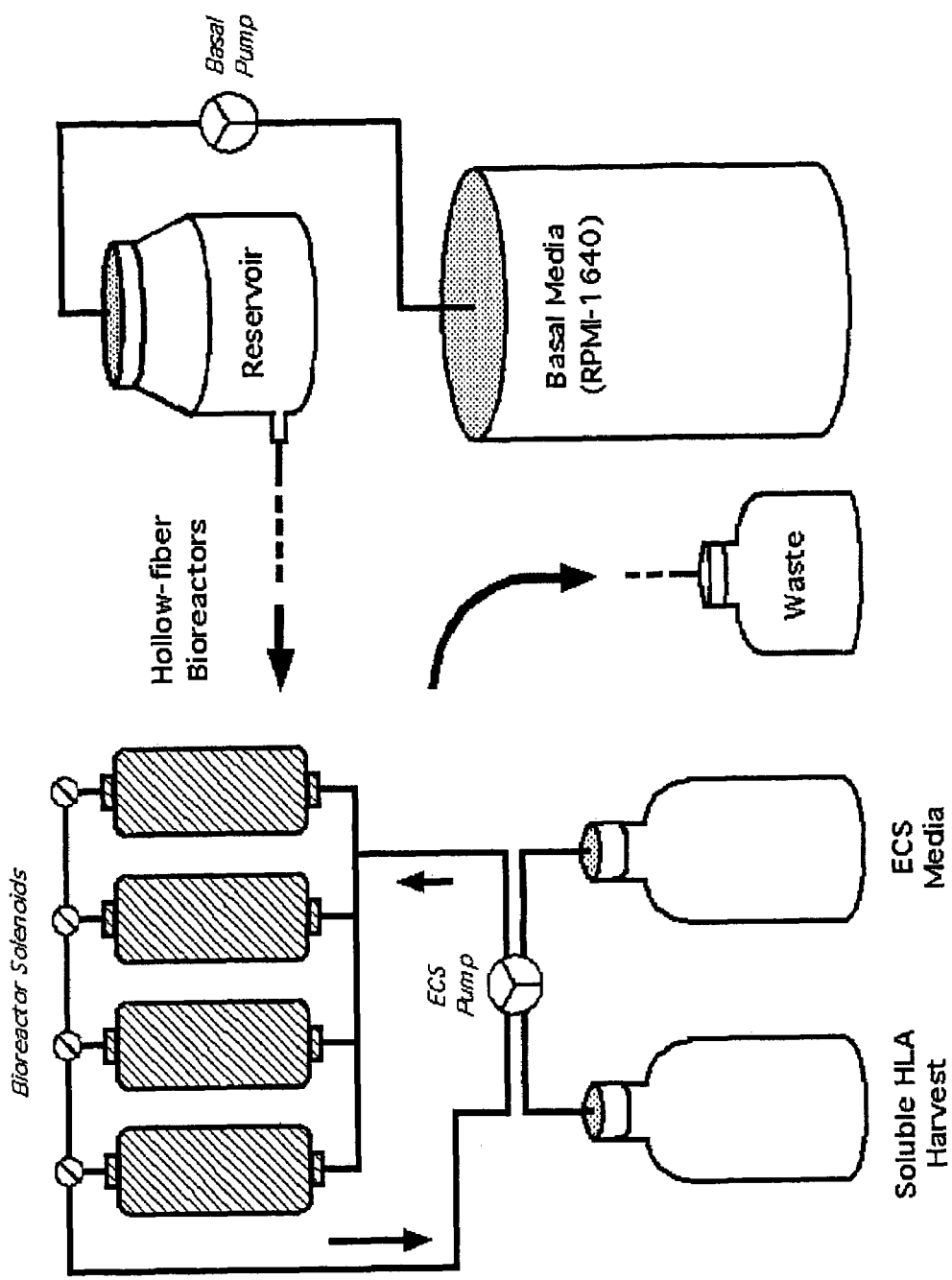
FIG. 9 is a graphical representation summarizing of the Unisyn Technologies CP-3000 basic flow path. The system was assembled and operated as described herein. Arrows indicate unidirectional media flow.

Since hollow-fiber bioreactors have been applied in place of in vivo hybridoma culture and MAb harvest from ascites (Evans et al. 1996) in order to continuously produce large quantities of pure immunoglobulins, they were utilized to produce and harvest the sHLA of the present invention. The Unisyn Technologies CP-3000, the standard flow path and primary components of which are diagrammatically simplified in FIG. 9, was selected for hollow-fiber bioreactor culture of successfully established transfectants. In this system, basal media is pumped into the fully-assembled system from a 200 L barrel; the media flows from the 4 L reservoir tank into the hollow-fiber networks of the four bioreactors, which provide 2.7 m$^2$ of surface area per cartridge, and then exits as waste. ECS media and sHLA harvest are tandemly pumped into and out of the 270 mL cartridges, respectively, with each bioreactor receiving/yielding equal media/harvest volumes as regulated by in-line solenoids.

Figure 10:
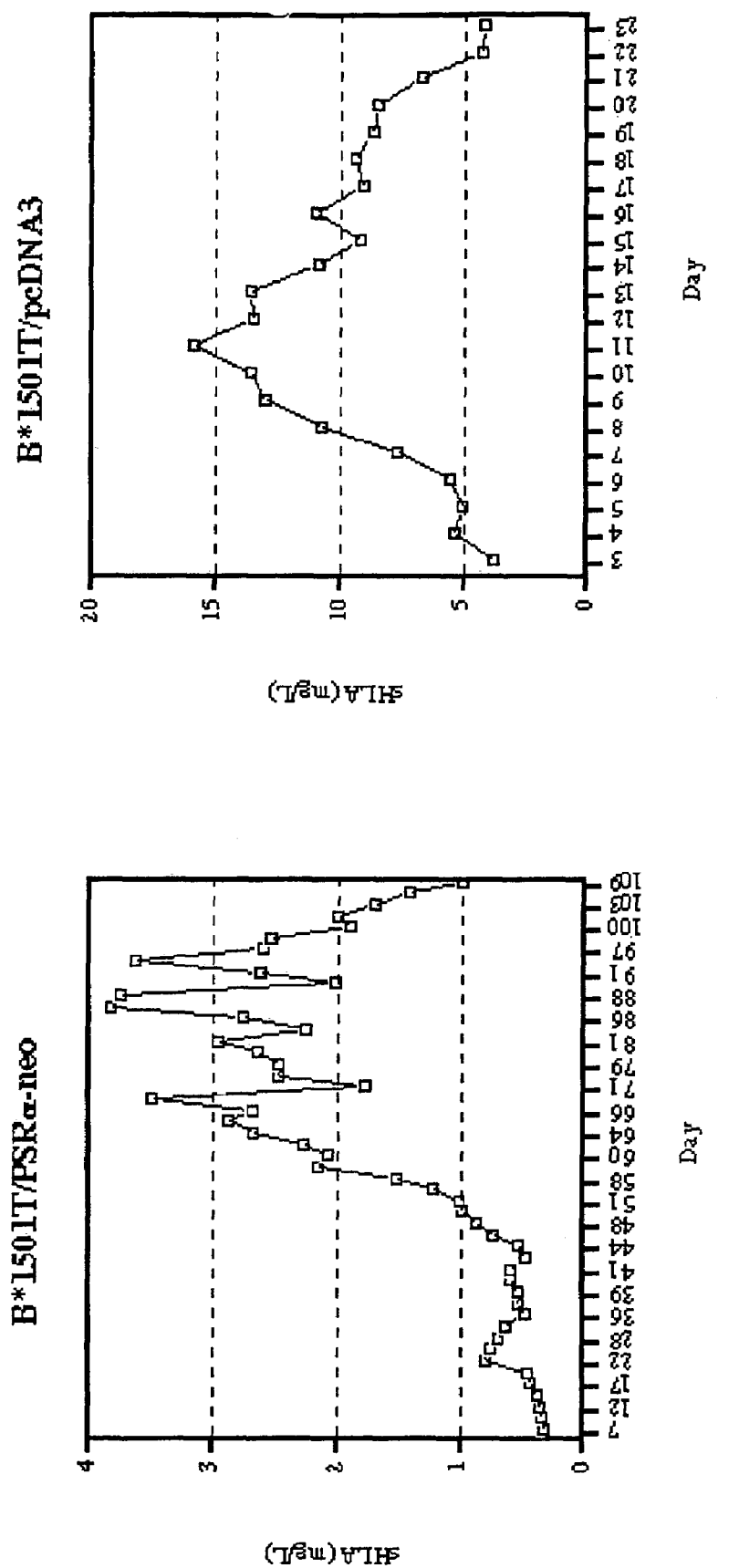
FIG. 10 is two graphs showing sHLA production during bioreactor runs with two different B*1501 transfectants. Constructs using $PSR_{\alpha\text{-}neo}$ and pcDNA3 for producing soluble B*1501 were separately transfected into B-LCL 721.221; subclones were then cultured in CP-3000 systems as described herein. Harvests samples drawn on the days indicated along the x-axis during each run were subjected to ELISA, yielding the representative sHLA production data shown.

The CP-3000 was set up according to the manufacturer's protocol. After the system was completely prepared, at least 1×10$^9$ viable cells of a transfectant were grown in roller bottles of RPMI-1640+2 mM L-glutamine+phenol red+10% FCS. The cells were pelleted and inoculated into the ECS of the bioreactor cartridges. ECS feed and harvest bottles were then attached to their corresponding lines, and the basal and recirculation rates were initially set to 100 and 1000 mL/h, respectively; the ECS was usually not activated until 24-36 h following inoculation. The system was then monitored at least twice daily over 4-6 weeks, with adjustments made as necessary. This involved checking the glucose concentration and pH from manually-drawn reservoir samples, checking DO readings, and regulating the basal and ECS rates accordingly (Prilliman et al. 1997; Prilliman et al. 1998). A fresh harvest sample was periodically extracted directly from the system to quantitate sHLA production by ELISA for production level monitoring (FIG. 10).

Cells were cultured in the bioreactor system during each un until the desired amount of sHLA had been produced and collected in harvests. Each of the bioreactor runs chronologically depicted in FIG. 10 was aborted once approximately 150 mg of sHLA was determined by ELISA to be contained in the respective harvests collected (Prilliman et al. 1997). The majority of runs were performed using 721.221 cells transfected with pcDNA3 or pcDNA3.1 (−) vector constructs, considering: (i) the significant differences in time frame between the runs performed using cell lines expressing soluble B*1501 from either the PSRα-neo or pcDNA3 vectors (3 months versus 1 month); and (ii) the fact that peptides extracted during each run produced identical motif results.

Upon completing a bioreactor un, sHLA complexes were purified from the harvests obtained (Prilliman et al. 1997). A 100 mL matrix of either the $β_2$m-specific MAb BBM.1 (Brodsky et al. 1979) or W6/32 (Barnstable et al. 1978) coupled to CNBr-activated Sepharose 4B (Amersham Pharmacia Biotech) according to the manufacturer's instructions was equilibrated with wash buffer (20 mM sodium phosphate, pH 7.2+0.02% sodium azide), and harvests were applied to the column using a GradiFrac LC system (Amersham Pharmacia Biotech); the load capacities for 100 mL matrices of the MAbs BBM.1 and W6/32 were approximated at 10 and 40 mg sHLA respectively, as monitored for saturation ELISA of screening pre- and post-column samples. The column was then washed, eluted with 0.2 N acetic acid, and neutralized with wash buffer. Both BBM.1 and W6/32 were used to affinity purify B*1501, the first molecule prepared. However, due to the differences in purification efficiency noted above between the two MAbs, W6/32 alone was employed to isolate the remaining molecules from bioreactor harvests. This MAb has been frequently used by others in purifying HLA (Falk et al. 1991; Barber et al. 1997).

The fractions collected during affinity column elution demonstrating UV absorbance at 280 nm were pooled, and glacial acetic acid was added to 10% volume to extract the peptides as described (Barber et al. 1995). Bound peptides were separated from heavy chains, $β_2$m, and BSA by passage through 3 kDa exclusion membrane filters (Amicon) (Prilliman et al. 1997). The ligand-containing eluate was then lyophilized.

To remove residual salts and free amino acids remaining from the extraction process, isolated peptides were purified of free amino acids and salts prior to fractionation. This was done on a 2.1×100 mm C18 column (Vydac) with a steep RP-HPLC gradient using a DYNAMAX HPLC system (Rainin). The gradient was generated by increasing to 100% buffer B (0.06% TFA in 100% acetonitrile) in 1 min, holding for 10 min, and returning to buffer A (0.1% TFA in HPLC-grade water) in 1 min. The column was loaded with peptides reconstituted in the minimum volume of buffer A required for solubilization. During the run, the region corresponding to absorbance at 214 nm was manually collected. Typically 1/100th of the total purified ligand collection volume was removed and subjected to Edman sequencing for 14 cycles on a 492A pulsed liquid-phase protein sequencer (Perkin-Elmer Applied Biosystems Division) according to established protocols (Falk et al. 1991; Barber et al. 1995).

Figure 11:
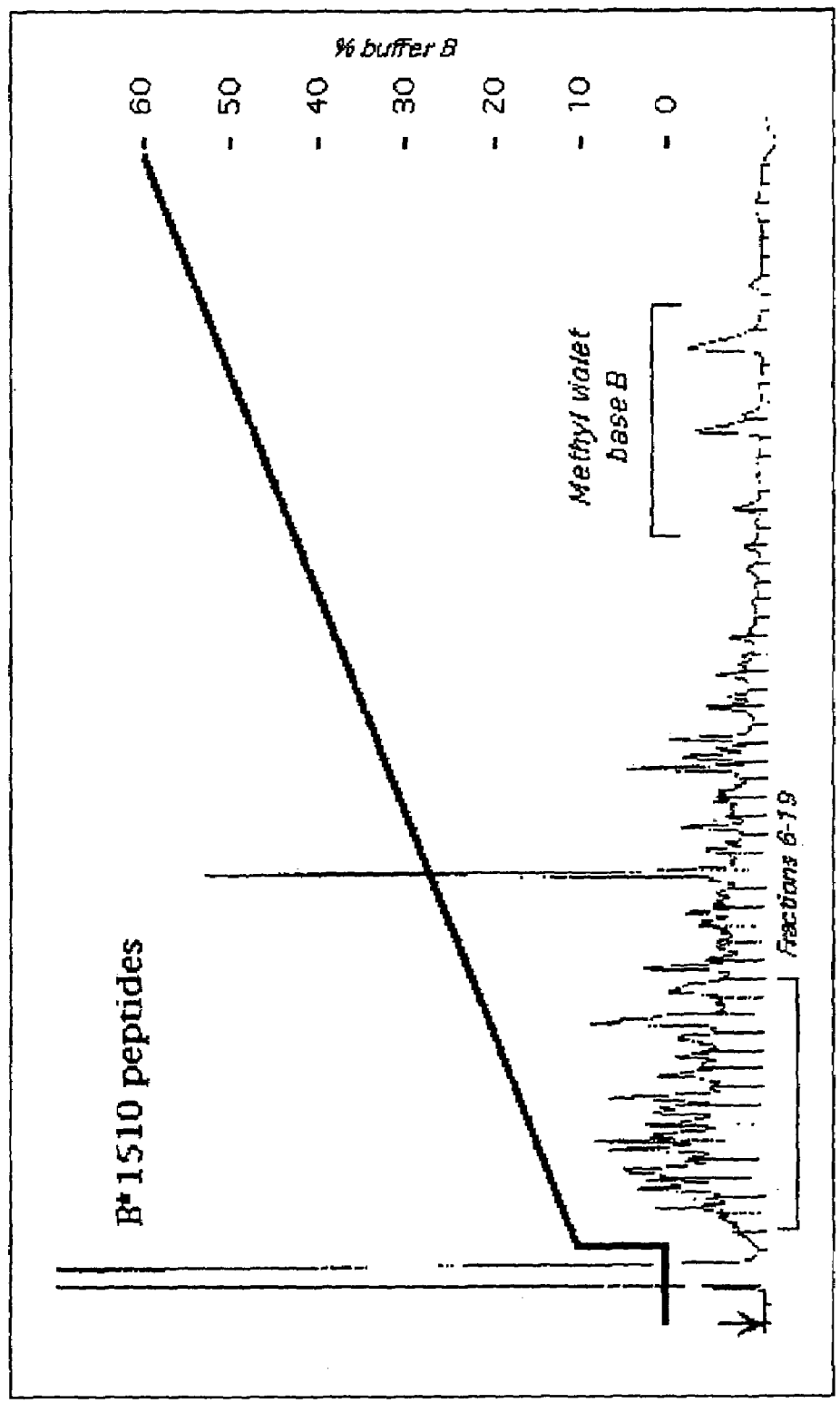
FIG. 11 is a graph showing RP-HPLC fractionation of peptides extracted from B*1510. The UV trace obtained during separation as described herein of approximately 400 μg of peptides extracted from B*1510 reveals the bulk of absorbance to occur along the gradient (black line) between 10-40% buffer B (indicated at the right). The three peaks associated with the control dye (methyl violet base B), as well as the primary region subjected to intensive mapping between B*1501, B*1503, B*1508, and B*1510 peptides (fractions 6-19), are indicated.

The purified ligands were next fractionated by RP-HPLC. For preliminary diversity assessment, approximately 150 µg of peptides, as calculated from the ELISA-based total mass of sHLA bound to the affinity column and an estimated 50% handling loss, were loaded in 10% acetic acid onto a 1.0×150 mm C18 column (Michrom Bioresources, Inc.) and separated using an initial gradient of 2-10% buffer B (0.085% TFA in 95% acetonitrile) in 0.02 min followed by a linear gradient of 10-60% buffer B in 60 min at 40 µL/min on a 2.1×150 mm C18 column (Michrom Bioresources, Inc.); buffer A was 0.1% TFA in 2% acetonitrile. Absorbance was monitored at 214 nm, and fractions were automatically collected every minute. For comparative analyses, approximately 400 µg of peptides were injected in 10% acetic acid containing 2 µg of the dye methyl violet base B to control for gradient consistency between runs (FIG. 11). The gradient formation parameters consisted of 2-10% buffer B in 0.02 min and 10-60% buffer B in 60 min at 180 µL/min. Absorbance was monitored at 214 nm, and fractions were automatically collected every minute. Edman sequencing of fractions, when performed, was conducted on 1/20th of each.

Figure 12:
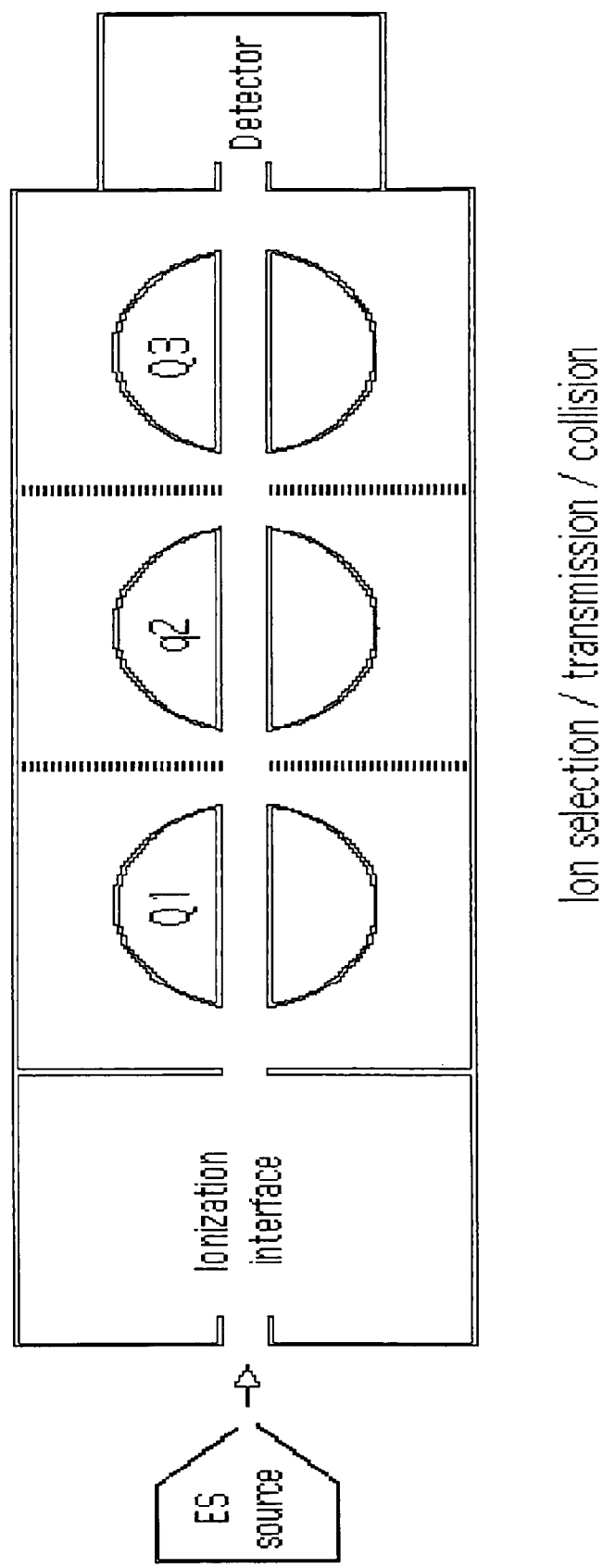
FIG. 12 is a schematic showing the generalized components of a triple quadrupole mass spectrometer. The basic constituents of the system described herein include: (A) an electrospray source/ionization interface for sample introduction; (B) three quadrupoles for ion manipulation, which includes mass filtration (Q1 or Q3), transmission (all quadrupoles), and/or collision (q2); and (C) a detector for amplifying transmitted ion signals so that they can be recorded and analyzed.

To map extracted peptides and obtain primary sequences, a triple quadrupole mass spectrometer with an ES ion source, as generically depicted in FIG. 12, was employed. By using a triple quadrupole instrument, not only are all of the ions present within a given fraction be summarized for a designated mass range (mass mapping), but ions may then be selectively fragmented in order to obtain information from which sequence information can be derived (characterization). This is due to the flexibility afforded by the quadrupole mass analyzers: Q1 and Q3 act as mass filters which can be set to generate alternating DC and RF voltage fields for selectively transmitting specific ions (Watson 1997). However, q2 is an enclosed transmission-only quadrupole; it can be pressurized with inert gas for the collisional dissociation of an ion transferred through Q1. The specific ionization interface, NanoES, chosen here as an ES source functions on the principles described by developers Wilm and Mann (Wilm and Mann 1996). To establish and validate the procedure, comprehensive peptide mapping and sequencing were first performed among fractions 6 through 19 (FIG. 11), which represented a region of relatively rich ligand concentration (data not shown), for B*1501, B*1503, B*1508, and B*1510; once this was accomplished, a more focused, and therefore less extensive, comparison was subsequently made between B*1501 and B*1512.

Prior to NanoES-MS, RP-HPLC fractions were completely dried by speed vac; the peptides were then resuspended in 0.1% acetic acid in 1:1 methanol:water. Aliquots from each of the individually concentrated fractions were loaded into 5 cm gold/palladium alloy-coated borosilicate pulled glass NanoES sample capillaries (Protana AIS). To begin sample flow and data collection, the loaded capillary tube was next carefully opened as described (Wilm and Mann 1996). The capillary was then positioned directly in front of the API III⁺ (PE SCIEX) triple quadrupole mass spectrometer's orifice, and 20-30 scans were collected as separate data files for the mass range 325-1400 m/z while operating the instrument at positive polarity. This procedure was performed sequentially to obtain constituent mass data for samples drawn from each RP-HPLC fraction.

Spectral "ion maps" were generated from the TICs acquired for each fraction. The maps obtained from corresponding fractions of peptides eluted from different HLA-B15 molecules were aligned (FIG. 13A), and ions of interest for NanoES-MS/MS were located. The ion maps were typically compared following baseline subtraction and smoothing. Putative ligand matches or, in the case of B*1512, mismatches among the ions were identified through a combination of data centroiding and direct visual assessment. Preference was placed upon selecting doubly-charged, or $[M+2H]^{2+}$, or higher ion forms commonly resulting from electrospray ionization for subsequent NanoES-MS/MS since the resulting daughter ion spectra were richer than those obtained from the collision of singly-charged, or $[M+H]^+$, ions (data not shown).

NanoES-MS/MS was performed by loading into a NanoES capillary tip, as described above, the desired volume of a fraction for which data was to be acquired. The volume loaded depended upon the relative sample flow rate achieved after opening the capillary tip and how long data acquisition was intended to proceed. Typically 3-4 µL were loaded at a time to collect MS/MS data for 20-25 mid- to low-intensity ions from a given fraction. Once loaded, the source head was positioned and the capillary opened as before. Separate data files were collected for each ion subjected to collisional dissociation.

Daughter ion spectra were generated from the TICs obtained in this manner for each ion chosen. The specific approach taken to interpet individual MS/MS spectra varied from ion to ion depending upon the quality of the data sets obtained but adhered to the general rules of MS/MS fragment interpretation (Roepstorff and Fohiman 1984). The Predict Sequence algorithm included as part of the BioMultiView software (BioToolBox package, PE SCIEX) was employed for the de novo sequence interpretation, and the sequences deduced were checked for identity with source proteins in various databases using the PeptideSearch algorithm (European Molecular Biology Laboratory; Mann and Wilm 1994) and performing advanced BLAST searches (Altschul et al. 1997) against the National Center for Biotechnology Information (National Institutes of Health) databases.

Figure 14:
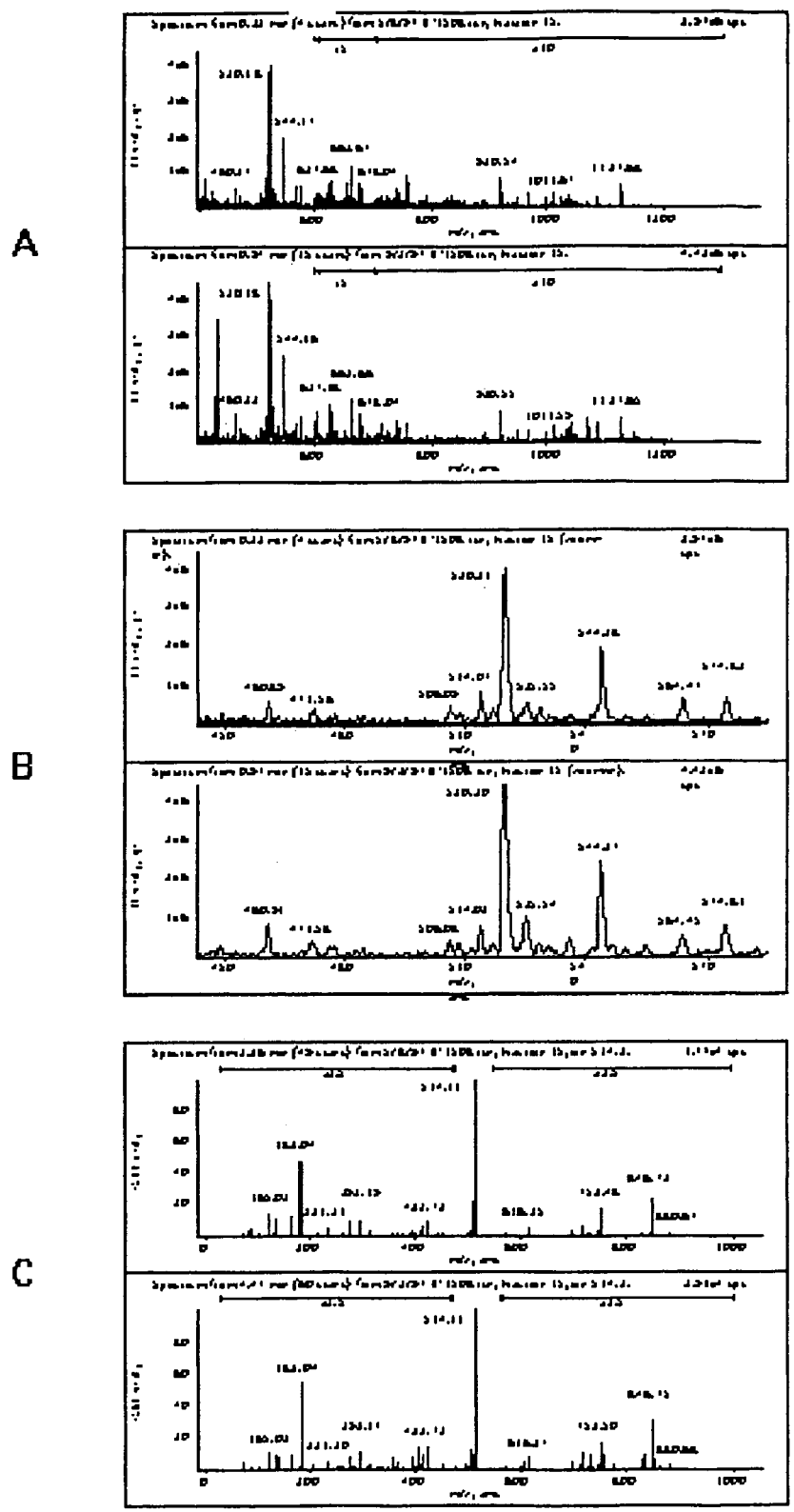
FIG. 14 is a graphical representation showing the reproducibility of the class I HLA ligand mapping and characterization strategy disclosed herein. Approximately 400 μg each of B*1508 ligands obtained from two separate bioreactor runs performed six months apart were fractionated by RP-HPLC as shown for B*1510 (FIG. 11). NanoES-MS ion mapping and comparison were then performed as described herein. As illustrated by the spectra of fraction 15 for each (A and B), the ion maps were consistent with one another; subjecting an ion (514.0) from each B*1508 fraction to NanoES-MS/MS further demonstrated reliability of the protocols employed.

Leu and Ile were indistinguishable unless suggested by Edman data and/or specific sequence matches, as were Gln and Lys since lysyl derivatization prior to fragmentation was not performed. NanoES-MS/MS data from ions of potentially overlapping peptides was aligned to confirm or refute the presence of shared ligands among different HLA-B15 molecules, as shown for one ion confirmed as an overlapping peptide across B*1501, B*1503, and B*1508 in FIG. 13, (B and C). Reproducibility of the protocol in its entirety is demonstrated in FIG. 14. To establish a numerical description ($N_{sum}/C_{sum}$) comparing ligand N- and C-regional occupancies for each allotype, N and C values for the four ligand positions at either terminus were determined by summing occurrence frequencies (using an arbitrarily-defined baseline of 10%); $N_{sum}$ was subsequently calculated from the four N values, and $C_{sum}$ was calculated from the four C values.

Peptides from HLA-B15 molecules were subjected to pooled Edman sequencing as well as more extensive examinations, including fractional Edman sequencing and mass spectrometric characterization of individual ligands. This was done to: (i) confirm the production/purification methods employed; and (ii) evaluate the relative nature and complexity of the peptides contained in extracts of naturally presented ligands.

Upon extracting peptides from each of six different B15 molecules, pooled Edman sequencing was performed. This was done both to validate results from the extraction of sHLA ligands with the techniques previously employed by others (B*1501 and B*1508, Falk et al. 1995; Barber et al. 1997), and to obtain novel motifs from the molecules that had not been previously examined (B*1503, B*1510, B*1512, and B*1518) for providing "traditional" points of reference.

Overall, the B*1501 motif (FIG. 15) was in agreement with the dominant P2 and P9 anchors (Gln and Tyr/Phe, respectively) previously defined (Falk et al. 1995; Barber et al. 1996; Barber et al. 1997). This result demonstrates that the peptides extracted from sHLA-B*1501 complexes were identical to those extracted by others from natural membrane-bound molecules. However, differences in the whole pool sequencing data arising from sHLA purified by BBM.1 (FIG. 15B) versus W6/32 (FIG. 15A) indicated that a greater number of peptides than originally realized should actually contribute to the consensus B*1501 motif.

First, while Gln and other residues including Leu, Met, and Val have been previously reported at P2 using W6/32 to isolate complexes, the aliphatic side chain Pro was strongly detected at P2 in the BBM.1-purified B*1501 motif as well. Though not employed by other groups pursuing similar studies, the $\beta_2$m-specific MAb BBM.1 was initially chosen here to avoid biases potentially imposed upon the class I heavy chain by bound peptides (Bluestone et al. 1992; Catipovic et al. 1992; Solheim et al. 1993). Of interest was that Pro has not been reported before as a strong or even weak P2 anchor in the B*1501 peptide motif. It has been suggested that B-locus allotypes that present peptides with Pro at P2 demonstrate a shallower B-pocket within their binding grooves than does B*1501, which exhibits a Ser at α-chain position 67 rather than a more constricting residue such as Phe (Barber et al. 1997).

This data suggests the possibility that Pro binds amicably within this deeper pocket but perhaps induces an altered heavy chain conformation that negatively biases purification of complexes by the W6/32 MAb typically used. The observation of a P2 Pro occupying a pocket with suboptimal physical complementarity is corroborated by a similar occurrence among peptides bound by the murine class I molecule $L^d$ (Corr et al. 1992; Balendiran et al. 1997). Purification methodology serves, therefore, as a factor in allele-specific motif predictions, and the whole pool sequencing with peptides extracted from both BBM.1 and W6/32-purified B*1501 complexes demonstrated that a strong Pro anchor at P2 is antibody dependent.

The pooled Edman motifs obtained for W6/32-purified molecules divergent from B*1501 are shown in FIG. 16. Like B*1501, each of the motifs reflected a nonameric consensus with distinct P2 and P9 anchors and internal auxiliary anchor preferences. The B*1508 motif, described by another group while its preparation was in progress during the development of this invention (Barber et al. 1997), was consistent between the two laboratories; it demonstrated a preference for the small side chains Pro and Ala at P2 and aromatic residues Tyr and Phe at P9. The B*1512 motif appeared nearly identical to that obtained from B*1501; by extension, considering that B*1519 differs from B*1512 in $\alpha_3$, which does not contribute to the peptide binding groove, it is predicted that B*1519 would bear the same motif as B*1501 and B*1512.

B*1503 diverges somewhat from the other three molecules presented above in showing a distinct preference for ligands with a neutral, polar Gln or positively-charged Lys as the P2 anchor; the aliphatic Met was evident here as well, though to a lesser degree than noted for the hydrophilic Gln and Lys residues (Prilliman et al. 1999). Like B*1501, B*1508, and B*1512 however, aromatic residues Tyr and Phe defined a hydrophobic P9 anchor. The only other class I molecules with motifs whose definitions thus far indicate a Lys at P2 are B*3902 (Falk et al. 1995) and B*4801 (Martinez-Naves et al. 1997), both of which structurally bear B-pockets identical to B*1503 except for a single L-T or L-E substitution, respectively, at the $\alpha_2$ helical residue 163 (Chelvanayagam 1996). The B-pocket of B*1503 is indistinguishable from that of B*4802 (Chelvanayagam 1996), whose motif remains undetermined but is likely to follow suit with those of B*1503 and these other molecules at the second ligand position. An assortment of polar, charged, and hydrophobic residues is evident at P3 of the B*1503 motif.

Figure 3:
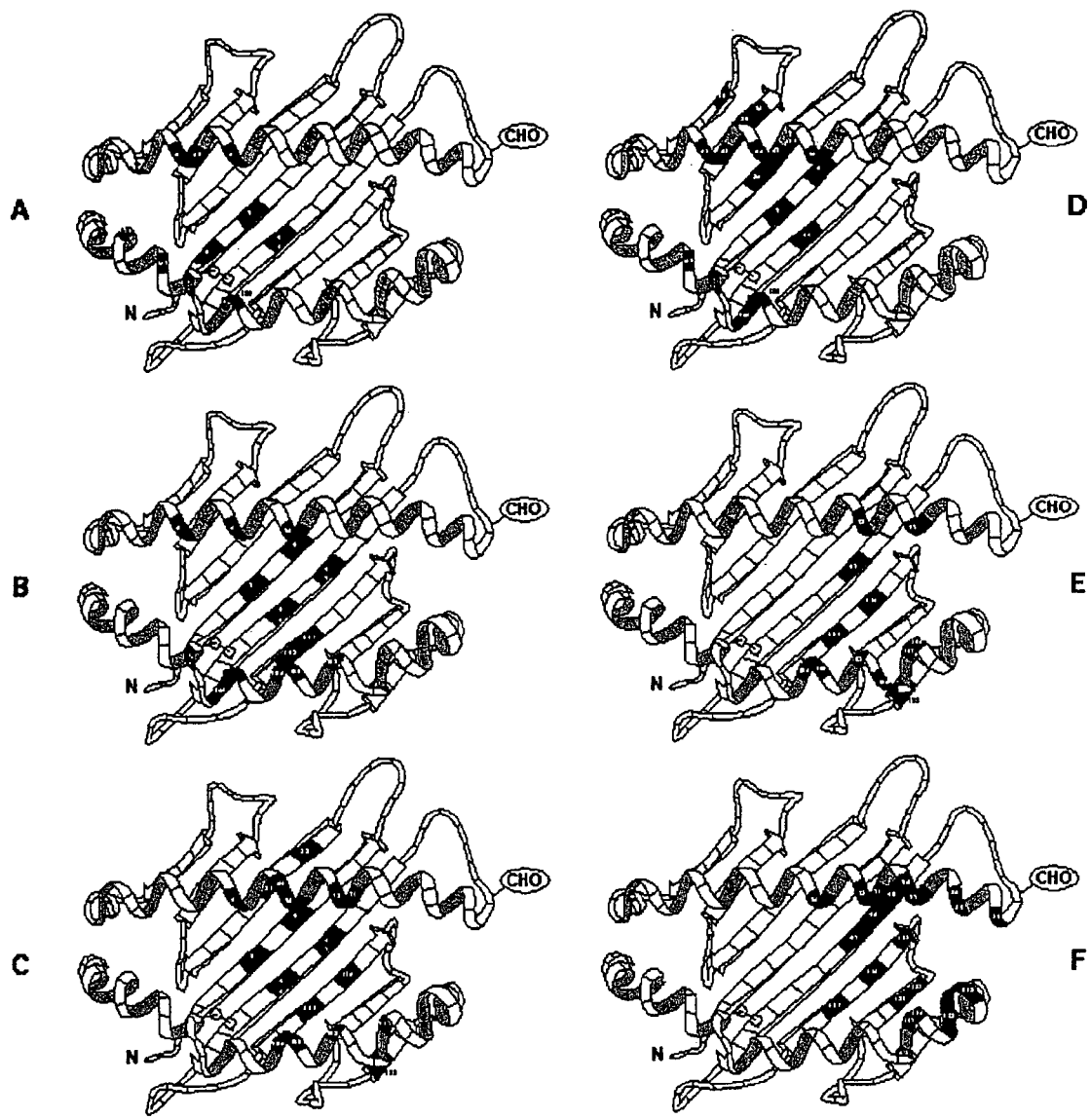
FIG. 3 is a graphical representation of the specificity determining pockets of the MHC class I ligand binding groove. The structural residues contributing to the six pockets (A through F) of the antigen binding groove formed by $\alpha_1$ and $\alpha_2$ are indicated in black and numbered from the N terminus of the mature class I $\alpha$-chain. The residues are as collectively defined in the literature (Saper et al. 1991; Matsumura et al. 1992; Chelvanayagam 1996). In terms of a nonameric ligand, the pockets are assumed to accommodate the amino acids occuring at given ligand positions as follows: A-pocket, P1; B-pocket, P2; C-pocket, P6; D-pocket, P3; E-pocket, P7; and F-pocket, P9. The majority of residues that contribute to these binding pockets are oriented such that they are solvent-inaccessible in mature trimers.

The B*1510 motif demonstrated a strict preference for ligands bearing a basic, hydrophilic His as a P2 anchor. A hydrophobic P9 anchor was described by residues including Leu and Phe. The B*1510 motif strongly resembled that previously defined for B*1509, which exhibits nearly identical anchor preferences with His at P2 and Leu, Phe, and Met at P9 (Barber et al. 1997). B*1510 and B*1509 differ structurally only by a substitution of N→D in $\alpha_2$ at the α-sheet floor position 114, which takes part in forming several specificity pockets within the peptide binding groove (FIG. 3).

By extrapolation from its structural neighbors, it was assumed that B*1518 would have for its motif a P2 anchor of His (as seen for B*1510 and B*1509) and a P9 of Tyr and Phe (as seen with B*1501, B*1503, B*1508, and B*1512). B*1518 differs from B*1510 solely at position 116; two other HLA-B molecules that differ exclusively at this position are B*3501 and B*3503: they differ by a S→F substitution here, which would sterically mimic the substitution between B*1518 and B*1510 and confer B*1510-like P9 preferences (Steinle et al. 1995; Kubo et al. 1998). Based upon this, and the fact that the P9 environments of B*1518/B*3501 and B*1510/B*3503 are similar (Chelvanayagam 1996), it was first predicted, and then confirmed following pooled sequencing, that B*1518 would bear the "hybrid motif" described.

Pooled Edman sequencing data therefore demonstrates that (i) the peptides extracted from sHLA complexes produced according to the methodology of the present invention are consistent with those previously extracted from native, cell surface-expressed complexes, and (ii) nonameric ligand lengths with anchor residues at P2 and P9 characteristic to specific polymorphisms are preferred. As for functional implications, the major anchors would predict natural ligand overlaps with B*1501 by B*1503 and B*1512.

Since class I peptide pools consist of thousands of different ligands, an early investigation during development of the analysis strategy and methods disclosed herein was to next fractionate and then Edman sequence the peptides extracted from one of the molecules. BBM.1-purified B*1501 (Prilliman, et al. 1997), the first soluble molecule produced by a non-repeatable precursor methodology to the fully repeatable and characterized methodology of the present invention, was initially examined to explore the general diversity around a pooled motif (Prilliman et al. 1998).

Figure 17:
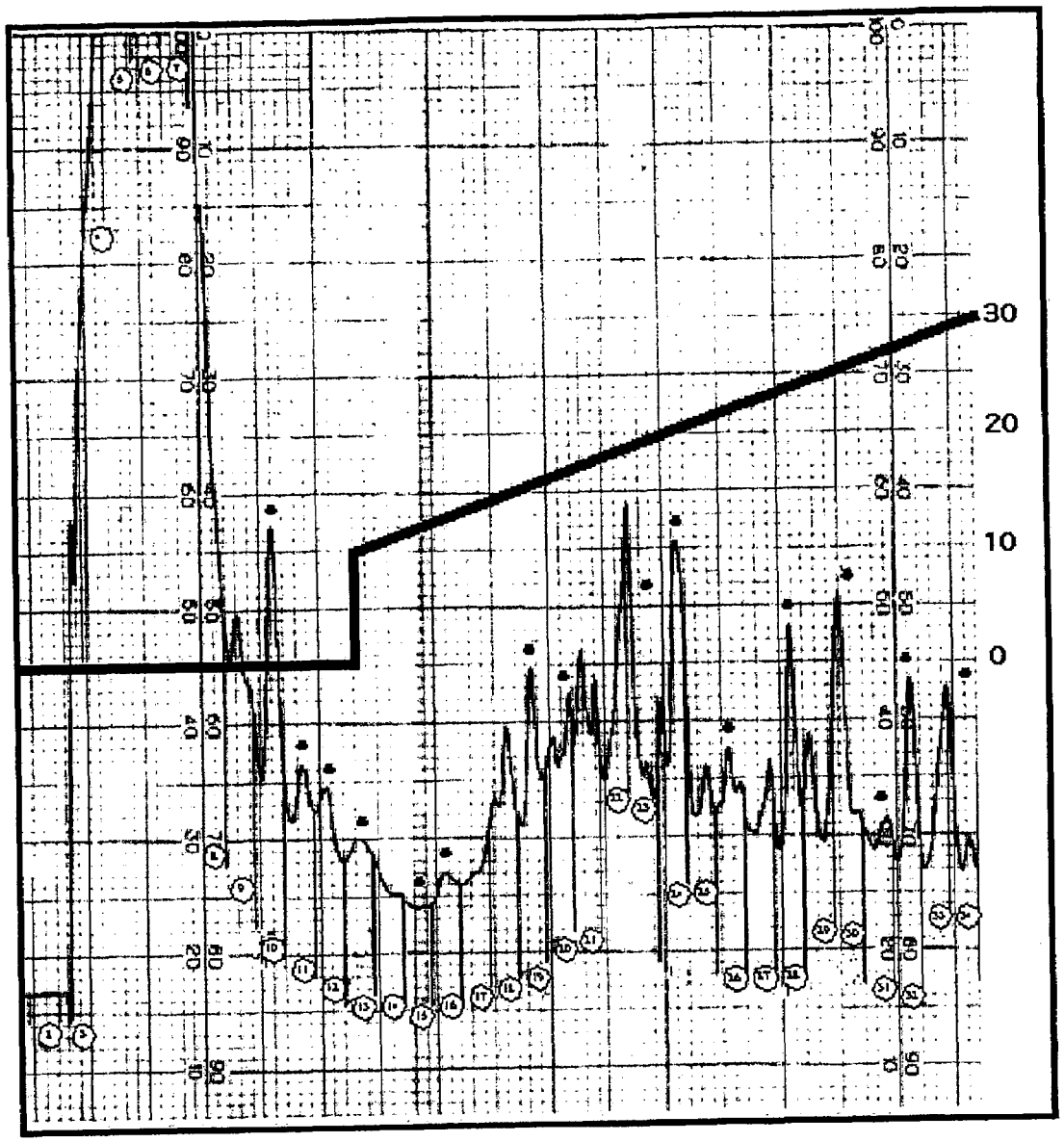
FIG. 17 is a graphical showing RP-HPLC separation of ligands from BBM.1-purified B*1501. The UV trace obtained during separation as described herein of approximately 150 μg of peptides extracted from BBM.1-purified B*1501 reveals the bulk of absorbance to occur along the gradient (black line) between 10-30% buffer B (indicated at the right). The fractions collected are numbered; although all fractions were examined, only those subsequently selected for analysis and data presentation in FIGS. 18 and 19 are marked by dots. It is noted that the chosen fractions were distributed evenly across the entire region of interest and included a wide variety that were of high as well as low UV absorbance and/or resolution.
Figure 18:
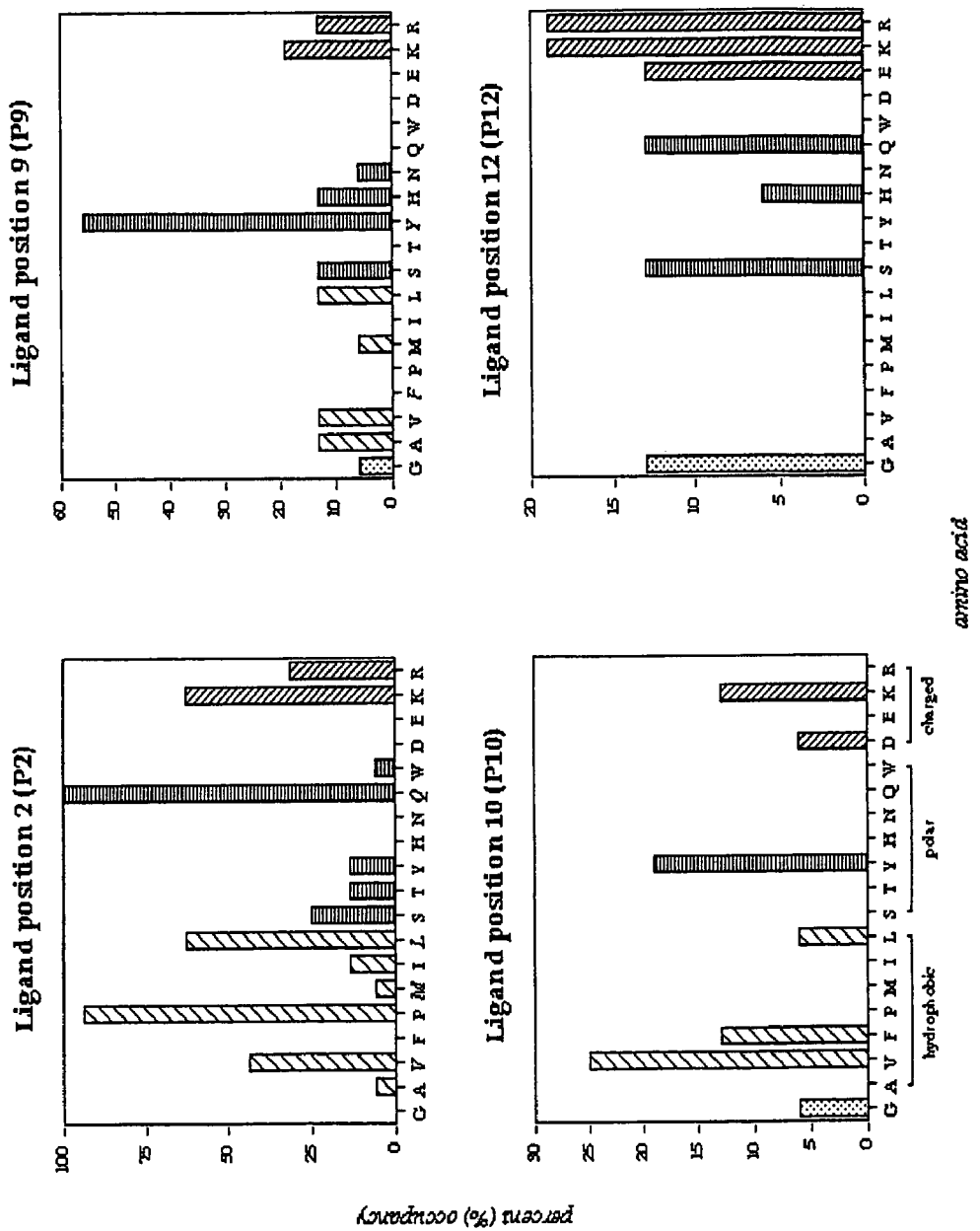
FIG. 18 is four graphs showing the percentages of RP-HPLC ligand fractions from BBM.1-purified B*1501 demonstrating particular amino acid occupancies by Edman degradation. Sequence complexity among the peptides was summarized by averaging the frequency of occurrence for amino acid residues at P2 through up to P12 for the fractions marked by dots in FIG. 17. Amino acids are grouped along the x-axis according to their physicochemical natures (charged, polar, or hydrophobic), as specifically designated in the chart for P10 and indicated within all four charts by differential shading. Residues observed at P2 and P9 in former B*1501 motif descriptions are indicated in bold italics. Since it was not derivatized, cysteine was undetectable and is therefore excluded.

Edman sequencing of peptide-containing fractions collected from the RP-HPLC gradient shown and described in FIG. 17 supported the existence of peptides up to 12 residues long and revealed significant positional diversity among the peptides isolated from B*1501. This positional diversity was illustrated in 16 representative fractions (FIG. 18). Assessment of dominant, strong, or weak amino acid residues present at the various positions indicated that the dominant anchors previously defined by whole pool sequencing did not necessarily predominate in fractions of the peptide pool (FIG. 19). In fractions 15 and 31 the dominant P2 Gln was replaced by a dominant Ala and a dominant Lys respectively, while the pooled motif Tyr fell below residues such as His and Lys at P9 in the same fractions. While variations on the consensus motif were prevalent at P2, this was not solely restricted to the N termini of bound peptides as shown in FIG. 18.

Among the 16 fractions studied, 12 demonstrated weak sequence yields out to 12 cycles of degradation; in nine of these fractions, P12 was occupied by the charged or polar residues Glu, Arg, Lys, Ser, His, or Gln. Additionally, the presence of numerous decamers within the B*1501 peptide population was suggested in that 11 of the fractions sequenced exhibited a typical P9 residue, Tyr or Phe, at P10. For example, in FIG. 19 the strong Phe presence at P10 in fraction 28 suggests that P10 serves as an anchor for a decamer(s) present within the fraction. The shifting of a P9 anchor preference to P10 is consistent with the P10 occupancies of individual decamers formerly characterized from B*1501 peptide pools (Falk et al. 1995; Barber et al. 1997). Although residues representing P9 anchors were seen at P10 and P12, amino acids unique in such longer ligands were also detected, suggesting that the shifting of a previously-reported P9 anchor is not the only means by which longer B*1501 peptides are bound within the peptide binding groove (Collins et al. 1994).

During the course of examining ligands from other sHLA molecules, which were purified alternatively with MAb W6/32, aliquots of RP-HPLC fractions from some were also subjected to Edman sequencing on occasion. The results from these random samplings of B*1501, B*1508, B*1503, and B*1510 fractions are summarized for major characteristics in Table 3. The characteristics recorded included preferences other than those seen in the pooled motifs at traditional anchor positions P2 and P9 and whether signal levels indicated the presence or not of residues beyond the nine cycles of degradation typically observed. Of additional interest, no Lys was observed among Edman sequenced fractions as an additional preference at P2 for B*1501 purified with W6/32, a finding contrary to the P2 preferences among fractions of BBM.1-purified material which lends further support to the argument for MAb bias, as discussed earlier, existing in complex purification.

In summary, the fractionation of B*1501 peptides prior to Edman analysis resulted in amino acid sequence data demonstrating that the components of a peptide pool can vary considerably from the overall motif (Prilliman et al. 1998). These data, as well as results obtained from other B15 molecules, suggested that peptides bound by the various molecules include: (i) species which are either longer or shorter than the nonameric size typically indicated by pool sequencing alone; and (ii) species that exhibit primary sequences different from those predicted by pooled sequencing. The additional data provided by further exploration of fractionated extracts from several of the B15 molecules in this manner expands the molecules with the potential for presenting B*1501-overlapping ligands to include not only B*1503 and B*1512 but B*1508 and B*1510 as well. Such diversity among fractions indicated that characterization of individual ligands would provide information not available in motifs.

Individual peptides from B*1501, B*1503, B*1508, B*1510, and B*1512 were comparatively examined to investigate whether the added flexibility observed through Edman degradation of RP-HPLC fractions would allow for natural ligand overlaps to occur across their respective polymorphisms.

More than 400 individual ligands extracted from the five distinct HLA-B15 allotypes were characterized according to the methodology of the present invention. The ligands characterized here were from ion map masses found in multiple B15 allotypes as demonstrated in FIG. 13A. Selected ions were then dissociated by NanoES-MS/MS, and the resulting fragment information was compared and interpreted, as described hereinabove, to determine if the ions represented sequence-identical or merely mass-identical ligand matches.

Individual peptide ligands characterized from the five B15 allotypes are listed in Tables A-E. The number of ligands for which either complete or partial sequences were obtained here was as follows: B*1501=126, B*1503=74, B*1508=96, B*1510=123, and B*1512=30. While the pooled motifs of peptides extracted respectively from the five molecules described nonamers with various P2 and P9 dominant anchors and P3 auxiliary anchor preferences (FIGS. 15 and 16), the single peptide sequences ranged from 7 to 12 amino acids in length and demonstrated (i) greater heterogeneity at their N-terminal/proximal regions than their C termini, and (ii) varying degrees of observed ligand overlap, both of which will be examined in the subsequent sections of this chapter.

Figure 20:
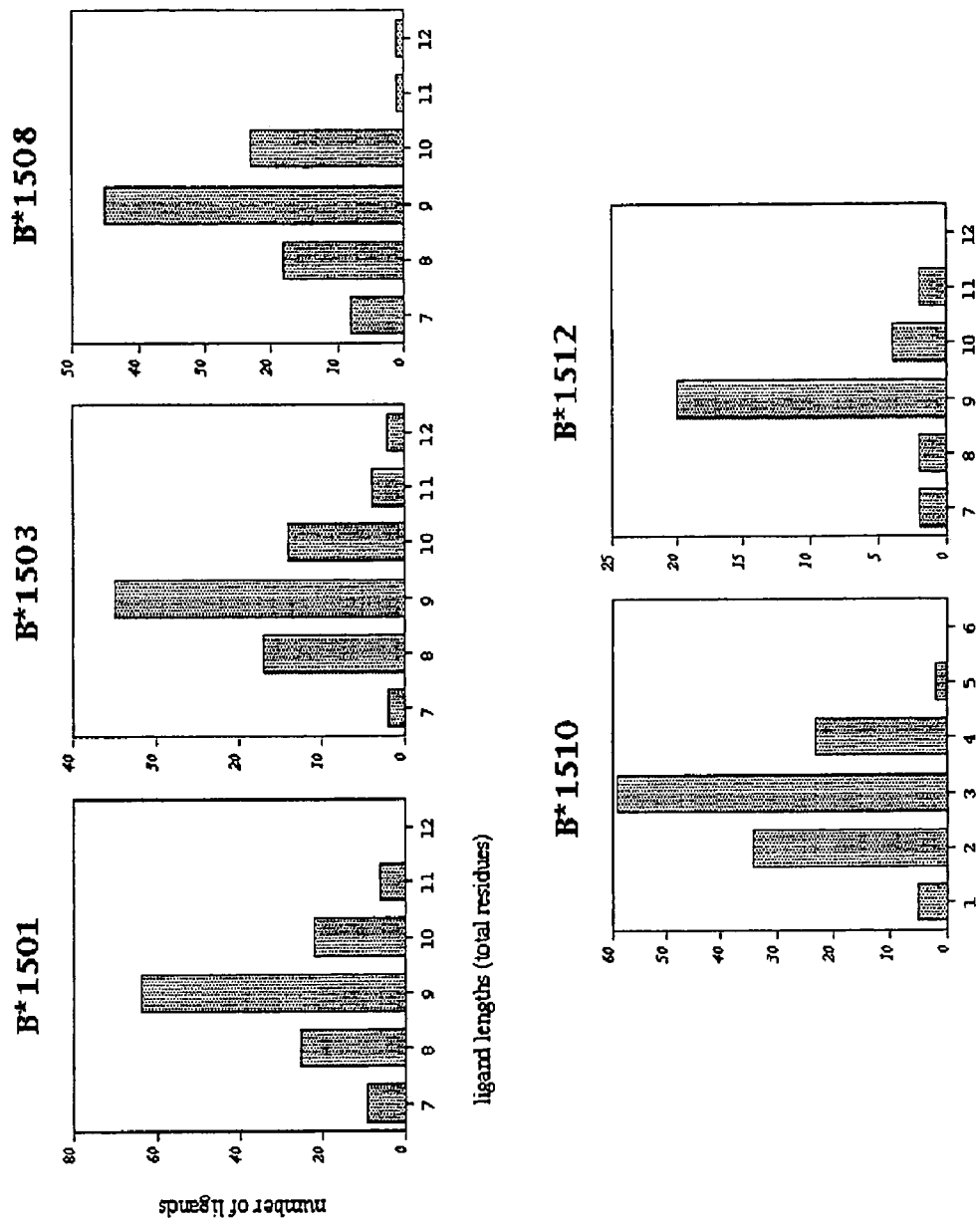
FIG. 20 is five graphs summarizing teh length diversity among the 449 characterized HLA-B15 ligands. Graphed data from the ligands listed in Tables A-E summarizes length diversity among the peptides respectively characterized from B*1501, B*1503, B*1508, B*1510, and B*1512.

In terms of length heterogeneity, the endogenous peptides eluted from B*1501, B*1503, B*1508, B*1510, and B*1512 varied in length from 7 to 12 amino acids as shown (FIG. 20). An overall length breakdown of the peptides listed in Tables A-E demonstrates that approximately 6% are heptamers, 21% are octamers, 50% are nonamers, 19% are decamers, 3% are undecamers, and 1% are dodecamers. Further emerging from the length characterization of individual ligands is the observation that peptides bound by each of the B15 molecules spanned ranges of 5 to 6 amino acids in length. For example, peptides eluted from B*1501, B*1510, and B*1512 were 7-11 amino acids in length, while those from B*1503 and B*1508 were 7-12 amino acids in length.

Coupling this length variability with the likewise varying degrees of regional sequence heterogeneity (which will be discussed) leaves only 23% of the endogenously loaded peptides characterized in Tables A-E as "ideal nonamers" with both P2 and P9 anchors in concordance with the dominant or strong preferences of the pooled Edman motifs from their respective source molecules. This finding is of principal significance in that a majority (77%) of potential ligands for any of these HLA-B15 molecules would therefore be overlooked if the length and sequence constraints of their pooled motifs were utilized as the primary criteria in searching for potential epitopes specific to them.

Examples of ligands from this study with homology to stretches of known proteins are shown in Table 4. The peptides yielding 100% identical BLAST database hits were grouped into seven categories, which were defined here according to the common natures of their potential source proteins: HLA ligands, replication/transcription/translation ligands, biosynthetic/degradative modification ligands, signalling/modulatory ligands, transporter/chaperone ligands, structural/cytokinesis ligands, and unknown function ligands. Aside from the HLA heavy chain-derived ligands, most appear to be derived from cytoplasmic or nuclear proteins, which illustrates that the typical endogenous pathway is involved in generating the majority of the class I-loaded peptides characterized (York and Rock 1996).

Of the 44 peptide sequences listed in Table 4, it is noteworthy that overlaps across other HLA-B15 molecules are evident within our data collection. The B*1510 tapasin$_{354-362}$ ligand HHSDGSVSL (SEQ ID NO:51), as well as both THTQPGVQL (SEQ ID NO:54) from septin 2 homolog$_{70-78}$ and SHANSAWL (SEQ ID NO:55) from β-adaptin$_{249-257}$, have also been sequenced from B*1509 extracts (Barber et al. 1997), and the B*1501/B*1508/B*1512 ubiquitin-protein ligase$_{83-91}$-derived ligand ILGPPGSVY (SEQ ID NO:41) was characterized from endogenously bound B*1502 peptides (Barber et al. 1997). The eIF3-p66$_{61-69}$ nonamer SQFGGGSQY (SEQ ID NO:29) (Falk et al. 1995; Barber et al. 1996) was found here within B*1501, B*1503, B*1508, and B*1512 extracts. The decamer YMIDPSGVSY (SEQ ID NO:42), which is homologous to proteasome subunit C8$_{150-159}$, was also previously described as a ligand for B*1502 (Barber et al. 1997), B*1508 (Barber et al. 1997), and B*4601 (Barber et al. 1996); it was found here presented by B*1501, B*1508, and B*1512. Some of the specific overlapping ligands identified in this study therefore overlap in antigen presentation with the HLA-B15 allotypes characterized by others.

Given the length heterogeneity observed among the ligands collectively characterized from B*1501, B*1503, B*1508, B*1510, and B*1512, analysis of peptide ligand primary structures proceeded through two separate alignments (N-and C-terminal) for each HLA-B15 allotype. The frequencies with which specific side chains occurred at (i) the N terminus and first three residues internal from it, and (ii) the C terminus and the first three residues internal to it were tabulated. As graphically summarized throughout parts A and B, respectively, of FIGS. 21-25, the salient features of these ligand regions and how they correlated with the structures of the molecules from which they were extracted can be examined.

The N-terminal/proximal regions for ligands from each of B*1501 (FIG. 21A), B*1503 (FIG. 22A), B*1508 (FIG. 23A), B*1510 (FIG. 24A), and B*1512 (FIG. 25A) clearly demonstrated acceptance of a variety of amino acid side chains, particularly at P3 and P4, by the portions of the binding groove assumed to interact with ligands at the designated positions. With the exception of B*1512 ligands, which were obtained from both a smaller and more biased collection of ions (see FIG. 25 legend), higher points in each of the graphs occur for certain side chains indicated along the P1 and, to a greater extent, P2 data lines, which represent the first and second positions, respectively, of the characterized ligands.

The results for P1 obtained from the HLA-B15 ligands characterized are of interest since the analysis of Edman sequencing data depends upon comparing relative increases between cycles and is therefore unreliable for making side chain determinations at this first position, especially when complex mixtures of peptides are examined (Stevanovic and Jung 1993). All five B15 allotypes demonstrated a number of side chains at P1, with preferences for residues including Ala, Leu/Ile, Gly, Ser, Thr, and Tyr observed in varying degrees among them (FIGS. 21-25, A). Overall, P1 appeared to be occupied in a majority of ligands by aliphatic amino acids.

Though the pooled motifs of B*1501 and B*1512 (FIGS. 15 and 16) as well as the spectral ion maps obtained from their RP-HPLC fractions (data not shown) were virtually identical, the substitution difference between the two molecules at A-pocket residue 167 suggested that ligands bound by these molecules might differ at P1. Performing NanoES-MS/MS upon a handful of ions, which appeared to be exclusive to B*1512, confirmed the presence of several ligands presented by B*1512 but not B*1501 (Table 5). Of the 16 sequenced, seven indicated His, two indicated Arg, and one indicated Lys at P1. In comparison, only a single B*1501 peptide each presented with His, Arg, or Lys at P1 out of 126 ligands characterized (Table A). An explanation for the existence of this subset of B*1512-restricted ligands with positively-charged N-termini could lie in the W→G substitution observed between B*1501 and B*1512 at α$_2$ position 167, which might sterically enhance the influence by the adjacent acidic residue at position 166 (Glu in B*1501 and Asp in B*1512) of B*1512 upon P1 in the A-pocket. Comparing individual ligands between B*1512 and B*1501 supports the notion that the polymorphism segregating them will confer distinct yet subtle effects upon peptide binding by other allotypes differing in this manner.

P2, which has been considered to act as a primary anchor for peptide ligands among most class I molecules described to date as based upon pooled Edman motifs, is classically accepted to associate with the B-pocket of the peptide binding groove. In terms of the motifs derived here by pooled sequencing (FIGS. 15 and 16) and the motifs previously established for other B15 family allotypes (Falk et al. 1995; Barber et al. 1996; Barber et al. 1997), a Gln at P2 is common to B*1501, B*1502, B*1503, B*1512, and B*1513 (Table 6). Three alleles, B*1502, B*1513, and B*1508, have a Pro at P2, while the lack of a strong Pro at P2 in both B*1501 and B*1503 corresponds to polymorphism at heavy chain positions 63 and 67. For example, B*1501 appears to lose the propensity for Pro at P2 due to polymorphism at position 63, while B*1508 appears to lose a Gln at P2 resulting from polymorphism at 67. Thus, comparisons within the B15 family highlight how substitutions at positions 63 and 67 of the class I heavy chain $\alpha_1$ helix appear to confer differential interaction with P2 of the peptide ligand.

While residue 63 modulates the size/conformation of P2, it can be seen that residues 24 and 45 influence the P2 charge nature propensities. A comparison of B*1501 and B*1503 illustrates how polymorphisms at positions 24 and 45 of the B-pocket influence P2 preferences in this manner; B*1503 is one of four B15 alleles with known motifs bearing a positively charged P2. Allotypes B*1509, B*1510, and B*1518 recognize a positively charged His at P2 and have the same residues at 24 and 45 as B*1503, but the differences at positions 63 and 67, which separate B*1503 from the other three molecules, again modulate the contour of P2 such that different positively charged P2 residues fit respectively into the B*1503 and B*1509/B*1510/B*1518 B-pocket categories.

It has previously been proposed that polymorphisms in the $\alpha_1$ helix prompt major changes in the repertoires of peptides bound by allotypes differing in this region (Barber et al. 1997). That any region, helical or sheet, of $\alpha_1$ would influence peptide P2 preferences more than $\alpha_2$ is of little surprise though since 14 of the 18 residues forming the B-pocket belong to the $\alpha_1$ domain (Table 6). A comparison of 12 known B15 motifs in the B-pocket suggests more refined rules for $\alpha_1$ in general, whereby polymorphisms in the helices sculpt the conformation and size of the amino acids that can fit into the peptide binding groove's B-pocket. Further analysis of the B15 motifs at P2 suggests that polymorphisms lining the floor of the groove tend to regulate the hydrophobic and/or charged nature of the residues at P2 of bound ligands. Perhaps in this way the walls and floor of the binding groove work in concert: the α-helical residues sterically control which amino acids can fit, while the β-sheet residues act to attract or repel particular side chains based on chemical compatibility within the ligand binding groove.

The interactions described for P2 here are, however, more relaxed than previously thought. For a majority of the allotypes shown in Table 6, three or more different side chains are observed by pooled Edman sequencing as dominant or strong B-pocket residents and/or the B-pockets of the molecules demonstrate abilities to naturally accommodate alternative P2 residues (Table 3 and FIGS. 21-25, A). Of specific interest, although Met appears in the B*1503 pooled motif as a strong P2 anchor residue (FIG. 16), only two of the peptides characterized for this allotype bear Met at P2 (FIG. 22A), while other residues including Gly, Pro, Ala, and Asn occur more often than Met at P2 among B*1503 ligands. The fact that Met appears in the pooled motif but fails to demonstrate a strong presence among the individual peptides indicates that disparate concentrations of ligands within extracts may skew pooled Edman sequencing results so as to be misleading.

Pro and Ala likewise appear with frequencies comparable to or exceeding those of the W6/32-purified pooled motif residues for B*1501 (FIG. 21A), and B*1508 ligands illustrate P2 inclinations for a rich array of side chains in addition to the motif-prescribed residues Pro and Ala which include Gly, Val, Met, Leu/Ile, Ser, Thr, and Gln/Lys. Similar variety is observed within the limited B*1512 ligand data set (FIG. 25A). In contrast, the B-pocket composition for B*1510 indicates His as the sole dominant/strong P2 occupant (Table 6), and among individual ligands characterized from B*1510 His is noted at a markedly higher degree than are alternative residues (FIG. 24A). However, amino acids including not only the positively charged Arg but to a greater extent Gly, Ala, Val, Leu/Ile, and Gln/Lys occur at P2 of some peptides are also characterized at P2 from this allotype. Thus the majority of HLA-B15 molecules demonstrate elastic N-proximal occupancies.

In comparison with the findings at the N-terminal/proximal regions, the C termini of ligands from each of B*1501 (FIG. 21B), B*1503 (FIG. 22B), B*1508 (FIG. 23B), B*1510 (FIG. 24B), and B*1512 (FIG. 25B) demonstrated a stricter acceptance of amino acid side chains. C-proximal ligand residues also revealed the existence of more distinct side chain tendencies.

Figure 24:
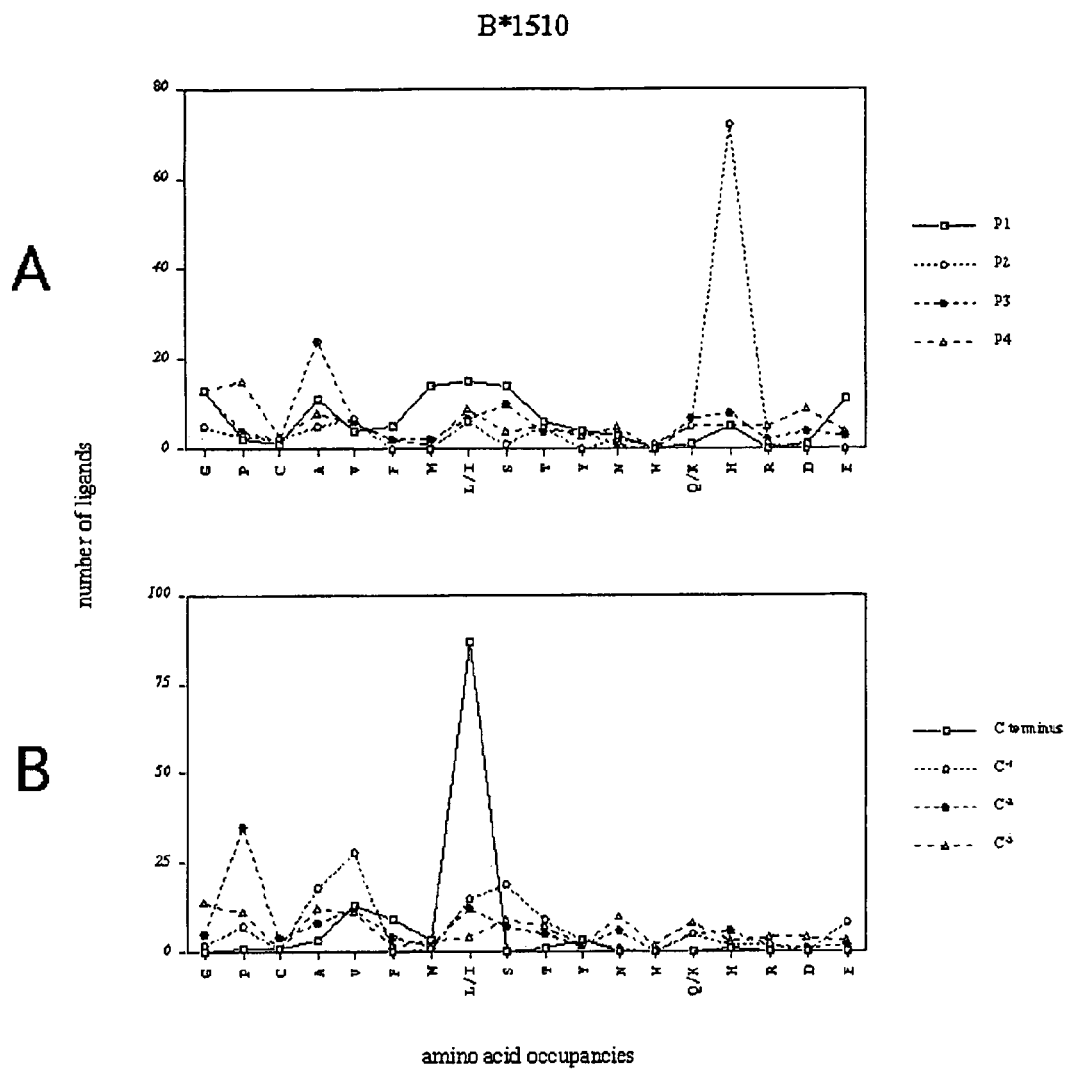
FIG. 24 is two graphs showing N- and C-regional diversity observed through alignments of B*1510 ligands. Frequency of occurrence for amino acids at the first (A) and final (B) four positions among the ligands characterized from B*1510 (Table D). The graphs were generated from separate N- and C-terminal data alignments.

For allotypes B*1501, B*1503, B*1508, and B*1512 a dominant C terminus was especially prominent among the ligands characterized from them, while B*1510 exhibited a P2 anchor nearly as strong as its primary C-terminal residue preference (FIG. 24, A and B). The aromatic residues Phe and, even more prominently, Tyr occupied the C-terminal positions of most peptides bound by the first four B 15 molecules, which appeared to agree with P9 of their respective motifs (FIGS. 15 and 16). The bulk of B*1510 ligands demonstrated Leu/Ile at their C termini; other occupants at this position included Phe and Val, an interesting observation in that more B*1510 peptides presented with Val, which is not included in either the pooled (FIG. 16) or fractional (Table 3) Edman motifs examined from this allotype, than Phe, which is identified as a strong P9 occupant by pooled sequencing. Such is the likely result of disparate peptide concentrations affecting the pooled Edman sequencing results as mentioned previously. Another factor includes the diminishing picomole yields per successive cycle of Edman degradation; this leads to progressively higher background signals and thus negatively affects sensitivity in examining the C-terminal/proximal regions of peptides (Stevanovic and Jung 1993).

The overwhelming conservation at the C termini of individual ligands (FIGS. 21-25, B) indicates that the C terminus acts as a dominant anchor for peptide ligands. P9 of pooled Edman motifs has classically been accepted to associate with the F-pocket of the peptide binding groove. C-terminal anchoring is observed here regardless of length heterogeneity (FIG. 20 and Tables A-E). For the majority (91%) of peptides greater than 9 residues long, this observation agrees with evidence that longer peptide ligands bulge centrally outward from the peptide binding groove. Sequencing individual ligands supports a concept that the C terminus of a ligand plays a dominant role as an anchor within the class I binding groove for the HLA-B15 allotypes examined.

With regard to pooled sequence motifs for HLA-B15 allotypes, all 12 molecules demonstrate chemical homogeneity at P9, with dominant/strong occupancies by hydrophobic residues (Table 7). The eight different F-pockets structurally represented among these allotypes show preferences for Tyr, Phe, Met, Leu, and Trp according to three functional group categories. This is in marked contrast with the B-pockets, for which eight different B-pockets among the same allotypes comprised seven distinct functional groups encompassing a mixture of both hydrophobic and hydrophilic side chains (Table 6).

It is interesting that, of these HLA-B15 molecules, nine have F-pocket functionality in the same category (B*1501, B*1502, B*1503, B*1508, B*1512, B*1516, B*1517, B*1518, and B*4601), with preferences for Tyr, Phe, and/or Met, despite the fact that they exhibit amino acid substitutions at nine different positions throughout the $\alpha_1$ helix and $\beta_2$ sheets. This redundancy demonstrates that, contrary to what was seen among structural residues affecting the B-pocket, the $\alpha_1$ helical polymorphism(s) shown for allotypes in the first category of Table 7 do not necessarily play a defined role in sculpting either the conformation or size preferences of ligands in this region of the peptide binding groove.

While the Edman-derived motifs for the B15 allotypes shown in FIGS. 15 and 16 clearly indicated P2 and P9 primary anchors and suggest an assortment of preferences at both P3 and P4, they fail to sufficiently capture the trends for auxiliary anchoring at the C-proximal regions of endogenously bound ligands which were perceptible throughout the individual peptide sequences. Additional preferences that likely serve as auxiliary anchors were evident at the C-proximal positions $C^{-1}$, $C^{-2}$, and $C^{-3}$ in the cases of nonamers, octamers, and heptamers, as well as in ligands longer than nonamers. A review of the positional frequencies observed among the HLA-B15 peptides shows that amino acids such as Val, Leu/Ile, Ser, Thr, and Gln/Lys tended to predominate at nearly all three of the C-proximal positions of ligands presented by B*1501, B*1503, B*1508, B*1510, and B*1512 (FIGS. 21-25, B). Of these residues, the hydrophilic, hydroxyl-containing Ser and Thr were especially frequent among these positions; nearly half (40%) of the ligands listed in Tables A-E, bear Ser and/or Thr at the designated C-proximal positions. In general, Glu occupied $C^{-1}$ and Gly occupied $C^{-3}$ to some extent among all five allotypes.

Val ($C^{-1}$) and Pro ($C^{-2}$) were especially prominent C-proximal residues observed among the B*1510 ligands; the overriding presence of Pro, which distinguished this region of B*1510-derived peptides from those of the other allotypes, can likely be attributed to steric influences imposed by the Tyr at $\alpha_2$ position 116 in B*1510, which additionally interacts with the C- and E-pockets of the peptide binding groove (FIG. 3). Further distinguishing several B*1510 ligands from but rare occurrences among B*1501, B*1503, B*1508, and B*1512, Pro frequently appeared as well in various C-proximal sequence combinations with Ala or Val (Table 8).

The amino acid residues characterized from each of the five HLA-B15 allotypes with occupancy rates of at least 10% for the first four (N-terminal/proximal) and last four (C-terminal/proximal) positions among ligands, respectively, are condensed in Tables 9-13. Presenting the data already discussed in this manner effectively emphasizes C-terminal dominance and N-proximal flexibility. By comparison, the data illustrates the limitations of pooled Edman motifs in being able to adequately reflect a consensus of the individual peptides contained within a given ligand extract. The $N_{sum}/C_{sum}$ quotients obtained as described for Tables 9-13 were less than 1.00 in the cases of all allotypes, thus providing a more fixed description to the C-terminal/proximal region (gray) as a whole with respect to the N-terminal/proximal region (black).

Among the N-regional position ligand residues occurring at >10%, nothing appears to prominently stand out at P3 and P4 although assignments were made to these positions via Edman sequencing. The occupancies that were observed were not necessarily captured by the motifs; a specific illustration of this is Ala (19.51%) at P3 of B*1510 (Table 12 and FIG. 16). This trend appeared likewise applicable at the P2 anchor, where with the exceptions of B*1508 and B*1510, occupants at this position among >10% of ligands from each of the remaining allotypes included additional side chains (for example, Ala at P2 in both B*1501 and B*1512) not accounted for by pooled sequencing. The C termini of each allotype are comprised of two amino acid specificities as shown by more than 80% of characterized peptides in all cases (Tables 9-13). In summary, comparing observed N- and C-regional occupancies among the characterized ligands underscores the flexibility of N-proximal versus the dominance of C-terminal preferences among the B*1501, B*1503, B*1508, B*1510, and B*1512 binding grooves.

A total of 40 specific ligands among the 449 characterized here (Tables A-E) overlapped across the peptide binding grooves of B*1501, B*1503, B*1508, and/or B*1512 (Table 14); as previously discussed from the information in Table 4, some of the overlapping ligands likewise coincided with ligands characterized by others from additional HLA-B15 allotypes including B*1502 and B*4601. Length variations among the overlapping ligands identified tended to mimic those observed among the entire set of ligands characterized, formerly discussed and illustrated in FIG. 15. Only seven overlapping ligands were longer than 9 amino acids in length (4 decamers and 3 undecamers), while 16 fell short of 9 residues long (6 heptamers and 10 octamers); less than 50% of the successful overlaps were therefore nonameric.

Throughout the mapping and sequencing approach that was developed and executed as outlined earlier (FIG. 6), an extensive comparison was first conducted upon ions occupying RP-HPLC fractions 6-19 from separations as shown in FIG. 11 of ~400 μg of peptides from each of B*1501, B*1503, B*1508, and B*1510, the first four B15 molecules prepared in the course of this study. From this, 21 peptide overlaps across B*1508 and B*1501 were defined. Similarly, eight ligands overlapping B*1501 and B*1503 were identified, and four ligands were found to overlap across B*1508, B*1503, and B*1501. A conservative estimate, based upon past examination of B*1501 ligands, is that the ion maps for each of the B15 allotypes represented at least 2,000 individual peptides per molecule (Prilliman et al. 1997), yet B*1510 was not observed to share ligand overlaps with B*1508, B*15011, or B*1503 (Table 14).

Figure 26:
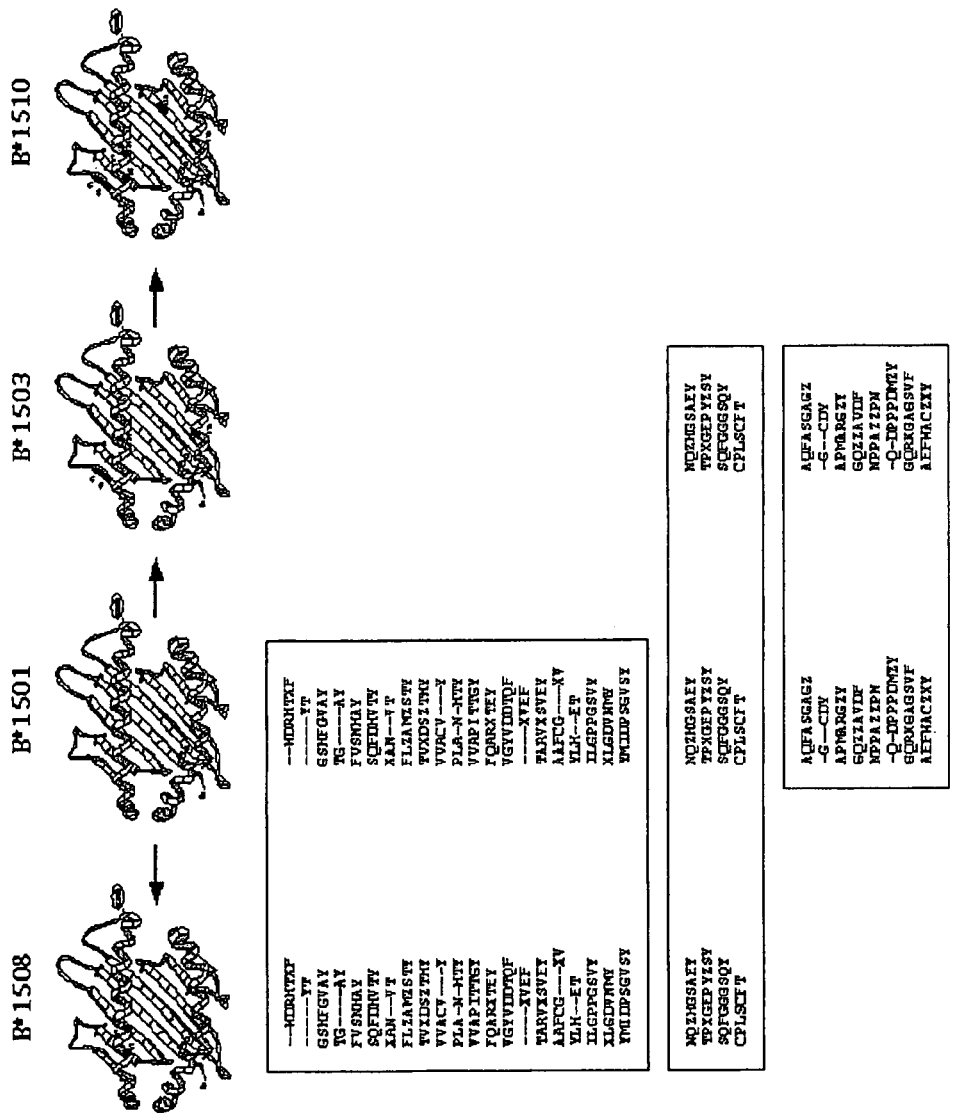
FIG. 26 is a graphical and tabular representation showing ligand overlaps identified by NanoES-MS mapping and characterized by NanoES-MSIMS during comparative analysis of B*1508, B*1501, B*1503, and B*1510 extracts. Ribbon diagrams of the class I antigen binding groove indicate residue substitutions (black, numbered from the first residue of the mature α-chain) between each B15 molecule with respect to B*1501. The peptides are categorized into three different groups from top to bottom as follows: ligands that overlap B*1508 and B*1501; ligands that overlap B*1508, B*1501, and B*1503; and ligands that overlap B*1501 and B*1503. Dashes represent positions at which amino acids could not be unambiguously assigned through the NanoES-MS/MS fragmentation patterns and/or Edman data obtained. Ligand residues that coincide with dominant and strong amino acids for the given motifs (FIGS. 15 and 16) are indicated in bold.

The sequence data indicates that overlapping ligands bind across divergent B*1508, B*1501, and B*1503 binding grooves but not B*1510. This pattern likewise accentuates an apparently dominant role for C-terminal anchors in natural peptide binding as discussed previously. FIG. 26 depicts, in the context of the class I peptide binding cleft, the locations of polymorphisms that individuate B*1508, B*1501, B*1503, and B*1510 and highlights the anchoring residues for the peptide overlaps according to the N-proximal and C-terminal specificities of their respective presenting molecule's motif (FIGS. 15 and 16). Bolding the amino acids of these overlapping ligands, which are in agreement with the traditional pooled motifs, underscores the trend whereby a C-terminal anchor sequence is conserved within overlaps while the N-proximal anchor is considerably more flexible in its location and/or sequence. A lack of overlaps with B*1510 could potentially be explained by the S→Y substitution observed between this allotype and the other three at $\alpha_2$ position 116. Thus, the conserved C-terminal anchors that facilitate the occurrence of B*1508, B*1501, and B*1503 overlaps fail to preferentially interact with the B*1510 C-terminal specificity pockets.

A further example provided here of how C-proximal auxiliary anchors might positively impact endogenous ligand binding is that eight of the peptides overlapping both the B*1508 and B*1501 antigen binding grooves bear Thr at $C^{-1}$, $C^{-2}$, or $C^{-3}$, and in four cases the peptides that bind B*1508/B*1501 or B*1508/B*1501/B*1503 are heptamers with Thr occupying P7, their C-terminal positions (FIG. 26). The prominent role of Thr as a C-terminal/proximal auxiliary anchor is dramatically illustrated by the B*1508/B*1501/B*1503 overlapping heptamer CPLSCFT (SEQ ID NO:60), where Thr provides a C-terminal anchor for this ligand not evident in the pooled motifs of the three allotypes.

Figure 27:
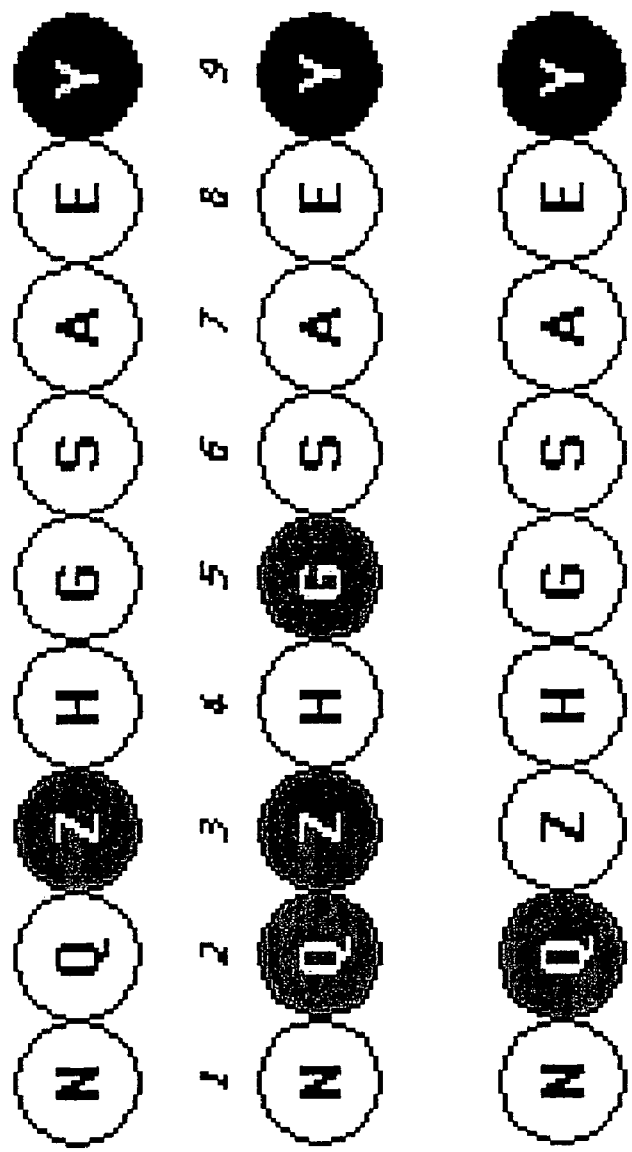
FIG. 27 is a pictorial representation of the proposed N-proximal and C-terminal anchoring of a nonamer overlapping B*1508, B*1501, and B*1503. The shared C-terminal anchoring preferences for Tyr in the NQZHGSAEY ligand among B*1508, B*1501, and B*1503 as defined by their respective motifs (FIGS. 15 and 16) are shaded black, while the varied N-proximal anchoring preferences likewise reflected in the motifs are cross-hatched. Ligand residues are numbered sequentially from the N terminus.

Distilling the data from the overlapping ligands among B*1501, B*1503, and B*1508 suggests a model for endogenous ligand binding whereby peptides are first anchored or held in the class I binding groove by their C termini. In order for a given peptide to remain stably fastened in the groove for successful trimer assembly and subsequent export from the cell, it is observed that following rigid anchoring at the C terminus as described, a ligand must be subsequently tethered into the class I antigen binding cleft at a more variably defined N-proximal position. Such is the case for peptide ligand NQZHGSAEY (SEQ ID NO:138), a nonamer that overlaps across B*1508, B*1501, and B*1503 (FIG. 24). According to this model (FIG. 27), a C-terminal Tyr securely anchors NQZHGSAEY (SEQ ID NO:138) into all three B15 allotypes, while a Gin at P2 anchors the peptide into B*1501 and B*1503 and a Gin/Lys (most likely a Lys based upon both motif assignments and fractional Edman sequencing data) at P3 provides additional anchoring for B*1501 and serves as the sole N-proximal anchor for B*1508. This model appears clearly applicable to at least 75% of the ligands presented in FIG. 26; for those peptides to which it does not evidently apply, the possible anchoring modes remain open to further speculation at the level of individual ligands.

Figure 22:
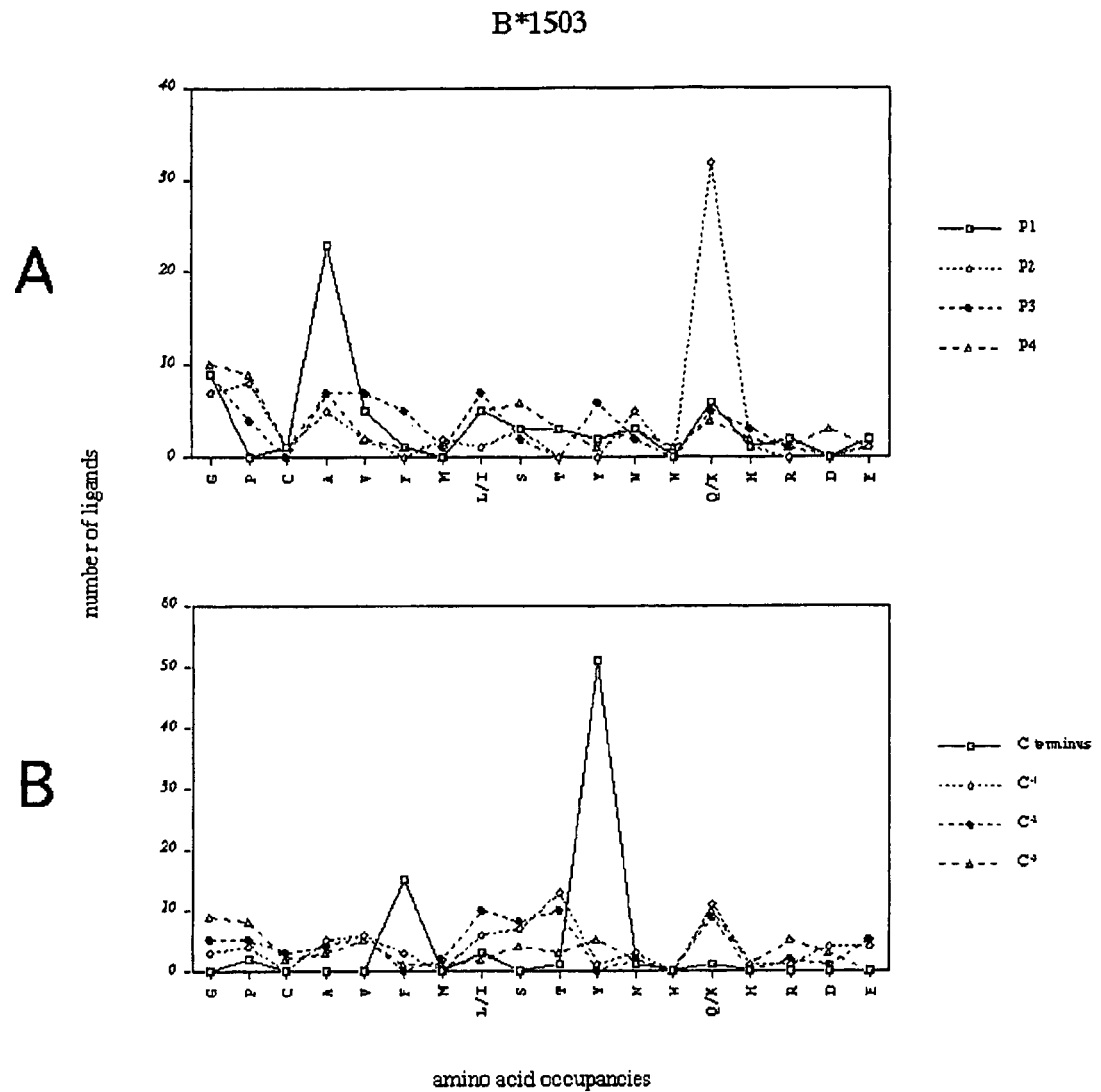
FIG. 22 is two graphs showing N- and C-regional diversity observed through alignments of B*1503 ligands. Frequency of occurrence for amino acids at the first (A) and final (B) four positions among the ligands characterized from B*1503 (Table B). The graphs were generated from separate N- and C-terminal data alignments.

For example, the B*1501/B*1503 overlap AQFASGAGZ (SEQ ID NO:135) (FIG. 26) may instead be additively stabilized through the N-proximal anchors indicated at P2 and P3 as well as at the N-terminal position, since Ala demonstrated significant P1 occupancy among both B*1501 and B*1503 ligands, as previously shown (FIGS. 21 and 22, A). Additionally, the four heptameric overlaps that were observed across B*1508/B*1501/B*1503, which terminate in Thr, could lie within the peptide binding groove such that they are anchored N-terminally/proximally and their C termini interact with the C-proximal regions of the groove, which have demonstrated preferences for Thr; these ligands might therefore fail to extend into the F-pocket. As compared with C-terminal sequences, both length and N-proximal specificity characteristics of ligands generally play secondary roles in the natural binding of B15 peptide epitopes.

Further stemming from the data obtained by comparatively examining B*1501, B*1503, B*1508, and B*1510 ligands, differential interactions with the chaperone tapasin specifically influence the loading of peptides into HLA-B15 molecules. Tapasin, an MHC-encoded chaperone discussed hereinabove (Herberg et al. 1998), is a recently-discovered 48 kDa transmembrane glycoprotein resident to the ER that directly interacts with both calreticulin and empty $\alpha$-chain/$\beta_2$m dimers to form a "loading complex" linked to TAP1/TAP2 (Sadasivan et al. 1996; Grandea III et al. 1997; Li et al. 1999). Tapasin is not a requirement for ligand loading via the typical endogenous processing pathway (Lewis et al. 1998; Peh et al. 1998), and aside from its proposed role in serving as a bridge between a class I dimer and the peptide transporter until release of mature trimers upon peptide binding, the exact role of tapasin during class I assembly is unknown (Pamer and Cresswell 1998). Interactions between nascent class I molecules and TAP1/TAP2 have, however, been shown to be influenced either directly or indirectly by $\alpha_3$ and positions 116 and 156 of $\alpha_2$ (Suh et al. 1999; Kulig et al. 1998; Neisig et al. 1996).

Of specific interest, past analysis of divergent HLA-B35 molecules has indicated that allotypes bearing an aromatic amino acid (Phe or Tyr) at position 116 interacted with TAP1/TAP2; allotypes bearing a Ser substitution at this site failed to demonstrate the interaction (Neisig et al. 1996). Likewise, data subsequently obtained for the sHLA transfectants utilized here according to established immunoprecipitation protocols (for example, Harris et al. 1998) indicates that although all four allotypes associate with calreticulin, B*1501, B*1503, and B*1508 do not associate with tapasin (and therefore not with TAP1/TAP2) whereas B*1510 does. Membrane-bound forms of B*1501 and B*1516 have previously been shown by others to not associate with TAP1/TAP2 (Neisig et al. 1996; de la Salle et al. 1997), demonstrating that results obtained from the sHLA transfects are in concordance with those of native molecules.

Though functionally divergent according to its pooled motif (FIG. 16) and the majority of peptides that it binds, B*1510 is capable of accommodating ligands with the properties favored by the B*1501, B*1503, and B*1508 binding grooves. Data both from individual ligands (Table D) and fractional Edman sequencing (Table 3) indicate that Tyr can occupy the C-terminal position, and specific examples in Table 4, including the spleen mitotic checkpoint BUB3$_{53-60}$ octamer YQHTGAVL (SEQ ID NO:32) and the splicing factor U2AF large chain$_{179-187}$ nonamer TQAPGNPVL (SEQ ID NO:37), attest to B-pocket flexibility. It is intriguing that among the peptides bound by B*1510 is the tapasin$_{354-362}$ nonamer HHSDGSVSL (SEQ ID NO:51); the peptide appears to occupy ligand extracts in a high copy number, as qualitatively based upon relative mass spectrometric ion intensities. Given this, as well as considering potential models of loading complex interactions suggested by others (Neisig et al. 1996; Elliott 1997), it can be extrapolated that a portion of tapasin, analogous to class II-associated invariant chain-derived peptides (Riberdy et al. 1992; Sette et al. 1992), extends into and blocks a region of the empty class I binding groove until it is displaced by an optimally-fitting ligand and/or secondary chaperone; this could also account for the differences in overall P2 flexibility observed between B*1510 peptides and those of the other three allotypes. Participating in ligand selection by this mechanism would describe a distinct peptide editing role for tapasin and could clarify the inability to detect overlaps between B*1510 and either B*1501, B*1503, or B*1508.

In addition to the initial search for overlaps across B*1501, B*1503, B*1508, and B*1510, a comparative analysis was performed between the ion maps of B*1501 and B*1512. As discussed previously hereinabove, such an examination is primarily important in revealing the presence of ligands bound by B*1512 but not B*1501 (Table 5). A number of overlapping ligands from B*1512, however, were additionally identified (Table 14). Conservative percentages of overlap subsequently observed among each of the four molecules from which ligands were characterized and the ancestral HLA-B15 allotype, B*1501, were determined as shown and described in Table 15.

As expected from an overview of their nearly identical ion maps, B*1501 and B*1512 demonstrated the highest overlap frequency between the allotypes at 70% among ions subjected to NanoES-MS/MS. After this, B*1503 and B*1508 respectively exhibited 14% and 9% overlap frequencies, while as shown earlier B*1510 completely failed to reveal overlaps with B*1501. The trend distinctly illustrates that the polymorphisms which distinguish the B*1503, B*1508, B*1510, and B*1512 peptide binding grooves from B*1501 are not functionally equivalent in terms of their impacts upon class I ligand association. However, it is also evident that they do not create concrete barriers to ligand binding. Because the repertoires of peptides bound by the various molecules examined may differ from B*1501 at frequencies greater than 80% (B*1508 and B*1503, Table 15) does not mean that they are unable to bind similar or completely identical peptides, a concept which has been incompletely addressed and occassionally negated by other studies grounded more upon pooled Edman sequencing, analysis of prominent extract constituents, or binding/reconstitution assays.

In particular and based upon previous research, the overlaps between B*1508 and B*1501 defined here would specifically not have been predicted (Barber et al. 1997); it may be anticipated by extension that other molecules differing solely by the polymorphism separating B*1508 and B*1501, for example B*1503 and B*1529 (Appendix A), yield similar overlap frequencies. Likewise, based upon the relatively high overlap frequency observed between B*1512 and B*1501, the substitutions at positions 166 and 167 distinguishing them exhibit a similarly subtle effect between A*2902 and A*2903 (which only differ from one another by the identical substitutions studied here; Prokupek et al. 1997) via mapping and sequencing of individual ligands. Systematically attempting to define the limits of overlap existence as conducted, therefore, demonstrates a critical departure from standard approaches which enhance predicting the abilities of different class I molecules to present overlapping ligands.

Comparative analyses of closely related soluble MHC class I molecules produced by the recombinant methods described herein, provide a means for assessing the functional impact of individual α-chain polymorphisms. The primary impetus for characterizing peptides extracted from class I molecules is to more precisely understand the influence of structural polymorphism upon the presentation of endogenous ligands. This is important since a fundamental realization of how naturally processed peptides bind to both individual and multiple class I allotypes can then be translated into protein and/or peptide-based therapies intended to elicit protective CTL responses. Therefore, an accurate interpretation of sequence data from such class I-bound peptides, either individual or pooled, should in turn further the selection of optimal viral and tumor-associated ligands to expedite the development of successful therapeutic applications.

The extensive examination of HLA-B15 ligands, as described herein, enhances understanding the rules that govern natural class I peptide presentation and is secondary evidence of the success and usefulness of the methodology for producing soluble MHC class I and II molecules described and claimed herein. By first building upon the traditional foundations provided by pooled Edman motifs (FIGS. 15 and 16), the data from over 400 individual peptides characterized from B*1501, B*1503, B*1508, B*1510, and B*1512 subsequently indicated that queries for potential epitopes specific to these allotypes would benefit from being optimized in three ways. First, although nonamers represent half of the ligand population, the other 50% of peptide epitopes range down to 7 and up to 12 amino acids in length. Second, effective N-proximal anchor requirements need not be strictly imposed at P2. Third, searches for ligands should weigh C-terminal/proximal sequence matches even more heavily than those of the N-region. The third trend revealed represent, the most substantial of the revised search criteria, since both length variations and lower sensitivity due to the diminishing returns and increasing backgrounds inherent to successive Edman sequencing cycles can C-regional motif trends (Stevanovic and Jung 1993). As stressed earlier, examples of this bias were evident here in both: (i) the stronger preference by B*1510 for peptides terminating in Val (absent from the pooled motif) rather than Phe (present in the pooled motif) (FIGS. 16 and 24B); and (ii) the inability of motifs to effectively reflect C-proximal auxiliary anchors (FIGS. 15; 16; and 21-25, B).

To illustrate the potential consequences of applying the modified search parameters described, the EBV structural antigen gp85, which has recently been implicated using a murine model as a favorable target against which protective CTLs might be generated (Khanna et al. 1999), was examined in the context of B*1501 to identify: (i) nonameric epitopes with motif-prescribed P2 and P9 occupancies; (ii) length variant epitopes with motif-prescribed P2 and P9 occupancies; and (iii) nonameric epitopes with flexible P2 occupancy (Table 16). Since only these three categories of ligands were designated, the inquiry was not exhaustive. However, the information extracted showed that, of the 98 possible epitopes identified, only the 22% within the first column would be placed under further experimental consideration if pooled motifs alone were applied in the search. This is not to imply that the data in this category is invalid but that it might be considerably incomplete for later applications. For example, if either of the $AMTSKFLMGTY_{172-182}$ (SEQ ID NO:205)(varying by length) or the $SAPLEKQLF_{123-131}$ (SEQ ID NO:246)(varying by P2 occupancy) peptides was demonstrated to elicit a more effective antigen-specific CTL response than any of the nonamers bearing standard motif P2/P9 assignments, this knowledge is pivotal to subsequent vaccine design; even if the two designated peptides evoked responses only equivalent to some of the nonamers, their non-motif length and/or sequences discrepancies could prove superior in conferring the ability to overlap multiple allotypes in addition to B*1501. This is advantageous since a vaccine consisting of a single or limited number of peptide specificities could theoretically be effective for protecting populations differing in HLA type (Loftus et al. 1995; Gulukota et al. 1996; Sidney et al. 1996c).

The majority of information collected from examining divergent HLA-B15 allotypes of sHLA molecules recombinantly produced according to the methodology of the present invention demonstrates that similar and occassionally identical peptide ligands are presented by the different B15 molecules so long as polymorphisms do not alter C-terminal anchoring pockets and while an N-proximal ligand residue can be subsequently anchored within the binding groove. Supporting data furthermore indicates that these principles additionally extend beyond the HLA-B15 allotypes described in specificity herein. Specifically, unpublished results by Ghosh and Wiley (noted in Bouvier and Wiley 1994) indicate that an octamer has been observed to successfully bind a class I molecule by its C terminus despite being shown through x-ray crystallography to not even reach the N-terminal pocket of the binding groove. In addition, a recently-described HIV-$gag_{197-205}$ CTL epitope presented by murine class 1 $K^d$ fails to show a motif-prescribed Tyr at P2 and instead associates stably through its conserved C terminus and an N-proximal preference for Gin at P3 (Mata et al. 1998). The rules established here through examination of hundreds of natural ligands from B*1501, B*1503, B*1508, B*1510, and B*1512 indicate that such occurrences may be more commonplace than exception, as both of these examples appear in agreement with the model in FIG. 27.

A step in developing therapies intended to elicit protective CTLs requires the selection of pathogen- and tumor-specific peptide ligands for presentation by MHC class I and class II molecules. Binding/reconstitution assays provide information that is biased due to their technical inconsistency and/or in vitro nature, while Edman sequencing of extracted class I peptide pools generates "motifs" that indicate that the optimal peptides are nonameric ligands bearing conserved P2 and P9 anchors; motifs have frequently been used to provide the search parameters for selecting potentially immunogenic epitopes that might be successfully presented by particular allotypes (Pamer et al. 1991; DiBrino et al. 1994; Kast et al. 1994; Davenport et al. 1995; Walden 1996; Holland et al.

1997; Zhang et al. 1997; Yoon et al. 1998; Chang et al. 1999). Therefore, to test the hypothesis that natural presentation overlaps exist despite the presence of various polymorphisms within the class I binding groove and thus determine how well pooled motifs actually represent their endogenously-derived constituents, ligands were purified from different sHLA molecules produced in hollow-fiber bioreactors, mapped by RP-HPLC and NanoES-MS, and sequenced by NanoES-MS/MS, all according to the methodology of the present invention.

Production of sHLA provides an efficient means of extracting large quantities of endogenous peptide ligands for the subsequent analyses, and comparative ion mapping of peptides extracted from distinct class I allotypes is a reliable method for detecting potential ligand overlaps. NanoES-MS/MS analysis then allows for sequence characterization to identify the overlap status of individual ion matches. The strategy developed to address overlap identification is additionally pertinent beyond the uses described herein. For example, similar mapping studies would be performed, with the primary intent instead of characterizing differences between maps, such as between pathogenically infected versus uninfected cell lines; the data obtained could contribute to identifying optimal vaccine epitopes. This concept is currently in the early stages of pursuit by several independent research teams (Veronese et al. 1996; van der Heeft et al. 1998). Successfully locating differences in a similar manner between B*1501 and B*1512 ion maps, as discussed herein, effectively supports this application.

Figure 5:
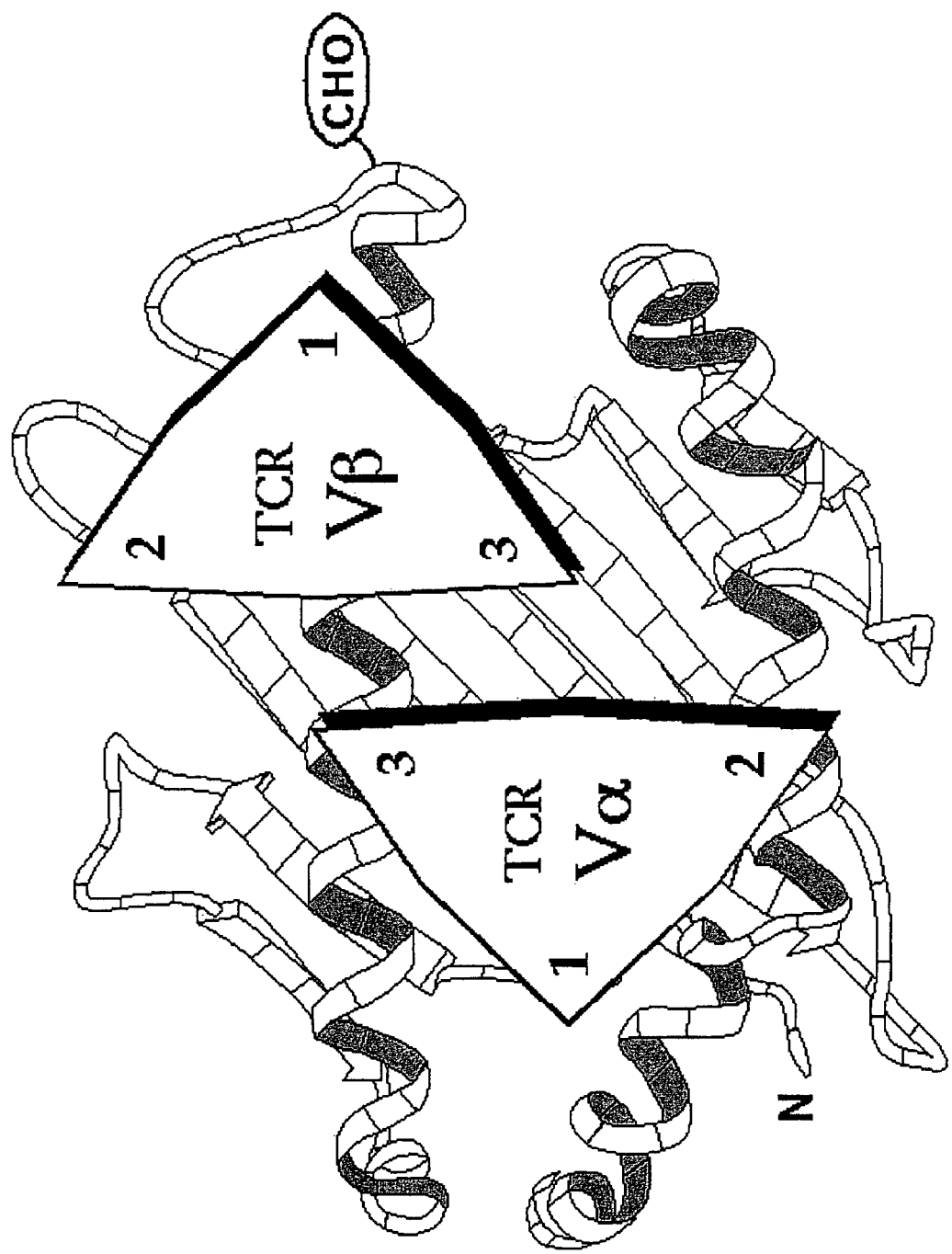
FIG. 5 is a schematic representation of the deduced contact region between the MHC class I $\alpha_1/\alpha_2$ and TCR $V_\alpha/B_\beta$ interfaces. From the diagonal orientation of the estimated binding footprints of CDRs 1, 2, and 3 (numbered) for each of TCR-$V_\alpha$ and $V_\beta$ with respect to the top of MHC-$\alpha_1$ and $\alpha_2$, the general interaction between TCR and MHC appears to predominantly involve $V_\alpha/V_\beta$ contact with both the class I solvent-accessible helical residues and the central portions of the bound ligand (not shown).
Figure 28:
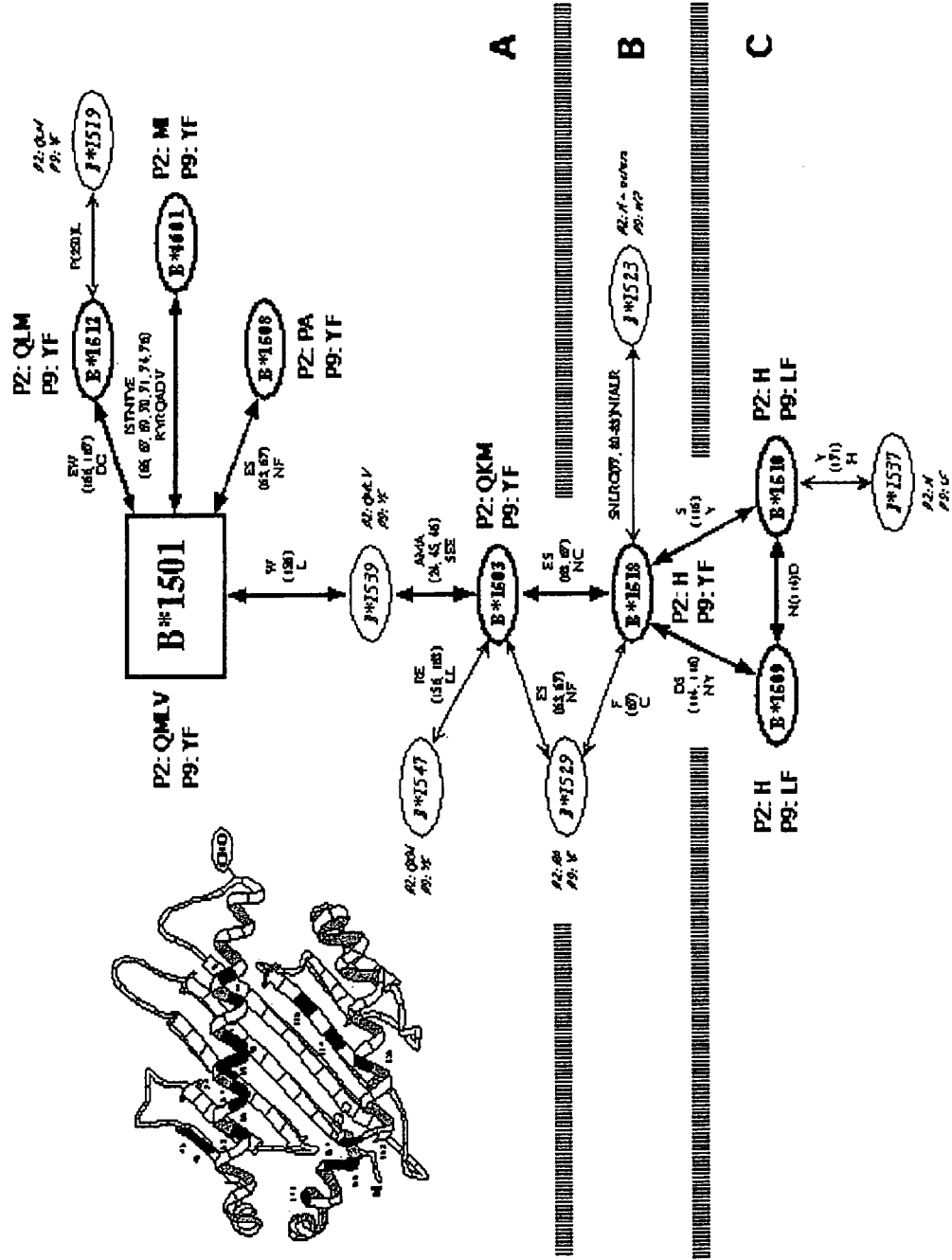
FIG. 28 is a pictorial schematic summarization the summary of structure-function relationships among the HLA-B15 allotypes from which ligands were characterized. HLA-B15 allotypes for which a motif is known are indicated in bold, while allotypes with currently undefined motifs are indicated in italics. Arrows are representative of single mutagenic events (which are specifically defined for each arrow); bold arrows emphasize evolutionary pathways between structures for which motifs have been described either here or elsewhere. P2 and P9 designations are listed. Tentative designations have been made for the italicized allotypes by extrapolation from known motifs in light of the polymorphisms present. P2/P9 specificities for B*1519 are based upon B*1512. P2/P9 specificities for B*1539 are based upon what has been observed between B*4402 and B*4403 (Fleischhauer et al. 1994). P2/P9 specificities for B*1529 are based upon B*1508. P2/P9 specificities for B*1523 are based upon what has been observed between B*1502 and B*1513 (Table 7), as well as observations between B*0801 and B*0802 (Arnett et al. 1998). P2/P9 specificities for B*1547 are based upon the relationship previously discussed between B*1503 and B*4801 (Martinez-Naves et al. 1997). P2/P9 specificities for B*1537 are based upon B*1402 (DiBrino et al. 1994). The three sections (A, B, and C) into which the molecules have been divided are discussed in the text. For reference, a ribbon diagram of the class I antigen binding groove indicating residue substitutions (black, numbered from the first residue of the mature α-chain) between the molecules with respect to B*1501 is provided.

FIG. 28 summarizes the α-chain substitutions and motif-derived P2 and P9 anchors for the HLA-B15 allotypes examined here, as well as additional allotypes indicated earlier in FIG. 5 that appear to serve as evolutionary intermediates between or extensions from B*1503, B*1510, B*1512, and B*1518. B*4601 is included since it differs from B*1501 by a single mutagenic event and overlaps with it were among peptides characterized in this study (Table 4). In section A, the allotypes B*1501, B*1503, B*1508, B*1512, and B*4601 have been shown to bind variously overlapping ligands; based upon the structurally-predicted motif anchors of the remaining molecules in this section including B*1519, B*1529, B*1539, and B*1547, it is suspected that ion mapping and characterization would reveal further overlaps according to the model shown in FIG. 27. Likewise, in section C the allotypes B*1509 and B*1510 have demonstrated overlapping ligands and will probably share some with B*1537.

Systematically mapping and characterizing 449 ligands from the related molecules B*1501, B*1503, B*1508, B*1510, and B*1512 demonstrates overall that the peptides bound by these allotypes: (i) vary in length from 7 to 12 residues; and (ii) are more conserved at their C termini that at their N-proximal positions. Flexibility at P2 in particular appears to arise at least in part from the combined effects of distinct steric and charge biases imposed respectively by α-helical and β-sheet structural residues throughout $\alpha_1$ and $\alpha_2$ of the various HLA-B15 molecules, while it is postulated that C-terminal preferences are influenced by tapasin-moderated loading selection within the ER.

Although not predictable from the pooled Edman motifs, the comparative peptide mapping strategy succeeded in identifying endogenously processed ligands which bind variously across the allotypes B*1501, B*1503, B*1508, and B*1512, but not B*1510. Overlapping peptide ligands appeared to favorably bind the first four B15 molecules since these allotypes share identical C-terminal anchoring pockets, whereas B*1510 diverges in this region. Endogenous peptide loading into the HLA-B15 allotypes therefore requires that a conserved C terminus be firmly anchored in the appropriate specificity pocket while N-proximal residues act more flexibly in terms of both location and sequence specificity to anchor the ligand into this binding groove region. Subsequently, the choice of allele-specific and/or overlapping peptide epitopes for CTL recognition may thus be contingent upon performing queries strongly based upon conserved C-terminal anchors.

Another embodiment of the present invention, as previously described herein-above, is the use of genomic DNA (gDNA) as the starting material for the production of the sHLA molecules described hereinbefore.

This alternative method of the present invention begins by obtaining genomic DNA which encodes the desired MHC class I or class II molecule. Alleles at the locus which encode the desired MHC molecule are PCR amplified in a locus specific manner. These locus specific PCR products may include the entire coding region of the MHC molecule or a portion thereof. In some cases a nested or hemi-nested PCR is applied to produce a truncated form of the class I or class II gene so that it will be secreted rather than anchored to the cell surface. In other cases the PCR will directly truncate the MHC molecule.

Locus specific PCR products are cloned into a mammalian expression vector and screened with a variety of methods to identify a clone encoding the desired MHC molecule. The cloned MHC molecules are DNA sequenced to insure fidelity of the PCR. Faithful truncated (i.e. sHLA) clones of the desired MHC molecule are then transfected into a mammalian cell line. When such cell line is transfected with a vector encoding a recombinant class I molecule, such cell line may either lack endogenous class I expression or express endogenous class I. It is important to note that cells expressing endogenous class I may spontaneously release MHC into solution upon natural cell death. In cases where this small amount of spontaneously released MHC is a concern, the transfected class I MHC molecule can be "tagged" such that it can be specifically purified away from spontaneously released endogenous class I molecules in cells that express class I molecules. For example, a DNA fragment encoding a His tail which will be attached to the protein may be added by the PCR reaction or may be encoded by the vector into which the gDNA fragment is cloned, and such His tail will further aid in purification of the class I molecules away from endogenous class I molecules. Tags beside a histidine tail have also been demonstrated to work and are logical to those skilled in the art of tagging proteins for downstream purification.

Cloned genomic DNA fragments contain both exons and introns as well as other non-translated regions at the 5' and 3' termini of the gene. Following transfection into a cell line which transcribes the genomic DNA (gDNA) into RNA, cloned genomic DNA results in a protein product thereby removing introns and splicing the RNA to form messenger RNA (mRNA), which is then translated into an MHC protein. Transfection of MHC molecules encoded by gDNA therefore facilitates reisolation of the gDNA, mRNA/cDNA, and protein. Production of MHC molecules in non-mammalian cell lines such as insect and bacterial cells requires cDNA clones, as these lower cell types do not have the ability to splice introns out of RNA transcribed from a gDNA clone. In these instances the mammalian gDNA transfectants of the present invention provide a valuable source of RNA which can be reverse transcribed to form MHC cDNA. The cDNA can then be cloned, transferred into cells, and then translated into protein. In addition to producing secreted MHC, such gDNA transfectants therefore provide a ready source of mRNA, and therefore cDNA clones, which can then be transfected into non-mammalian cells for production of MHC. Thus, the present invention which starts with MHC genomic DNA clones allows for the production of MHC in cells from various species.

A key advantage of starting from gDNA is that viable cells containing the MHC molecule of interest are not needed. Since all individuals in the population have a different MHC repertoire, one would need to search more than 500,000 individuals to find someone with the same MHC complement as a desired individual—this is observed when trying to find a match for bone marrow transplantation. Thus, if it is desired to produce a particular MHC molecule for use in an experiment or diagnostic, a person or cell expressing the MHC allele of interest would first need to be identified. Alternatively, in the method of the present invention, only a saliva sample, a hair root, an old freezer sample, or less than a milliliter (0.2 ml) of blood would be required to isolate the gDNA. Then, starting from gDNA, the MHC molecule of interest could be obtained via a gDNA clone as described herein, and following transfection of such clone into mammalian cells, the desired protein could be produced directly or in mammalian cells or from cDNA in several species of cells using the methods of the present invention described herein.

Current experiments to obtain an MHC allele for protein expression typically start from mRNA, which requires a fresh sample of mammalian cells that express the MHC molecule of interest. Working from gDNA does not require gene expression or a fresh biological sample. It is also important to note that RNA is inherently unstable and is not easily obtained as is gDNA. Therefore, if production of a particular MHC molecule starting from a cDNA clone is desired, a person or cell line that is expressing the allele of interest must traditionally first be identified in order to obtain RNA. Then a fresh sample of blood or cells must be obtained; experiments using the methodology of the present invention show that $\geq 5$ milliliters of blood that is less than 3 days old is required to obtain sufficient RNA for MHC cDNA synthesis. Thus, by starting with gDNA, the breath of MHC molecules that can be readily produced is expanded. This is a key factor in a system as polymorphic as the MHC system; hundreds of MHC molecules exist, and not all MHC molecules are readily available from mRNA. This is especially true of MHC molecules unique to isolated populations or of MHC molecules unique to ethnic minorities. Starting class I or class II protein expression from the point of genomic DNA simplifies the isolation of the gene of interest and insures a more equitable means of producing MHC molecules for study; otherwise, one would be left to determine whose MHC molecules are chosen and not chosen for study, as well as to determine which ethnic population from which fresh samples cannot be obtained should not have their MHC molecules included in a diagnostic assay.

While cDNA may be substituted for genomic DNA as the starting material, production of cDNA for each of the desired HLA class I types will require hundreds of different, HLA typed, viable cell lines, each expressing a different HLA class I type. Alternatively, fresh samples are required from individuals with the various desired MHC types. The use of genomic DNA as the starting material allows for the production of clones for many HLA molecules from a single genomic DNA sequence, as the amplification process can be manipulated to mimic recombinatorial and gene conversion events. Several mutagenesis strategies exist whereby a given class I gDNA clone could be modified at either the level of gDNA or at the cDNA resulting from this gDNA clone. The process of the present invention does not require viable cells, and therefore the degradation which plagues RNA is not a problem. Thus, from a given gDNA clone, any number of gDNA and cDNA MHC molecules can be produced.

Three useful products can be obtained from the mammalian cell line expressing HLA class I molecules from such a genomic DNA construct. The first product is the soluble class I MHC protein, which may be purified and utilized in various experimental strategies, including but not limited to epitope testing. Epitope testing is a method for determining how well discovered or putative peptide epitopes bind individual, specific class I or class II MHC proteins. Epitope testing with secreted individual MHC molecules has several advantages over the prior art, which utilized MHC from cells expressing multiple membrane-bound MHCs. While the prior art method could distinguish if a cell or cell lysate would recognize an epitope, such method was unable to directly distinguish in which specific MHC molecule the peptide epitope was bound. Lengthy purification processes might be used to try and obtain a single MHC molecule, but doing so limits the quantity and usefulness of the protein obtained. The novelty of the current approach is that individual MHC specificities can be utilized in sufficient quantity through the use of recombinant, soluble MHC proteins. Because MHC molecules participate in numerous immune responses, studies of vaccines, transplantation, immune tolerance, and autoimmunity can all benefit from individual MHC molecules provided in sufficient quantity.

A second important product obtained from mammalian cells secreting individual MHC molecules is the peptide cargo carried by MHC molecules. Class I and class II MHC molecules are really a trimolecular complex consisting of an alpha chain, a beta chain, and the alpha/beta chain's peptide cargo to be reviewed by immune effector cells. Since it is the peptide cargo, and not the MHC alpha and beta chains, which marks a cell as infected, tumorigenic, or diseased, there is a great need to characterize the peptides bound by particular MHC molecules. For example, characterization of such peptides will greatly aid in determining how the peptides presented by a person with MHC-associated diabetes differ from the peptides presented by the MHC molecules associated with resistance to diabetes. As stated above, having a sufficient supply of an individual MHC molecule, and therefore that MHC molecules bound peptides, provides a means for studying such diseases. Because the method of the present invention provides quantities of MHC protein previously unobtainable, unparalleled studies of MHC molecules and their important peptide cargo can now be facilitated.

The methodology for producing sHLA from gDNA, while similar to the methodology for producing sHLA from cDNA, is different and as such requires different and/or unique steps and/or processes for its completion. One exemplary detailed production methodology for use gDNA as the starting material for the production of MHC class I or II molecules is described herein below.

Genomic DNA Extraction

Figure 29:
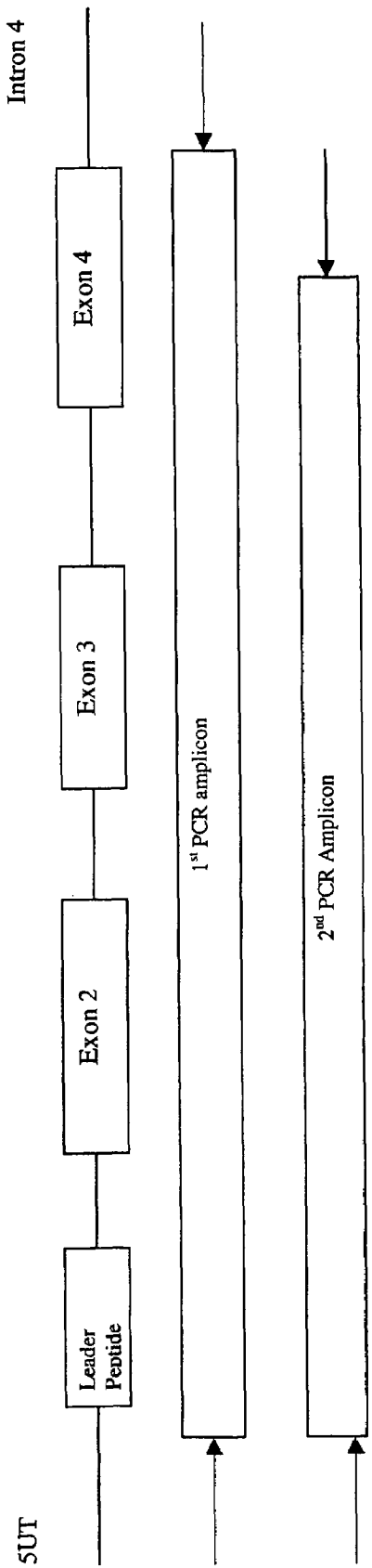
FIG. 29 is a pictorial representation of the PCR strategy for the production of soluble HLA from gDNA according to the methods of the present invention.

Greater than or equal to 200 ul of sample either blood, plasma, serum, buffy coat, body fluid or up to $5 \times 10^6$ lymphocytes in 200 ul phosphate buffered saline was used to extract genomic DNA using the QIAampr DNA Blood Mini Kit blood and body fluid spin protocol. Genomic DNA quality and quantity was assessed using optical density readings at 260 nm and 280 nm PCR Strategy Primers have been designed for HLA-A, -B and -C loci in order to produce a truncated amplicon of the human class I MHC using a two-stage PCR strategy. The first stage PCR uses a primer set that amplify from the 5' Untranslated region to Intron 4. This amplicon is used as a template for the second PCR which results in a truncated version of the MHC Class I gene by utilizing a 3' primer that sits down in exon 4 at codon 298 (including the leader peptide), the 5' primer remains the same as the 1$^{st}$ PCR. An overview of this PCR strategy can be seen in FIG. 29. The primers for each locus are listed in Table 17. Different HLA-B locus alleles require primers with different restriction cut sites depending on the nucleotide sequence of the allele. Hence there are two 5' and two 3' truncating primers for the HLA-B locus.

1. Primary PCR Materials

An Eppendorf Gradient Mastercycler is used for all PCR. H$_2$O: Dionized ultra filtered water (DIUF) Fisher Scientific, W2-4,41. PCR nt mix (10 mM each deoxyribonucleoside triphosphate [dNTP]), Boehringer Manheim, #1814, 362. 10× Pfx Amplification buffer, pH 9.0, GibcoBRLR, part #52806, formulation is proprietary information. 50 mM MgSO$_4$, GibcoBRLR, part #52044. Platinumâ Pfx DNA Polymerase (B Locus only), GibcoBRLR,11708-013. Pfu DNA Polymerase (A and C Locus), Promega, M7741. Pfu DNA Polymerase 10× reaction Buffer with MgSO$_4$, 200 mM Tris-HCL, pH 8.8, 100 mM KCL, 100 mM (NH$_4$)$_2$SO$_4$, 20 mMMgSO$_4$, 1 mg/ml nuclease free BSA, 1% TritonrX-100. gDNA Template. Amplification primers (in ng/ul):
a. A locus: 5' sense PP5UTA (300); 3'antisense PPI4A (300)
b. B locus (Not B*39's): sense PP5UTB (300); antisense PPI4B (300)
c. B locus (B*39's): sense 5UTB39 (300); antisense PPI4B (300)
d. C Locus: sense 5PKCE (300); antisense PPI4C (300).

B. Secondary PCR (also used for colony PCR)

H$_2$O: Dionized ultra filtered water (DIUF) Fisher Scientific, W2-4,41. PCR nt mix (10 mM each deoxyribonucleoside triphosphate [dNTP]), Boehringer Manheim, #1814, 362. Pfu DNA Polymerase, Promega, M7741. Pfu DNA Polymerase 10× reaction Buffer with MgSO$_4$, 200 mM Tris-HCL, pH 8.8, 100 mM KCL, 100 mM (NH$_4$)$_2$SO$_4$, 20 mM MgSO$_4$, 1 mg/ml nuclease free BSA, 1% TritonrX-100. Template 1:100 dilution of the primary PCR product. Amplification primers (in ng/ul):
a. A-locus: 5' sense PP5UTA (300), 3' antisense PP3PEI (300)
b. B-locus: sense PP5UTB (300), antisense PP3PEI (300)
c. B-locus: sense PP5UT (300), antisense PP3PEIH (300)
d. B-locus B39's: sense 5UTB39 (300), antisense PP3PEIH (300)
e. C-locus: sense 5PKCE (300), antisense PP3PEI (300)
f. C-locus Cw*7's: sense 5PKCE (300), antisense 3PEIHC7 (300)

C. Gel Purification of PCR Products and Vectors

Dark Reader Transilluminator Model DR-45M, Clare Chemical Research. SYBR Green, Molecular Probes Inc. Quantum Prep Freeze 'N Squeeze DNA Gel Extraction Spin Columns, Bio-Rad Laboratories, 732-6165.

D. Restriction Digests, Ligation and Transformation

Restriction enzymes from New England Biolabs: EcoR I #RO101S; Hind III #R0104S; Xba I #R0145S. T4 DNA Ligase, New England Biolabs, #M0202S. pcDNA3.1(−), Invitrogen Corporation, V795-20. 10× Buffers from New England Biolabs. EcoR I buffer, 500 mM NaCl, 1000 mM Tris-HCL, 10 mM MgCL$_2$, 0.25% Triton-X 100, pH 7.5. T4 DNA ligase buffer, 500 mM Tris-HCL, 100 mM MgCL$_2$, 100 mM DTT, 10 mM ATP, 250 ug/ml BSA, pH 7.5. NEB buffer 2, 500 mM NaCl, 100 mM Tris-HCl, 100 mM MgCl$_2$, 10 mM DDT, pH 7.9. 100× BSA, New England Biolabs. Z-Competent *E. coli* Transformation Buffer Set, Zymo Research, T3002. *E. coli* strain JM109. LB Plates with 100 ug/ml ampicillin. LB media with 100 ug/ml ampicillin E. Plasmid Extraction Wizard Plus SV minipreps, Promega, #A1460

3. Sequencing of Clones

Thermo Sequenase Primer Cycle Sequencing Kit, Amersham Pharmacia Biotech, 25-2538-01. CY5 labeled primers (Table 18). Alfexpress automated DNA sequencer, Amersham Pharmacia Biotech.

4. Gel Casting

PagePlus 40% concentrate, Amresco, E562, 500 ml. Urea, Amersham Pharmacia Biotech, 17-0889-01,500 g. N'N'N'N'-tetramethylethyleneiamine (TEMED), APB. Ammonium persulphate (10% solution), APB. Boric acid, APB. EDTA-disodium salt, APB. Tris, APB. Bind-Saline, APB. Isopropanol, Sigma. Glacial Acetic Acid, Fisher Biotech. DIUF water, Fisher Scientific. Ethanol 200-proof.

5. Plasmid Preparation for Electroporation

Qiagen Plasmid Midi kit, Qiagen Inc., 12143.

A. Electroporation

Biorad Gene Pulser with capacitance extender, Bio-Rad Laboratories. Gene Pulser Cuvette, Bio-Rad Laboratories. Cytomix: 120 mM KCl, 0.15 mM CaCl$_2$, 10 mMK$_2$HPO$_4$/KH$_2$PO$_4$, pH 7.6, 25 mM Hepes, pH 7.6, 2 mM EGTA, pH 7.6, 5 mM MgCl$_2$, pH 7.6 with KOH. RPMI 1640+20% Foetal Calf Serum+Pen/strep. Haemacytometer. Light Microscope. CO$_2$ 37° Incubator. Cells in log phase.

Methods used for the production of soluble human HLA Class I and II proteins in mammalian cells from gDNA.

1. Primary PCR

| A. A-Locus and C-Locus | |
|---|---|
| 10x Pfu buffer | 5 ul |
| 5' Primer (300 ng/ul) | 1 ul |
| 3' Primer (300 ng/ul) | 1 ul |
| dNTP's (10 mM each) | 1 ul |
| gDNA (>>50 ng/ul) | 10 ul |
| DIUF H$_2$0 | 31.4 ul |
| Pfu DNA Polymerase | 0.6 ul |
| 96° C.   2 min. | |
| 95° C.   1 min | x35 |
| 58° C.   1 min | x35 |
| 73° C.   5 min | x35 |
| 73° C.   10 min | |
| B. B-locus | |
| 10x Pfx buffer | 5 ul |
| 5' Primer (300 ng/ul) | 1 ul |
| 3' Primer (300 ng/ul) | 1 ul |
| dNTP's (10 mM each) | 1.5 ul |
| MgSO$_4$ (50 mM) | 1 ul |
| gDNA (100 ng/ul) | 1 ul |
| DIUF H$_2$O | 40 ul |
| Pfx DNA Polymerase | 0.5 ul |
| 94° C.   2 min. | |
| 94° C.   1 min | x35 |
| 60° C.   1 min | x35 |
| 68° C.   3.5 min | x35 |
| 68° C.   5 min | |

2. Gel Purification of PCR (all PCR and Plasmids are Gel Purified)

Mix primary PCR with 5 ul of 10× SYBR green and incubate at room temperature for 15 minutes then load on a 2% agarose gel. Visualize on the Dark Reader and purify using the Quantum Prep Freeze and Squeeze extraction kit according to the manufacturers instructions.

3. Secondary PCR of A, B and C Loci

| | |
|---|---|
| 10x Pfu buffer | 5 ul |
| 5' Primer (300 ng/ul) | 1.0 ul |
| 3' Primer (300 ng/ul) | 1.0 ul |
| dNTP's (10 mM each) | 1 ul |
| 1:100 1° PCR | 10 ul |
| DIUF H$_2$0 | 31.4 ul |
| Pfu DNA Polymerase | 0.6 ul |
| 96° C. 2 min. | |
| 95° C. 1 min | x35 |
| 56° C. 1 min | x35 |
| 73° C. 4 min | x35 |
| 73° C. 7 min | |

4. Restriction Digests

| | |
|---|---|
| 2° PCR (gel purified) | 30 ul |
| Restriction enzyme 1 | X ul |
| Restriction enzyme 2 | X ul |
| 10x buffer | 5 ul |
| 100x BSA | 0.5 ul |
| DIUF H$_2$O | 10.5 ul |

The cut sites incorporated into the PCR primers for each individual PCR will determine the enzymes used. The expression vector pcDNA3.1 (−) will be cut in a similar manner.

5. Ligation

| | |
|---|---|
| pcDNA3.1(−) cut with same enzymes as PCR | x ng |
| Cut PCR | y ng |
| 10x T4 DNA ligase buffer | 2 ul |
| T4 DNA Ligase | 1 ul |
| DIUF H$_2$0 | up to 20 ul |

The ratio of vector to insert will vary between samples, a good starting point is a ratio of 1:6

6. Transformation

Transform JM109 using competent cells made using Z-competent *E. coli* Transformation Kit and Buffer Set.

7. Colony PCR and Restriction Digests

Either following the secondary PCR protocol or carrying out another restriction digest can be used to screen the vector for the appropriate insert.

8. Mini Preps of Colonies with Insert

Use the Wizard Plus SV minipreps and follow the manufacturers instructions. Make glycerol stocks before beginning extraction protocol.

9. Sequencing of Positive Clones and Gel Casting

Using the Thermo Sequenase Primer Cycle Sequencing Kit

| | |
|---|---|
| A, C, G or T mix | 3 ul |
| CY5 Primer 1 pm/ul | 1 ul |
| DNA template 100 ng/ul | 5 ul |
| 96° C. 2 min | |
| 96° C. 30 sec | x25 |
| 61° C. 30 sec | x25 |

Add 6 ul formamide loading buffer and load 10 ul onto sequencing gel Analyse sequence for good clones with no misincorporations.

10. Gel Casting

A. Prepare a 10× TBE stock solution for the sequencing gel mix:

| | 500 mL |
|---|---|
| Tris | 60.5 g |
| EDTA | 1.85 g |
| Boric Acid | 25.5 g |
| Fisher DIUF H$_2$O | 440 mL |

Filter using a 0.22m or 0.45m filter and store at 4° C. until required.

11. Prepare a 10× TBE Stock Solution for the Running Buffer:

| | 1 L |
|---|---|
| Tris | 121.0 g |
| EDTA | 3.7 g |
| Boric Acid | 51.0 g |
| Ultra pure H$_2$O | 880 mL |

12. Prepare the Sequencing Gel Mix:

| | 1 Gel, 6% PagePlus |
|---|---|
| Urea | 19.8 g |
| PagePlus 40% conc. | 7.95 mL |
| 10x TBE | 5.5 mL |
| Fisher DIUF H$_2$O | 25.3 mL |

Filter using a 0.22 m or 0.45 m filter.

Initiate polymerization of the sequencing gel by adding 330 uL of a freshly made 10% APS solution and 33 uL of TEMED. Cast a 0.5 mm sequencing gel and allow it to polymerize for 5 hours.

13. Midi Preps

Prepare plasmid for electroporation using the Qiagen Plasmid Midi Kit according to the manufacturers instructions.

14. Electroporation

Electroporations are performed as described in "The Bw4 public epitope of HLA-B molecules confers reactivity with natural killer cell clones that express NKb1, a putative HLA receptor. Gumperz, J. E., V. Litwin, J. H. Phillips, L. L. Lanier and P. Parham. J. Exp. Med. 181:1133-1144, 1995," which is herein expressly incorporated by reference in its entirety.

15. Screening for Production of Soluble HLA

An ELISA is used to screen for the production of soluble HLA, see ELISA protocol.

ELISA Protocol

Solutions:

3 N H$_2$SO$_4$:

| For 500 ml: | 200 ml | H$_2$O |
|---|---|---|
| | 300 ml | 5 N H$_2$SO$_4$ |

Store at Room-Temperature

10× PBS (PH 7.4):

|  | 26.8 mM | KCl |
|---|---|---|
|  | 14.7 mM | KH$_2$PO$_4$ |
|  | 1.37 M | NaCl |
|  | 81 mM | Na$_2$HPO$_4$ |
| For 1000 ml: | 2 g | KCl |
|  | 2 g | KH$_2$PO$_4$ anhydrous |
|  | 80 g | NaCl |
|  | 11.5 g | Na$_2$HPO$_4$ |

Add H$_2$O
Adjust pH to 7.4
Add up with H$_2$O to 1000 ml
Filter
Store at 4° C.

TBS Coating Buffer (pH 8.5):

|  | 25 mM |  | Tris-HCl |  | pH 8.5 |
|---|---|---|---|---|---|
|  | 150 mM |  | NaCl |  |  |
| For 1000 ml: | 100 ml |  | 10x | TBS | pH 8.5 |
|  |  |  | 900 ml | H$_2$O |  |

Store at 4° C.

10% BSA

| For 250 ml: | 25 g | BSA |
|---|---|---|

Add H$_2$O
Stir to dissolve
Add H$_2$O up to 225 ml
Filter
Store at 4° C.
(Add 10x PBS prior to use)

ELISA WASH

|  | 2.68 mM |  | KCl |  |
|---|---|---|---|---|
|  | 1.47 mM |  | KH$_2$PO$_4$ |  |
|  | 137 mM |  | NaCl |  |
|  | 8.1 mM |  | Na$_2$HPO$_4$ |  |
|  | 0.05% |  | Tween-20 |  |
| For 4000 ml: | 400 ml |  | 10x | PBS |
|  |  |  | 3598 ml | H$_2$O |
|  |  |  | 2 ml | Tween-20 |

Store at 4° C.

OPD Substrate Solution for HRP:

|  | 0.05 M |  | Na$_2$HPO$_4$ | pH 5.0 |
|---|---|---|---|---|
|  | 0.025 M |  | Citrate |  |
|  | 0.4 mg/ml |  | OPD |  |
|  | 0.012% |  | H$_2$O$_2$ |  |
| For 10 ml: | 10 ml | 0.05 M | Phosphate-citrate buffer | pH 5.0 |
|  |  | 2 tablets | OPD (2 mg ea) | (Sigma; P-6787) |
|  |  | 4 µl | 30% Hydrogen peroxide (H$_2$O$_2$) | (Sigma; H1009) |

Always prepare fresh
Use within 1 hour of preparation
Add fresh 30% H$_2$O$_2$ immediately prior to use 0.05 M Phosphate-Citrate Buffer:

|  | 0.05 M |  | Na$_2$HPO$_4$ | pH 5.0 |
|---|---|---|---|---|
|  | 0.025 M |  | Citrate |  |
| For 1000 ml: | 7.10 g |  | Na$_2$HPO$_4$ anhydrous (Dibasic) |  |
|  | 5.25 g |  | Citric acid monohydrate |  |

Add ddH$_2$O
Adjust pH to 5.0, if necessary
Add ddH$_2$O to a final volume of 1000 ml
Filter
Store at room temperature The HLA ELISA Procedure For biochemical analysis, monomorphic monoclonal antibodies are particularly useful for identification of HLA locus products and their subtypes W6/32 is one of the most common monoclonal antibodies (mAb) used to characterize human class I major histocompatibility complex (MHC) molecules. It is directed against monomorphic determinants on HLA-A, -B and -C heavy chains, which recognizes only mature complexed class I molecules and recognizes a conformational epitope on the intact MHC molecule containing both beta2-microglobulin (b2m) and the heavy chain (HC). W6/32 binds a compact epitope on the class I molecule that includes both residue 3 of beta2m and residue 121 of the heavy chain (Ladasky J J, Shum B P, Canavez F, Seuanez H N, Parham P. Residue 3 of beta2-microglobulin affects binding of class I MHC molecules by the W6/32 antibody. Immunogenetics 1999 April;49(4):312-20.). The constant portion of the molecule W6/32 binds to is recognized by CTLs and thus can inhibit cytotoxicity. The reactivity of W6/32 is sensitive to the amino terminus of human beta2-microglobulin (Shields M J, Ribaudo R K. Mapping of the monoclonal antibody W6/32: sensitivity to the amino terminus of beta2-microglobulin. Tissue Antigens 1998 May;51(5):567-70). W6/32 is available biotinylated (Serotec MCA81B) offering additional variations in ELISA Procedures.

Anti-human b2m (HRP) (DAKO P0174) recognizes denatured as well as complexed b2m. Although in principle anti-b2m reagents could be used for the purpose of identification of HLA molecules, they are less suitable when association of heavy chain and b2m is weak. The patterns of class I molecules precipitated with W6/32 and anti-b2m are usually indistinguishable [Vasilov, 1983 #10].

Rabbit anti-b2-microglobulin dissociates b2-microglobulin from heavy chain as a consequence of binding (Rogers, M. J., Appella, E., Pierotti, M. A., Invemizzi, G., and Parmiani, G. (1979) Proc Natl. Acad. Sci. U.S.A. 76, 1415-1419). It also has been reported that rabbit anti-human b2-microglobulin dissociates b2-microglobulin from HLA heavy chains upon binding (Nakamuro, K., Tanigaki, N., and Pressman, D. (1977) Immunology 32,139-146.). This anti-human b2m antibody is also available unconjugated (DAKO A0072).

The W6/32-HLA Sandwich ELISA

Sandwich assays can be used to study a number of aspects of protein complexes. If antibodies are available to different components of a heteropolymer, a two-antibody assay can be designed to test for the presence of the complex. Using a variation of these assays, monoclonal antibodies can be used to test whether a given antigen is multimeric.

The W6/32-anti-b2m antibody sandwich assay is one of the best techniques for determining the presence and quantity of sHLA. Two antibody sandwich assays are quick and accurate, and if a source of pure antigen is available, the assay can be used to determine the absolute amounts of antigen in unknown samples. The assay requires two antibodies that bind to non-overlapping epitopes on the antigen. This assay is particularly useful to study a number of aspects of protein complexes.

To detect the antigen (sHLA), the wells of microtiter plates are coated with the specific (capture) antibody W6/32 followed by the incubation with test solutions containing antigen. Unbound antigen is washed out and a different antigen-specific antibody (anti-b2m) conjugated to HRP is added, followed by another incubation. Unbound conjugate is washed out and substrate is added. After another incubation, the degree of substrate hydrolysis is measured. The amount of substrate hydrolyzed is proportional to the amount of antigen in the test solution.

The major advantages of this technique are that the antigen does not need to be purified prior to use and that the assays are very specific. The sensitivity of the assay depends on 4 factors:

(1) The number of capture antibody
(2) The avidity of the capture antibody for the antigen
(3) The avidity of the second antibody for the antigen
(4) The specific activity of the labeled second antibody Use an ELISA protocol template and label a clear 96-well polystyrene assay plate. Polystyrene is normally used as a microtiter plate. (Because it is not translucent, enzyme assays that will be quantitated by a plate reader should be performed in polystyrene and not PVC plates).

| Company | Plate | Specificity | Cat# |
|---|---|---|---|
| Nunc | Maxisorp StarWell Modules Framed 8-well strips | standard/untreated | 441653 |

Coating of the W6/32 should be performed in Tris buffered saline (TBS); pH 8.5. Prepare a coating solution of 8.0 µg/ml of specific W6/32 antibody in TBS (pH 8.5). Although this is well above the capacity of a microtiter plate, the binding will occur more rapidly. Higher concentrations will speed the binding of antigen to the polystyrene but the capacity of the plastic is only about 100 ng/well (300 ng/cm$^2$), so the extra protein will not bind. If using W6/32 of unknown composition or concentration, first titrate the amount of standard antibody solution needed to coat the plate versus a fixed, high concentration of labeled antigen. Plot the values and select the lowest level that will yield a strong signal. Do not include sodium azide in any solutions when horseradish peroxidase is used for detection.

Immediately coat the microtiter plate with 100 µl per well using a multichannel pipet. Standard polystyrene will bind antibodies or antigens when the proteins are simply incubated with the plastic. The bonds that hold the proteins are non-covalent, but the exact types of interactions are not known. Shake the plate to ensure that the antigen solution is evenly distributed over the bottom of each well. Seal the plate with plate sealers (sealplate adhesive sealing film, nonsterile, 100 per unit; Phenix (1-800 767-0665); LMT-Seal-EX) or sealing tape to Nunc-Immuno™ Modules (# 236366). Incubate at 4° C. overnight. Avoid detergents and extraneous proteins. Next day, remove the contents of the well by flicking the liquid into the sink or a suitable waste container. Remove last traces of solution by inverting the plate and blotting it against clean paper toweling. Complete removal of liquid at each step is essential for good performance. Wash the plate 10 times with Wash Buffer (PBS containing 0.05% Tween-20) using a multi-channel ELISA washer.

After the last wash, remove any remaining Wash Buffer by inverting the plate and blotting it against clean paper toweling. After the W6/32 is bound, the remaining sites on the plate must be saturated by incubating with blocking buffer made of 3% BSA in PBS. Fill the wells with 200 µl blocking buffer. Cover the plates with an adhesive strip and incubate overnight at 4° C. Alternatively, incubate for at least 2 hours at room temperature which is, however, not the standard procedure. Blocked plates may be stored for at least 5 days at 4° C. Good pipetting practice is most important to produce reliable quantitative results. The tips are just as important a part of the system as the pipette itself. If they are of inferior quality or do not fit exactly, even the best pipette cannot produce satisfactory results.

When maximum levels of accuracy are stipulated, prewetting should be used at all times. To do this, the required set volume is first drawn in one or two times using the same tip and then returned. Prewetting is absolutely necessary on the more difficult liquids such as 3% BSA. Do not prewet, if your intention is to mix your pipetted sample thoroughly with an already present solution. However, prewet only for volumes greater than 10 µl. In the case of pipettes for volumes less than 10 µl the residual liquid film is as a rule taken into account when designing and adjusting the instrument. The tips must be changed between each individual sample. With volumes <10 µl special attention must also be paid to drawing in the liquid slowly, otherwise the sample will be significantly warmed up by the frictional heat generated. Then slowly withdraw the tip from the liquid, if necessary wiping off any drops clinging to the outside. To dispense the set volume hold the tip at a slight angle, press it down uniformly as far as the first stop.

In order to reduce the effects of surface tension, the tip should be in contact with the side of the container when the liquid is dispensed. After liquid has been discharged with the metering stroke, a short pause is made to enable the liquid running down the inside of the tip to collect at its lower end. Then press it down swiftly to the second stop, in order to blow out the tip with the extended stroke with which the residual liquid can be blown out. In cases that are not problematic (e.g. aqueous solutions) this brings about a rapid and virtually complete discharge of the set volume. In more difficult cases, a slower discharge and a longer pause before actuating the extended stroke can help. To determine the absolute amount of antigen (sHLA), sample values are compared with those obtained using known amounts of pure unlabeled antigen in a standard curve.

For accurate quantitation, all samples have to be run in triplicate, and the standard antigen-dilution series should be included on each plate. Pipetting should be preformed without delay to minimize differences in time of incubation between samples. All dilutions should be done in blocking buffer. Thus, prepare a standard antigen-dilution series by successive dilutions of the homologous antigen stock in 3% BSA in PBS blocking buffer. In order to measure the amount of antigen in a test sample, the standard antigen-dilution series needs to span most of the dynamic range of binding. This range spans from 5 to 100 ng sHLA/ml.

A stock solution of 1 µg/ml should be prepared, aliquoted in volumes of 300 µl and stored at 4° C. Prepare a 50 ml batch of standard at the time. (New batches need to be compared to the old batch before used in quantitation). Use a tube of the standard stock solution to prepare successive dilutions according to the scheme below. While standard curves are necessary to accurately measure the amount of antigen in test samples, they are unnecessary for qualitative "yes/no" answers.

For accurate quantitation, the test solutions containing sHLA should be assayed over a number of at least 4 dilutions to assure to be within the range of the standard curve. Prepare serial dilutions of each antigen test solution in blocking buffer (3% BSA in PBS). Standard dilutions for purified, crude or flow through samples are given below:

After mixing, prepare all dilutions in disposable U-bottom 96 well microtiter plates before adding them to the W6/32-coated plates with a multipipette. Add 150 µl in each well. To further proceed, remove any remaining blocking buffer and wash the plate as described above. The plates are now ready for sample addition. Add 100 µl of the sHLA containing test solutions and the standard antigen dilutions to the antibody-coated wells. Cover the plates with an adhesive strip and incubate for exactly 1 hour at room temperature. After incubation, remove the unbound antigen by washing the plate 10× with Wash Buffer (PBS containing 0.05% Tween-20) as described.

Prepare the appropriate developing reagent to detect sHLA. Use the second specific antibody, anti-human b2m-HRP (DAKO P0174/0.4 mg/ml) conjugated to Horseradish Peroxidase (HRP). Dilute the anti-human b2m-HRP in a ratio of 1:1,000 in 3% BSA in PBS. (Do not include sodium azide in solutions when horseradish peroxidase is used for detection).

|      | No. of plates | Total Antibody | anti-b2m-HRP | 3% BSA in PBS |
|------|---------------|----------------|--------------|---------------|
| Mix: | 1             | 10 ml          | 10 µl        | 10 ml         |
|      | 2             | 20 ml          | 20 µl        | 20 ml         |
|      | 3             | 30 ml          | 30 µl        | 30 ml         |
|      | 4             | 40 ml          | 40 µl        | 40 ml         |
|      | 5             | 50 ml          | 50 µl        | 50 ml         |

Add 100 µl of the secondary antibody dilution to each well. All dilutions should be done in blocking buffer. Cover with a new adhesive strip and incubate for 20 minutes at room temperature. Prepare the appropriate amount of substrate prior to the wash step. Bring the substrate to room temperature. OPD (o-Phenylenediamine) is a peroxidase substrate suitable for use in ELISA procedures. The substrate produces a soluble end product that is yellow in color. The OPD reaction is stopped with 3 N $H_2SO_4$, producing an orange-brown product and read at 492 nm. Prepare OPD fresh from tablets (Sigma, P6787; 2 mg/tablet). The solid tablets are convenient to use when small quantities of the substrate are required.

After second antibody incubation, remove the unbound secondary reagent by washing the plate 10× with Wash Buffer (PBS containing 0.05% Tween-20). After the final wash, add 100 µl of the OPD substrate solution to each well and allow to develop at room temperature for 10 minutes. Reagents of the developing system are light-sensitive, thus, avoid placing the plate in direct light. Prepare the 3 N $H_2SO_4$ stop solution. After 10 minutes, add 100 µl of stop solution per 100 µl of reaction mixture to each well. Gently tap the plate to ensure thorough mixing. Read the ELISA plate at a wavelength of 490 nm within a time period of 15 minutes after stopping the reaction.

The background should be around 0.1. If the background is higher, the substrate may have been contaminated with a peroxidase. If the subtrate background is low and the background in your assay is high, this may be due to insufficient blocking. Finally analyze your readings. Prepare a standard curve constructed from the data produced by serial dilutions of the standard antigen. To determine the absolute amount of antigen, compare these values with those obtained from the standard curve.

After running the ELISA on various transfectants it is possible to determine which ones will produce the highest levels of soluble HLA molecules. These "good producers" are grown to the point where a cell pharm can be seeded. The harvest from the cell pharm is then used to extract the soluble HLA using the following purification protocol.

To start the chromatography procedure, prepare the ÄKTA™ prime system. The system can be used immediately but the spectrophotometers full ability will not be obtained until after 1 hour of lamp warm-up. To prepare the system for a run, check that the buffer inlet tubings are immersed in the correct buffer vessels and the waste tubings are put into a waste bottle. Only use degassed and filtered liquids to make sure that the liquid remains free from air bubbles. Degass by applying a vacuum to the solution. Prepare and hook up the buffers necessary for a sHLA purification:

| Buffer Valve (A) | |
|---|---|
| 1. PBS, pH 7.4 | (Wash buffer) |
| 2. 20% Ethanol/70% Ethanol | (Cleaning solutions) |
| 3. 0.1 N NaO | (MOK elution buffer) |
| 4. 50 mM Diethylamine (DEA), pH 11.3 | (MOK elution buffer) |
| 5. Protein sample | (The line is stored in PBS/ 0.05% Na Azide, pH 7.4) |
| 6. 0.2 N Acetic acid, pH ~2.7 | (Cleaning &MOK solution) |
| 7. 0.1 M Citric acid, pH 3.0 | (Protein A elution buffer) |
| 8. 0.1 M Glycine, pH 11.0 | (sHLA elution buffer) |

It is important to purge the lines after a new hook-up with about 50 ml of liquid to get the air out of the system. Purging can be done manually through the inlets of the buffer valve (A1-A8), while carefully immersing the tubing in the respective liquid. To remove any trapped air bubbles in the flow path, purge the pump in the order PBS/20% ethanol/PBS/final buffer solution. Next, prepare the recorder to monitor the purification. Autozero the built-in UV spectrophotometer with PBS as reference. Equilibrate all material to the temperature at which the chromatography will be performed. For large scale purifications, attach the column entrance/exit to the system.

Equilibrate the column by passing 10 bed-volumes of PBS over the matrix. Before starting any column purification, the protein concentration in the sample solution should be determined using a quantitative ELISA procedure. The sample volume loaded will depend on the size and loading capacity of the column and the concentration of the sample. Calculate the volume of the sample solution maximally saturating the column according to the columns capacity to bind the antigen.

| (A) Antigen concentration: | mg/ml antigen |
|---|---|
| (B) Antigen binding capacity: | mg antigen/ml gel |
| (C) Matrix volume: | ml gel |
| (D) Maximal amount of antigen: (B * C) | mg |
| (E) Sample volume: (D/A) | ml |

Since the binding capacity of the column will realistically not be reached, a much lower volume of sample solution should be chosen. A value between 40 to 50% of the calculated volume is more accurate which also will not result in the waste of lots of unbound antibody within the flow-through. Prepare the antibody sample solution for purification. Spin crude harvest at 5,000 rpm for 25 minutes (JA10 rotor) to remove lipid and cell debris. The antigen solution must be free of particulate matter. Pour the supernatant into a suitable container. Prevent air bubble formation.

Name of the Crude Harvest:

Volume used: ml

Amount of sample: mg

The simplest method to bind the antigen to the antibody/Sepharose 4B matrix is to apply the sample through the system pump and pass the protein solution down the column. Set appropriate parameters to record the loading conditions on the recorder.

|  | Chart Speed | Conductivity | Optical Density |
| --- | --- | --- | --- |
| Load | 0.1 mm/min | 0.5 V | 1.0 V |

Save a 1 ml probe from the starting material (LOAD) before the purification procedure for analysis purposes. Set the buffer valve to position 5 and the injection valve to position LOAD. Make sure the inlet tubings are purged with sample buffer without any air-bubbles present. To have a purged sample line, disconnect shortly the column before loading and circulate the sample within the system with higher flow rate. Pass the solution slowly through the column with a flow rate of approximately 1.0 ml/min or lower to give the protein time to bind more efficiently. Higher flow rates will decrease efficiency. A disruption in flow may cause a rapid rise in back-pressure. If this occurs, immediately shut off the pump and check the gel bed for compression.

Collect the flow-through in an appropriate container. Keep until you are sure all material has bound to the column and negligible amounts are in the flow through. Take a sample at the end of the run (Ft) which should be analyzed. Wash the column with PBS at 10 ml/min until UV absorbance at 280 nm is zero. For a large column use 2000-3000 ml wash buffer (PBS). Save the wash in a container until after the purification.

|  | Chart Speed | Conductivity | Optical Density |
| --- | --- | --- | --- |
| Wash | 0.5 mm/min | 0.5 V | 1.0 V |

Prepare borosilicate collection tubes by adding 1.2 ml of 1 M Tris-HCl, pH 7.0 per 4.8 ml of fraction to be collected (1:4). Neutralization is a safety measure to preserve the activity of the eluted molecule. MHC class I (SHLA) molecules are best eluted from a W6/32 column by 0.1 M glycine, pH 11.0. Absorbance is used for generating a protein elution profile.

|  | Chart Speed | Conductivity | Optical Density |
| --- | --- | --- | --- |
| Elution | 0.5 mm/sec | 0.2 V | 0.1 V |

Place the collector arm over the first collection tube. Elute 4.8 ml per fraction at 10 ml/min. Immediately afterwards, mix each tube gently to bring the pH back to neutral. As with all protein solutions, avoid bubbling or frothing as this denatures the proteins. If a very low amount of protein is expected, change the conductivity on the recorder to a lower value. Identify the antigen-containing fractions by absorbance at 280 nm on the chart and combine them during up-concentration. Up-concentrate immediately and buffer exchange into PBS using MACROSEP™ centrifugal concentrators (Pall Filtron; Northborough, Mass.; MACROSEP 10K; OD010C37). Keep the protein on ice at all times and centrifuge at 4° C. After the buffer exchange, prepare the sample for storage at 4° C. Filter the pure samples through a 0.2μ filter and aliquot directly into sterile, screw cap tubes. Label appropriately.

Determine the absorbance at 280 nm as well as the protein concentration with the Micro BCA kit. Activity can be determined with a regular ELISA procedure. The purity of the eluted sHLA can be assessed by SDS-PAGE, Western blotting or performing a Superdex column analysis. After the elution, quickly re-equilibrate the column with PBS to avoid denaturation of the W6/32 antibody linked to it. For analytical work in which more than one allele will be purified on the same column, extreme care must be taken. To be able to re-use the column, start a maintenance procedure after the re-equilibration. Cleaning-in-place is a procedure, which removes contaminants such as lipids, precipitates or denatured proteins that may remain in the column after regeneration. Such contaminations are especially likely when working with crude materials. The procedure helps to maintain the capacity, flow properties and general performance.

Mock elute the column using buffers with alternating pH. Start running over 10 gel volumes of 0.2 N acetic acid followed by 10 gel volumes of 50 mM diethylamine, pH 11.3 at a speed of 10 ml/min. Repeat three times and always equilibrate with 10 gel volumes PBS between buffer changes.

|  | Chart Speed | Conductivity | Optical Density |
| --- | --- | --- | --- |
| Mok-elution | 1.0 mm/min | 0.2 V | 0.1 V |

After Mok-elution, store the column at 4° C. in PBS/0.05% Na Azide. Sanitization inactivates microbial contaminants in the packed column and related equipment. One generally recommended procedure is to wash alternately with high and low pH buffers as performed in the coupling reaction. For sanitization, disassemble the column and wash the matrix alternately with low pH wash buffer (0.1 M sodium acetate containing 0.5 M NaCl, pH 4.0) and high pH wash buffer (0.1 M Tris-HCl containing 0.5 M NaCl, pH 8.0) for 3 times followed by re-equilibration with PBS. Re-assemble the cleaned and sterilized column and store it at 4° C. in PBS containing 0.05% sodium azide.

After the column is removed, the ÄKTA™ prime system has to be cleaned carefully. Start with the cleaning of line 5, where the sample was hooked up. Rinse the system pump and include the fraction collector line. First clean the inlet tubings, by manually running the system pump and flushing with 0.2 N acetic acid at 30 ml/min followed by 0.1 N NaOH. Always equilibrate with PBS. Don't forget to add a line between the injection valve and the UV detector as a bridge, as replacement of the column. Finally, rinse with 20% ethanol. If the column was sanitized because of bacterial contamination, rinse with 70% ethanol.

In order to test whether or not the sHLA molecules produced were conformational, an assay was developed using a variety of different antibodies:

1. w6/32, recognizes conformational intact trimer
2. hc10, recognizes denatured HLA molecules
3. anti $b_2M$, recognizes free and non-covalently associated Beta 2 microglobulin The methodology for this assay is essentially the same as the standard Elisa described above, except that instead of coating the plate with w6/32, the soluble HLA molecules are coated directly to it. The three different antibodies are then utilized in three different ways to detect the bound HLA. W6/32 is biotin labeled, therefore Vectastain kit and OPD are used for detection, anti $b_2M$ is conjugated to horse radish peroxidase and so can be directly detected using OPD and with hc10 a secondary anti-mouse IgG horse radish peroxidase conjugated antibody and OPD are used.

Results for sHLA Production Using gDNA as the Starting Material Using sample 3A394

Genomic DNA Extraction.

Using 200 ul whole blood, a Qiagen DNA extraction was performed. Table 19 shows the optical density readings and concentration of this extraction.

Primary PCR of 3A394

| 10x pfu buffer | 5 ul |
|---|---|
| PP5UTA | 1 ul |
| 3PPI4A | 1 ul |
| dNTP | 1 ul |
| gDNA | 10 ul |
| H₂O | 31.4 ul |
| Pfu | 1 ul |

Figure 30:
FIG. 30 is a gel image of the primary PCR of 3A394.

See FIG. 30 for the gel image of this PCR.

FIG. 30. 2% agarose gel showing the primary PCR product of 3A394 (5$^{th}$ lane from the right) at approximately 2 kb in size.

The PCR product was gel purified and this along with unpurifed PCR was used in the secondary PCR at a 1:100 dilution.

Secondary PCR of 3A394

| 10x pfu buffer | 5 ul |
|---|---|
| dNTP | 1 ul |
| PP5UTA | 1 ul |
| PP3PEI | 1 ul |
| 1:100 1° PCR | 10 ul |
| H₂O | 31.4 ul |
| Pfu | 0.6 ul |

Figure 31:
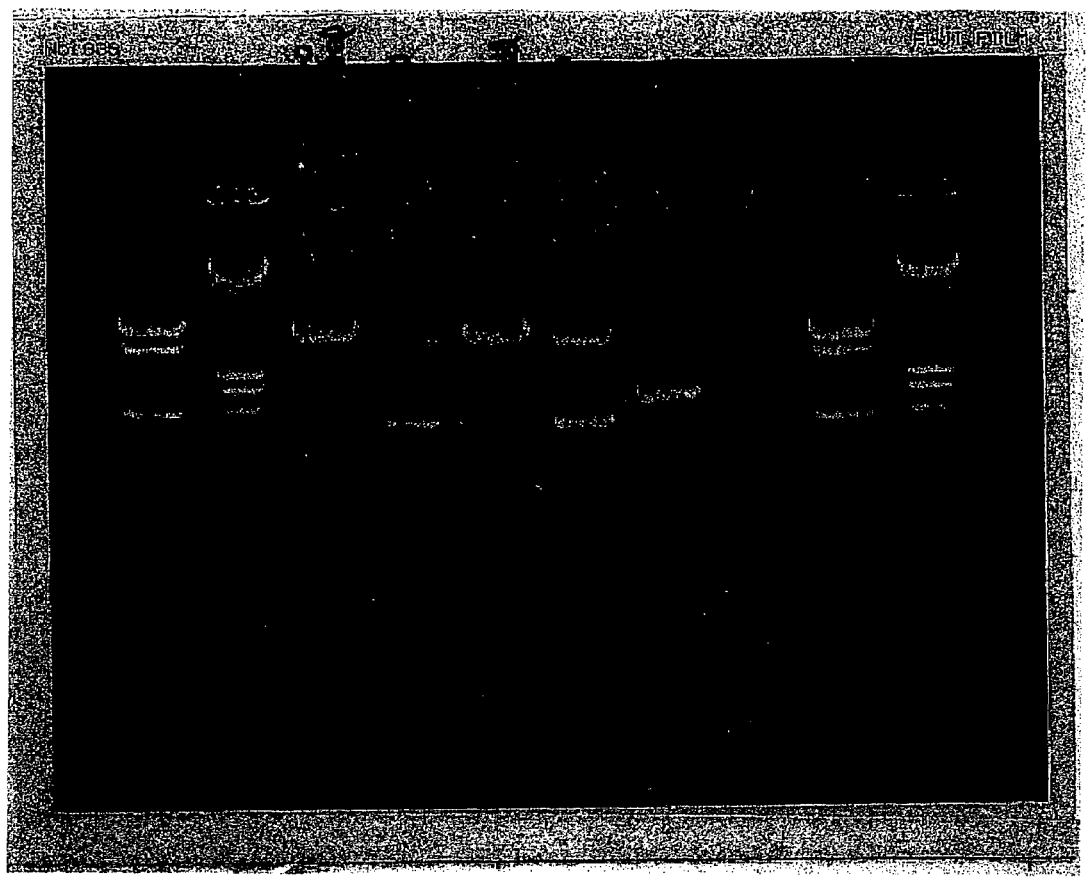
FIG. 31 is a gel image of the secondary PCR of 3A394.

The results of this can be seen in FIG. 31. Secondary PCR of 3A394. Gel purified and unpurified can be seen in lanes 2 and 3 of FIG. 31.

Figure 32:
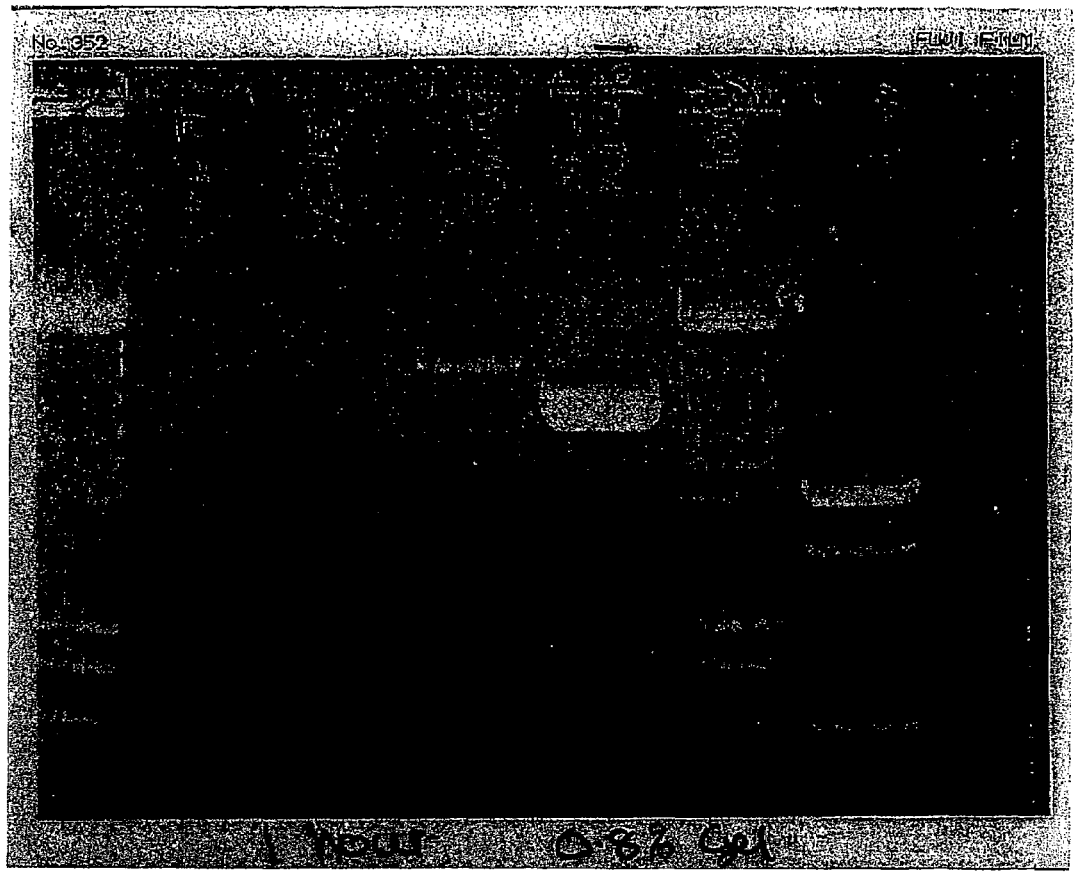
FIG. 32 is a gel image showing 3A394 and pcDNA3.1 digested with EcoR I and Xba I.

The PCR product derived from gel purified primary PCR was in turn gel purified and used in the restriction digest in order to ligate into pcDNA 3.1 (−), FIG. 32.

Figure 33:
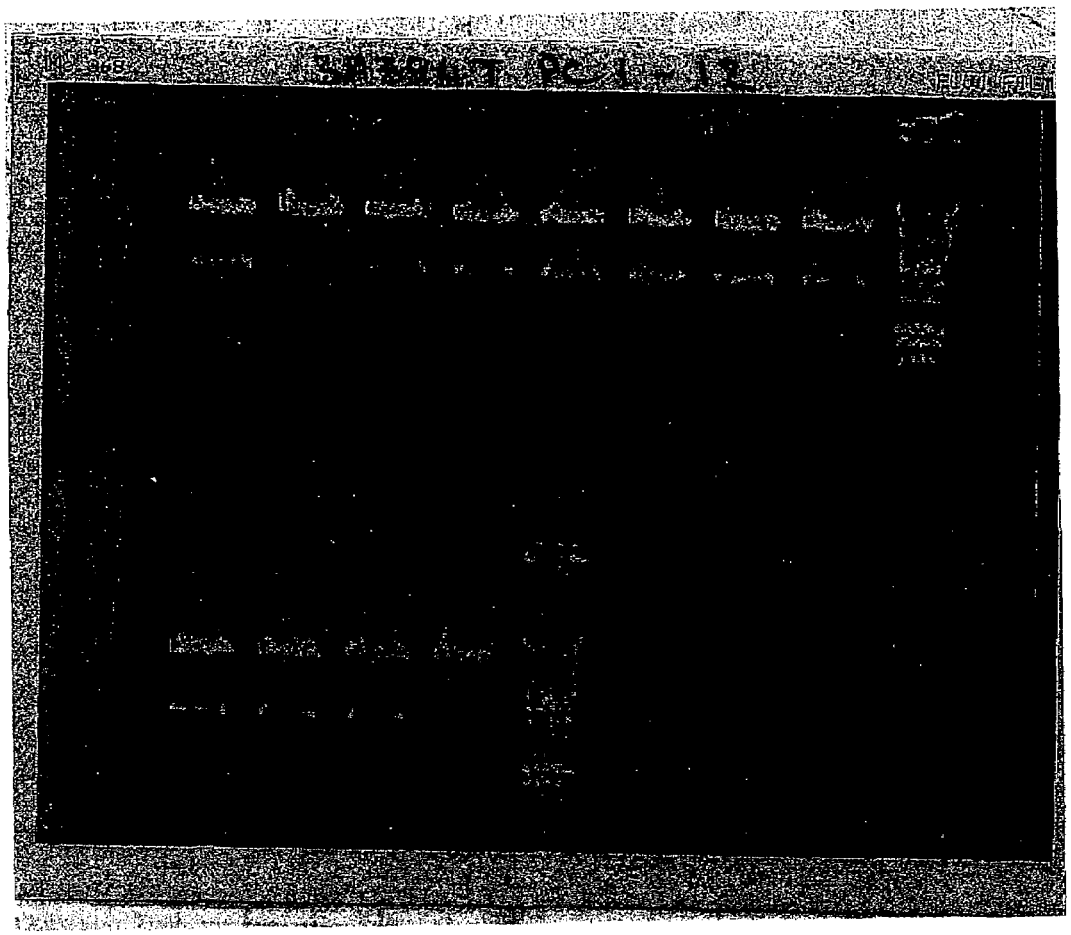
FIG. 33 is a gel image showing the restriction digests of 3A394 clones.

FIG. 32 is a gel showing 3A394 and pcDNA3.1 digested with EcoR I and Xba I. Once the ligations, at three different insert to vector ratios, and transformation were completed colonies were picked, grown overnight and then the plasmid DNA was extracted. A restriction digest was performed to screen for insert as shown in FIG. 33 is a restriction digests of 3A394 clones. A vector to insert ratio of 1:6 is the most efficient.

Following identification of positive clones the concentration of the vector was established by optical density (Table 20) and then diluted to 500 ng/ul.

Cycle sequencing was then performed on sample 3A394TPC1 and it was established that this was a good clone of HLA-A*1102 truncated at codon 298.

The clone 3A394PC1 was then grown up and the plasmid containing A*1102 Truncated (A*11021) was prepared for electroporation by performing a large scale plasmid extraction. The concentration of this was determined using optical density which can be seen in Table 21.

30 ug of this was then electroporated into the cell line LCL 721.221 with the decay times being recorded then, after 2 days the viability of the cells was determined, Table 22.

The cells were then placed under G418 selection to screen for positive transfectants, those exhibiting G418 resistance were screened for soluble HLA production using the Elisa, Table 23. Only two replicates were tested for this sample and all were done using undiluted supernatant.

Samples 3A394TPC1 wells 1 and 2 were grown further and eventually well 1 cells were seeded into a cell pharm. This protocol has been performed on many HLA types as can be seen by the production of soluble HLA molecules in Table 24.

Due to the fact that the monoclonal antibody w6/32 only recognizes the folded trimer complex of heavy chain-light chain-peptide the results of the ELISA demonstrate that we are producing conformational molecules originally derived from genomic DNA.

Figure 34:
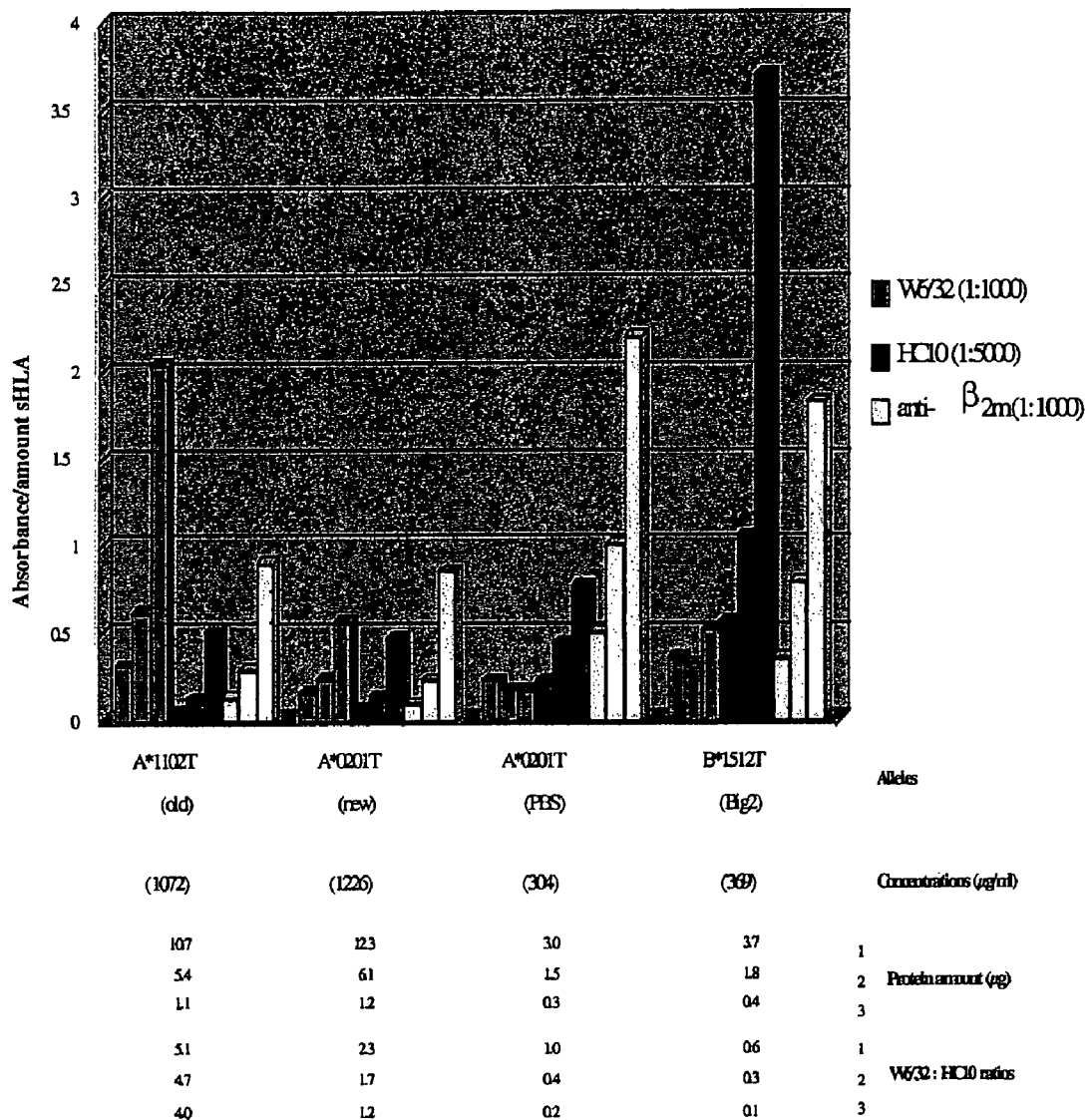
FIG. 34 is a graph showing the comparative binding of three monoclonal antibodies to four soluble HLA molecules.

FIG. 34 is a graph showing the comparative binding of three monoclonal antibodies to four different soluble HLA molecules. A*1102T is sample 3A394TPC1 well 1 from genomic DNA the other three are produced from cDNA. Three different amounts of soluble HLA were coated to the plate for each allele.

The results of the comparative binding assay demonstrate several properties of the soluble HLA produced from genomic DNA. Coating a plate with more protein will not necessarily yield a higher signal to protein ratio. Soluble HLA from genomic DNA gives results comparable to that of cDNA constructs. The fact that all three antibodies bind this confirms the correct epitopes of the recombinant molecules are present.

Due to the polymorphic nature of the HLA system production of many alleles as soluble molecules is very difficult as a viable cell line is required in order to make cDNA and quite often this is not available. Thus a method that allows us to produce many different alleles from a readily available starting point is invaluable. Production of the sHLA from genomic DNA provides such a starting point. We have shown here that two simple PCR reactions allows us to clone many, if not all, HLA Class I alleles from genomic. DNA.

The Elisa data allows us to test how functional these molecule are. By using w6/32 and anti $b_2M$ to establish production levels we also provide information as to how much of the protein is in a trimeric form. The comparative Elisa data helps back this up as the ratio of w6/32:hc10 needs to be greater than 1.0 in order for there to be more conformational molecule than denatured, this is shown to be the case. In summary we have developed a technique that will allow the production of virtually any HLA Class I molecule in a soluble form on demand.

An exemplary useful product which can be obtained from the mammalian cell line expressing such a genomic DNA construct is a cDNA clone encoding the desired class I or class II molecule. The cDNA clone encoding the desired class I or class II molecule is formed from the mRNA molecule encoding the desired class I molecule isolated from such mammalian cell line. The cDNA clone may be utilized for functional testing, as described in more detail herein below. Thus, gDNA clones can be used as a mechanism to obtain cDNA clones of the desired class I or class II HLA molecule.

The cDNA clones may be transfected into a cell which is unable to splice introns and process the mRNA molecule and therefore would not express the MHC molecule encoded by the genomic DNA, such as insect cells or bacterial cells. In addition, these cell lines will also be deficient in peptide processing and loading, and therefore the soluble MHC molecules expressed from such cells will not contain peptides bound therein (referred to as free heavy chain HLA). Such soluble, free heavy chain HLA can effectively be tested for epitope binding as well. That is, MHC made in cells which do not naturally load peptide can be experimentally loaded with the peptide of choice. The heavy chain, light chain, peptide trimer can be reassembled in vitro using a high affinity peptide to facilitate assembly. Alternatively, a cell deficient in peptide processing can be pulsed with peptide such that the trimolecular MHC complex forms. DNA encoding a peptide (also encoding an appropriate targeting signal) could also be co-transfected into the cell with the MHC so that the MHC molecule which emerges from the cell is loaded only with the desired peptide. In this way MHC molecules could be loaded with a single low affinity peptide so that replacement with test peptides in a binding assay are more controlled.

Note that an advantage of secreting individual MHC molecules from a cell that naturally loads peptide is that the MHC molecule of interest is naturally loaded with thousands of different peptides. When used in a peptide binding assay, a synthetic peptide can therefore be compared to thousands of naturally loaded peptides.

Another use for the sHLA produced functional testing, according to the methodology of the present invention is the peptide-MHC complex can be multimerized to form soluble peptide-MHC dimers or tetramers, or other multiple soluble peptide-MHC-mers, such as fivemers, sixmers, etc. which serve as ligands for CTLs. The tetramers can be mixed with CTLs in vitro or with CTLs from the blood of human subjects to identify antigenic peptides responsible for immune responses in humans. Altman et al (Science, 1996), herein expressly incorporated by reference in its entirety, discloses a method of functional testing using tetramer technology; however, the method of Altman, however, only discloses one soluble MHC molecule which has been utilized in such a method, and Altman's method faces the same disadvantages and defects described above for the prior art, that is, the method envisions isolating individual mRNA/cDNA molecules from hundreds of different, typed cell lines, and then manipulating the cDNA molecules to produce the desired soluble MHC molecule. The methods of the present invention envision combining the tetramer technology with amplification of genomic DNA, cloning the genomic DNA fragment, and transfection of the resulting construct into a mammalian cell line followed by isolation of cDNA from such transfected cell line and transfection into a cell line deficient in peptide processing and loading, thereby removing the need to isolate hundreds of different, typed cell lines for obtaining the different cDNAs.

MHC/peptide tetramers are widely utilized in the phenotypic analysis of T cells and in the study of T cell responses to pathological conditions such as viral infections and cancer. Current methodology for tetramer production consists of expressing the MHC class I heavy chain in bacterial or insect cells and refolding the heavy chain in the presence of β-2-microglobulin and a specific peptide ligand in vitro.

The methodology of the present invention had two specific aims, although this should not be regarded as limiting: 1) to engineer a cDNA construct of a class I heavy chain containing a BirA substrate peptide (bsp) sequence at its 3' end (C-terminus) which would enable its subsequent biotinylation and 2) to develop a novel means of tetramer production using a mammalian expression system. The mammalian system used was a B cell/T cell hybrid, the antigen-processing mutant cell line CEM×721.174.T2 (T2). When pulsed with established HLA B*0702-presented peptides from HIV-infected CD4+ T cells, T2 cells transfected with the recombinant, truncated B*0702 HLA heavy chain secreted specific MHC/peptide complexes. Following enzymatic biotinylation, these complexes were combined with avidin to form B7 tetramers. A mammalian expression system affords several advantages over a prokaryotic system, such as allowing normal glycosylation of the class I heavy chain and eliminating the need to refold the MHC/peptide complex in vitro following expression. The MHC class I molecules are therefore naturally folded in the cell rather than artificially folded outside the cell. Indeed, such artificial folding of the MHC class I molecules outside of the cell results in a MHC class I molecule which differs from one found in a "natural" system (i.e. a human immune system) and as such, is not an appropriate basis upon which to conduct vaccine development.

Abbreviations: MHC, major histocompatibility complex; $\beta_2m$, $\beta_2$-microglobulin; HLA, human leukocyte antigen; sHLA, soluble human leukocyte antigen; bsp, BirA substrate peptide or biotinylation substrate peptide; CTL, cytotoxic T lymphocytes; PCR, polymerase chain reaction; ELISA, enzyme-linked immunosorbent assay; HRP, horseradish peroxidase; PE, phycoerythrin; PBS, phosphate buffered saline; TAP, Transporters associated with Antigen Processing; TCR, T cell receptor; ER, endoplasmic reticulum; kDa, kiloDaltons.

Figure 1:
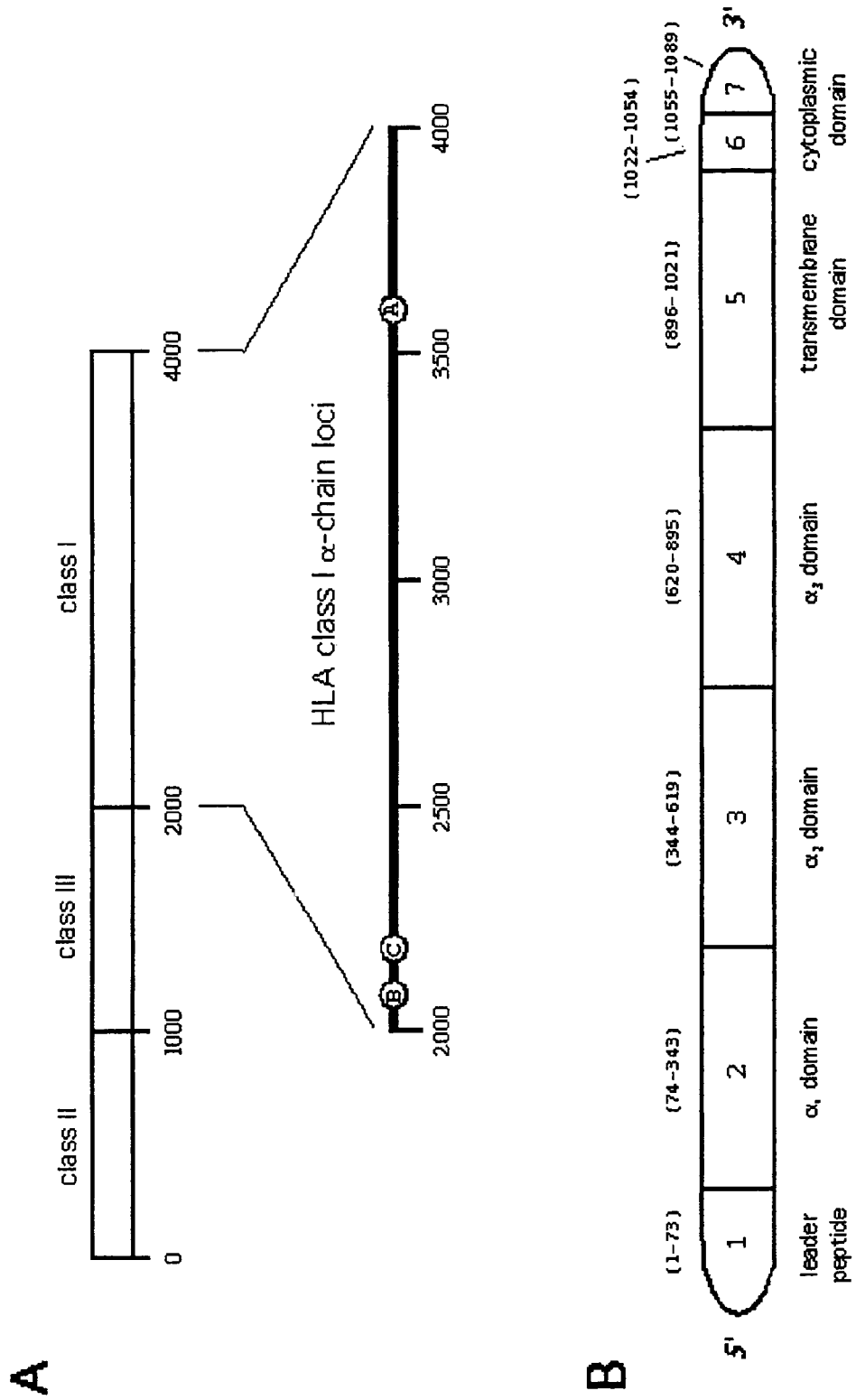
FIG. 1 is a graphical representation of MHC class I location and heavy chain coding region. (A) Simple map of the human MHC region, specifically highlighting the B, C, and A loci that encode the class I heavy chains as simplified from (Janeway and Travers 1994). Genetic distances are estimated in kilobases. Other genes (not shown) including heavy chains and transporter/chaperone proteins (class II) and complement proteins and cytokines (class II) are encoded within the remaining MHC regions. (B) The basic exon structure of MHC class I transcripts. A total of seven exons encode the leader peptide (1), $\alpha_1$ domain (2), $\alpha_2$ domain (3), $\alpha_3$ domain (4), transmembrane domain (5), and cytoplasmic domains (6-7). Specific exon regions are indicated in parentheses for HLA-B*15011 (accession number U03859, Hildebrand et al. 1994), which encodes the HLA-B*1501 heavy chain.
Figure 2:
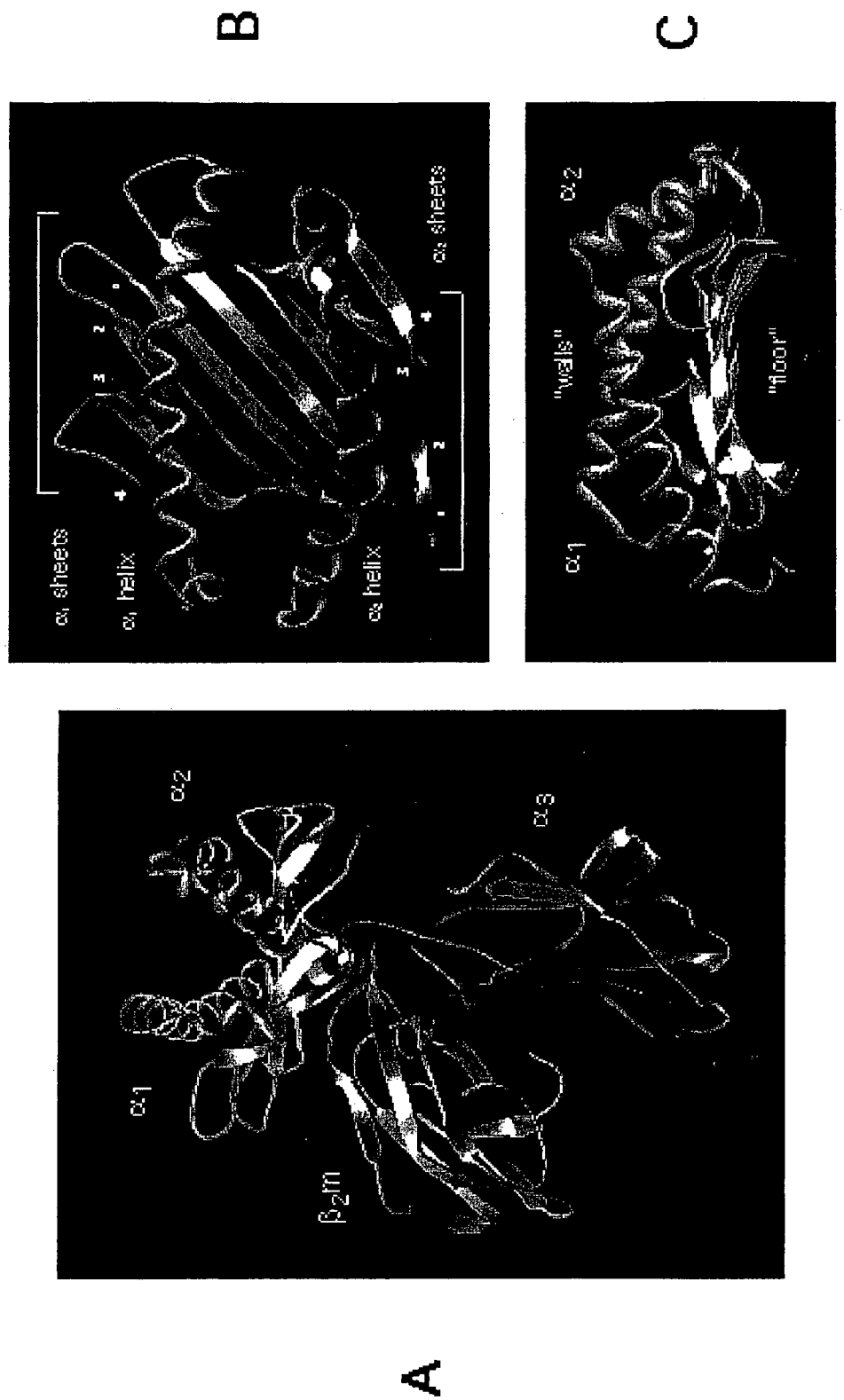
FIG. 2 is a three-dimensional graphical representation of the configuration of the MHC class I extracellular domains. (A) The complete extracellular portion of the class I molecule HLA-B*3501, revealing the three domains ($\alpha_1$, $\alpha_2$, and $\alpha_3$) of the heavy chain as well as the noncovalently associated light chain, $\beta_2$m. Top (B) and side (C) views of the basket-like antigen binding groove formed by $\alpha_1$ and $\alpha_2$; the $\alpha$-helix and $\beta$-sheets for each domain are respectively indicated in (B). These three images were rendered from the HLA-B*3501 Protein Data Bank (Brookhaven National Laboratory) crystal structure coordinate file, 1A1N (Smith et al. 1996a), using the Swiss-PdbViewer 3.01 software (Guex and Peitsch 1996). The CHO linked to $\alpha_1$ residue 86 is not shown.
Figure 35:
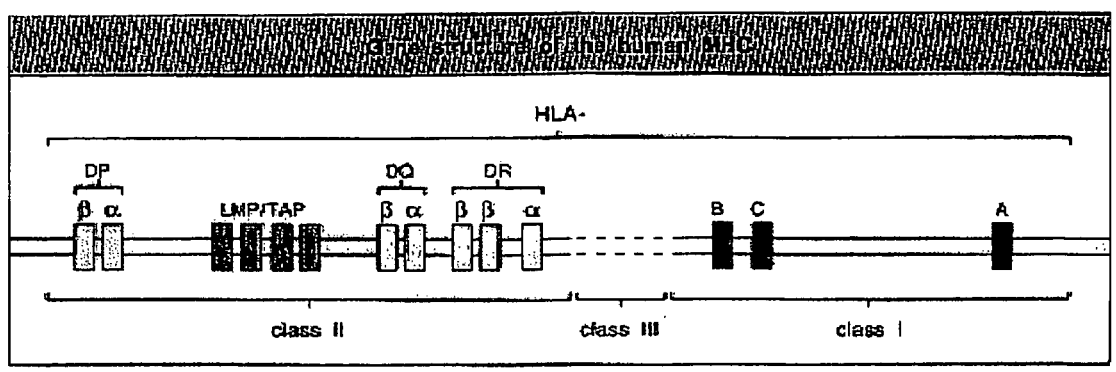
FIG. 35 is a pictorial representation of the MHC.

The structure and function of MHC class I. Unlike B lymphocytes which can interact with antigen in its intact form, T lymphocytes only recognize protein antigen broken down into peptide fragments and presented in association with specialized cell-surface molecules. These molecules are the gene products of the major histocompatibility complex (MHC) (FIGS. 1 and 35), a region on chromosome six known to encode proteins that are critical for immunologic specificity and transplantation histocompatitiblity. MHC molecules, also termed human leukocyte antigens (HLA), are cell-surface glycoproteins that function primarily in communicating to T cells the presence of intracellular or extracellular invaders. MHC/peptide complexes are recognized by the T cell receptor (TCR), an interaction enabling T cells to discriminate between MHC molecules bearing "foreign" antigen (viral/tumor/bacterial peptides) and MHC molecules displaying "self" peptides. An immune response can then be initiated against cells determined to harbor foreign antigen on the basis of the avidity of this binding interaction.

MHC molecules are of two types, designated class I and class II. In general, class II molecules are located on antigen presenting cells (APCs), such as macrophages or dendritic cells, and present peptides from exogenously synthesized protein, usually the breakdown products from phagocytosed bacteria or protozoa. Thus, class II molecules primarily function to warn the immune system of extracellular invaders. The class II/peptide complex is recognized by and interacts with TCRs of CD4+ T cells (T helper or Th cells). Class I molecules are located on platelets and all nucleated cells of the body and bind peptides derived from endogenously synthesized proteins. Examples of endogenously synthesized proteins which may be broken up and presented by class I molecules include both "self" proteins, such as those normally produced in healthy cells, and "foreign" proteins, such as the viral proteins in virus-infected cells or the abnormal proteins produced in tumor cells. Thus, class I molecules primarily function to report to the immune system the health of the intracellular environment. The TCRs of CD8+ cytotoxic T lymphocytes (CTLs) interact with the MHC class II/peptide complex.

Figure 36:
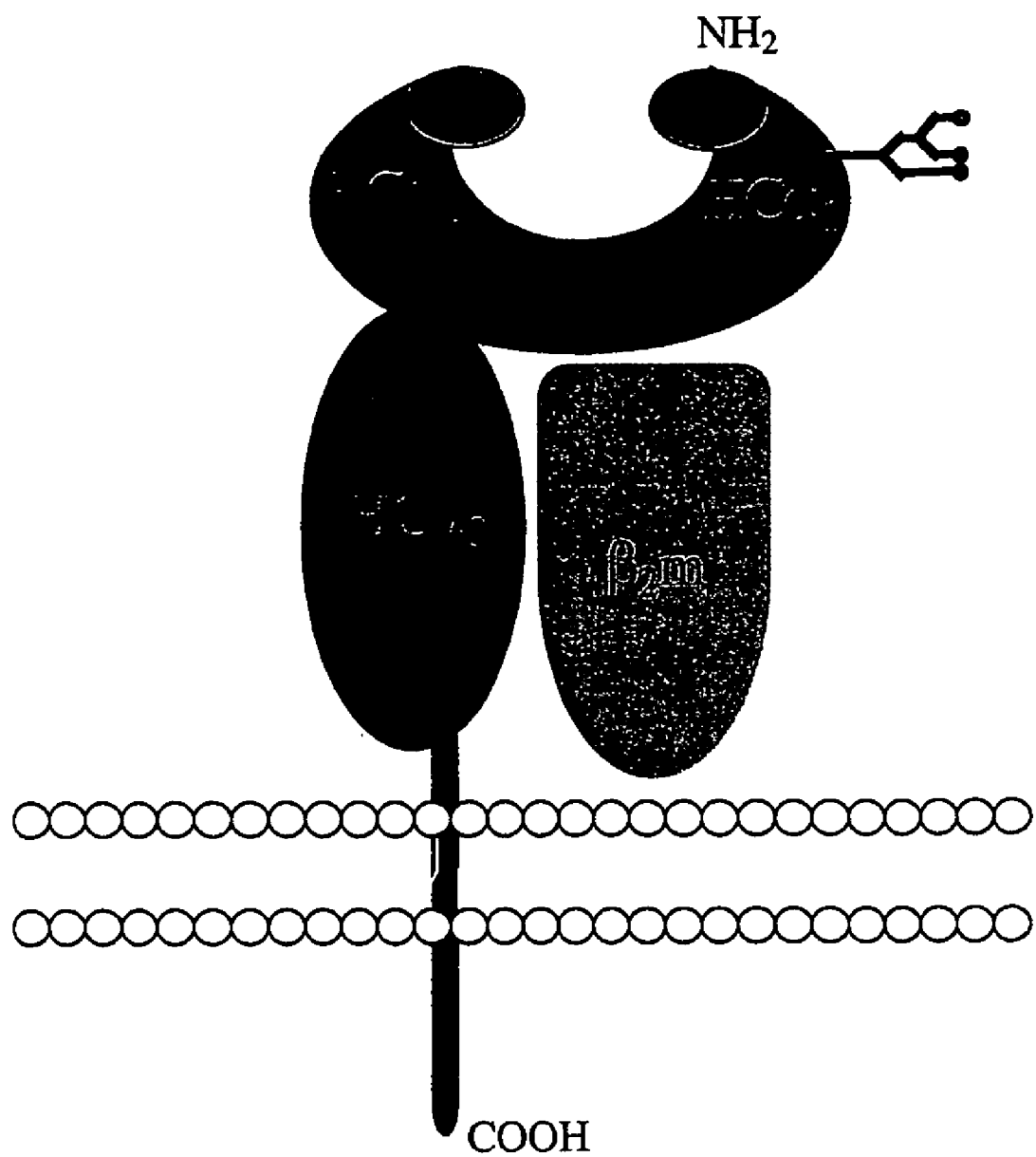
FIG. 36 is a pictorial representation of an HLA molecule.
Figure 37:
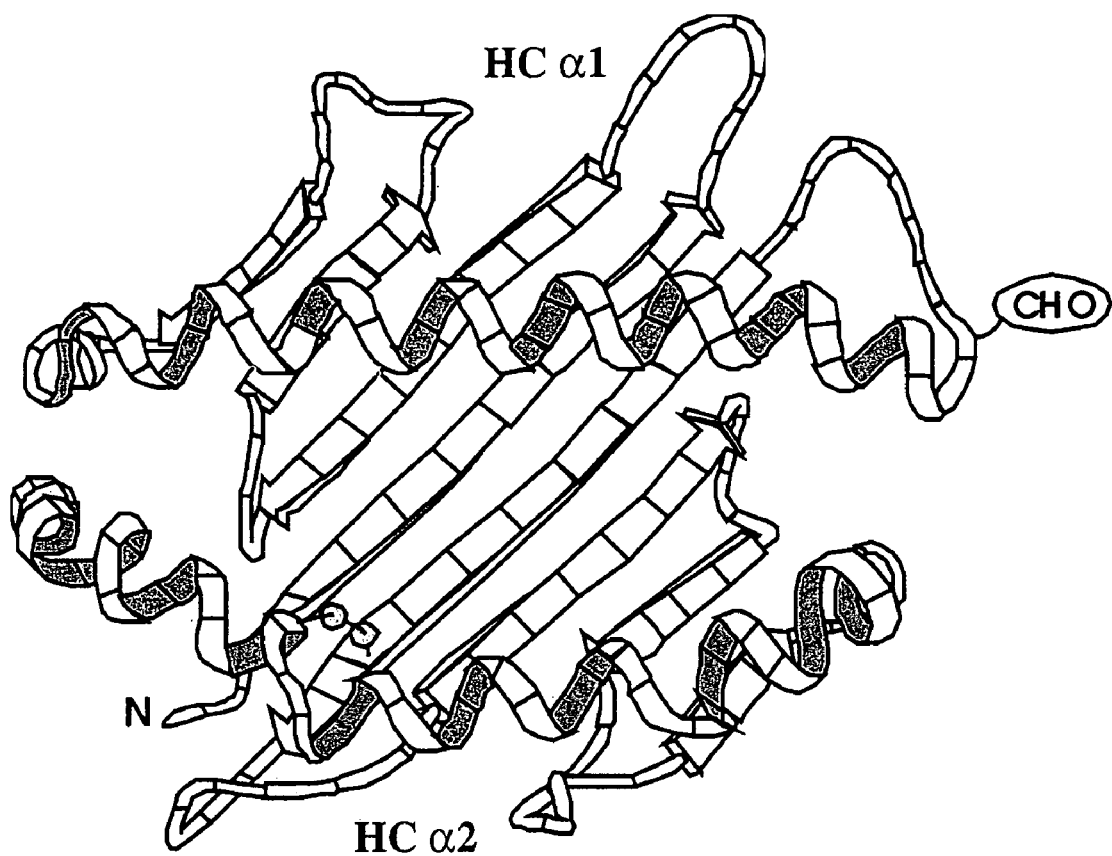
FIG. 37 is a pictorial representation of the HLA binding groove that binds antigenic peptides.

Structurally, class I molecules are heterodimers comprised of two noncovalently bound polypeptide chains, a larger "heavy" chain ($\alpha$) and a smaller "light" chain ($\beta$2-microglobulin, or $\beta_2$m). The polymorphic, polygenic heavy chain (45 kDa), encoded within the MHC on chromosome six, is subdivided into three extracellular domains (designated $\alpha_1$, $\alpha_2$, and $\alpha_3$), one intracellular domain, and one transmembrane domain (FIG. 36). The two outermost extracellular domains, $\alpha_1$ and $\alpha_2$, together form the groove that binds antigenic peptide (FIG. 37). Thus, interaction with the TCR occurs at this region of the protein. The $\alpha_3$ domain of the molecule contains the recognition site for the CD8 protein on the CTL; this interaction serves to stabilize the contact between the T cell and the APC.

The invariant light chain (12 kDa), encoded outside the MHC on chromosome 15, consists of a single, extracellular polypeptide. In the recombinant truncated HLA class I molecule (soluble HLA or sHLA, approximately 47 kDa), the C-terminal intracellular and transmembrane domains of the heavy chain are not amplified by PCR and thus deleted, resulting in a functional MHC/peptide complex that is secreted from the cell and still capable of interaction with the TCR.

Figure 38:
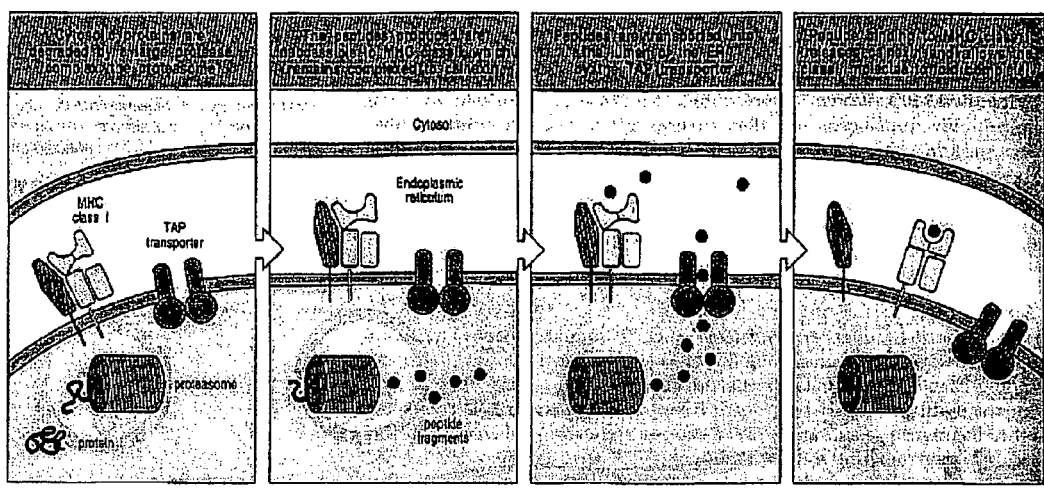
FIG. 38 is a pictorial representation of the antigen processing and assembly of the MHC class II/peptide complex.

Antigen processing and assembly of the MHC class II/peptide complex. The heavy chain of the class I heterodimer is cotranslationally inserted into the lumen of the ER (FIG. 38). The extracellular (intralumenal) domains of newly synthesized $\alpha$ chains are glycosylated and become immediately associated with the ER chaperone protein calnexin. Calnexin is a membrane-bound molecule that functions to temporarily keep the heavy chain in a partially folded state. The subsequent noncovalent interaction of free $\beta_2$m with the heavy chain causes the release of calnexin, and the heavy chain/$\beta_2$m complex becomes sequentially associated with the chaperones calreticulin and tapasin. These chaperones position the class I heterodimer in a manner that enables it to be loaded with the processed peptides once they are transported into the ER by the TAP (transporter associated with antigen processing) complex, located within the ER membrane.

Figure 39:
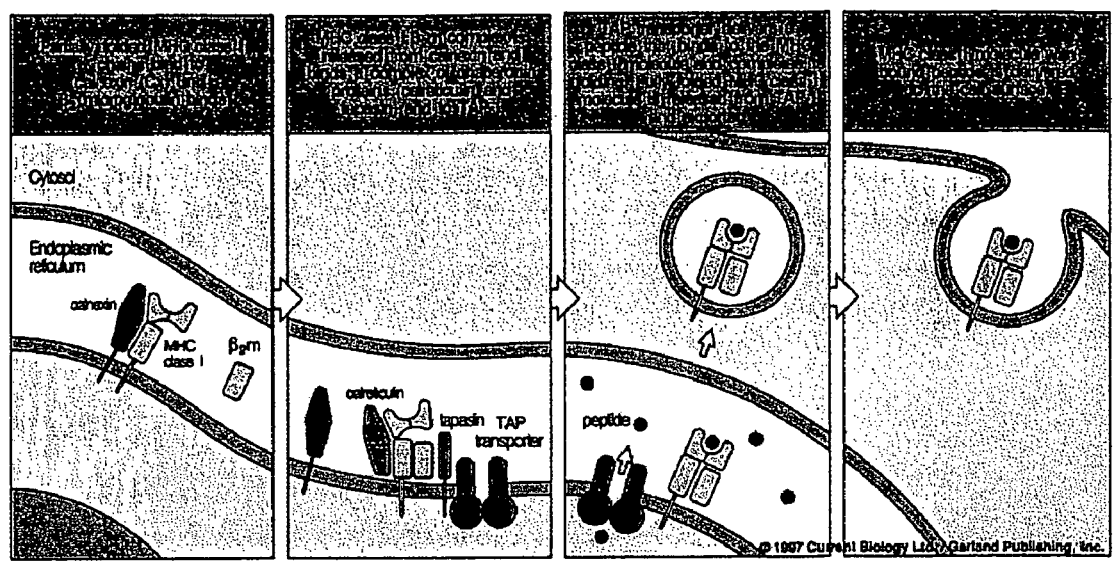
FIG. 39 is a pictorial representation of HLA peptide loading and movement of the HLA molecule to the cell surface.

In the cytosol, a multisubunit, multicatalytic protease complex called the proteosome functions to prepare the endogenously synthesized proteins for presentation by MHC class I molecules. Once proteins (viral or otherwise) are cleaved into peptides of various lengths by the proteosome, the TAP complex actively transports the peptides into the ER where the MHC heterodimer awaits. In the ER lumen, peptides are further trimmed to lengths of 8-11 amino acids. If possessing the requisite binding affinity to the particular class I allele, a peptide will be loaded into the binding cleft of the class I heavy chain to form the MHC heavy chain/light chain/peptide heterotrimeric complex, which is subsequently routed to the cell surface via the Golgi apparatus (FIG. 39).

Cells incapable of antigen processing, for reasons such as inhibition of the proteosome or mutation of TAP, will likewise be deficient in the cell-surface expression of the class I/peptide complex since the class I heterodimer cannot leave the ER until it binds peptide. A particular cell line called T2, which is TAP-deficient and therefore has no cell-surface class I expression, is widely utilized in antigen processing studies. Additionally, it has been shown that abundant exogenous peptide can be pinocytosed, enter an intracellular trafficking pathway, and be delivered to the ER compartment directly in a TAP-independent way. High affinity peptides delivered to the ER in this manner can then bind to de novo-synthesized MHC class I molecules and be subsequently displayed at the cell surface. Thus, T2 cells, the system of mammalian expression utilized in the experiments herein, are capable of cell surface MHC class I expression when pulsed with exogenous peptide of sufficient affinity for the particular class I allele.

Figure 40:
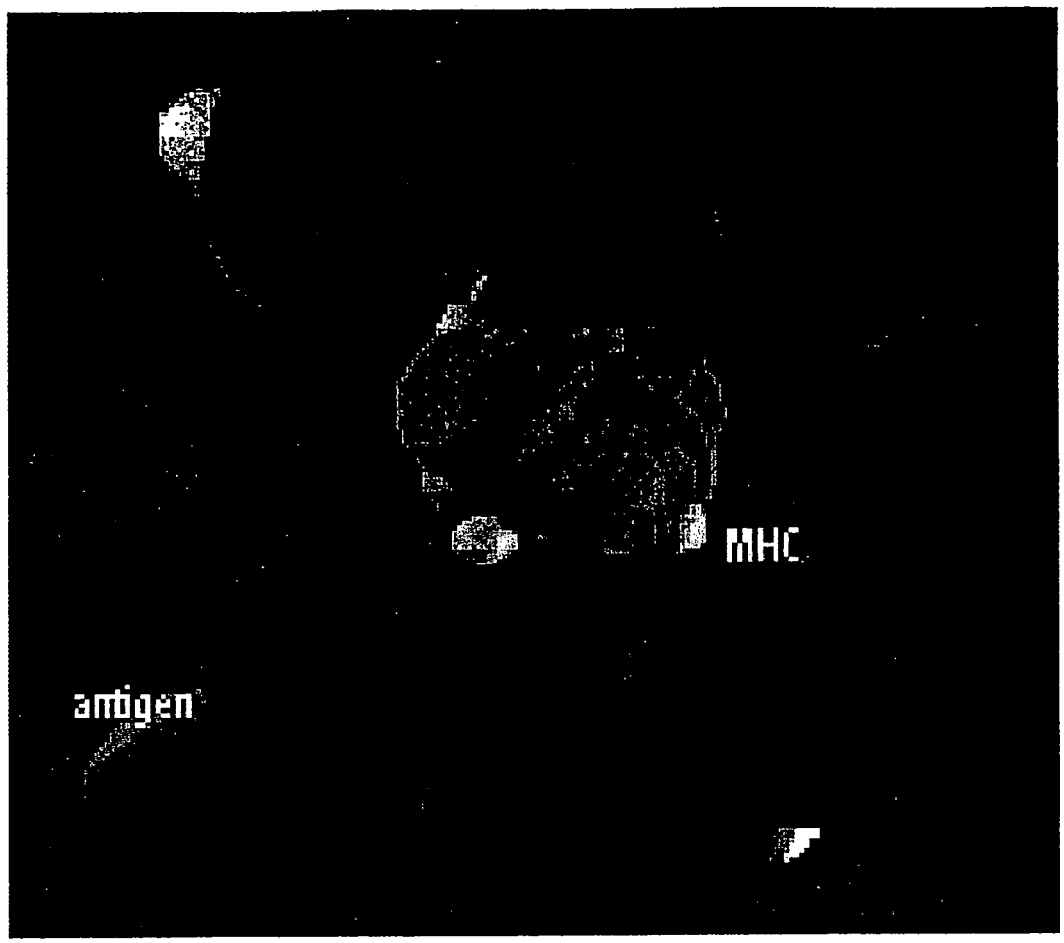
FIG. 40 is a pictorial representation of a tetramer biotinylated sHLA complex of the present invention.

The interaction of the MHC/peptide complex with the TCR is the central event in the initiation of most antigen-specific immune responses. The TCR recognizes the antigen complex by forming intermolecular contacts with both the class I molecule and the antigenic peptide. The outcome of this interaction (i.e. whether or not an immune response is generated) is dependent upon the density and duration of the TCR-MHC/peptide binding. Thus, an immunogenic MHC/peptide complex will bind the TCR with greater avidity than a non-immunogenic MHC antigen complex. Furthermore, it is known that a monomeric MHC/peptide complex, even if immunogenic, dissociates rapidly from a TCR, indicating that multiple TCRs must interact with multiple MHC/peptide complexes in order to activate T cells. In light of this information, Altman et al. disclosed a suggested methodology to analyze antigen-specific T cell populations by multimerizing the MHC/peptide complex into tetramers. Essentially, a tetramer consists of four biotinylated MHC/peptide complexes noncovalently bound to an avidin molecule (FIG. 40). Compared to a monomeric MHC/peptide complex, tetramers have slower rates of dissociation from CTLs since they are able to bind more than one TCR on that particular CTL. This unique characteristic makes tetramers very useful as immunological stains.

Until now, tetramers have incorporated MHC/peptide complexes that were made by expressing a recombinant class I heavy chain in bacteria and subsequently refolding the heavy chain in vitro in the presence of $\beta_2$m and a specific peptide ligand. The purpose of this project was to make tetramers using MHC/peptide complexes synthesized in mammalian cells, specifically cells of the antigen-processing mutant cell line T2 so that every MHC/peptide complex secreted would contain the same antigenic peptide. It is desirable to reflect as much as possible the actual in vivo interaction between human cells expressing cell-surface MHC/peptide complexes and cytotoxic T lymphocytes.

The three following oligonucleotide primers, designated A, B, and C, were purchased from commercially available sources (i.e. operon):

```
Primer A, a 5' primer:
5'_GGGCCTCGAGGGACTCAGAATCTCCCCAGACGCCGAG_3'    (SEQ ID NO:634)

Primer B, a 3' primer:
5'_CCGCAAGCTTCCATCTCAGGGTGAGGGGCT_3'           (SEQ ID NO:635)

Primer C, a 3' primer:
5'_CCGCGAATTCTTATTCGTGCCATTCGATTTTCTG_3'       (SEQ ID NO:636)
```

Figure 41:
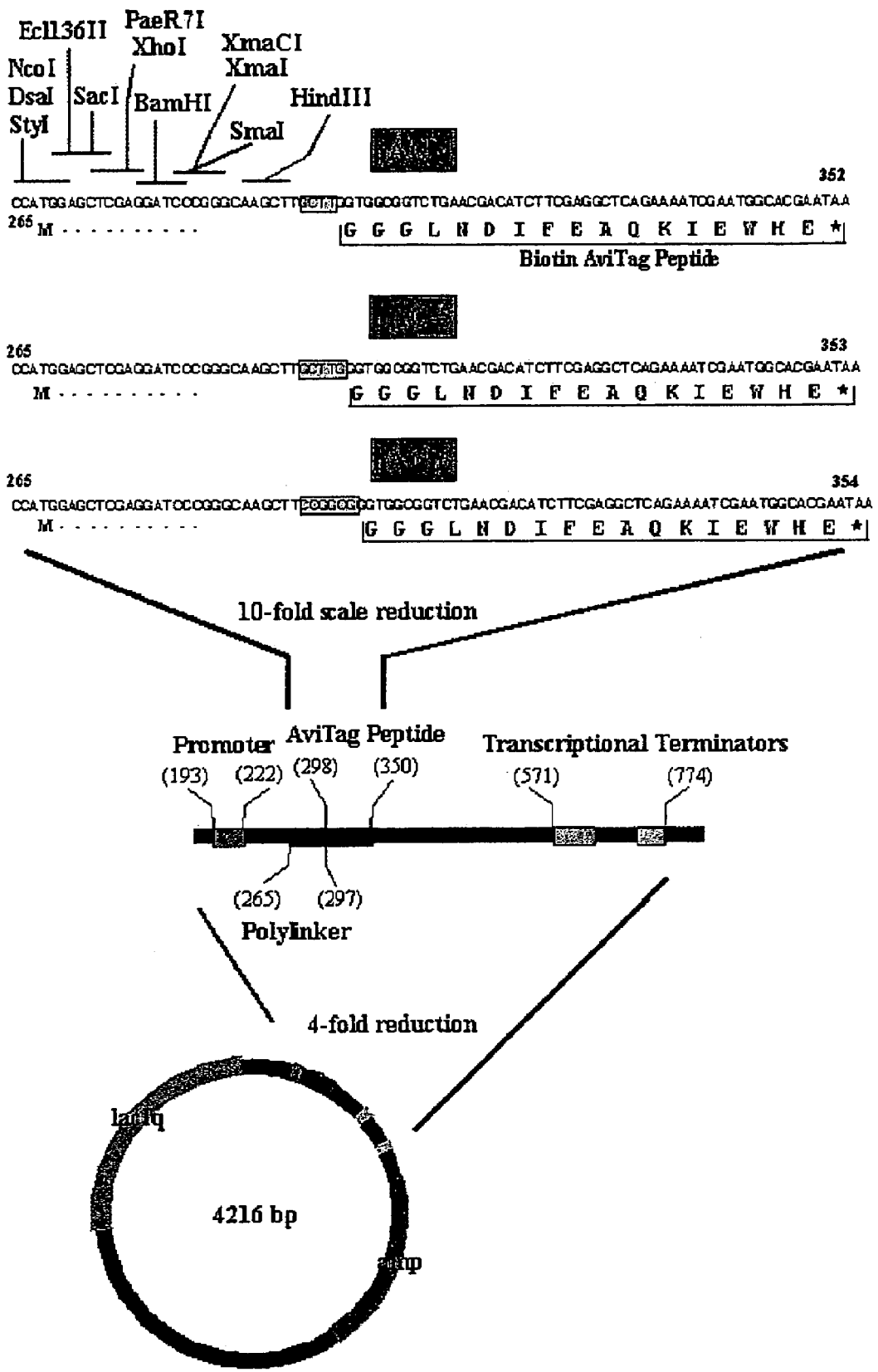
FIG. 41 is a pictorial representation of a bacterial expression vector encoding a biotinylation substrate peptide sequence.

Primers A and B were used in PCR #1 and the template cDNA was a recombinant sHLA-B*0702 truncated gene with a 6-histidine tail in pcDNA3.1(−), a mammalian expression vector. PCR #1 was designed to incorporate 5' Xho I (CTC GAG) and 3' Hind III (MG CTT) cut sites and to amplify the truncated B*0702 heavy chain lacking a 3' stop codon. All PCR reactions for this project were performed with a proof-reading taq polymerase (PFU Polymerase, Promega) and were subjected to 25 cycles of 95° C. for 1 minute (strand separation), 59° C. for 1 minute (primer annealing), and 72° C. for 2 minutes (DNA synthesis), followed by a final extension time of 7 minutes at 72° C. The product of PCR #1 was purified using a QIAquick PCR purification kit (QIAGEN) and was subsequently digested for 2 hr at 37° C. with Xho I and Hind III. Concurrently, a bacterial expression vector (C-Terminal Biotin AviTag Vector, Avidity; catalog number pAC-6) (FIG. 41) encoding the biotinylation substrate peptide sequence GLNDIFEAQKIEWHE (residues 3-17 of SEQ ID NO:631) was digested with the same restriction enzymes under the same conditions. The digest products were gel purified using a Freeze N Squeeze kit (BioRad) and ligated together for 2.5 hours at room temperature. Competent cells of $E.$ $coli$ strain JM1ø9 were transformed with the ligated DNA, plated on LB/ampicillin agar, and incubated for 16 hours at 37° C. Using colony PCR, colonies were screened for insert of the gene into the vector.

The B*0702t-no stop/AviTag vector DNA was isolated and prepared using a DNA Miniprep kit (Promega) and served as the template cDNA for PCR #2. Primers A and C were used in PCR #2, which was designed to maintain a 5' Xho I cut site, incorporate a 3' EcoR I cut site (GM TTC) distal to the bsp, and amplify the B*0702t gene with the bsp on its 3' end. The PCR product was purified with the QIAquick purification kit and, along with the mammalian expression vector pcDNA3.1 (−), was digested with Xho I and EcoR I restriction enzymes. Digest products were gel purified (Freeze N Squeeze), ligated together, and transformed into competent JM1ø9 $E.$ $coli$ cells, which were then incubated overnight at 37° C. on LB/ampicillin agar. Colony PCR was performed to check selected colonies for insert of the B*0702t-bsp gene into pcDNA(−). DNA from clones with insert was prepared (Miniprep kit) and sequenced using cycle sequencing. Sequences were analyzed and a good clone was identified. The plasmid DNA of the good clone was isolated and prepared for transfection using a DNA Midiprep kit (QIAGEN).

Cells of the human cell line T2 were cultured in RPMI 1640 media+20% fetal calf serum, 1% penicillin/streptomycin, and 0.25% phenol red. A total of $1.7 \times 10^7$ T2 cells were transfected with 30 µg of B*0702t-bsp/pcDNA3.1(−) DNA by electroporation using the Gene Pulser (BioRad) at 0.25 V and 960 µFD. Transfected cells were selected in a medium containing 40% RPMI 1640, 40% conditioned media, 20% fetal calf serum, 2% penicillin/streptomycin, 0.2% phenol red, and 1.5 mg/mL G418 neomycin (Celigro). Surviving cells were pulsed with the synthetic HIV GAG peptide $NH_2$—S—P—R-T-L-N-A-W—V—COOH (SEQ ID NO:637) at 20 ug/mL and then incubated for 24 hours at 37° C. Transfectants were then screened by ELISA using W6/32 (8 µg/mL), which is directed against the entire HLA heavy chain/light chain ($\beta_2$m)/peptide complex, as the primary (capture) antibody and anti-$\beta_2$m conjugated to HRP (diluted 1:1000) as the secondary (conjugate) antibody (Dako).

High-producing cells were then expanded and cultured (continuously being repulsed with peptide), and their supernatant was collected and centrifuged to remove cell debris. The specific MHC/peptide complexes were purified using an affinity chromatography system (AKTA™ prime). In brief, the supernatant was passed over a 38 mL bed volume XK 26 column of cyanogen bromide-activated Sepharose 4B (Amersham Pharmacia Biotech) coupled to W6/32. The protein was then eluted intact in basic buffer (0.1 M glycine-NaOH, pH 11.0). To neutralize the eluate, 1.0 M Tris was added in a 1 to 4 ratio of neutralization buffer:elution buffer, resulting in a final solution of 0.25 M tris/0.075 M glycine, pH ~8.0. Immediately, the eluted protein was concentrated and buffer-exchanged to PBS+0.05% Na Azide using MACROSEP centrifugal concentrators (Pall Filtron, MACROSEP 10K). Purified protein was quantified using ELISA.

Figure 42:
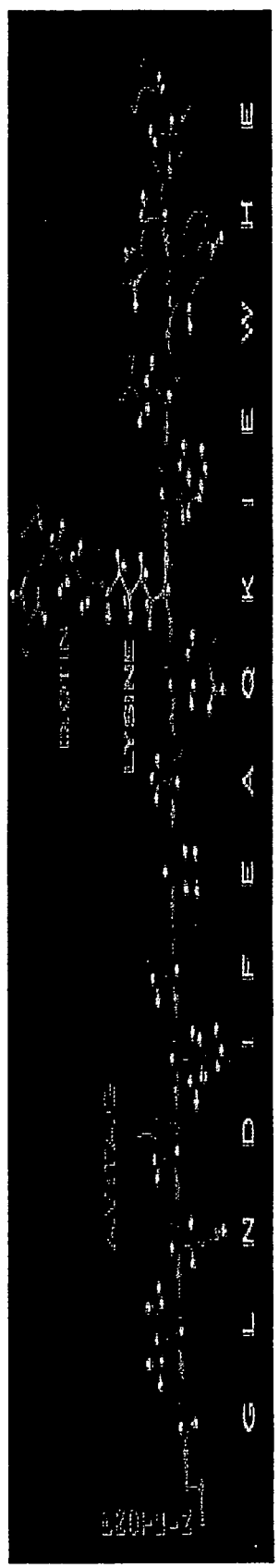
FIG. 42 is a pictorial representation of the biotinylation of sHLA.

The purified sHLA-bsp/peptide complex was enzymatically biotinylated on a single lysine residue within the bsp by incubation with BirA (Avidity; other names for this enzyme include biotin protein ligase, biotin ligase, biotin operon repressor protein, biotin holoenzyme synthetase, and biotin-[acetyl-CoA carboxylase]synthetase) (FIG. 42).

Figure 43:
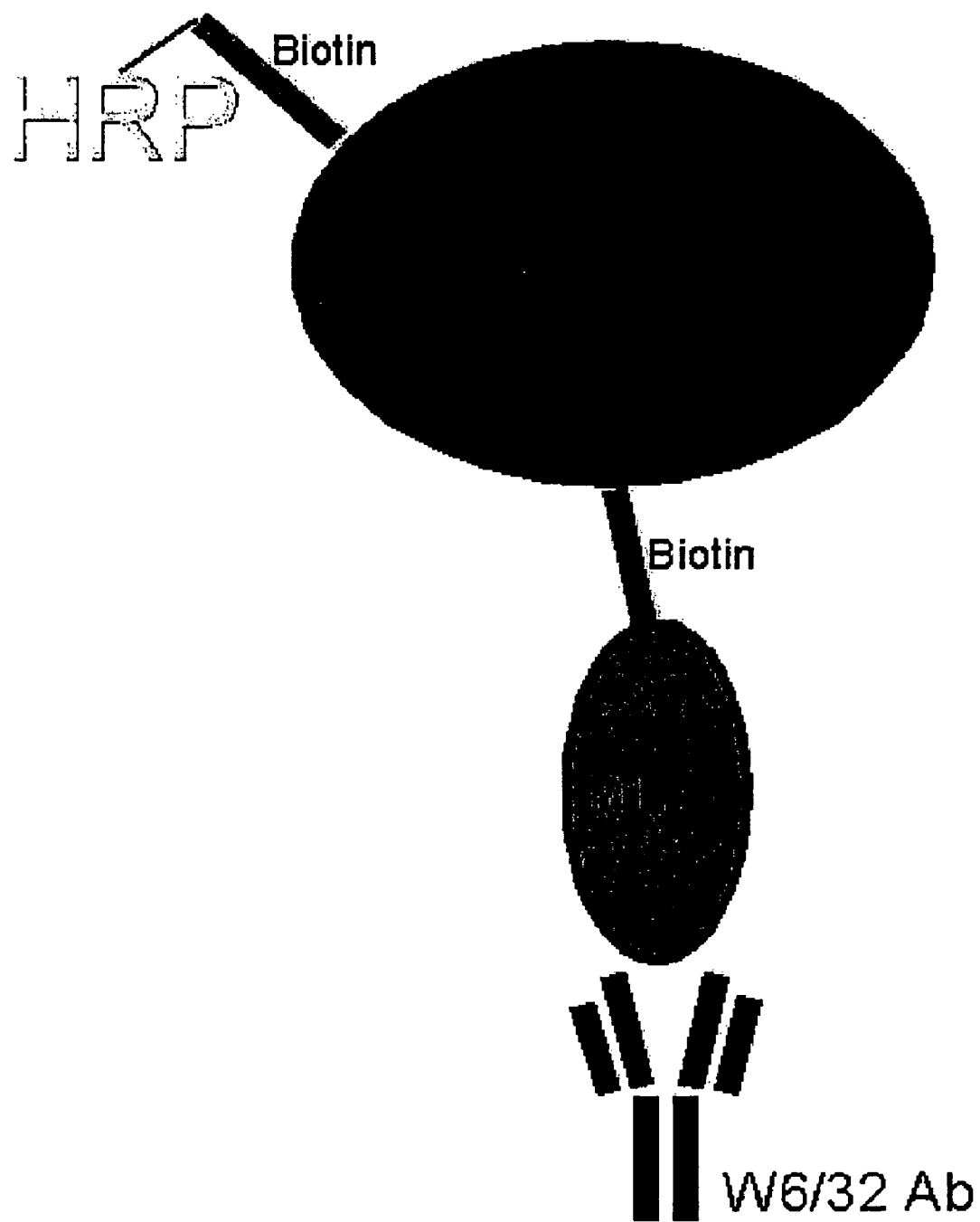
FIG. 43 is a pictorial representation of the conjugate used to confirm biotinylation of the sHLA molecule.

Incubation time was varied under constant conditions to determine the time required for maximum biotinylation efficiency. Four identical reactions were incubated for either 1, 4, 8, or 16 hours at 37° C. Biotinylation mixture components were as follows: sHLA-bsp, 6 µM; MgOAc (Biomix B, Avidity), 1.9 mM; adenosine triphosphate (Biomix B, Avidity), 1.9 mM; BirA, 0.8 µM; Tris-HCl, pH 8.0, 9.4 mM; biotin (Biomix B, Avidity), 10 µM; Pefabloc SC Plus (Roche), a protease inhibitor, 0.42 mM. Biotinylation was confirmed using a modified ELISA, with W6/32 (8 µg/mL) as the capture antibody and ABC Vectastain (Vector Laboratories), a kit containing avidin and biotinylated HRP, as the conjugate (FIG. 43).

Biotinylated sHLA was separated from free biotin by applying the biotinylation reaction product to a Bio-Spin chromatography column (BioRad, Bio-Spin 30 Tris columns). Tetrameric sHLA/peptide complexes were produced by the stepwise addition ($\frac{1}{10}^{th}$ volume, waiting 10 minutes between each addition) of the conjugate UltraAvidin-R-phycoerythrin (UltraAvidin-R-PE; Leinco Technologies) to the biotinylated class I complex. The final mixture contained a 1:4 molar ratio of UltraAvidin-R-PE:biotinylated class I, which is the same as a 1:1 molar ratio UltraAvidin-R-PE biotin binding sites:biotinylated class I. The volumes of avidin and biotinylated class I were determined by calculating the molar concentrations of each (in moles/µL) and then making certain that the number of moles of biotin binding sites in the avidin equaled the number of moles of biotinylated class I. (Because the biotinylation assay was qualitative rather than quantitative, the assumption that biotinylation efficiency was high (~90%) was made prior to making these calculations.) Tetramers were purified by gel filtration on a Superdex S-200 column (Pharmacia; Molecular Biology Resource Facility, University of Oklahoma Health Sciences Center).

Figure 44:
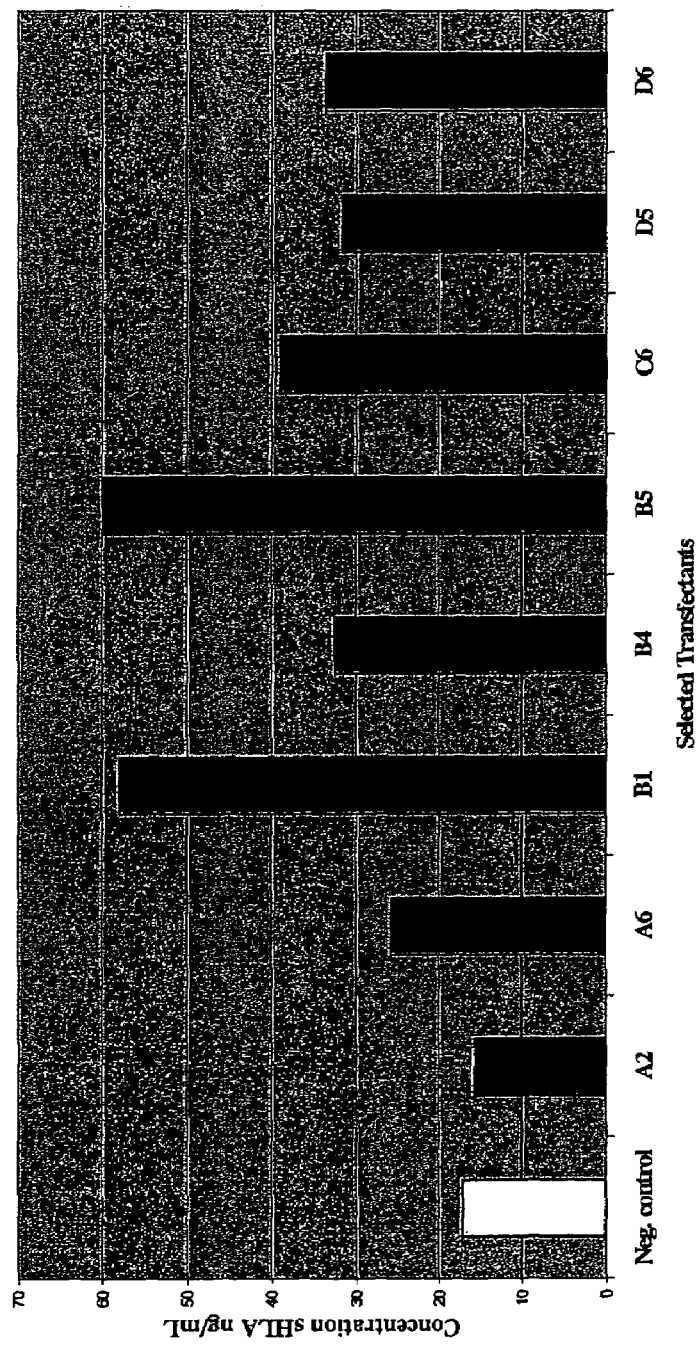
FIG. 44 is a graph showing production of sHLA-B*0702 by $T_2$ transfectants after peptide pulsing.

The construct successfully created using the AviTag bsp vector contained a 7-residue sequence (W-K-L-P-A-G-G) (SEQ ID NO:638) between the truncated B7 heavy chain at its C-terminus and the bsp. Despite the fact that the peptide binding groove is at the N-terminus of the heavy chain, it was undetermined at the time of transfection whether this 7-residue linker would in any way affect MHC protein folding or peptide binding capability. Because class I molecules must be properly folded and loaded with peptide before being directed to the cell surface, only the specific MHC/peptide complexes should be in the supernatant. Additionally, the W6/32 monoclonal capture antibody of the ELISA positively identified the presence of MHC-bsp/peptide complexes secreted into the supernatant by producing transfectants (FIG. 44). Thus, the 7 residue linker did not alter protein folding or peptide loading.

Figure 45:
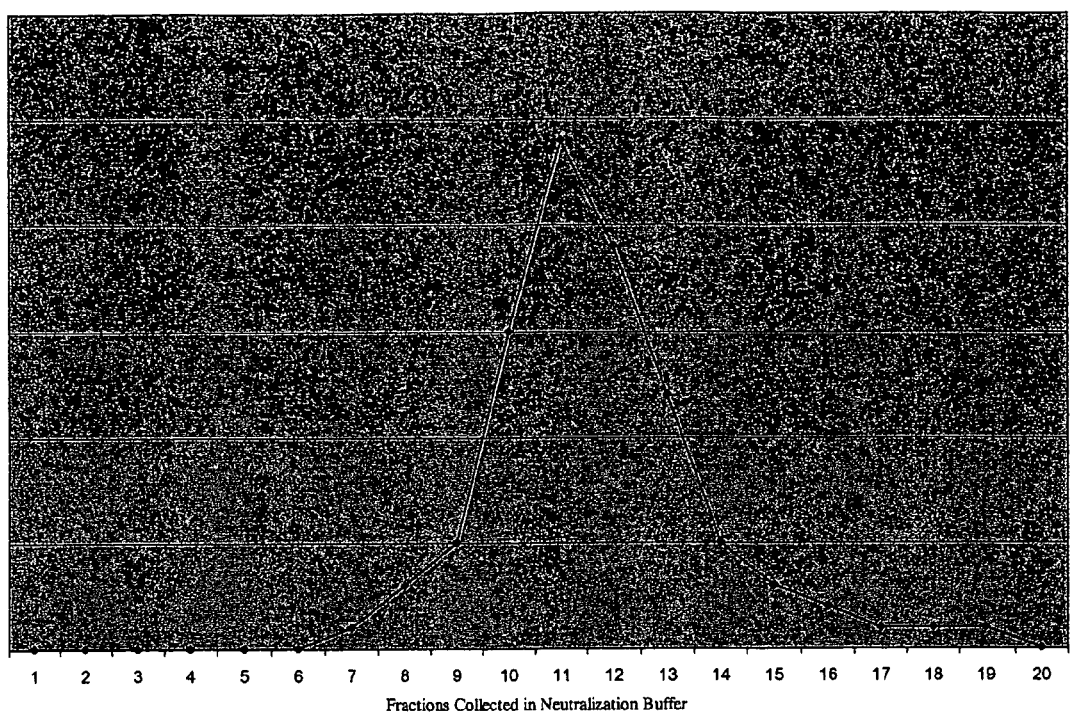
FIG. 45 is a graph showing the elution curve of the Elisa assay used to confirm sHLA production.

With regard to the purification of the class I-bsp molecule via affinity column chromatography, the bsp addition to the molecule perhaps affected column loading, as only ~50% recovery of the purified protein was achieved when pre-column and post-column protein amounts were compared. A large percentage of this "lost" protein was detected both in the wash, indicating non-specific binding to the column during loading, and in the flow-thru, possibly indicating that the additional 22 amino acids (15 amino acids in the bsp and 7 amino acids linking the bsp to the class I, discussed above) on the C-terminus of the molecule interfered with loading. If the latter occurred, then ELISA results quantifying sHLA-bsp production by T2's may be underestimated, since the same W6/32 antibody used as the capture in the ELISA is also coupled the column. The elution curve (FIG. 45), produced as a result of the spectrophotometric (OD280) measurements of the column system during elution, allowed determination of which eluted fractions contained protein. These fractions were then pooled and the purified protein was concentrated and biotinylated.

Figure 46:
FIG. 46 is a graph showing that an increase in time results in greater biotinylation.

In a 1993 paper, Peter Shatz demonstrated that an array of BirA substrate peptide sequences, all having in common a lysine residue at position 9 or 10, existed and were capable of being biotinylated. However, some bsp sequences biotinylate more robustly than other sequences. It is important, therefore, to determine the reaction time required to optimally biotinylate a given protein with its specific bsp, so as to not waste the protein in future biotinylation reactions. FIG. 46 demonstrates that increasing the incubation time of the biotinylation reaction, with all other variables unchanged, allows for greater biotinylation.

Figure 47:
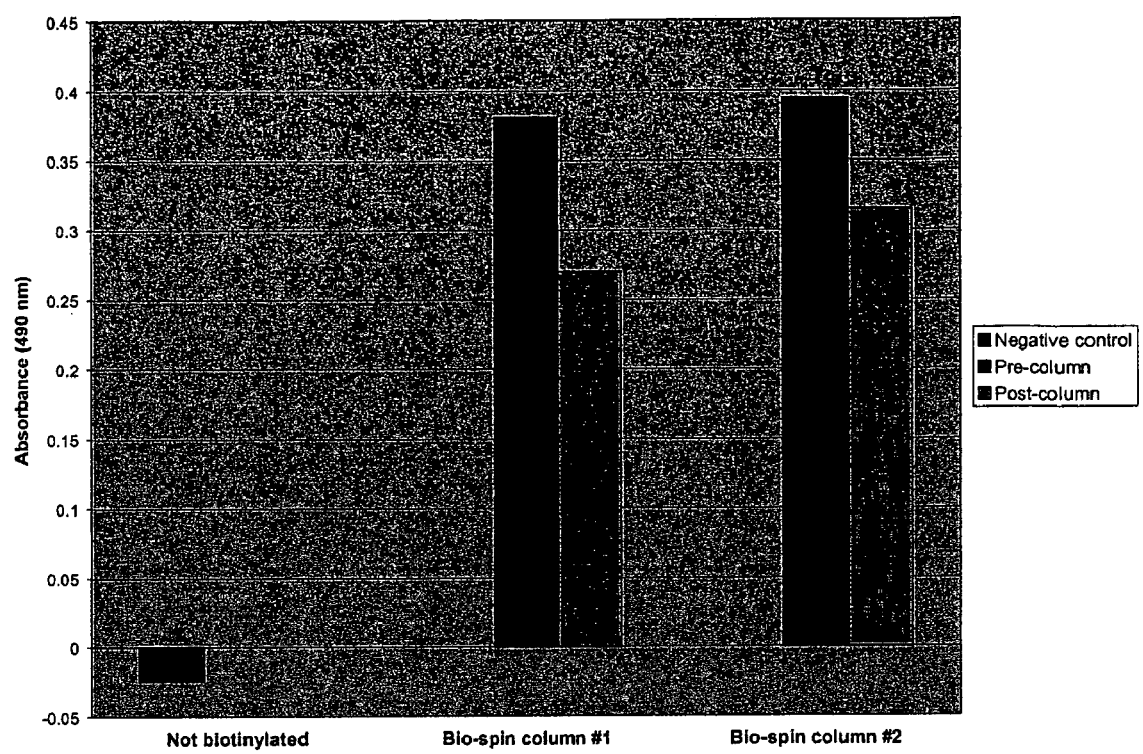
FIG. 47 is a graph showing separation of biotinylated class I from free biotin.

Importantly, purifying the biotinylated class I molecules from any free biotin remaining in the reaction mixture was performed prior to making tetramers, as free biotin may assume one or more of the four biotin binding sites on the avidin molecule in place of a biotinylated class I molecule. FIG. 47 indicates that some biotinylated protein was lost in this step. However, this purification ideally eliminates any "contamination" from monomers, dimers, or trimers when making tetramers, optimizing tetramer yield.

Upon purification of the tetramers via gel filtration (Superdex-200), tetramers (MW 498.6 kDa) were separated on the basis of size from any other possibly-present molecule contained in the reaction mixture [free avidin-PE conjugate (300 kDa—avidin 60 kDa and Phycoerythrin 240 kDa); free biotinylated class I (49.65 kDa); unbiotinylated class I-bsp, since biotinylation efficiency was not likely 100% (49.4 kDa); free biotin, despite the purification step (243 Daltons); monomers (349.65 kDa); dimers (399.3 kDa); or trimers (448.94 kDa)].

The present use of tetramers as reagents to stain T cells specific to an epitope is widely known and utilized. Additionally, the use of tetramers in vaccine development and immune modulation is a reality in present biomedical research. Several potential applications of tetramers in modulating the human immune system include tolerance induction in autoimmune diseases and adoptive transfer of antigen-specific T cells in the clinic. If the specific epitope causing the immune response in an autoimmune disease is known, a tetrameric complex specific to the patient's HLA type and containing the immunogenic epitope could be made and, in theory, given therapeutically to the patient in a dose large enough to induce tolerance. Liposomes, which are artificial antigen presenting cells that can be made and have incorporated in their membranes specific MHC/peptide complexes, are a cousin to the tetramer and would likely be used, rather than tetramers, for this type of immune modulation. Adoptive transfer of T cells specific to an antigen of a disease causing agent (tumor or viral) could be achieved by using tetramers (specific to the patient and the antigen) to sort live T cells, culturing these T cells in vitro to increase their numbers, and then transferring the cells back into the patient in hopes of enhancing the patient's immune response.

Thus, as the potential therapeutic use of tetramers in the clinic becomes a reality, it is evident that a tetramer molecule containing MHC molecules expressed in mammalian cells would more so reflect the protein produced in vivo. Although it is not known for certain the significance of the role of MHC glycosylation in in vivo intra- and inter-molecular interactions, it is important both in research and clinical therapy to use a system that emulates the actual interaction as much as possible. Likewise, it is not known if the class I trimeric complex formed inside mammalian cells is structurally identical to that formed outside the cell, and for this reason we choose to load sHLA class I molecules inside the cell. In summary, we show that class I molecules can be loaded with peptide inside a mammalian cell, secreted from the cell, biotinylated, and that these biotinylated class I molecules interact with streptavidin.

Alternatively, a cell line deficient in peptide processing but still efficient in peptide loading may be utilized for both epitope and functional testing, so that a putative epitope can be expressed or pulsed into a cell and loaded into the HLA molecule in the ER of such cell. The cDNA construct isolated as described above may be ligated into a mammalian expression vector which also contains a DNA fragment encoding a peptide of interest attached to a fragment encoding a signal peptide so that the peptide of interest will be retained in the ER of the cell for loading, and such construct transfected into the mammalian cell line deficient in peptide processing but which retains the ability to load peptide in the HLA molecules, such as the T2 cell line. In this manner, the peptide of interest is produced together with the HLA molecule. The soluble HLA molecule (with or without a His or biotinylation signal tail) can then be purified and utilized as a reagent that has been produced in mammalian cells (fully glycosylated, etc.) and is loaded with the single co-transfected peptide. Optionally, random oligomers could be made and cloned into such a mammalian expression vector, and the soluble HLA molecules could again be purified and used to characterize T cells or other immune effector cells. In a further alternative, rather than expressing the peptides with the HLA molecule, the cells expressing the HLA molecule could be pulsed with a single synthetic peptide or multiple synthetic peptides and analyzed as described above to identify bound peptides. Any of the HLA molecule-peptide complexes could be multimerized to form dimers, tetramers, etc. and tested for their ability to serve as ligands for CTLs and induce immune responses in humans.

In summary, the method of the present invention involves production of MHC class I and class II molecules beginning from gDNA and/or cDNA. The gDNA clones encoding a given MHC molecule can be truncated to be secreted rather than bound at the cell surface. This truncated version of the MHC molecule can be produced in mammalian or insect/bacterial cells such that milligram or greater quantities of an individual class I or class II molecule can be obtained. The secreted MHC class I molecules can be naturally loaded with thousands of endogenous peptides in mammalian cells, while the secreted MHC class II molecules can be naturally loaded with thousands of endocytic peptides in mammalian cells. Alternatively, the secreted MHC proteins can be produced in cells that do not load the MHC molecule with peptide ligand. Production of MHC proteins in cells which do not load the MHC molecule with peptide facilitates the loading of the MHC molecule via co-transfection with constructs encoding a given peptide(s). Alternatively, the MHC peptide-loading deficient MHC transfectant can be pulsed with peptides or DNA encoding peptides. The resulting individual secreted MHC molecules are useful for studies of peptide loading (i.e. in vaccine development), for characterizing human immune responses to a given MHC molecule loaded with a particular peptide(s), and to the development of diagnostics where one needs sufficient MHC protein in order to directly assess reactivity to different MHC proteins.

Another important component of the secreted MHC molecules described here is that naturally loaded peptides can be eluted from the MHC molecules and characterized. Substantial quantities of peptide can be obtained from individual MHC molecules, and the peptides can be selectively characterized. Unique information results from having a sufficient supply of eluted peptide, and this information is essential to databases and predictive algorithms which are essential to the vaccine architect.

Thus, in accordance with the present invention, there has been provided a methodology for producing and manipulating Class I and Class II MHC molecules from gDNA as well as the sHLA molecules and their uses that fully satisfies the objectives and advantages set forth herein above. Although the invention has been described in conjunction with the specific drawings, experimentation, results and language set forth herein above, it is evident that many alternatives, modifications, and variations will be apparent to those skilled in the art. Accordingly, it is intended to embrace all such alternatives, modifications and variations that fall within the spirit and broad scope of the invention.

REFERENCES

Altschul, S. F., T. L. Madden, A. A. Schäffer, J. Zhang, Z. Zhang, W. Miller and D. J. Lipman (1997). Gapped BLAST and PSI-BLAST: a new generation of protein database search programs. *Nuc. Acids Res.* 25: 3389-3402.

Antao, A. B., V. G. Chinchar, T. J. McConnell, N. W. Miller, L. W. Clem and M. R. Wilson (1999). MHC class I genes of the channel catfish: sequence analysis and expression. *Immunogenetics* 49: 303-311.

Appella, E., E. A. Padlan and D. F. Hunt (1995). Analysis of the structure of naturally processed peptides bound by class I and class II major histocompatibility complex molecules. In *Interface between Chemistry and Biochemistry*. P. Jollés and H. Jörnvall, eds. EXS series. Basel; Birkhäuser Verlag 73: 105-119.

Arnett, K. L., W. Huang, N. M. Valiante, L. D. Barber and P. Parham (1998). The Bw4/Bw6 difference between HLA-B*0802 and HLA-B*0801 changes the peptides endogenously bound and the stimulation of alloreactive T cells. *Immunogenetics* 48: 56-61.

Arrand, J. R., L. Rymo, J. E. Walsh, E. Bjorck, T. Lindahl and B. E. Griffin (1981). Molecular cloning of the complete Epstein-Barr virus genome as a set of overlapping restriction endonuclease fragments. *Nuc. Acids Res.* 9: 2999-3014.

Balendiran, G. K., J. C. Solheim, A. C. M. Young, T. H. Hansen, S. G. Nathenson and J. C. Sacchettini (1997). The three-dimensional structure of an H-2 $L^d$-peptide complex explains the unique interaction of $L^d$ with beta-2 microglobulin and peptide. *Proc. Natl. Acad. Sci. USA* 94: 6880-6885.

Ballard, J. D., R. J. Collier and M. N. Starnbach (1996). Anthrax toxin-mediated delivery of a cytotoxic T-cell epitope in vivo. *Proc. Natl. Acad. Sci. USA* 93:12531-12534.

Barber, L. D., B. Gillece-Castro, L. Percival, X. Li, C. Clayberger and P. Parham (1995). Overlap in the repertoires of peptides bound in vivo by a group of related class I HLA-B allotypes. *Curr. Biol.* 5: 179-190.

Barber, L. D., L. Percival, K. L. Arnett, J. E. Gumperz, L. Chen and P. Parham (1997). Polymorphism in the α1 helix of the HLA-B heavy chain can have an overriding influence on peptide-binding specificity. *J. Immunol.* 158: 1660-1669.

Barber, L. D., L. Percival, N. M. Valiante, L. Chen, C. Lee, J. E. Gumperz, J. H. Phillips, L. L. Lanier, J. C. Bigge, R. B. Parekh and P. Parham (1996). The inter-locus recombinant HLA-B*4601 has high selectivity in peptide binding and functions characteristic of HLA-C. *J. Exp. Med.* 184: 735-740.

Barnstable, C. J., W. F. Bodmer, G. Brown, G. Galfre, C. Milstein, A. F. Williams and A. Ziegler (1978). Production of monoclonal antibodies to group A erythrocytes, HLA and other human cell surface antigens: new tools for genetic analysis. *Cell* 14: 9-20.

Bertoletti, A., C. Ferrari, F. Fiaccadori, A. Penna, R. Margolskee, H. J. Schlicht, P. Fowler, S. Guilhot and F. V. Chisari (1991). HLA class I-restricted human cytotoxic T-cells recognize endogenously synthesized hepatitis B virus nucleocapsid antigen. *Proc. Natl. Acad. Sci. USA* 88: 10445-10449.

Björkman, P. J. (1997). MHC restriction in three dimensions: a view of T cell receptor/ligand interactions. *Cell* 89: 167-170.

Björkman, P. J. and P. Parham (1990). Structure, function and diversity of class I major histocompatibility molecules. *Annu. Rev. Biochem.* 59: 253-288.

Björkman, P. J., M. A. Saper, B. Samraoui, W. S. Bennett, J. L. Strominger and D. C. Wiley (1987a). Structure of the human class I histocompatibility antigen, HLA-A2. *Nature* 329: 506-512.

Björkman, P. J., M. A. Saper, B. Samraoui, W. S. Bennett, J. L. Strominger and D. C. Wiley (1987b). The foreign antigen binding site and T cell recognition regions of class I histocompatibility antigens. *Nature* 329: 512-518.

Bluestone, J. A., S. Jameson, S. Miller and R. Dick (1992). Peptide-induced conformational changes in class I heavy chains alter major hisotocompatibility complex recognition. *J. Exp. Med.* 176: 1757-1761.

Boisgerault, F., V. Tieng, M. C. Stolzenberg, N. Dulphy, I. Khalil, R. Tamouza, D. Charron and A. Toubert (1996). Differences in endogenous peptides presented by HLA-B*2705 and B*2703 allelic variants: implications for susceptibility to spondylarthropathies. *J. Clin. Invest.* 98: 2764-2770.

Borges, L., M. L. Hsu, N. Fanger, M. Kubin and D. Cosman (1997). A family of human lymphoid and myeloid Ig-like receptors, some of which bind to MHC class I molecules. *J. Immunol.* 159: 5192-5196.

Bouvier, M. and D. C. Wiley (1994). Importance of peptide amino and carboxyl termini to the stability of MHC class I molecules. *Science* 265: 398-402.

Brodsky, F. M., W. F. Bodmer and P. Parham (1979). Characterization of a monoclonal anti-β2-microglobulin antibody and its use in the genetic and biochemical analysis of major histocompatibility antigens. *Eur. J. Immunol* 9: 536-545.

Brooks, J. M., R. J. Murray, W. A. Thomas, M. G. Kurilla and A. B. Rickinson (1993). Different HLA-B27 subtypes present the same immunodominant Epstein-Barr virus peptide. *J. Exp. Med.* 178: 879-887. Calin-Laurens, V., M. -C. Trescol-Biémont, D. Gerlier and C. Rabourdin-Combe (1993). Can one predict antigenic peptides for MHC class I-restricted cytotoxic T lymphocytes useful for vaccination? *Vaccine* 11: 974-978.

Carrington, M., G. W. Nelson, M. P. Martin, T. Kissner, D. Vlahov, J. J. Goedert, R. Kaslow, S. Buchbinder, K. Hoots and S. J. O'Brien (1999). HLA and HIV-1: heterozygote advantage and B*35-Cw*04 disadvantage. *Science* 283: 1748-1752.

Catipovic, B., J. Dal Porto, M. Mage, T. E. Johansen and J. P. Schneck (1992). Major histocompatibility complex conformational epitopes are peptide specific. *J. Exp. Med.* 176: 1611-1618.

Chang, K. -M., N. H. Gruener, S. Southwood, J. Sidney, G. R. Pape, F. V. Chisari and A. Sette (1999). Identification of HLA-A3 and -B7-restricted CTL response to hepatitis C virus in patients with acute and chronic hepatitis C. *J. Immunol.* 162: 1156-1164.

Chapman, J. R. (1996). Mass spectrometry: ionization methods and instrumentation. In *Protein and Peptide Analysis by Mass Spectrometry*. J. R. Chapman, ed. Methods in Molecular Biology series. Totowa, N.J.; Humana Press Inc. 61: 9-28.

Chelvanayagam, G. (1996). A roadmap for HLA-A, HLA-B, and HLA-C peptide binding specificities. *Immunogenetics* 45: 15-26.

Chen, B. P. and P. Parham (1989). Direct binding of influenza peptides to class I HLA molecules. *Nature* 337: 743-745.

Choo, S. Y., L. -a. Fan and J. A. Hansen (1991). A novel HLA-B27 allele maps B27 allospecificity to the region around position 70 in the $\alpha_1$ domain. *J. Immunol.* 147:174-180.

Choo, S. Y., L. -a. Fan and J. A. Hansen (1993). Allelic variations clustered in the antigen binding sites of HLA-Bw62 molecules. *Immunogenetics* 37:108-113.

Clark, W. R., C. M. Walsh, A. A. Glass, F. Hayashi, M. Matloubian and R. Ahmed (1995). Molecular pathways of CTL-mediated cytotoxicity. *Immunol Rev.* 146: 33-44.

Collins, E. J., D. N. Garboczi and D. C. Wiley. (1994). Three-dimensional structure of peptide extending from one end of a class I MHC binding site. *Nature* 371: 626-629.

Collins, E. J., D. N. Garboczi, M. N. Karpusas and D. C. Wiley (1995). The three-dimensional structure of a class I major histocompatibility complex molecule missing the $\alpha_3$ domain of the heavy chain. *Proc. Natl. Acad. Sci. USA* 92: 1218-1221.

Corr, M., L. F. Boyd, S. R. Frankel, S. Kozlowski, E. A. Padlan and D. H. Margulies (1992). Endogenous peptides of a soluble major histocompatibility complex class I molecule, $H-2L^d$s: sequence motif, quantitative binding, and molecular modeling of the complex. *J. Exp. Med.* 176: 1681-1692.

Cosman, D., N. Fanger, L. Borges, M. Kubin, W. Chin, L. Peterson and M. L. Hsu (1997). A novel immunoglobulin superfamily receptor for cellular and viral MHC class I molecules. *Immunity* 7: 273-282.

Coulie, P. G., M. Somville, F. Lehmann, P. Hainaut, F. Brasseur, R. Devos and T. Boon (1992). Precursor frequency analysis of human cytolytic T lymphocytes directed against autologous melanoma cells. *Int. J. Cancer* 50: 289-297.

Coux, O., K. Tanaka and A. L. Goldberg (1996). Structure and functions of the 20S and 26S proteasomes. *Annu. Rev. Biochem.* 65: 801-847.

Cox, A. L., J. Skipper, Y. Chen, R. A. Henderson, T. L. Darrow, J. Shabanowitz, V. H. Engelhard, D. F. Hunt and C. L. Slingluff. (1994). Identification of a peptide recognized by five melanoma-specific human cytotoxic T cell lines. *Science* 264: 716-719.

Craiu, A., T. Akopian, A. Goldberg and K. L. Rock (1997). Two distinct proteolytic processes in the generation of a major histocompatibility complex class I-presented peptide. *Proc. Natl. Acad. Sci. USA* 94:10850-10855.

Dausset, J. (1958). Lso-leuco-anticorps. *Acta Haematol.* 20: 156-166.

Davenport, M. P., I. A. P. Ho Shon and A. V. S. Hill (1995). An empirical method for the prediction of T-cell epitopes. *Immunogenetics* 42: 392-397.

Davenport, M. P., K. J. Smith, D. Barouch, S. W. Reid, W. M. Bodnar, A. C. Willis, D. F. Hunt and A. V. S. Hill (1997). HLA class I binding motifs derived from random peptide libraries differ at the COOH terminus from those of eluted peptides. *J. Exp. Med.* 185: 367-371.

Day, P. M., J. W. Yewdell, A. Porgador, R. N. Germain and J. R. Bennink (1997). Direct delivery of exogenous MHC class I molecule-binding oligopeptides to the endoplasmic reticulum of viable cells. *Immunology* 94: 8064-8069.

de la Salle, H., E. Houssaint, M. -A. Peyrat, D. Arnold, J. Salamero, D. Pinczon, S. Stevanovic, H. Bausinger, D. Fricker, E. Gomard, W. Biddison, P. Lehner, F. UytdeHaag, M. Sasportes, L. Donato, H. -G. Rammensee, J. -P. Cazenare, D. Hanau, M. -M. Tongio and M. Bonneville. (1997). Human peptide transporter deficiency: importance of HLA-B in the presentation of TAP-independent EBV antigens. *J. Immunol.* 158: 4555-4563.

del Guercio, M. -F., J. Sidney, G. Hermanson, C. Perez, H. M. Grey, R. T. Kubo and A. Sette (1995). Binding of a peptide antigen to multiple HLA alleles allows definition of an A2-like supertype. *J. Immunol.* 154: 685-693.

DiBrino, M., K. C. Parker, D. H. Margulies, J. Shiloach, R. V. Turner, W. E. Biddison and J. E. Coligan (1994). The HLA-B14 peptide binding site can accommodate peptides with different combinations of anchor residues. *J. Biol. Chem.* 269: 32426-32434.

DiBrino, M., K. C. Parker, J. Shiloach, R. V. Turner, T. Tsuchida, M. Garfield, W. E. Biddison and J. E. Coligan (1994). Endogenous peptides with distinct amino acid anchor residue motifs bind to HLA-A1 and HLA-B8. *J. Immunol.* 152: 620-631.

Domena, J. D., A. -M. Little, J. A. Madrigal, W. H. Hildebrand, L. Johnston-Dow, E. du Toit, W. B. Bias and P. Parham (1993). Structural heterogeneity in HLA-B70, a high frequency antigen of black populations. *Tissue Antigens* 42: 509-517.

Donnelly, J. J., J. B. Ulmer, L. A. Hawe, A. Friedman, X. -P. Shi, K. R. Leander, J. W. Shiver, A. I. Oliff, D. Martinez, D. Montgomery and M. A. Liu (1993). Targeted delivery of peptide epitopes to class I major histocompatibility molecules by a modified *Pseudomonas* exotoxin. *Proc. Natl. Acad. Sci. USA* 90: 3530-3534.

Drijfhout, J. W., R. M. Brandt, J. D'Amaro, W. M. Kast and C. J. Melief (1995). Detailed motifs for peptide binding to HLA-A*0201 derived from large random sets of peptides using a cellular binding assay. *Hum. Immunol.* 43: 1-12.

Elliott, T. J. (1991). How do peptides associate with MHC class I molecules? *Immunol. Today* 12: 386-388.

Elliott, T. (1997). How does TAP associate with MHC class I molecules? *Immunol. Today* 18: 375-379.

Elliott, T., M. Smith, P. Driscoll and A. McMichael (1993). Peptide selection by class I molecules of the major histocompatibility complex. *Curr. Biol.* 3: 854-866.

Engelhard, V. H. (1994). Structure of peptides associated with class I and class II MHC molecules. *Annu. Rev. Immunol.* 12: 181-207.

Ennis, P. D., A. P. Jackson and P. Parham (1988). Molecular cloning of bovine class I MHC cDNA. *J. Immunol.* 141: 642-651.

Ennis, P. D., J. Zemmour, R. D. Salter and P. Parham (1990). Rapid cloning of HLA-A, B cDNA by using the polymerase chain reaction: frequency and nature of errors produced in amplification. *Proc. Natl. Acad. Sci. USA* 87: 2833-2837.

Evans, T. L. and R. A. Miller (1988). Large-scale production of murine monoclonal antibodies using hollow fiber bioreactors. *Biotechniques* 6: 762-767.

Falk, F., O. Rötzschke, M. Takiguchi, V. Gnau, S. Stevanovic, G. Jung and H. -G. Rammensee (1995). Peptide motifs of HLA-B58, B60, B61, and B62 molecules. *Immunogenetics* 41: 165-168.

Falk, K., O. Rötzschke, S. Stevanovic, G. Jung and H. -G. Rammensee (1991). Allele-specific motifs revealed by sequencing of self peptides eluted from MHC molecules. *Nature* 351: 290-293.

Falk, K., O. Rötzschke, M. Takiguchi, V. Gnau, S. Stevanovic, G. Jung and H. -G. Rammensee (1995). Peptide motifs of HLA-B38 and B39 molecules. *Immunogenetics* 41: 162-164.

Ferris, R. L., C. Buck, S. A. Hammond, A. S. Woods, R. J. Cotter, M. Takiguchi, Y. Igarashi, Y. Ichikawa and R. F. Siliciano (1996). Class I-restricted presentation of an HIV-1 gp41 epitope containing an N-linked glycosylation site: implications for the mechanism of processing of viral envelope proteins. *J. Immunol.* 156: 834-840.

Flad, T., B. Spengler, H. Kalbacher, P. Brossart, D. Baier, R. Kaufmann, P. Bold, S. Metzger, M. Blüggel, H. E. Meyer, B. Kurz and C. A. Muller (1998). Direct identification of major histocompatibility complex class I-bound tumor-associated peptide antigens of a renal carcinoma cell line by a novel mass spectrometric method. *Cancer Res.* 58: 5803-5811.

Fleischhauer, K., D. Avila, F. Vilbois, C. Traversari, C. Bordignon and H. -J. Wallny (1994). Characterization of natural peptide ligands for HLA-B*4402 and -B*4403: implications for peptide involvement in allorecognition of a single amino acid change in the HLA-B44 heavy chain. *Tissue Antigens* 44: 311-317.

Frelinger, J. A., F. M. Gotch, H. Zweerink, E. Wain and A. J. McMichael (1990). Evidence of widespread binding of HLA class I molecules to peptides. *J. Exp. Med.* 172: 827-834.

Fremont, D. H., M. Matsumura, E. A. Stura, P. A. Peterson and I. A. Wilson (1992). Crystal structures of two viral peptides in complex with murine MHC class I H-2K$^b$. *Science* 257: 919-927.

Fruci, D., P. Rovero, R. H. Butler, R. Sorrentino, R. Tosi and N. Tanigaki (1993). HLA class I binding of synthetic nonamer peptides carrying major anchor residue motifs of HLA-B27 (B*2705)-binding peptides. *Immunogenetics* 38: 41-46.

Gaczynska, M., K. L. Rock, T. Spies and A. L. Goldberg (1994). Peptidase activities of proteasomes are differentially regulated by the major histocompatibility complex-encoded genes for LMP2 and LMP7. *Proc. Natl. Acad. Sci. USA* 91: 9213-9217.

Garboczi, D. N., P. Ghosh, U. Utz, Q. R. Fan, W. E. Biddison and D. C. Wiley (1996). Structure of thecomplex between human T cell receptor, viral peptide, and HLA-A2. *Nature* 384: 134-141.

Garcia, K. C., M. Degano, R. L. Stanfield, A. Brunmark, M. R. Jackson, P. A. Peterson, L. Teyton and I. A. Wilson (1996). An αβT cell receptor structure at 2.5 Å and its orientation in the TCR-MHC complex. *Science* 274: 209-219.

Garrett, T. P. J., M. A. Saper, P. J. Bjorkman, J. L. Strominger and D. C. Wiley (1989). Specificity pockets for the side chains of peptide antigens in HLA-Aw68. *Nature* 342: 692-696.

Germain, R. N. (1994). MHC-dependent antigen processing and peptide presentation: providing ligands for T lymphocyte activation. *Cell* 76: 287-299.

Germain, R. N. and D. H. Margulies (1993). The biochemistry and cell biology of antigen processing and presentation. *Annu. Rev. Immunol.* 11: 403-450.

Glithero, A., J. Tormo, J. S. Haurum, G. Arsequell, G. Valencia, J. Edwards, S. Springer, A. Townsend, Y. L. Pao, M. Wormald, R. A. Dwek, E. Y. Jones and T. Elliott (1999). Crystal structures of two H-2 D$^b$/glycopeptide complexes suggest a molecular basis for CTL cross-reactivity. *Immunity* 10: 63-74.

Gnjatic, S., B. Bressac-de Paillerets, J. G. Guillet and J. Choppin (1995). Mapping and ranking of potential cytotoxic T epitopes in the p53 protein: effect of mutations and polymorphism on peptide binding to purified and refolded HLA molecules. *Eur. J. Immunol.* 25: 1638-1642.

Goletz, T. J., K. R. Klimpel, N. Arora, S. H. Leppla, J. M. Keith and J. A. Berzofsky (1997). Targeting HIV proteins to the major histocompatibility complex class I processing pathway with a novel gp120-anthrax toxin fusion protein. *Proc. Natl. Acad. Sci. USA* 94: 12059-12064.

Gooding, L. R. and K. A. O'Connell (1983). Recognition by cytotoxic T lymphocytes of cells expressing fragments of the SV40 tumor antigen. *J. Immunol* 131: 2580-2586.

Gorer, P. A. (1936). The detection of antigenic differences in mouse erythrocytes by the employment of immune sera. *Br. J. Exp. Pathol.* 17: 42-50.

Gorer, P. A. (1937). The genetic and antigenic basis of tumor transplantation. *J. Pathol. Bacteriol.* 44: 691-697.

Gotch, F., A. McMichael and J. Rothbard (1988). Recognition of influenza A matrix protein by HLA-A2 restricted T lymphocytes: use of analogues to orientate the matrix peptide in the HLA-A2 binding site. *J. Exp. Med.* 168: 2045-2057.

Grandea III, A. G., M. J. Androlewicz, R. S. Athwal, D. E. Geraghty and T. Spies (1995). Dependence of peptide binding by MHC class I molecules on their interaction with TAP. *Science* 270: 105-108.

Grandea III, A. G., P. J. Lehner, P. Cresswell and T. Spies (1997). Regulation of MHC class I heterodimer stability and interaction with TAP by tapasin. *Immunongenetics* 46: 477-483.

Guex, N. and M. C. Peitsch (1996). Swiss-PdbViewer: a fast and easy-to-use PDB viewer for Macintosh and PC. *Prot. Data Bank Quart. Newsletter* 77: 7.

Gulukota, K. and C. DeLisi (1996). HLA allele selection for designing peptide vaccines. *Genet Anal.* 13: 81-86.

Gumperz, J. E., V. Litwin, J. H. Phillips, L. L. Lanier and P. Parham (1995). The Bw4 public epitope of HLA-B molecules confers reactivity with natural killer cell clones that express NKb1, a putative HLA receptor. *J. Exp. Med.* 181: 1133-1144.

Guo, H. -C., T. S. Jardetzky, T. P. J. Garrett, W. S. Lane, J. L. Strominger and D. C. Wiley (1992). Different length peptides bind to HLA-Aw68 similarly at their ends but bulge out in the middle. *Nature* 360: 364-366.

Harris, M. R., Y. L. Y. Yik, C. S. Kindle, T. H. Hansen and J. C. Solheim (1998). Calreticulin and calnexin interact with different protein and glycan determinants during the assembly of MHC class I. *J. Immunol.* 160: 5404-5409.

Harty, J. T. and M. J. Bevan (1992). CD8$^+$ T cells specific for a single nonamer epitope of *Listeria monocytogenes* are protective in vivo. *J. Exp. Med.* 175: 1531-1538.

Heemels, M. -T. and H. Ploegh (1995). Generation, translocation, and presentation of MHC class I-restricted peptides. *Annu. Rev. Biochem.* 64: 463-491.

Henderson, R. A., A. L. Cox, K. Sakaguchi, E. Appella, J. Shabanowitz, D. F. Hunt and V. H. Engelhard (1993). Direct identification of an endogenous peptide recognized by multiple HLA-A2.1-specific cytotoxic T cells. *Proc. Natl. Acad. Sci. USA* 90: 10275-10279.

Henderson, R. A., H. Michel, K. Sakaguchi, J. Shabanowitz, E. Appella, D. F. Hunt and V. H. Engelhard (1992). HLA-A2.1-associated peptides from a mutant cell line: a second pathway of antigen presentation. *Science* 255: 1264-1266.

Herberg, J. A., S. Beck and J. Trowsdale (1998). TAPASIN, DAXX, RGL2, HKE2 and four new genes (BING 1, 3 to 5) form a dense cluster at the centromeric end of the MHC. *J. Mol. Biol.* 10: 839-857.

Heslop, H. E., C. Y. C. Ng, C. Li, C. A. Smith, S. K. Loftin, R. A. Krance, M. K. Brenner and C. M. Rooney (1996). Long-term restoration of immunity against Epstein-Barr virus infection by adoptive transfer of gene-modified virus-specific T lymphocytes. *Nature Med.* 2: 551-555.

Hildebrand, W. H., J. D. Domena, S. Y. Shen, M. Bunce, S. G. E. Marsh, W. B. Bias and P. Parham (1994). HLA-B15: a widespread and diverse family of HLA-B alleles. *Tissue Antigens* 43: 209-218.

Hill, A. V. S., C. E. M. Allsopp, D. Kwiatkowski, N. M. Anstey, P. Twumasi, P. A. Rowe, S. Bennett, D. Brewster, A. J. McMichael and B. M. Greenwood (1991). Common West African HLA antigens are associated with protection from severe malaria. *Nature* 352: 595-600.

Hill, A. V. S., J. Elvin, A. C. Willis, M. Aidoo, C. E. M. Allsopp, F. M. Gotch, X. Ming Gao, M. Takiguchi, B. M. Greenwood, A. R. M. Townsend, A. J. McMichael and H. C. Whittle (1992). Molecular analysis of the association of HLA-B53 and resistance to severe malaria. *Nature* 360: 434-439.

Hogan, K. T., D. P. Eisinger, S. B. Cupp, 3rd, K. J. Lekstrom, D. D. Deacon, J. Shabanowitz, D. F. Hunt, V. H. Engelhard, C. L. Slingluff, Jr. and M. M. [0465] Ross (1998). The peptide recognized by HLA-A68.2-restricted, squamous cell carcinoma of the lung-specific cytotoxic T lymphocytes is derived from a mutated elongation factor 2 gene. *Cancer Res.* 58: 5144-5150.

Hogan, K. T., N. Shimojo, S. F. Walk, V. H. Engelhard, W. L. Maloy, J. E. Coligan and W. E. Biddison (1988). Mutations of the $\alpha_2$ helix of HLA-A2 affect presentation but do not inhibit binding of influenza virus matrix peptide. *J. Exp. Med.* 168: 725-736.

Holland, M. J., D. J. Conway, T. J. Blanchard, O. M. Mahdi, R. L. Bailey, H. C. Whittle and D. C. Mabey (1997). Synthetic peptides based upon *Chlamydia trachomatis* antigens identify cytotoxic T lymphocyte responses in subjects from a trachoma-endemic population. *Clin. Exp. Immunol.* 107: 44-49.

Hsu, V. W., L. C. Yuan, J. G. Nuchtem, J. Lippincott-Schwartz, G. J. Hämmerling and R. D. Klausner (1991). A recycling pathway between the endoplasmic reticulum and the Golgi apparatus for retention of unassembled MHC class I molecules. *Nature* 352: 441-444.

Huczko, E. L., W. M. Bodnar, D. Benjamin, K. Sakasuchi, N. Z. Zhu, J. Shabanowitz, R. A. Henderson, E. Appella, D. F. Hunt and V. H. Engelhard (1993). Characteristics of endogenous peptides eluted from the class I MHC molecule HLA-B7 determined by mass spectrometry and computer modeling. *J. Immunol.* 151: 2572-2587.

Hughes, A. L. and M. Nei (1988). Pattern of nucleotide substitution at major histocompatibility complex class I loci reveals overdominant selection. *Nature* 335: 167-170.

Hughes, A. L. and M. Yeager (1998). Natural selection at major histocompatibility complex loci of vertebrates. *Annu. Rev. Genet* 32: 415-435.

Hunt, D. F., R. A. Henderson, J. Shabanowitz, K. Sakaguchi, H. Michel, N. Sevilir, A. L. Cox, E. Appella and V. H. Engelhard (1992). Characterization of peptides bound to the class I MHC molecule HLA-A2.1 by mass spectrometry. *Science* 255: 1261-1263.

Ikonomidis, G., Y. Paterson, F. J. Kos and D. A. Portnoy (1994). Delivery of a viral antigen to the class I processing and presentation pathway by *Listeria monocytogenes*. *J. Exp. Med.* 180: 2209-2218.

Jackson, L. R., L. J. Trudel, J. G. Fox and N. S. Lipman (1996). Evaluation of hollow fiber bioreactors as an alternative to murine ascites production for small scale monoclonal antibody production. *J. Immunol. Methods* 189: 217-231.

Jamieson, B. D., L. D. Butler and R. Ahmed (1987). Effective clearance of a persistent viral infection requires cooperation between virus-specific Lyt2$^+$ cells and nonspecific bone marrow-derived cells. *J. Virol.* 61: 3930-3937.

Figure 4:
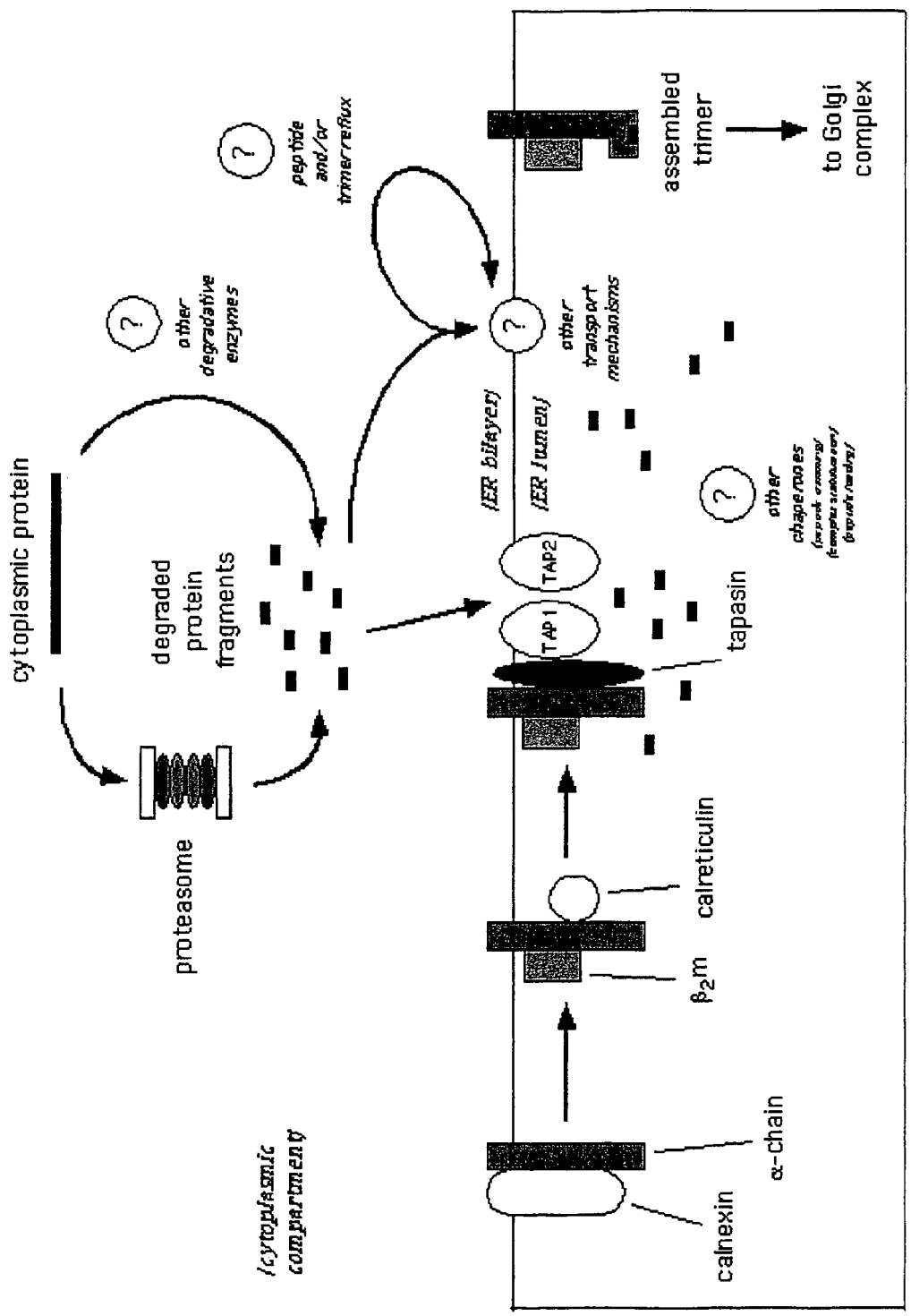
FIG. 4 is a pictorial representation summarizing MHC class I trimer assembly and transport. The typical endogenous processing pathway shown is simplified from the description disclosed herein. Major proteins participating in the processes are specifically illustrated and labelled. Some alternative processing and/or transport mechanisms currently under investigation are designated in the diagram by question marks. Assembled trimers travel through the Golgi complex prior to vesicular delivery to the surface membrane of the cell (not shown).

Janeway, Jr., C. A. and P. Travers (1994). *Immunobiology: The Immune System in Health and Disease*. C. A. Janeway, Jr. and P. Travers, eds. London; Current Biology Ltd.: FIG. 4.16.

Jardetzky, T. S., W. S. Lane, R. A. Robinson, D. R. Madden and D. C. Wiley (1991). Identification of self peptides bound to purified HLA-B27. *Nature* 353: 326-329.

Kast, W. M., R. M. P. Brandt, J. Sidney, J. -W. Drijfhout, R. T. Kubo, H. M. Grey, C. J. M. Melief and A. Sette (1994). Role of HLA-A motifs in identification of potential CTL epitopes in human papillomavirus type 16 E6 and E7 proteins. *J. Immunol.* 152: 3904-3912.

Kaufman, J., K. Skjoedt and J. Salomonsen (1990). The MHC molecules of nonmammalian vertebrates. *Immunol. Rev.* 113: 83-117.

Kavathas, P., F. H. Bach and R. DeMars (1980). Gamma ray-induced loss of expression of HLA and glyoxalase I alleles in lymphoblastoid cells. *Proc. Natl. Acad. Sci. USA* 77: 4251-4255.

Kawakami, Y., S. Eliyahu, K. Sakaguchi, P. F. Robbins, L. Rivoltini, J. R. Yannelli, E. Appella and S. A. Rosenberg (1994). Identification of the immunodominant peptides of the MART-1 human melanoma antigen recognized by the majority of HLA-A2-restricted tumor infiltrating lymphocytes. *J. Exp. Med.* 180: 347-352.

Khanna, R., M. Sherritt and S. R. Burrows (1999). EBV structural antigens, gp350 and gp85, as targets for ex vivo virus-specific CTL during acute infectious mononucleosis: potential use of gp350/gp85 CTL epitopes for vaccine design. *J. Immunol.* 162: 3063-3069.

Kikuchi, A., T. Sakaguchi, K. Miwa, Y. Takamiya, H. -G. Rammensee, Y. Kaneko and M. Takiguchi (1996). Binding of nonamer peptides to three HLA-B51 molecules which differ by a single amino acid substitution in the A-pocket. *Immunogenetics* 43: 268-276.

Kim, D. T., D. J. Mitchell, D. G. Brockstedt, L. Fong, G. P. Nolan, C. G. Fathmann, E. G. Engleman and J. B. Rothbard (1997). Introduction of soluble proteins into the MHC class I pathway by conjugation to an HIV tat peptide. *J. Immunol.* 159:1666-1668.

Kiftlesen, D. J., L. W. Thompson, P. H. Gulden, J. C. Skipper, T. A. Colella, J. A. Shabanowitz, D. F. Hunt, V. H. Engelhard and C. L. Slingluff, Jr. (1998). Human melanoma patients recognize an HLA-A1-restricted CTL epitope from tyrosinase containing two cysteine residues: implications for tumor vaccine development. *J. Immunol.* 160: 2099-2106.

Konya, J., G. Stuber, A. Bjomdal, E. M. Fenyo and J. Dillner (1997). Primary induction of human cytotoxic lymphocytes against a synthetic peptide of the human immunodeficiency virus type 1 protease. *J. Gen. Virol.* 78: 2217-2224.

Kostyu, D. D., L. I. Hannick, J. L. Traweek, M. Ghanayem, D. Heilpem and D. Dawson (1997). HLA class I polymorphism: structure and function and still questions. *Hum. Immunol.* 57: 1-18.

Kozlowski, S., M. Corr, T. Takeshita, L. F. Boyd, C. D. Pendleton, R. N. Germain, J. A. Berzofsky and D. H. Margulies (1992). Serum angiotensin-1 converting enzyme activity processes a human immunodeficiency virus 1 gp 160 peptide for presentation by major histocompatibility complex class I molecules. *J. Exp. Med.* 175:1417-1422.

Kubo, H., Y. Ikeda-Moore, A. Kikuchi, K. Miwa, K. Nokihara, C. Schönbach and M. Takiguchi (1998). Residue 116 determines the C-terminal anchor residue of HLA-B*3501 and -B*5101 binding peptides but does not explain the general affinity difference. *Immunogenetics* 47: 256-263.

Kubo, R. T., A. Sette, H. M. Grey, E. Appella, K. Sakaguchi, N. -Z. Zhu, D. Amoft, N. Sherman, J. Shabanowitz, H. Michel, W. M. Bodnar, T. A. Davis and D. F. Hunt (1994). Definition of specific peptide motifs for four major HLA-A alleles. *J. Immunol.* 152: 3913-3924.

Kuhner, M. K., D. A. Lawlor, P. D. Ennis and P. Parham (1991). Gene conversion in the evolution of the human and chimpanzee MHC class I loci. *Tissue Antigens* 38: 152-164.

Kulig, K., D. Nandi, I. Bacik, J. J. Monaco and S. Vukmanovic (1998). Physical and functional association of the major histocompatibility complex class I heavy chain $\alpha_3$ domain with the transporter associated with antigen processing. *J. Exp. Med.* 187: 865-874.

Kulkarni, A. B., P. L. Collins, I. Bacik, J. W. Yewdell, J. R. Bennink, J. E. Crowe, Jr. and B. R. Murphy (1995). Cytotoxic T-cells specific for a single peptide on the M2 protein of respiratory syncytial virus are the sole mediators of resistance induced by immunization with M2 encoded by a recombinant vaccinia virus. *J. Virol.* 69: 1261-1264.

Lanier, L. L. and J. H. Phillips (1996). Inhibitory MHC class I receptors on NK cells and T cells. *Immunol. Today* 17: 86-91.

Lawlor, D. A., E. Warren, F. E. Ward and P. Parham (1990). Comparison of class I MHC alleles in humans and apes. *Immunol. Rev.* 113: 147-185.

Lehner, P. J. and P. Cresswell (1996). Processing and delivery of peptides presented by MHC class I molecules. *Curr. Op. Immunol.* 8: 59-67.

Lewis, J. W., A. Sewel and T. Elliott (1998). HLA-A*0201 presents TAP-dependent peptide epitopes to cytotoxic T lymphocytes in the absence of tapasin. *Eur. J. Immunol.* 28: 3214-3220.

Li, S., K. M. Paulsson, H. O. Sjogren and P. Wang (1999). Peptide-bound major histocompatibility complex class I molecules associate with tapasin before dissociation from transporter associated with antigen processing. *J. Biol. Chem.* 274: 8649-8654.

Lin, A. Y., B. Devaux, A. Green, C. Sagerström, J. D. Elliott and M. M. Davis (1990). Expression of T cell antigen receptor heterodimers in a lipid-linked form. *Science* 249: 677-679.

Lin, L., K. Tokunaga, H. Tanaka, F. Nakajima, T. Imanishi, K. Kashiwase, M. Bannai, S. Mizuno, T. Akaza, K. Tadakoro, Y. Shibata and T. Juji (1996). Further molecular diversity in the HLA-B15 family. *Tissue Antigens* 47: 265-274.

Lin, Y. L. and B. A. Askonas (1981). Biological properties of an influenza A virus-specific killer T cell clone: inhibition of virus replication in vivo and induction of delayed-type hypersensitivity reactions. *J. Exp. Med.* 154: 225-234.

Lindquist, J. A., O. N. Jensen, M. Mann and G. J. Hämmerling (1998). ER-60, a chaperone with thiol-dependent reductase activity involved in MHC class I assembly. *EMBO J.* 17: 2186-2195.

Ljunggren, H. G., N. J. Stam, C. Ohlen, J. J. Neefjes, P. Hoglund, M. T. Heemels, J. Bastin, T. N. Schumacher, A. Townsend, K. Karre and H. L. Ploegh (1990). Empty MHC class I molecules come out in the cold. *Nature* 346(6283): 476480.

Loftus, D. J., R. T. Kubo, K. Sakaguchi, E. Celis, A. Sette and E. Appella (1995). Analysis of MHC-specific peptide motifs: applications in immunotherapy. In *Advances in Experimental Medicine and Biology*. M. Z. Atassi and G. S. Bixler, eds. New York; Plenum Press 383: 201-210.

Lombardi, G., M. Matusi, R. Moots, G. Aichinger, S. Sidhu, R. Batchelor, J. Frelinger and R. Lechler (1991). Limited regions of the $\alpha_2$-domain $\alpha$-helix control anti-A2 allorecognition: an analysis using a panel of A2 mutants. *Immunogenetics* 34: 149-156.

Luckey, C. J., G. M. King, J. A. Marto, S. Venketeswaran, B. F. Maier, V. L. Crotzer, T. A. Colella, J. Shabanowitz, D. F. Hunt and V. H. Engelhard (1998). Proteasomes can either generate or destroy MHC class I epitopes: evidence for nonproteasomal epitope generation in the cytosol. *J. Immunol.* 161: 112-121.

Madden, D. R. (1995). The three-dimensional structure of peptide-MHC complexes. *Annu. Rev. Immunol.* 13: 587-622.

Madden, D. R., D. N. Garboczi and D. C. Wiley (1993). The antigenic identity of peptide-MHC complexes: a comparison of the conformations of five viral peptides presented by HLA-A2. *Cell* 75: 693-708.

Madden, D. R., J. C. Gorga, J. L. Strominger and D. C. Wiley (1991). The structure of HLA-B27 reveals nonamer self-peptides bound in an extended conformation. *Nature* 353: 321-325.

Madden, D. R., J. C. Gorga, J. L. Strominger and D. C. Wiley (1992). The three-dimensional structure of HLA-B27 at 2.1 Å resolution suggests a general mechanism for tight peptide binding to MHC. *Cell* 70: 1035-1048.

Malarkannan, S., F. Gonzalez, V. Nguyen, G. Adair and N. Shastri (1996). Alloreactive CD8+ T cells can recognize unusual, rare, and unique processed peptide/MHC complexes. *J. Immunol.* 157: 4464-4473.

Mann, M. and M. Wilm (1994). Error-tolerant identification of peptides in sequence databases by peptide sequence tags. *Anal. Chem.* 66: 4390-4399.

Manning, T. C., C. J. Schlueter, E. A. Brodnicki, E. A. Parke, J. A. Speir, K. C. Garcia, L. Teyton, I. A. Wilson and D. M. Kranz (1998). Alanine scanning mutagenesis of an $\alpha\beta$ T cell receptor: mapping the energy of antigen presentation. *Immunity* 8: 413-425.

Martinez-Naves, E., L. D. Barber, J. A. Madrigal, C. M. Vullo, C. Clayberger, S. C. Lyu, R. C. Williams, C. Gorodezky, T. Markow, M. L. Petzl-Erler and P. Parham (1997). Interactions of HLA-B*4801 with peptide and CD8. *Tissue Antigens* 50: 258-64.

Mata, M., P. J. Travers, Q. Liu, F. R. Frankel and Y. Paterson (1998). The MHC class I-restricted immune response to HIV-gag in BALB/c mice selects a single epitope that does not have a predictable MHC-binding motif and binds to $K^d$ through interactions between a glutamine at P3 and pocket D. *J. Immunol.* 161: 2985-2993.

Matsui, M., C. E. Hioe and J. A. Frelinger (1993). Roles of the six peptide-binding pockets of the HLA-A2 molecule in allorecognition by human cytotoxic T-cell clones. *Proc. Natl. Acad. Sci. USA* 90: 674-678.

Matsumura, M., D. H. Fremont, P. A. Peterson and I. A. Wilson (1992). Emerging principles for the recognition of peptide antigens by MHC class I molecules. *Science* 257: 927-934.

Melief, C. J. (1992). Tumor eradication by adoptive transfer of cytotoxic T lymphocytes. *Adv. Cancer. Res.* 58: 143-75.

Monaco, J. J., S. Cho and M. Attaya (1990). Transport protein genes in the murine MHC: possible implications for antigen processing. *Science* 250: 1723-1726.

Moore, M. W., F. R. Carbone and M. J. Bevan (1988). Introduction of soluble protein into the class I pathway of antigen processing and presentation. *Cell* 54: 777-785.

Moots, R. J. (1993). In the groove: the fine detail of antigen presentation to cytotoxic T lymphocytes. *Clin. Sci.* 84: 585-591.

Mosse, C. A., L. Meadows, C. J. Luckey, D. J. Kittlesen, E. L. Huczko, C. L. Slingluff, Jr., J. Shabanowitz, D. F. Hunt and V. H. Engelhard (1998). The class I antigen-processing pathway for the membrane protein tyrosinase involves translation in the endoplasmic reticulum and processing in the cytosol. *J. Exp. Med.* 187: 37-48.

Muul, L. M., P. J. Spiess, E. P. Director and S. A. Rosenberg (1987). Identification of specific cytolytic immune responses against autologous tumor in humans bearing malignant melanoma. *J. Immunol.* 138: 989-995.

Nathenson, S. G., H. Uehara, B. M. Ewenstein, T. J. Kindt and J. E. Coligan (1981). Primary structural analysis of transplantation antigens of the murine H-2 major histocompatibility complex. *Annu. Rev. Biochem.* 50: 1025-1052.

Neefjes, J. J., G. J. Hammerling and F. Momburg (1993). Folding and assembly of major histocompatibility complex class I heterodimers in the endoplasmic reticulum of intact cells precedes the binding of peptide. *J. Exp. Med.* 178:1971-1980.

Nei, M., and A. L. Hughes (1992). Balanced polymorphism and evolution by the birth-and-death process in the MHC loci. In *Proceedings of the Eleventh International Histocompatibility Workshop and Conference.* K. Tsuji, M. Aizawa and T. Sasazuki, eds. Oxford; Oxford University Press 2: 27-38.

Neisig, A., R. Wubbolts, X. Zang, C. Melief and J. Neefjes (1996). Allele-specific differences in the interaction of MHC class I molecules with transporters associated with antigen processing. *J. Immunol.* 156: 3196-3206.

Nößner, E. and P. Parham (1995). Species-specific differences in chaperone interaction of human and mouse major histocompatibility complex class I molecules. *J. Exp. Med.* 181: 327-337.

Ooba, T., H. Hayashi, S. Karaki, M. Tanabe, K. Kano and M. Takiguchi (1989). The structure of HLA-B35 suggests that it is derived from HLA-Bw58 by two genetic mechanisms. *Immunogenetics* 30: 76-80.

Orr, H. T., J. A. López de Castro, D. Lancet and J. L. Strominger (1979). Complete amino acid sequence of a papain-solubilized human histocompatibility antigen, HLA-B7.2: sequence determination and search for homologies. *Biochemistry* 18: 5711-5720.

Pamer, E. and P. Cresswell (1998). Mechanisms of MHC class I-restricted antigen processing. *Annu. Rev. Immunol.* 16: 323-358.

Pamer, E. G., J. T. Harty and M. J. Bevan (1991). Precise prediction of a dominant class I MHC-restricted epitope of *Listera monocytogenes. Nature* 353: 852-855.

Papayannopoulos, I. A. (1995). The interpretation of collision-induced dissociation tandem mass spectra of peptides. *Mass Spectrom. Rev.* 14: 49-73.

Paradela, A., M. Garcia-Peydró, J. Vazquez, D. Rognan and J. López de Castro (1998). The same natural ligand is involved in allorecognition of multiple HLA-B27 subtypes by a single T cell clone: role of peptide and the MHC molecule in alloreactivity. *J. Immunol.* 161: 5481-5490.

Parham, P. (1990). Transporters of delight. *Nature* 348: 674-675.

Parham, P. (1992). Evolution of class I HLA polymorphism: selection and drift. In *Proceedings of the Eleventh International Histocompatibility Workshop and Conference.* K. Tsuji, M. Aizawa, and T. Sasazuki, eds. Oxford; Oxford University Press 2: 72-82.

Parham, P. (1996). Pictures of MHC restriction. *Nature* 384: 109-110.

Parham, P., E. J. Adams and K. L. Arnett (1995). The origins of HLA-A, B, and C polymorphism. *Immunol. Rev.* 143: 141-180.

Parham, P., D. A. Lawlor, C. E. Lomen and P. D. Ennis (1989). Diversity and diversification of HLA-A, B, C alleles. *J. Immunol.* 142: 3937-3950.

Parham, P., D. A. Lawlor, R. D. Salter, C. E. Lomen and P. D. Ennis (1989). HLA-A, B, C: patterns of polymorphism in peptide binding proteins. In *Immunobiology of HLA.* B. Dupont, ed. New York; Springer-Verlag 2:10-33.

Parham, P., C. E. Lomen, D. A. Lawlor, J. P. Ways, N. Holmes, H. L. Coppin, R. D. Salter, A. M. Wan and P. Ennis (1988). Nature of polymorphism in HLA-A, B, C molecules. *Proc. Natl. Acad. Sci. USA* 85: 4005-4009.

Parker, K. C., M. A. Bednarek and J. E. Coligan (1994). Scheme for ranking potential HLA-A2 binding peptides based on independent binding of individual peptide sidechains. *J. Immunol.* 152: 163-75.

Payne, R., B. Amos, D. Kostyu, C. P. Engelfriet, P. M. van den Berg-Loonen, E. S. Curtoni and P. Richiardi (1978). Subdivisions of the HLA-B5 and Bw35 complex. *Tissue Antigens* 11: 302-314.

Payne, R. and E. Hackel (1961). Inheritance of human leukocyte antigens. *Am. J. Human Genet* 13: 306-319.

Peh, C. A., S. R. Burrows, M. Bamden, R. Khanna, P. Cresswell, D. J. Moss and J. McCluskey (1998). HLA-B27-restricted antigen presentation in the absence of tapasin reveals polymorphism in mechanisms of HLA class I peptide loading. *Immunity* 8: 531-542.

Pohla, H., W. Kuon, P. Tabaczewski, C. Doemer and E. H. Weiss (1989). Allelic variation in HLA-B and HLA-C sequences and the evolution of the HLA-B alleles. *Immunogenetics* 29: 297-307.

Prilliman, K., D. Lawlor, M. Ellexson, N. McElwee, D. Confer, D. K. C. Cooper, R. C. Kennedy and W. Hildebrand (1996). Characterization of baboon class I major histocompatibility complex molecules: implications for baboon-to-human xenotransplantation. *Transplantation* 61: 989-996.

Prilliman, K., M. Lindsey, Y. Zuo, K. W. Jackson, Y. Zhang and W. Hildebrand (1997). Large-scale production of class I bound peptides: assigning a signature to HLA-B*1501. *Immunogenetics* 45: 379-385.

Prilliman, K., N. Steiner, M. Ellexson, D. Stewart, M. Lau, P. Terasaki, C. Hurley and W. Hildebrand (1996). Novel alleles HLA-B*7802 and B*51022: evidence for convergency in the HLA-B5 family. *Tissue Antigens* 47: 49-57.

Prilliman, K. R., M. Lindsey, K. W. Jackson, J. Cole, R. Bonner and W. H. Hildebrand (1998). Complexity among constituents of the HLA-B*1501 peptide motif. *Immunogenetics* 48: 89-97.

Prilliman, K. R., M. Lindsey, J. Wang, K. W. Jackson and W. H. Hildebrand (1999). Peptide motif of the class I molecule HLA-B*1503. *Immunogenetics* 49: 144-146.

Prokupek, B., P. Dunn, J. Ross, F. Jordan, R. Holman, J. A. Madrigal and A. -M. Little (1997). HLA-A*2903 expresses an epitope shared with HLA-A*8001. *Tissue Antigens* 51: 115-118.

Rammensee, H. -G., J. Bachmann and S. Stevanovic (1997). The Function. In *MHC Ligands and Peptide Motifs*. H. -G. Rammensee, J. Bachmann, and S. Stevanovic, eds. Molecular Biology Intelligence Unit series. Austin, Tex.; Landes Bioscience: 217-369.

Rammensee, H. -G., K. Falk and O. Rötzschke (1993). Peptides naturally presented by MHC class I molecules. *Annu. Rev. Immunol.* 11: 213-244.

Reid, S. W., S. McAdam, K. J. Smith, P. Klenerman, C. A. O'Callaghan, K. Harlos, B. K. Jakobsen, A. J. McMichael, J. I. Bell, D. I. Stuart and E. Y. Jones (1996). Antagonist HIV-1 Gag peptides induce structural changes in HLA B8. *J. Exp. Med.* 184: 2279-2286.

Riberdy, J. M., J. R. Newcomb, M. J. Surman, J. A. Barbosa and P. Cresswell (1992). HLA-DR molecules from an antigen-processing mutant cell line are associated with invariant chain peptides. *Nature* 360: 474-477.

Riddell, S. R., K. S. Watanabe, J. M. Goodrich, M. E. Agha and P. D. Greenberg (1992). Restoration of viral immunity in immunodeficient humans by the adoptive transfer of CTL clones. *Science* 257: 238-241.

Robbins, P. A., D. N. Garboczi and J. L. Strominger (1995). HLA-A*0201 complexes with two 10-mer peptides differing at the P2 anchor residue have distinct refolding kinetics. *J. Immunol.* 154: 703-709.

Robey, E. and B. J. Fowlkes (1994). Selective events in T cell development. *Annu. Rev. Immunol.* 12: 675-705.

Rodriguez, S. G., M. Bei, A. Inamdar, D. Stewart, A. H. Johnson and C. K. Hurley (1996). Molecular and serological characterization of HLA-B71 in association with different class I haplotypes or in different ethnic groups. *Tissue Antigens* 47: 58-62.

Rodriguez, S. G., A. H. Johnson and C. K. Hurley (1993). Molecular characterization of HLA-B71 from an African American individual. *Hum. Immunol.* 37: 192-194.

Roelse, J., M. Grommé, F. Momburg, G. Hämmerling and J. Neefjes (1994). Trimming of TAP-translocated peptides in the endoplasmic reticulum and in the cytosol during recycling. *J. Exp. Med.* 180: 1591-1597.

Roepstorff, P. and J. Fohlman (1984). Proposal for a common nomenclature for sequence ions in mass spectra of peptides. *Biomed. Mass Spectrom.* 11: 601.

Rohren, E. M., L. R. Pease, H. L. Ploegh and T. N. M. Schumacher (1993). Polymorphisms in the pockets of major histocompatibility complex class I molecules influence peptide preference. *J. Exp. Med.* 177: 1713-1721.

Rojos, S., P. Aparicio, S. Y. Choo, J. A. Hansen and J. A. López de Castro (1987). Structural analysis of an HLA-B27 population variant, B27f: multiple patterns of amino acid changes within a single polypeptide segment generates polymorphism in HLA-B27. *J. Immunol.* 139: 831-836.

Rötzschke, O. and K. Falk (1991). Naturally-occurring peptide antigens derived from the MHC class-I-restricted processing pathway. *Immunol. Today* 12: 447-455.

Rötzschke, O., K. Falk, K. Deres, H. Schild, M. Norda, J. Metzger, G. Jung and H. -G. Rammensee (1990). Isolation and analysis of naturally processed viral peptides as recognized by cytotoxic T cells. *Nature* 348:252-254.

Ruppert, J., J. Sidney, E. Celis, R. T. Kubo, H. M. Grey and A. Sette (1993). Prominent role of secondary anchor residues in peptide binding to HLA-A2.1 molecules. *Cell* 74: 929-937.

Sadasivan, B., P. J. Lehner, B. Ortmann, T. Spies and P. Cresswell (1996). Roles for calreticulin and a novel glycoprotein, tapasin, in the interaction of MHC class I molecules with TAP. *Immunity* 5: 103-114.

Sadovnikova, E., X. Zhu, S. M. Collins, J. Zhou, K. Vousden, L. Crawford, P. Beverley and H. J. Stauss (1993). Limitations of predictive motifs revealed by cytotoxic T lymphocyte epitope mapping of the human papilloma virus E7 protein. *Int. Immunol.* 6: 289-296.

Salter, R. D. (1994). Intracellular transport of class I HLA molecules is affected by polymorphic residues in the binding groove. *Immunogenetics* 39: 266-271.

Salter, R. D., D. N. Howell and P. Cresswell (1985). Genes regulating HLA class I antigen expression in T-B lymphoblast hybrids. *Immunogenetics* 21: 235-246.

Saper, M. A., P. J. Björkman and D. C. Wiley (1991). Refined structure of the human histocompatibility antigen HLA-A2 at 2.6 Å resolution. *J. Mol. Biol.* 219: 277-319.

Schmitz, J. E., M. J. Kuroda, S. Santra, V. G. Sasseville, M. A. Simon, M. A. Lifton, P. Racz, K. Tenner-Racz, M. Dalesandro, B. J. Scallon, J. Ghrayeb, M. A. Forman, D. C. Montefiori, E. P. Rieber, N. L. Letvin and K. A. Reimann (1999). Control of viremia in simian immunodeficiency virus infection by $CD8^+$ lymphocytes. *Science* 283: 857-860.

Sette, A., S. Ceman, R. T. Kubo, K. Sakaguchi, E. Appella, D. F. Hunt, T. A. Davis, H. Michel, J. Shabanowitz, R. Ruders dorf, H. M. Grey and R. DeMars (1992). Invariant chain peptides in most HLA-DR molecules of an antigen-processing mutant. *Science* 258: 1801-1804.

Sette, A., J. Sidney, M. -F. del Guercio, S. Southwood, J. Ruppert, C. Dahlberg, H. M. Grey and R. Kubo (1994). Peptide binding to the most frequent HLA-A class I alleles measured by quantitative molecular binding assays. *Mol. Immunol.* 31: 813-822.

Shichijo, S., M. Nakao, Y. Imai, H. Takasu, M. Kawamoto, F. Niiya, D. Yang, Y. Toh, H. Yamana and K. Itoh (1998). A gene encoding antigenic peptides of human squamous cell carcinoma recognized by cytotoxic T lymphocytes. *J. Exp. Med.* 187: 277-288.

Sidney, J., M. -F. del Guercio, S. Southwood, V. H. Engelhard, E. Appella, H. -G. Rammensee, K. Falk, O. Rötzschke, M. Takiguchi, R. T. Kubo, H. M. Grey and A. Sette (1995). Several HLA alleles share overlapping peptide specificities. *J. Immunol.* 154: 247-259.

Sidney, J., H. M. Grey, S. Southwood, E. Celis, P. A. Wentworth, M. -F. del Guercio, R. T. Kubo, R. W. Chestnut and A. Sette (1996a). Definition of an HLA-A3-like supermotif demonstrates the overlapping peptide-binding repertoires of common HLA molecules. *Hum. Immunol.* 45: 79-93.

Sidney, J., S. Southwood, M. -F. del Guercio, H. M. Grey, R. W. Chestnut, R. T. Kubo and A. Sette (1996b). Specificity and degeneracy in peptide binding to HLA-B7-like class I molecules. *J. Immunol.* 157: 3480-3490.

Sidney, J., H. M. Grey, R. T. Kubo and A. Sette (1996c). Practical, biochemical, and evolutionary implications of the discovery of HLA class I supermotifs. *Immunol. Today* 17: 261-266.

Silver, M. L., K. C. Parker and D. C. Wiley (1991). Reconstitution by MHC-restricted peptides of HLA-A2 heavy chain with $\beta_2$-microglobulin, in vitro. *Nature* 350: 619-622.

Simmons, W. A., S. G. Summerfield, D. C. Roopenian, C. A. Slaughter, A. R. Zuberi, S. J. Gaskell, R. S. Bordoli, J. Hoyes, C. R. Moomaw, R. A. Colbert, L. Y. -W. Leong, G. W. Butcher, R. E. Hammer and J. D. Taurog (1997). Novel HY peptide antigens presented by HLA-B27. *J. Immunol.* 159: 2750-2759.

Skipper, J. C. A., D. J. Kittlesen, R. C. Hendrickson, D. D. Deacon, N. L. Harthun, S. N. Wagner, D. F. Hunt, V. H. Engelhard and C. L. Slingluff, Jr. (1996). Shared epitopes for HLA-A3-restricted melanoma-reactive human CTL include a naturally processed epitope from Pme-17/gp100. *J. Immunol.* 157: 5027-5033.

Smith, J. D., J. C. Solheim, B. M. Carreno and T. H. Hansen (1995). Characterization of class I MHC folding intermediates and their disparate interactions with peptide and $\beta_2$-microglobulin. *Mol. Immunol.* 32: 531-540.

Smith, K. D. and C. T. Lutz (1997). Alloreactive T cell recognition of MHC class I molecules: the T cell receptor interacts with limited regions of the MHC class I long a helices. *J. Immunol.* 158: 2805-2812.

Smith, K. J., S. W. Reid, D. I. Stuart, A. J. McMichael, E. Y. Jones and J. I. Bell (1996a). An altered position of the alpha 2 helix of MHC class I is revealed by the crystal structure of HLA-B*3501. *Immunity* 4: 203-213.

Smith, K. J., S. W. Reid, K. Harlos, A. J. McMichael, D. l. Stuart, J. I. Bell and E. Y. Jones (1996b). Bound water structure and polymorphic amino acids act together to allow the binding of different peptides to MHC class I HLA-B53. *Immunity* 4: 215-228.

Snyder, H. L., J. W. Yewdell and J. R. Bennink (1994). Trimming of antigenic peptides in an early secretory compartment. *J. Exp. Med.* 180: 2389-2394.

Sobao, Y., N. Tsuchiya, M. Takiguchi and K. Tokunaga (1999). Overlapping peptide-binding specificities of HLA-B27 and B39: evidence for a role of peptide supermotif in the pathogenesis of spondylarthropathies. *Arthritis Rheum.* 42: 175-181.

Solheim, J. C., B. M. Carreno, J. D. Smith, J. Gorka, N. B. Myers, Z. Wen, J. M. Martinko, D. R. Lee and T. Hansen (1993). Binding of peptides lacking consensus anchor residue alters H-2L$^d$ serologic recognition. *J. Immunol.* 151: 5387-5397.

Spee, P. and J. Neefjes (1997). TAP-translocated peptides specifically bind proteins in the endoplasmic reticulum, including gp96, protein disulfide isomerase and calreticulin. *Eur. J. Immunol.* 27: 2441-2449.

Steinle, A., K. Falk, O. Rötzschke, V. Gnau, S. Stevanovic, G. Jung, D. J. Schendel and H. -G. Rammensee (1995). Motif of HLA-B*3503 peptide ligands. *Immunogenetics* 43: 105-107.

Stevanovic, S. and G. Jung (1993). Multiple sequence analysis: pool sequencing of synthetic and natural peptide libraries. *Anal. Biochem.* 212: 212-220.

Storkus, W. J., J. Alexander, J. A. Payne, J. R. Dawson and P. Cresswell (1989). Reversal of natural killing susceptibility in target cells expressing transfected class I HLA genes. *Proc. Natl. Acad. Sci. USA* 86: 2361-2364.

Sudo, T., N. Kamikawaji, A. Kimura, Y. Date, C. J. Savoie, H. Nakashima, E. Furuichi, S. Kuhara and T. Sasazuki (1995). Differences in MHC class I self peptide repertoires among HLA-A2 subtypes. *J. Immunol.* 155: 4749-4756.

Suh, W. -K., M. A. Derby, M. F. Cohen-Doyle, G. J. Schoenhals, K. Früh, J. A. Berzofsky and D. B. Williams (1999). Interaction of murine MHC class I molecules with tapasin and TAP enhances peptide loading and involves the heavy chain $\alpha_3$ domain. *J. Immunol.* 162:1530-1540.

Suh, W. -K., E. K. Mitchell, Y. Yang, P. A. Peterson, G. L. Waneck and D. B. Williams (1996). MHC class I molecules form ternary complexes with calnexin and TAP and undergo peptide-regulated interaction with TAP via their extracellular domains. *J. Exp. Med.* 184: 337-348.

Takamiya, Y., C. Schönbach, K. Nokihara, S. Ferrone, M. Yamaguchi, K. Kano, K. Egawa and M. Takiguchi (1994). HLA-B*3501-peptide interactions: role of anchor residues of peptides in their binding to HLA-B*3501 molecules. *Int. Immunol.* 6: 255-261.

Tan, T. L., A. Geluk, M. Toebes, T. H. Ottenhoff and J. W. Drijfhout (1997). A novel, highly efficient peptide-HLA class I binding assay using unfolded heavy chain molecules: identification of HIV-1 derived peptides that bind to HLA-A*0201 and HLA-A*0301. *J. Immunol. Methods* 205: 201-209.

Tanigaki, N. (1992). The specificity and efficiency of endogenous peptides in the induction of HLA class I $\alpha$ chain refolding. *Eur. J. Immunol.* 22: 2177-2180.

Tieng, V., N. Dulphy, F. Boisgérault, R. Tamouza, D. Charron and A. Toubert (1997). HLA-B*2707 peptide motif: Tyr C-terminal anchor is not shared by all disease-associated subtypes. *Immunogenetics* 47: 103-105.

Tomer, K. B., M. A. Moseley, L. J. Deterding and C. E. Parker (1994). Capillary liquid chromatography/mass spectrometry. *Mass Spectrom. Rev.* 13: 431-457.

Townsend, A. and H. Bodmer (1989). Antigen recognition by class I restricted T lymphocytes. *Annu. Rev. Immunol.* 7: 601-624.

Townsend, A., T. Elliott, V. Cerundolo, L. Foster, B. Barber and A. Tse (1990). Assembly of MHC class I molecules analyzed in vitro. *Cell* 62: 285-295.

Townsend, A., C. Ohlen, J. Bastin, H. Ljungren, L. Foster and K. Karre (1990). Association of class I major histocompatibility heavy and light chains induced by viral peptides. *Nature* 340: 443-448.

Townsend, A., C. Ohlen, L. Foster, J. Bastin, H. G. Ljunggren and K. Karre (1989). A mutant cell in which association of class I heavy and light chains is induced by viral peptides. *Cold Spring Harb. Symp. Quant. Biol.* 54: 299-308.

Townsend, A. R. M., F. M. Gotch and J. Davey (1985). Cytotoxic T cells recognize fragments of the influenza nucleoprotein. *Cell* 42: 457-467.

Tragardh, L., L. Rask, K. Wiman and P. A. Peterson (1979). Primary structure of pooled, papain-solubilized HLA-A, B, and C antigens. *Scand. J. Immunol.* 10: 597-600.

Trowsdale, J. (1995). "Both man & bird & beast": comparative organization of MHC genes. *Immunogenetics* 41: 1-17.

Tsomides, T. J., B. D. Walker and H. N. Eisen (1991). An optimal viral peptide recognized by CD8$^+$ T cells binds very tightly to the restricting class I major histocompatibility complex protein on intact cells but not to the purified class I protein. *Proc. Natl. Acad. Sci. USA* 88: 11276-11280.

Tussey, L. G., M. Matsui, S. Rowland-Jones, R. Warburton, J. A. Frelinger and A. McMichael (1994). Analysis of mutant HLA-A2 molecules: differential effects on peptide binding and CTL recognition. *J. Immunol.* 152: 1213-1221.

Tzeng, C. -M., E. J. Adams, J. E. Gumperz, L. Percival, R. S. Wells, P. Parham and L. D. Barber (1996). Peptides bound endogenously by HLA-Cw*0304 expressed in LCL 721.221 cells include a peptide derived from HLA-E. *Tissue Antigens* 48: 325-328.

Urban, R. G., R. M. Chicz, W. S. Lane, J. L. Strominger, A. Rehm, M. J. H. Kenter, F. G. C. M. UytdeHaag, H. Ploegh, B. Uchanska-Ziegler and A. Ziegler (1994). A subset of HLA-B27 molecules contains peptides much longer than nonamers. *Proc. Natl. Acad. Sci. USA* 91: 1534-1538.

van der Heeft, E., G. J. ten Hove, C. A. Herberts, H. D. Meiring, C. A. C. M. van Els and A. P. J. M. de Jong (1998). A microcapillary column switching HPLC-electrospray ionization MS system for the direct identification of peptides presented by major histocompatibility complex class I molecules. *Anal. Chem.* 70: 3742-3751.

van Rood, J. J. (1969). Leucocyte grouping and organ transplantation. *Br. J. Haematol.* 16: 211-219.

Veronese, F. M., D. Arnoft, V. Barnaba, D. J. Loftus, K. Sakaguchi, C. B. Thompson, S. Salemi, C. Mastroianni, A. Sette, J. Shabanowitz, D. F. Hunt and E. Appella (1996). Autoreactive cytotoxic T lymphocytes in human immunodeficiency virus type 1-infected subjects. *J. Exp. Med.* 183: 2509-2516.

Vose, B. M. and G. D. Bonnard (1982). Human tumour antigens defined by cytotoxicity and proliferative responses of cultured lymphoid cells. *Nature* 296: 359-361.

Walden, P. (1996). T-cell epitope determination. *Curr. Opin. Immunol.* 8: 68-74.

Walker, B. D., C. Flexner, T. J. Paradis, T. C. Fuller, M. S. Hirsch, R. T. Schooley and B. Moss (1988). HIV-1 reverse transcriptase is a target for cytotoxic T-lymphocytes in infected individuals. *Science* 240: 64-66.

Wang, W., P. H. Gulden, R. A. Pierce, J. A. Shabanowitz, S. T. Man, D. F. Hunt and V. H. Engelhard (1997). A naturally processed peptide presented by HLA-A*0201 is expressed at low abundance and recognized by an alloreactive CD8+ cytotoxic T cell with apparent high affinity. *J. Immunol.* 158: 5797-5804.

Wang, Y., D. S. Guttoh and M. J. Androlewicz (1998). TAP prefers to transport melanoma antigenic peptides which are longer than the optimal T-cell epitope: evidence for further processing in the endoplasmic reticulum. *Melanoma Res.* 8: 345-353.

Watson, J. T. (1997). Types of mass spectrometers. In *Introduction to Mass Spectrometry*. J. T. Watson, ed. Philadelphia, Pa.; Lippincott-Raven: 64-108.

Wilm, M. and M. Mann (1996). Analytical properties of the nanoelectrospray ion source. *Anal. Chem.* 68: 1-8.

Winkler, C., A. Schultz, S. Cevario and S. O'Brien (1989). Genetic characterization of FLA, the cat major histocompatibility complex. *Proc. Natl. Acad. Sci. USA* 86: 943-947.

Woods, A. S., A. Y. C. Huang, R. J. Cotter, G. R. Pasternack, D. M. Pardoll and E. M. Jaffee (1995). Simplified high-sensitivity sequencing of a major histocompatibility complex class I-associated immunoreactive peptide using matrix assisted laser desorption/ionization mass spectrometry. *Anal. Biochem.* 226: 15-25.

Yagüe, J., J. Vázquez and J. A. López de Castro (1998). A single amino acid change makes the peptide specificity of B*3910 unrelated to B*3901 and closer to a group of HLA-B proteins including the malaria-protecting allotype HLA-B53. *Tissue Antigens* 52: 416-421.

Yap, K. L., G. L. Ada and I. F. C. McKenzie (1978). Transfer of specific cytotoxic T lymphocytes protects mice inoculated with influenza virus. *Nature* 273: 238-239.

Yewdell, J. W. and J. R. Bennink (1990). The binary logic of antigen processing and presentation to T cells. *Cell* 62: 203-206.

Yokoyama, W. M. (1993). Recognition structures on natural killer cells. *Curr. Opin. Immunol.* 5: 67-73.

Yoon, H., M. K. Chung, S. S. Min, H. G. Lee, W. D. Yoo, K. T. Chung, N. P. Jung and S. N. Park (1998). Synthetic peptides of human papillomavirus type 18 E6 harboring HLA-A2.1 motif can induce peptide-specific cytotoxic T-cells from peripheral blood mononuclear cells of healthy donors. *Virus Res.* 54: 23-29.

York, I. A. and K. L. Rock (1996). Antigen processing and presentation by the class I major histocompatibility complex. *Annu. Rev. Immunol.* 14: 369-396.

Young, A. C., S. G. Nathenson and J. C. Sacchettini (1995). Structural studies of class I major histocompatibility complex proteins: insights into antigen presentation. *FASEB J.* 9: 26-36.

Young, N. T., A. Mulder, V. Cerundolo, F. H. Claas and K. I. Welsh (1998). Expression of HLA class I antigens in transporter associated with antigen processing (TAP)-deficient mutant cell lines. *Tissue Antigens* 52: 368-373.

Zeh III, H. J., G. H. Leder, M. T. Lotze, R. D. Salter, M. Tector, G. Stuber, S. Modrow and W. J. Storkus (1994). Flow-cytometric determination of peptide-class I complex formation: identification of p53 peptides that bind to HLA-A2. *Hum. Immunol.* 39: 79-86.

Zhang, C., J. L. Cornette, J. A. Berzofsky and C. DeLisi (1997). The organization of human leucocyte antigen class I epitopes in HIV genome products: implications for HIV evolution and vaccine design. *Vaccine* 15: 1291-1302.

Zinkernagel, R. M. and P. C. Doherty (1974). Restriction of in vitro T cell-mediated cytotoxicity in lymphocytic choriomeningitis within a syngeneic or semiallogeneic system. *Nature* 248: 701-702.

---

We claim:

1. A method for the production of soluble Class I MHC complexes in a hollow fiber bioreactor unit having an appropriate growth media therein, comprising the steps of:
   obtaining gDNA from a sample wherein a portion of the gDNA encodes a desired individual Class I MHC heavy chain molecule;
   producing a PCR product encoding a soluble form of the desired Class I MHC heavy chain molecule by PCR amplification of the gDNA, wherein the amplification utilizes at least one locus-specific primer having a stop codon incorporated into a 3' primer thereby resulting in a PCR product that does not encode the cytoplasmic and transmembrane domains of the desired Class I MHC heavy chain molecule, thereby producing a PCR product that encodes a soluble Class I MHC heavy chain molecule;
   inserting the PCR product into a mammalian expression vector to form a plasmid containing the PCR product encoding the soluble Class I MHC heavy chain molecule;
   electroporating the plasmid containing the PCR product into at least one suitable host cell; and
   inoculating the hollow fiber bioreactor unit with the at least one suitable host cell containing the plasmid such that the hollow fiber bioreactor unit produces soluble Class I MHC complexes having the desired Class I MHC heavy chain molecule associated with native beta-2-microglobulin and loaded with endogenously produced peptides, wherein the beta-2-microglobulin is native to and endogenously produced in the host cell.

2. The method according to claim 1, further comprising the step of harvesting the soluble Class I MHC complexes from the hollow fiber bioreactor unit.

3. The method according to claim 1, wherein the gDNA is obtained from blood, saliva, hair, semen, or sweat.

4. The method according to claim 1, wherein the mammalian expression vector contains a promoter that facilitates increased expression of the PCR product.

5. The method according to claim 1, wherein the suitable host cell lacks expression of Class I MHC molecules.

6. A method for the production of soluble Class I MHC complexes in a hollow fiber bioreactor unit having an appropriate growth media therein, comprising the steps of:
   obtaining gDNA from a sample, wherein a portion of the gDNA encodes a desired individual Class I MHC heavy chain molecule;
   transfecting the gDNA into a cell line, wherein the cell line transcribes the gDNA into mRNA;
   isolating mRNA and reverse transcribing the mRNA to obtain cDNA, wherein the cDNA contains cDNA encoding the desired Class I MHC heavy chain molecule;
   producing a PCR product encoding a soluble form of the desired Class I MHC heavy chain molecule by PCR amplification of the cDNA encoding the desired Class I MHC heavy chain molecule, wherein the amplification utilizes at least one locus-specific primer and results in a PCR product that does not encode the cytoplasmic and transmembrane domains of the desired Class I MHC heavy chain molecule, thereby producing a PCR product that encodes a soluble Class I MHC heavy chain molecule;
   inserting the PCR product into a mammalian expression vector to form a plasmid containing the PCR product;
   electroporating the plasmid containing the PCR product into at least one suitable host cell; and
   inoculating the hollow fiber bioreactor unit with the at least one suitable host cell containing the plasmid such that the hollow fiber bioreactor unit produces soluble Class I MHC complexes having the desired Class I MHC heavy chain molecule associated with native beta-2-microglobulin and loaded with endogenously produced peptides, wherein the beta-2-microglobulin is native to and endogenously produced in the host cell.

7. The method according to claim 6, further comprising the step of harvesting the soluble Class I MHC complexes from the hollow fiber bioreactor unit.

8. The method according to claim 6, wherein the gDNA is obtained from blood, saliva, hair, semen, or sweat.

9. The method according to claim 6, wherein the locus-specific primer includes a sequence encoding a tail such that the soluble Class I MHC heavy chain molecule encoded by the PCR product contains a tail attached thereto that facilitates in purification of the soluble Class I MHC complexes produced therefrom.

10. The method according to claim 6, wherein the mammalian expression vector contains a promoter that facilitates increased expression of the PCR product.

11. The method according to claim 6, wherein the suitable host cell lacks expression of Class I MHC molecules.

12. The method according to claim 6, wherein the soluble Class I MHC complexes are folded naturally and are trafficked through the host cell in such a way that they are identical in functional properties to a Class I MHC complex expressed from the Class I MHC heavy chain allele mRNA and thereby bind peptide ligands in an identical manner as full-length, cell-surface-expressed Class I MHC complexes.

* * * * *

UNITED STATES PATENT AND TRADEMARK OFFICE
CERTIFICATE OF CORRECTION

| | | |
|---|---|---|
| PATENT NO. | : 7,521,202 B2 | Page 1 of 4 |
| APPLICATION NO. | : 11/099283 | |
| DATED | : April 21, 2009 | |
| INVENTOR(S) | : William H. Hildebrand and Kiley R. Prillman | |

It is certified that error appears in the above-identified patent and that said Letters Patent is hereby corrected as shown below:

Page 2, Under Publications: missing the following reference:
"LARGE-SCALE PRODUCTION OF CLASS I BOUND PEPTIDES; ASSIGNING A SIGNATURE TO HLA-B* 1501", Prillman et al., Immunogenetics, 45(6): 379-385 (1997).

Column 1, line 11-12: After "THEREOF," delete "now published"

Column 4, line 63: Delete "(Zinkemagel" and replace with -- Zindemagel --

Column 10, line 63: Delete "(class II)" and replace with -- (class III) --

Column 14, line 56: Delete "MSIMS" and replace with -- MS/MS --

Column 15, line 58: After "MHC" delete "class II/peptide" and
     replace with --class I/peptide --

Column 18, line 64: Delete "$CD8_+$" and replace with -- $CD8^+$ --

Column 22, line 61: Delete "un" and replace with -- run --

Column 23, line 7: Delete "un" and replace with -- run --

Column 24, line 37: Delete "AIS)" and replace with -- A/S --

Column 25, line 11: Delete "Fohiman" and replace with -- Fohlman --

Column 25, line 21: Delete "lie" and replace with -- Ile --

Column 25, line 22: Delete "GIn" and replace with -- Gln --

Column 25, line 54: Delete "(Gin" and replace with -- (Gln --

Column 25, line 64: Delete "GIn" and replace with -- Gln --

Column 26, line 43: Delete "GIn" and replace with -- Gln --

Column 26, line 46: Delete "Gin" and replace with -- Gln --

UNITED STATES PATENT AND TRADEMARK OFFICE
CERTIFICATE OF CORRECTION

PATENT NO. : 7,521,202 B2
APPLICATION NO. : 11/099283
DATED : April 21, 2009
INVENTOR(S) : William H. Hildebrand and Kiley R. Prillman It is certified that error appears in the above-identified patent and that said Letters Patent is hereby corrected as shown below:

Column 27, line 46: Delete "Gin" and replace with -- Gln --

Column 29, line 43: Delete "SHANSAWL" and replace with -- SHANSAVVL --

Column 30, line 59: Delete "Gin" and replace with -- Gln --

Column 30, line 66: Delete "GIn" and replace with -- Gln --

Column 31, line 59: Delete "Gin/Lys." and replace with -- Gln/Lys. --

Column 31, line 67: Delete "Gin/Lys" and replace with -- Gln/Lys --

Column 33, line 15: Delete "Gin/Lys" and replace with -- Gln/Lys --

Column 34, line 12: Delete "FIG. 15." and replace with -- FIG. 18. --

Column 35, line 15: Delete "Gin" and replace with -- Gln --

Column 35, line 16: Delete "Gin/Lys" and replace with -- Gln/Lys --

Column 38, line 49: Delete "Gin" and replace with -- Gln --

Column 43, line 36: Delete "KCL" and replace with -- KCl --

Column 43, line 56: Delete "#RO101S;" and replace with -- #R0101S; --

Column 48, line 49: Delete "Invemizzi" and replace with -- Invernizzi --

Column 53, line 55: Delete "(SHLA)" and replace with -- (sHLA) --

Column 55, line 1: Delete "orderto" and replace with -- order to --

Column 56, line 2: Delete "vectorwas" and replace with -- vector was --

Column 56, line 8: Delete "(A*11021)" and replace with -- (A*1102T) --

Column 56, line 32: Delete "otherthree" and replace with -- other three --

UNITED STATES PATENT AND TRADEMARK OFFICE
CERTIFICATE OF CORRECTION

PATENT NO. : 7,521,202 B2
APPLICATION NO. : 11/099283
DATED : April 21, 2009
INVENTOR(S) : William H. Hildebrand and Kiley R. Prillman It is certified that error appears in the above-identified patent and that said Letters Patent is hereby corrected as shown below:

Column 58, line 61: Delete "wam" and replace with -- warn --

Column 59, line 7: Delete "class II/peptide" and replace with -- class I/peptide --

Column 59, line 30: Delete "class II/pep-" and replace with -- class I/pep- --

Column 61, line 5: Delete "(MG CTT)" and replace with -- (AAG CTT) --

Column 61, line 31: Delete "(GM TTC)" and replace with -- (GAA TTC) --

Column 62, line 12: Delete "complexwas" and replace with -- complex was --

Column 62, line 32: Delete "sHLAwas" and replace with -- sHLA was --

Column 62, line 33: Delete "productto" and replace with -- product to --

Column 68, line 1: Delete "Lso-" and replace with -- Iso- --

Column 69, line 57: Delete "thecomplex" and replace with -- the complex --

Column 71, line 54: Delete "Nuchtem," and replace with -- Nuchtern, --

Column 72, line 66: Delete "Bjomdal" and replace with -- Bjorndal --

Column 73, line 4: Delete "Heilpem" and replace with -- Heilpern --

Column 73, line 19: Delete "Amoft," and replace with -- Arnott, --

Column 76, line 39: Delete "Bamden," and replace with -- Barnden --

Column 76, line 44: Delete "Doemer" and replace with -- Doerner --

Column 79, line 10: After "class I long" delete "a" and replace with -- α --

Column 80, line 47: Delete "Frelingerand" and replace with -- Frelinger and --

UNITED STATES PATENT AND TRADEMARK OFFICE
CERTIFICATE OF CORRECTION

PATENT NO. : 7,521,202 B2
APPLICATION NO. : 11/099283
DATED : April 21, 2009
INVENTOR(S) : William H. Hildebrand and Kiley R. Prillman It is certified that error appears in the above-identified patent and that said Letters Patent is hereby corrected as shown below:

Column 81, line 1: Delete "Amoft," and replace with -- Arnott --

Column 81, line 35: Delete "Pastemack," and replace with -- Pasternack --

Signed and Sealed this

Twenty-third Day of June, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 7,521,202 B2 | Page 1 of 1 |
| APPLICATION NO. | : 11/099283 | |
| DATED | : April 21, 2009 | |
| INVENTOR(S) | : William H. Hildebrand and Kiley R. Prillman | |

It is certified that error appears in the above-identified patent and that said Letters Patent is hereby corrected as shown below:

Column 4, line 63: Delete "(Zinkemagel" and replace with -- (Zinkernagel --

Signed and Sealed this

Eighth Day of September, 2009

David J. Kappos
*Director of the United States Patent and Trademark Office*